US009134318B2

(12) United States Patent
Madian et al.

(10) Patent No.: US 9,134,318 B2
(45) Date of Patent: Sep. 15, 2015

(54) DETECTION OF OXIDIZED POLYPEPTIDES

(75) Inventors: Ashraf G. Madian, West Lafayette, IN (US); Fred E. Regnier, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/515,102

(22) PCT Filed: Dec. 10, 2010

(86) PCT No.: PCT/US2010/059828
§ 371 (c)(1),
(2), (4) Date: Aug. 27, 2012

(87) PCT Pub. No.: WO2011/072197
PCT Pub. Date: Jun. 16, 2011

(65) Prior Publication Data
US 2012/0309040 A1 Dec. 6, 2012

Related U.S. Application Data

(60) Provisional application No. 61/285,830, filed on Dec. 11, 2009.

(51) Int. Cl.
*C12Q 1/37* (2006.01)
*G01N 33/68* (2006.01)

(52) U.S. Cl.
CPC ........ *G01N 33/6848* (2013.01); *G01N 33/6842* (2013.01)

(58) Field of Classification Search
CPC .............. G01N 15/05; G01N 33/6842; G01N 33/6848; G01N 33/6893; G01N 2496/05; G01N 2496/00; G01N 2291/2466; G01N 2033/50; G01N 2030/8831; G01N 2800/7009; G01N 2800/7004; G01N 2800/02; G01N 2800/44; G01N 2800/70; C12Q 1/37; C12Q 1/6883
See application file for complete search history.

(56) References Cited

U.S. PATENT DOCUMENTS

| 6,864,099 | B2 | 3/2005 | Regnier |
| 6,872,575 | B2 | 3/2005 | Regnier |
| 7,449,170 | B2 | 11/2008 | Regnier et al. |
| 2002/0037532 | A1* | 3/2002 | Regnier et al. ................ 435/7.1 |
| 2003/0129769 | A1 | 7/2003 | Regnier |
| 2007/0087448 | A1* | 4/2007 | Nelsestuen ................... 436/173 |
| 2008/0145863 | A1 | 6/2008 | Regnier |
| 2008/0299542 | A1 | 12/2008 | Loscalzo |
| 2009/0148952 | A1 | 6/2009 | Regnier et al. |
| 2009/0226884 | A1 | 9/2009 | Tsujimoto et al. |

FOREIGN PATENT DOCUMENTS

| WO | WO 01/86306 A2 | 11/2001 |
| WO | WO 01/86306 A3 | 3/2003 |
| WO | WO 03/027682 A2 | 4/2003 |
| WO | WO 2003/027682 A3 | 2/2004 |
| WO | WO 2006/039456 A1 | 4/2006 |
| WO | WO 2009/134439 A2 | 11/2009 |
| WO | WO 2009/134439 A3 | 3/2010 |

OTHER PUBLICATIONS

Dalle-Donne I. et al., Protein carbonyl groups as biomarkers of oxidative stress, Clinica Chimica Acta, 2003, vol. 329, pp. 23-38.*
Madian A.G. et al., Identification of Differentially Expressed Oxidized Proteins in the Plasma of Type II Diabetic Zucker Rats, a Poster, No. 505, presented on Nov. 18-23, 2009 in San Francisco, USA, at the meeting for the Society for Free Radical Biology and Medicine (16th SFRBM-2009).*
Krijnen P.A.J. et al., Clusterin: a protective mediator for ischemic cardiomyocytes? Am. J. Physiol. Heart. Circ. Physiol., 2005, vol. 289, pp. H2193-H2202.*
Katz N. R. et al., Synthesis and secretion of hemopexin in primary cultures of rat hepatocytes Demonstration of an intracellular pr 酮同 of hemopexin, Eur. J. Biochem., 1985, vol. 146, pp. 1 55-159.*
Vivekanadan-Giri et al., Mass spectrometric quantification of amino acid oxidation products identifies oxidative mechanisms of diabetic end-organ damage, Rev. Endocr. Metab. Disord., Dec. 2008, vol. 9, No. 4, pp. 275-287.*
Aldini et al., "Mass spectrometric characterization of covalent modification of human serum albumin by 4-hydroxy-*trans*-2-nonenal," *J. Mass Spectrom.*, 2006, 41(9): 1149-1161. Published online Aug. 3, 2006.
Barreiro et al., "Expression and carbonylation of creatine kinase in the quadriceps femoris muscles of patients with chronic obstructive pulmonary disease." *Am. J. Respir. Cell Mol. Biol.* 33:636-642; 2005. Published in Press as DOI: 10.1165/rcmb.2005-0114OC on Sep. 15, 2005.
Berglund et al., "A Genecentric Human Protein Atlas for Expression Profiles Based on Antibodies," *Mol. Cell. Proteomics*, 2008, 7(10): 2019-2027. Published, MCP Papers in Press, Jul. 31, 2008, DOI 10.1074/mcp.R800013-MCP200.
Bolgar et al., "Determination of the Sites of 4-Hydroxy-2-nonenal Adduction to Protein by Electrospray Tandem Mass Spectrometry," *Anal. Chem.* Jul. 15, 1996, 68(14): 2325-2330. Abstract published in *Advance ACS Abstracts*, May 15, 1996.

(Continued)

*Primary Examiner* — Satyendra Singh
(74) *Attorney, Agent, or Firm* — Brown Rudnick LLP; Adam M. Schoen

(57) ABSTRACT

A diagnostic method for determining the absence or presence of a disease is provided. The method generally includes assaying the amount and/or types of oxidized peptides in a sample from a subject, and comparing these to the amount and types of reference oxidized polypeptides. The method may include the use of stable isotope label, affinity selection, to identify and quantify changes in oxidized peptides or oxidized proteins associated with diseases such as type II diabetes mellitus, breast cancer, and Parkinson's disease, to monitor a patient's response to a therapeutic agent (e.g., an antioxidant), and/or to monitor disease recurrence.

10 Claims, 35 Drawing Sheets

(56) References Cited

OTHER PUBLICATIONS

Bolgar et al., "First direct evidence for lipid/protein conjugation in oxidized human low density lipoprotein." *J. Biol. Chem.* 271:27999-28001; Nov. 8, 1996.

Borisov Oleg et al., "Low-Energy Collision-Induced Dissociation Fragmentation Analysis of Cysteinyl-Modified Peptides,"*Anal. Chem*, 2002, 74(10): 2284-2292. Published on Web Apr. 9, 2002.

Boyd-Kimball et al., "Proteomic identification of proteins oxidized by Aβ(1-42) in synaptosomes: Implications for Alzheimer's disease." *Brain Res.* 1044:206-215; 2005. Available online Apr. 15, 2005.

Brancia et al., "Comprehensive analysis of glycated human serum albumin tryptic peptides by off-line liquid chromatography followed by MALDI analysis on a time-of-flight/curved field reflectron tandem mass spectrometer." *J. Mass Spectrom.* 41:1179-1185; 2006. Published online Aug. 21, 2006.

Brock et al., "Proteomic analysis of the site specificity of glycation and carboxymethylation of ribonuclease." *J. Proteome Res.* 2:506-513; 2003. Published on Web Jul. 1, 2003.

Brown et al., "Hypoxia and oxidative stress in breast cancer Oxidative stress: its effects on the growth, metastatic potential and response to therapy of breast cancer," *Breast Cancer Research* 2001, 3:323-327. Available online at <http://breast-cancer-research.com/content/3/5/323>; 5 pages. Published: Jul. 23, 2001.

Brown et al., "Investigation of Doxorubicin Resistance in MCF-7 Breast Cancer Cells Using Shot-Gun Comparative Proteomics with Proteolytic $^{18}$O Labeling," *J. Proteome Res.*, 2004, 3(3): 455-462. Published on Web Feb. 13, 2004.

Brownlee, "Biochemistry and molecular cell biology of diabetic complications," *Nature*, Dec. 13, 2001, 414: 813-820.

Brownlee, "The Pathobiology of Diabetic Complications," *Diabetes*, Jun. 2005, 54(6): 1615-1625.

Bruenner et al., "Direct Characterization of Protein Adducts of the Lipid Peroxidation Product 4-Hydroxy-2-nonenal Using Electrospray Mass Spectrometry," *Chem. Res. Toxicol.*, 1995, 8(4): 552-559. Abstract published in Advance ACS Abstracts, Apr. 15, 1995.

Bruno et al., "Protein Carbonyl Formation in Response to Propiconazole-Induced Oxidative Stress."*J. Proteome Res.* 8:2070-2078; 2009. Published on Web Jan. 27, 2009.

Camargo et al., "Green tea exerts antioxidant action in vitro and its consumption increases total serum antioxidant potential in normal and dyslipidemic subjects," *Nutr. Res.*, Dec. 2006, 26(12): 626-631.

Canet-Aviles et al., "The Parkinson's Disease Protein DJ-1 is Neuroprotective Due to Cysteine-Sulfuric Acid-DrivenMitochondrial Localization," *PNAS*, Jun. 15, 2004, 101(24): 9103-9108.

Carbone et al., "Modification of heat shock protein 90 by 4-hydroxynonenal in a rat model of chronic alcoholic liver disease." *J. Pharmacol. Exp. Ther.* 315:8-15; Oct. 2005. Epub Jun. 10, 2005 Presented in part at the *44th annual meeting of the Society of Toxicology*, Mar. 6-10, New Orleans, LA.

Castegna et al., "Proteomic identification of oxidatively modified proteins in Alzheimer's disease brain. Part II: dihydropyrimidinase-related protein 2, a-enolase and heat shock cognate 71," *J. Neurochem.*, 2002, 82, 1524-1532.

Chaudhuri et al., "Detection of protein carbonyls in aging liver tissue: a fluorescence-based proteomic approach." *Mech. Ageing Dev.* 127:849-861; 2006. Available online Sep. 26, 2006.

Chavez et al., "New role for an old probe: affinity labeling of oxylipid protein conjugates by N'-aminooxymethylcarbonylhydrazino d-biotin." *Anal Chem* 78:6847-6854; 2006. Published on Web Aug. 30, 2006.

Chua et al., "Cell Cycle Arrest Induced by Hydrogen Peroxide is Associated with Modulation of Oxidative Stress Related Genes in Breast Cancer Cells," *Experimental Biology and Medicine*, Sep. 2009, 234: 1086-1094.

Chung et al., "Detection of carbonyl-modified proteins in interfibrillar rat mitochondria using N'-aminooxymethylcarbonylhydrazino-D-biotin as an aldehyde/keto-reactive probe in combination with Western blot analysis and tandem mass spectrometry." *Electrophoresis* 29:1317-1324; Mar. 2008.

Cocklin et al., "Identity and localization of advanced glycation end products on human beta 2-microglobulin using matrixassisted laser desorption/ionization time-of-flight mass spectrometry." *Anal. Biochem.* 314:322-325; 2003.

Cos et al., "In Vitro Antioxidant Profile of Phenolic Acid Derivatives," *Free Radical Res.*, 2002, 36(6): 711-716.

Creasy and Cottrell, "Error tolerant searching of uninterpreted tandem mass spectrometry data." *Proteomics* 2:1426-1434; 2002.

Davies et al., "Preferential degradation of oxidized proteins by the 20S proteasome may be inhibited in aging and in inflammatory neuromuscular diseases," *Neurology*, 2006, 66(2, Suppl. 1): S93-S96.

Dennis et al., "DAVID: Database for Annotation, Visualization, and Integrated Discovery," *Genome Biol.*, 2003, 4: R60; 11 pages. Published: Aug. 14, 2003.

Dorts et al., "Oxidative stress, protein carbonylation and heat shock proteins in the black tiger shrimp, *Penaeus monodon*, following exposure to endosulfan and deltamethrin." *Environ. Toxicol. Pharmacol.* 28:302-310; 2009. Available online May 20, 2009.

D'Souza et al., "Detection of catalase as a major protein target of the lipid peroxidation product 4-HNE and the lack of its genetic association as a risk factor in SLE." *BMC Med. Genet.* 9:62, 8 pages; 2008. Published: Jul. 7, 2008.

Eliuk Shannon et al., "Active site modifications of the brain isoform of creatine kinase by 4-hydroxy-2-nonenal correlate with reduced enzyme activity: mapping of modified sites by Fourier transform-ion cyclotron resonance mass spectrometry." *Chem Res Toxicol* 20:1260-1268; 2007. Published on Web Aug. 16, 2007.

Evans et al., "Are Oxidative Stress-Activated Signaling Pathways Mediators of Insulin Resistance and β-Cell Dysfunction?" *Diabetes*, Jan. 2003, 52:1-8.

Evans et al., "Oxidative Stress and Stress-Activated Signaling Pathways: A Unifying Hypothesis of Type 2 Diabetes," *Endocrine Reviews*, 2002, 23: 599-622.

Fenaille et al., "Immunoaffinity purification and characterization of 4-hydroxy-2-nonenal- and malondialdehyde-modified peptides by electrospray ionization tandem mass spectrometry." *Anal Chem* 74:6298-6304; Dec. 15, 2002. Published on Web Nov. 15, 2002.

Fenaille et al., "Study of protein modification by 4-hydroxy-2-nonenal and other short chain aldehydes analyzed by electrospray ionization tandem mass spectrometry." *J Am Soc Mass Spectrom* 14:215-226; 2003. Published online Jan. 24, 2003.

Feng et al., "Quantitative proteomic profiling of muscle type-dependent and age-dependent protein carbonylation in rat skeletal muscle mitchondria." *J. Gerontol., Ser. A* 63A:1137-1152; Nov. 2008.

Gadgil et al., "Screening and sequencing of glycated proteins by neutral loss scan LC/MS/MS method." *Anal Chem* 79:5991-5999; Aug. 1, 2007. Published on Web Jun. 16, 2007.

Georgetti et al., "Evaluation of the Antioxidant Activity of Different Flavonoids by the Chemiluminescence Method," *AAPS PharmSci*, 2003, 5(2): E20, 5 pages. Published: Jun. 13, 2003.

Gonenc et al., "Plasma malondialdehyde (MDA) levels in breast and lung cancer patients," *Journal of Clinical Pharmacy and Therapeutics*, 2001, 26:141-144.

Gong et al., "Different Immunoaffinity Fractionation Strategies to Characterize the Human Plasma Proteome," *J. Proteome Res.* 2006, 5(6): 1379-1387. Published on Web May 4, 2006.

Gontarev et al., "Application of phenylboronic acid modified hydrogel affinity chips for high-throughput mass spectrometric analysis of glycated proteins." *Rapid Communications in Mass Spectrometry* 21:1-6; Jan. 1, 2007.

Green and Toms, "Properties of subunits of avidin coupled to Sepharose." *Biochem. J.* 133:687-700; 1973.

Green, "Avidin." *Adv. Protein Chem.* 29:85-133; 1975.

Greibrokk et al., "Separating proteins by pI-values—Can 2D LC replace 2D GE?" *LC-GC Eur.* 18:355-360; 2005.

(56) References Cited

OTHER PUBLICATIONS

Grimsrud et al., "Carbonylation of Adipose Proteins in Obesity and Insulin Resistance," *Mol. Cell. Proteomics*, 2007, 6: 624-637. Published, MCP Papers in Press, Jan. 6, 2007, DOI 10.1074/mcp.M600120-MCP200.

Han et al., "Design, Synthesis, and Application of a Hydrazide-Functionalized Isotope-Coded Affinity Tag for the Quantification of Oxylipid-Protein Conjugates."*Anal. Chem.* (Washington, DC, U. S.) 79:3342-3354; May 1, 2007. Published on Web Mar. 27, 2007.

Hermans et al., "Challenges and Pitfalls in Antioxidant Research," *Curr. Med. Chem.*, Feb. 2007, 14(4): 417-430.

Hermans et al., "Method development and validation for monitoring in vivo oxidative stress: Evaluation of lipid peroxidation and fat-soluble vitamin status by HPLC in rat plasma," *J. Chromatogr., B: Anal. Technol. Biomed. Life Sci.*, 2005, 822(1-2): 33-39. Available online Jun. 28, 2005.

Huang et al., "Systematic and integrative analysis of large gene lists using DAVID bioinformatics resources," *Nat. Protoc.*, 2009, 4: 44-57. Published online Dec. 18, 2008; doi:10.1038/nprot.2008.211.

Hussain et al., "Modifications of proteins by 4-hydroxy-2-nonenal in the ventilatory muscles of rats." *Am. J. Physiol.* 290:L996-L1003; 2006.

Ishii et al., "Molecular Basis of Enzyme Inactivation by an Endogenous Electrophile 4-Hydroxy-2-nonenal: Identification of Modification Sites in Glyceraldehyde-3-phosphate Dehydrogenase." *Biochemistry* 42:3474-3480; 2003. Published on Web Mar. 8, 2003.

Isom et al., Modification of *Cytochrome c* by 4-hydroxy-2-nonenal: evidence for histidine, lysine, and arginine-aldehyde adducts. *J. Am. Soc. Mass Spectrom.* 15:1136-1147; 2004.

Issaq et al., "Serum and Plasma Proteomics," *Chem. Rev.*, Aug. 2007, 107(8): 3601-20. Published on Web Jul. 18, 2007.

Jacobs et al. "Utilizing Human Blood Plasma for Proteomic Biomarker Discovery," *J. Proteome Res.*, 2005, 4(4): 1073-1085. Published on Web May 20, 2005.

Kapphahn et al., "Retinal proteins modified by 4-hydroxynonenal: identification of molecular targets." *Exp. Eye Res.* 83:165-175; 2006. Available online Mar. 10, 2006.

Keshishian et al., "Quantitative, multiplexed assays for low abundance proteins in plasma by targeted mass spectrometry and stable isotope dilution." *Mol. Cell. Proteomics* 6.12:2212-2229; 2007. Published, MCP Papers in Press, Oct. 15, 2007, DOI 10.1074/mcp.M700354-MCP200.

Kristensen et al., "Identification of oxidised proteins in the matrix of rice leaf mitochondria by immunoprecipitation and two-dimensional liquid chromatography-tandem mass spectrometry." *Phytochemistry (Elsevier)* 65:1839-1851; 2004. Available online May 10, 2004.

Kuo et al., "Urinary 8-hydroxy-2'-deoxyguanosine (8-OHdG) and genetic polymorphisms in breast cancer patients," *Mutation Research* 2007, 631:62-68. Available online Apr. 20, 2007.

Lapolla et al., "Advanced glycation end products: a highly complex set of biologically relevant compounds detected by mass spectrometry," *Journal of Mass Spectrometry*, 2001, 36(4): 370-378. Paper presented at the *18th Informal Meeting on Mass Spectrometry*, Prague, Czech Republic, Apr. 30-May 3, 2000.

Lapolla et al., "Enzymatic digestion and mass spectrometry in the study of advanced glycation end products/peptides".*J Am. Soc. Mass Spectrom.* 15:496-509; 2004. Published online Feb. 2, 2004.

Lee et al., "Method to site-specifically identify and quantitate carbonyl end products of protein oxidation using oxidation-dependent element coded affinity tags (O-ECAT) and nanoliquid chromatography Fourier transform mass spectrometry," *J. Proteome Res.*, 2006, 5(3): 539-547. Published on Web Feb. 15, 2006.

Levine et al., "Determination of Carbonyl Content in Oxidatively Modified Proteins," *Methods Enzymol.*, 1990, 186(Oxygen Radicals Biol. Syst., Pt. B): 464-478.

Li et al., "A novel approach of proteomics to study the mechanism of action of grape seed proanthocyanidin extracts on diabetic retinopathy in rats," *Chin. Med. J. (Engl. Ed.)*, Dec. 20, 2008, 121(24): 2544-2552.

Liu et al., "Mass spectroscopic characterization of protein modification by 4-hydroxy-2-(E)-nonenal and 4-oxo-2-(E)-nonenal." *Chemical Research in Toxicology* 16:901-911; 2003.

Logan et al., "Engineered Disulfide Bonds Restore Chaperone-like Function of DJ-1 Mutants Linked to Familial Parkinson's Disease," *Biochemistry*, 2010, 49(27): 5624-5633. Published on Web Jun. 8, 2010.

Madian et al., "Profiling Carbonylated Proteins in Human Plasma." *J. Proteome Res.*, 2010, 9(3): 1330-1343. Published on Web Feb. 1, 2010.

Madian et al., "Proteomic Identification of Carbonylated Proteins and their Oxidation Sites." *J. Proteome Res.*, 2010, 9(8): 3766-3780. Published on Web Jun. 4, 2010.

Madian et al., "Differential carbonylation of proteins as a function of in vivo oxidative stress," Sep. 2, 2011 *J. Prot. Res.* 10:3959-3972. Available online on Jul. 29, 2011.

Madian et al., "Oxidative stress induced carbonylation in human plasma," Oct. 19, 2011 *J. Proteomics* 74:2395-2416. Available online on Jul. 30, 2011.

Madian et al., "Determining the effects of antioxidants on oxidative stress induced carbonylation of proteins," Dec. 15, 2011 *Anal. Chem.* 83:9328-9336. Available online on Nov. 2, 2011.

Madian et al., "Effect of Single Amino Acid Substitution on Oxidative Modifications of the Parkinson's Disease-related Protein, DJ-1." *Mol. Cell. Proteomics*, 2012, 11:M111.010892; 15 pages. Published, MCP Papers in Press, Nov. 21, 2011, DOI 10.1074/mcp.M111.010892.

Maeda et al., "Detection of oxidized proteins in muscles of diabetic rats." *J. Mass Spectrom. Soc. Jpn.* 51:509-515; 2003. English language abstract included.

Magni et al., "Characterisation of adducts of the lipid peroxidation product 4-hydroxy-2-nonenal and amyloid βpeptides by liquid chromatography/electrospray ionisation mass spectrometry," *Rapid Commun. Mass Spectrom.*, 2002, 16(15): 1485-1493.

Mann and Jensen, "Proteomic analysis of post-translational modifications." *Nat. Biotechnol.* 21:255-261; 2003.

Marotta et al., "Accurate mass measurements by Fourier transform mass spectrometry in the study of advanced glycation end products/peptides." *J. Mass Spectrom.* 38:196-205, 2003. Published online Jan. 14, 2003.

Mashiba et al., "In Vivo Complex Formation of Oxidized $\alpha_1$-Antitrypsin and LDL," *Arterioscler., Thromb., Vasc. Biol.*, 2001, 21(11): 1801-1808.

McKay et al., "The development of multiple reaction monitoring assays for liver-derived plasma proteins." *Proteomics: Clin. Appl.* 1:1570-1581; Dec. 2007. Epub Nov. 16, 2007.

Meany et al., "Identification of carbonylated proteins from enriched rat skeletal muscle mitochondria using affinity chromatography-stable isotope labeling and tandem mass spectrometry." *Proteomics* 7:1150-1163; Apr. 2007. Article first published online. Mar. 27, 2007.

Mirzaei and Regnier, "Enrichment of Carbonylated Peptides Using Girard P Reagent and Strong Cation Exchange Chromatography." *Anal. Chem.* 78:770-778; Feb. 1, 2006. Published on Web Dec. 17, 2005.

Mirzaei and Regnier, "Identification and quantification of protein carbonylation using light and heavy isotope labeled Girard's P reagent," *Journal of Chromatography, A*, 2006, 1134(1-2): 122-133. Available online Sep. 22, 2006.

Mirzaei and Regnier, "Protein:protein aggregation induced by protein oxidation." *J Chromatogr B Analyt Technol Biomed Life Sci* 873:8-14; 2008. Available online Apr. 23, 2008.

Miyagi et al., "Proteolytic $^{18}$O-Labeling Strategies for Quantitative Proteomics," *Spectrometry Reviews*, 2007, 26(1): 121-136. Published online Nov. 3, 2006.

Nabeshi et al., "Proteomic analysis for protein carbonyl as an indicator of oxidative damage in senescence-accelerated mice." *Free Radical Res.* 40:1173-1181; Nov. 2006.

Newton et al., "Liver Proteome Analysis in a Rodent Model of Alcoholic Steatosis." *J Proteome Res.* 8:1663-1671; 2009. Published on Web Feb. 5, 2009.

Nistala et al., "Redox control of renal functions and hypertension," *Antioxid. Redox Signaling*, Dec. 2008, 10(12): 2047-2089.

(56) References Cited

OTHER PUBLICATIONS

Noda et al., "Identification of enzymes and regulatory proteins in *Escherichia coli* that are oxidized under nitrogen, carbon, or phosphate starvation." *Proc. Natl. Acad. Sci. U. S. A.* 104:18456-18460; Nov. 20, 2007. Epub Nov. 14, 2007.
Obama et al., "Analysis of modified apolipoprotein B-100 structures formed in oxidized low-density lipoprotein using LC-MS/MS," *Proteomics*, Jun. 2007, 7(13): 2132-2141.
Oh-Ishi et al., "Proteomic method detects oxidatively induced protein carbonyls in muscles of a diabetes model Otsuka Long-Evans Tokushima Fatty (OLETF) rat." *Free Radical Biol. Med.* 34:11-22; 2003. X.
Oikawa et al., "Proteomic identification of carbonylated proteins in the monkey hippocampus after ischemia-reperfusion." *Free Radical Biol. Med.* 46:1472-1477; Jun. 1, 2009. Available online Mar. 9, 2009.
Orioli et al., "LC-ESI-MS/MS determination of 4-hydroxy-trans-2-nonenal Michael adducts with cysteine and histidine-containing peptides as early markers of oxidative stress in excitable tissues." *J Chromatogr B Analyt Technol Biomed Life Sci* 827:109-118; 2005. Available online May 23, 2005.
Ounjaijean et al., "Effect of green tea on iron status and oxidative stress in iron-loaded rats," *Med. Chem.*, Jul. 2008, 4(4): 365-370.
Park et al., "Identification of the binding site of methylglyoxal on glutathione peroxidase: methylglyoxal inhibits glutathione peroxidase activity via binding to glutathione binding sites Arg 184 and 185." *Free radical research* 37:205-211; 2003.
Pennathur et al., "A hydroxyl radical—like species oxidizes cynomolgus monkey artery wall proteins in early diabetic vascular disease," *J Clin. Invest.*, Apr. 2001, 107: 853-860.
Perez et al., "Protein Stability and Resistance to Oxidative Stress Are Determinants of Longevity in the Longest-Living Rodent, the Naked Mole-Rat," *PNAS*, Mar. 3, 2009, 106(9): 3059-3064. Epub Feb. 17, 2009.
Perkins et al., "Probability-based protein identification by searching sequence databases using mass spectrometry data." *Electrophoresis* 20:3551-3567; 1999.
Perluigi et al., "Redox proteomics identification of 4-hydroxynonenal-modified brain proteins in Alzheimer's disease: Role of lipid peroxidation in Alzheimer's disease pathogenesis." *Proteomics: Clin. Appl.* 3:682-693; Jun. 1, 2009.
Peterson et al., "Zucker Diabetic Fatty Rat as a Model for Non-insulin-dependent Diabetes Mellitus," *ILAR News*, 1990, 32:16-19.
Podmore et al., "Vitamin C exhibits pro-oxidant properties," *Nature*, 1998, 392(6676): 559.
Poon et al., "Proteomic analysis of specific brain proteins in aged SAMP8 mice treated with alphalipoic acid: implications for aging and age-related neurodegenerative disorders." *Neurochem. Int.* 46:159-168; 2005. Available online Nov. 23, 2004.
Poon et al., "Quantitative proteomics analysis of differential protein expression and oxidative modification of specific proteins in the brains of old mice." *Neurobiol. Aging* 27:1010-1019; 2006. Available online Jun. 23, 2005.
Prokai et al., "Mass spectrometrybased survey of age-associated protein carbonylation in rat brain mitochondria." *J. Mass Spectrom.* 42:1583-1589; Dec. 2007. Paper presented at the *25th Informal Meeting on Mass Spectrometry*, Nyiregyháza-Sóstó, Hungary, May 6-10, 2007.
Radfar et al., "Chloroquine mediates specific proteome oxidative damage across the erythrocytic cycle of resistant Plasmodium falciparum." *Free Radical Biol. Med.* 44:2034-2042; 2008. Available online Mar. 20, 2008.
Rauniyar et al., "Characterization of 4-Hydroxy-2-nonenal-Modified Peptides by Liquid Chromatography-Tandem Mass Spectrometry Using Data-Dependent Acquisition: Neutral Loss-Driven MS3 versus Neutral Loss-Driven Electron Capture Dissociation." *Anal. Chem.* 81:782-789; Jan. 15, 2009. Published on Web Dec. 12, 2008.
Rauniyar et al., "Fourier transform ion cyclotron resonance mass spectrometry of covalent adducts of proteins and 4-hydroxy-2-nonenal, a reactive end-product of lipid peroxidation." *Anal. Bioanal. Chem.* 389:1421-1428; 2007. Published online: Sep. 6, 2007.
Reed et al., T"Redox proteomic identification of 4-Hydroxy-2-nonenal-modified brain proteins in amnestic mild cognitive impairment: Insight into the role of lipid peroxidation in the progression and pathogenesis of Alzheimer's disease." *Neurobiol. Dis.* 30:107-120; 2008. Available online Jan. 5, 2008.
Regnier, Fred E., "Mitochondrial Proteomics of Aging," Grant Abtract, Grant No. R01AG025362 [online]. National Institute on Aging, National Institutes of Health, project dates Sep. 30, 2004 to Jan. 31, 2010 [retrieved on May 14, 2013]. Retrieved from the Internet: http://projectreporter.nih.gov/pr_Prj_info_desc_dtls.cfm?aid=7479678&icde=16304281&ddparam=&ddvalue=&ddsub=&cr=1&csb=default&cs=ASC&print=yes>; 2 pgs.
Regnier, Fred E., "APT: The Analytical Proteomics Team," Grant Abstract, Grant No. U24CA126480 [online] National Cancer Institute, National Institutes of Health, project dates Sep. 28, 2006 to Aug. 31, 2012 [retrieved on May 14, 2013]. Retrieved from the Internet: <http://projectreporter.nih.gov/project_info_description.cfm?aid=8133592&icde=16304190&ddparam=&ddvalue=&ddsub=&cr=-1&csb=default&cs=ASC>; 2 pgs.
Roe et al., "Proteomic mapping of 4-hydroxynonenal protein modification sites by solid-phase hydrazide chemistry and mass spectrometry." *Analytical chemistry* 79:3747-3756; May 15, 2007. Published on Web Apr. 17, 2007.
Rossner et al., "Relationship between Urinary 15-$F_{2t}$-Isoprostane and 8-Oxodeoxyguanosine Levels and Breast Cancer Risk," *Cancer Epidemiology, Biomarkers & Prevention*, Apr. 2006, 15: 639-644.
Rossner et al., "Plasma protein carbonyl levels and breast cancer risk," *J. Cell. Mol. Med.*, Sep.-Oct. 2007, 11(5): 1138-1148.
Salman-Tabcheh et al., "Nitration of Tyrosyl-Residues From Extra- and Intracellular Proteins in Human Whole Blood," *Free Radical Biol. Med.*, 1995, 19(5): 695-698.
Santos-Gonzalez et al., "Modifications of plasma proteome in long-lived rats fed on a coenzyme $Q_{10}$-supplemented diet," *Exp. Gerontol.*, 2007, 42(8): 798-806. Available online May 10, 2007.
Schmitt et al., "Characterization of advanced glycation end products: mass changes in correlation to side chain modifications." *Anal Biochem* 346:101-106; 2005. Available online Aug. 15, 2005.
Sener et al., "Lipid peroxidation and total antioxidant status in patients with breast cancer," *Cell Biochemistry and Function*, 2007, 25: 377-382. Published online Jan. 30, 2006.
Shipitsin et al., "Molecular Defmition of Breast Tumor Heterogeneity," *Cancer Cell*, Mar. 2007, 11: 259-273. Published: Mar. 12, 2007.
Soreghan et al., "High-throughput proteomic-based identification of oxidatively induced protein carbonylation in mouse brain." *Pharm Res* 20:1713-1720; Nov. 2003.
Stadman et al., "Metal-catalyzed Oxidation of Proteins," *J. Biol. Chem.*, Feb. 5, 1991, 266: 2005-2008.
Stadtman et al., "Protein Oxidation in Aging and Age-Related Diseases," *Ann. N.Y. Acad. Sci.*, 2000, 928: 22-38.
Stadtman et al., "Methionine oxidation and aging," *Biochim. Biophys. Acta*, 2005, 1703(2): 135-140. Available online Sep. 9, 2004.
Stahl-Zeng et al., "High sensitivity detection of plasma proteins by multiple reaction monitoring of N-glycosites." *Mol. Cell. Proteomics* 6:1809-1817; 2007. Published, MCP Papers in Press, Jul. 20, 2007, DOI 10.1074/mcp.M700132-MCP200.
Stevens et al., "Rapid characterization of covalent modifications to rat brain mitochondrial proteins after ex vivo exposure to 4-hydroxy-2-nonenal by liquid chromatography-tandem mass spectrometry using data-dependent and neutral loss-driven MS3 acquisition." *J Mass Spectrom* 42:1599-1605; Dec. 2007; Article first published online: Dec. 17, 2007. Paper presented at the *25th Informal Meeting on Mass Spectrometry*, Nyiregyháza-Sóstó, Hungary, May 6-10, 2007.
Tas et al., "Oxidative Stress in Breast Cancer," *Med. Oncol.*, 2005, 22(1): 11-15.
Temple et al., "Identification of Specific Protein Carbonylation Sites in Model Oxidations of Human Serum Albumin," *J. Am. Soc. Mass Spectrom.*, 2006, 17(8): 1172-1180. Published online Jun. 5, 2006.

(56) References Cited

OTHER PUBLICATIONS

Tsaytler et al., "Immediate Protein Targets of Photodynamic Treatment in Carcinoma Cells." *J. Proteome Res.* 7:3868-3878; 2008. Published on Web Jul. 25, 2008.
Uttara et al., "Oxidative Stress and Neurodegenerative Diseases: A Review of Upstream and Downstream Antioxidant Therapeutic Options," *Curr. Neuropharmacol.*, Mar. 2009, 7(1): 65-74.
Vincent et al., "Oxidative Stress in the Pathogenesis of Diabetic Neuropathy," *Endocrine Reviews*, Aug. 2004, 25: 612-628.
Wang et al., "Differential Proteomics Analysis of Specific Carbonylated Proteins in the Temporal Cortex of Aged Rats: The Deterioration of Antioxidant System." *Neurochem. Res* 35:13-21; 2009. Published online: Jun. 28, 2009.
Wautier and Schmidt, "Protein glycation." *Circ. Res.* 95:233-238; Aug. 6, 2004.
Weinreb et al., "A novel approach of proteomics and transcriptomics to study the mechanism of action of the antioxidant—iron chelator green tea polyphenol (−)-epigallocatechin-3-gallate," *Free Radical Biol. Med.*, Aug. 15, 2007, 43(4): 546-556. Available online May 16, 2007.
Yeh et al., "No effect of cigarette smoking dose on oxidized plasma proteins," *Environ. Res.*, Feb. 2008, 106(2): 219-225. Epub Nov. 9, 2007.
Yoo and Regnier, "Proteomic analysis of carbonylated proteins in two-dimensional gel electrophoresis using avidin-fluorescein affinity staining." *Electrophoresis* 25:1334-1341; 2004.
Zhang et al., "Application of electron transfer dissociation mass spectrometry in analyses of non-enzymatically glycated peptides." *Rapid Comnun Mass Spectrom* 21:661-666; Mar. 15, 2007. Article first published online: Feb. 5, 2007.
Zhang et al., "Enrichment and analysis of nonenzymatically glycated peptides: boronate affinity chromatography coupled with electron-transfer dissociation mass spectrometry." *J. Proteome Res* 6:2323-2330; Jun. 2007. Published on Web May 9, 2007.
Zhang et al., "Proteomic Profiling of Nonenzymatically Glycated Proteins in Human Plasma and Erythrocyte Membranes," *J. Proteome Res.*, May 2008, 7(5): 2025-2032. Published on Web Apr. 9, 2008.
Zhou et al., "The Oxidation State of DJ-1 Regulates its Chaperone Activity Toward α-Synuclein," *J. Molecular Biology*, 2006, 356(4): 1036-1048. Available online Dec. 27, 2005.
Zipprich et al., "Plasma Protein Carbonyls and Breast Cancer Risk in Sisters Discordant for Breast Cancer from the New York Site of the Breast Cancer Family Registry," *Cancer Res.*, Apr. 1, 2009, 69: 2966-2972.
Amici et al., "Conversion of amino acid residues in proteins and amino acid homopolymers to carbonyl derivatives by metal-catalyzed oxidation reactions," *J. Biol. Chem.*, Feb. 25, 1989, 264(6): 3341-3346.
Barelli et al., "Oxidation of proteins: basic principles and perspectives for blood proteomics," *Proteomics: Clin. Appl.*, 2008, 2(2): 142-157.
Butterfield et al., Proteomics for the identification of specifically oxidized proteins in brain: technology and application to the study of neurodegenerative disorders, *Amino Acids*, 2003, 25(3-4): 419-425. Available online on Aug. 21, 2003.
Butterfield et al., "Proteomics: a new approach to investigate oxidative stress in Alzheimer's disease brain," *Brain Res.*, 2004, 1000(1-2): 1-7.
Dalle-Donne et al., "Protein carbonyl groups as biomarkers of oxidative stress," *Clin. Chim. Acta.*, 2003, 329(1-2): 23-38.

Dalle-Donne et al., "Protein carbonylation in human diseases," *Trends in Mol. Med.*, Apr. 2003, 9(4): 169-176.
Dalle-Donne et al., "Protein carbonylation, cellular dysfunction, and disease progression," *J Cell. Mol. Med.*, 2006, 10(2): 389-406.
Dalle-Donne et al., "Proteins as sensitive biomarkers of human conditions associated with oxidative stress," *Redox Proteomics*, John Wiley & Sons, Inc., Hoboken, NJ, 2006, pp. 487-525.
Haulica et al., "Free radical between health and disease," *Rom. J. Physiol.*, 2002, 37(1-4): 15-27.
Jana et al., "Specificity of age-related carbonylation of plasma proteins in the mouse and rat," *Arch. Biochem. Biophys.*, Jan. 15, 2002, 397(2): 433-439.
Jones, "Redefining Oxidative Stress," *Antioxid. Redox Signal*, 2006, 8(9-10): 1865-1879.
Levine et al., "Carbonyl modified proteins in cellular regulation, aging, and disease," *Free Radic. Biol. Med.*, 2002, 32(9):790-796.
Mirzaei et al., "Affinity Chromatographic Selection of Carbonylated Proteins Followed by Identification of Oxidation Sites Using Tandem Mass Spectrometry." *Anal. Chem.* Apr. 15, 2005, 77(8): 2386-2392. Available online on Mar. 10, 2005.
Mirzaei et al., "Creation of Allotypic Active Sites During Oxidative Stress." *J Proteome Res.*, 2006, 5(9): 2159-2168. Available online on Jul. 13, 2006.
Mirzaei et al., "Protein—RNA Cross-Linking in the Ribosomes of Yeast under Oxidative Stress." *J Proteome Res.*, 2006, 5(12): 3249-3259. Available online on Oct. 26, 2006.
Mirzaei et al., "Identification of Yeast Oxidized Proteins Chromatographic Top-Down Approach for Identification of Carbonylated, Fragmented and Cross-Linked Proteins in Yeast." *J Chromatogr. A*, 2007, 1141(1): 22-31. Available online on Dec. 22, 2006.
Requena et al., "Glutamic and aminoadipic semialdehydes are the main carbonyl products of metal-catalyzed oxidation of proteins," *PNAS*, Jan. 2, 2001, 98(1): 69-74.
Stadtman et al., "Free radical-mediated oxidation of free amino acids and amino acid residues in proteins," *Amino Acids*, 2003, 25(3-4): 207-218. Available online Jul. 29, 2003.
Castegna Alessandra et al., "Proteomic identification of oxidatively modified proteins in Alzheimer's disease brain. Part 1: Creatine Kinase BB, glutamine synthase, and ubiquitin carboxy-terminal hydrolase L-1", Free Radical Biology and Medicine, Elsevier Science, US, vol. 33, No. 4, Aug. 15, 2002, pp. 562-571, XP009169551, ISSN: 0891-5849.
Castegna Alessandra et al., "Proteomic identification of oxidatively modified proteins in Alzheimer's disease brain. Part 2: Dihydropyrimidinase-related protein 2, alpha-enolase and heat shock cognate 71", Journal of Neurochemistry, Wiley Interscience, New York, NY, US, vol. 82, No. 6, Sep. 1, 2002, pp. 1524-1532, XP009169552, ISSN: 0022-3042.
Mirzaei Hamid et al., "Identification of oxidized proteins in rat plasma using avidin chromatography and tandem mass spectrometry", Proteomics, Wiley—VCH Verlag, Weinheim, DE, vol. 8, No. 7, Apr. 1, 2008, pp. 1516-1527, XP009169547, ISSN: 1615-9853.
Madian Ashraf G et al., "Profiling Carbonylated Proteins in Human Plasma", Journal of Proteome Research, ACS, Washington, DC, US, vol. 9, No. 3, Mar. 5, 2010, pp. 1330-1343, XP009169555, ISSN: 1535-3893.
Madian Ashraf G et al., "Profiling of the Human Plasma Oxidized Proteome", Free Radical Biology & Medicine, vol. 45, No. Suppl. 1, 2008, p. S122, XP9169607, & 15th Annual Meeting of the Society-for-free-radical-biology-and-medic INE, Indianapolis, IN, US, Nov. 19-23, 2008, ISSN: 0891-5849.

* cited by examiner

■ Number of proteins identified by both MALDI and ESI ionization methods
☐ Number of proteins identified by ESI only
■ Number of proteins identified by MALDI only

Figure 13

| Extracellular compartment | Membrane | Cytoplasm | Nucleus | Unspecified |
|---|---|---|---|---|
| Transthyretin<br>IGHV1OR15-1　IGHM　APOC3<br>des-Arg9-bradykinin<br>　　　　　　　　　APOA4<br>　IGHG4　LAMC2　APOA2<br>IGKC　Fibronectin<br>　C3b　C1qc　Transferrin<br>IGHG2　IGHG1　HABP2　APOB<br>　C3a<br>IGKV1-5　Fibrinogen (fibrin)　C4Ba<br>HBD<br>Ceruloplasmin　Thrombin　C4B protein<br>IGHA2　HPRG　C4Bb　A2M　USH2A<br>　　　Alpha 1-antitrypsin<br>IGHG3　C3c　　　　　　KNG<br>　PRG4　APOC4　C3dg　des-Arg10-kallidin<br>F13B　　IC3b　　HBB<br>Igλ　APOC1　HP<br>　　Bradykinin<br>　IGHA1　　　　APOE<br>IGKV3-20<br>　　Albumin　Vitronectin　C3<br>　　　　　　　　Hemopexin<br>FHR-1　C1qa　AIM (CD5L)　Factor H<br>　Kallidin　APOL1　C4BP alpha<br>IGLC<br>p90 fibronectin　p140 Fibronectin | ZAN<br>Plexin C1<br>HLA-E | SNX13　PON1<br>LRRC49　Titin<br>CENP-F<br>　　　TBK1<br>BPAG1<br>　　　PRDX2<br>KLHL4<br>　　MTMR13<br>KIAA1043<br>Oxygen-regulated protein 1<br>Nesprin 1<br>Myosin Vb<br>HOOK2<br>KIF16B (SNX23/C20orf23)<br>PSF<br>KATNB1<br>SPTA1<br>MAP4 | KLHL7<br>GANP<br>ORC4L | USP43<br>T-A2MG<br>LSM2<br>KRT9<br>VPS13D<br>WDR89<br>MYO3A<br>Myosin IIIA |

Figure 14

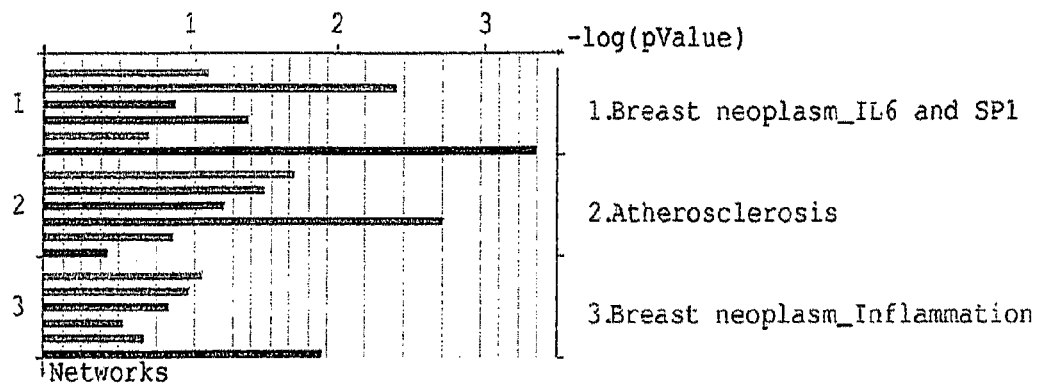

1. Breast neoplasm_IL6 and SP1
2. Atherosclerosis
3. Breast neoplasm_Inflammation Networks

Figure 15

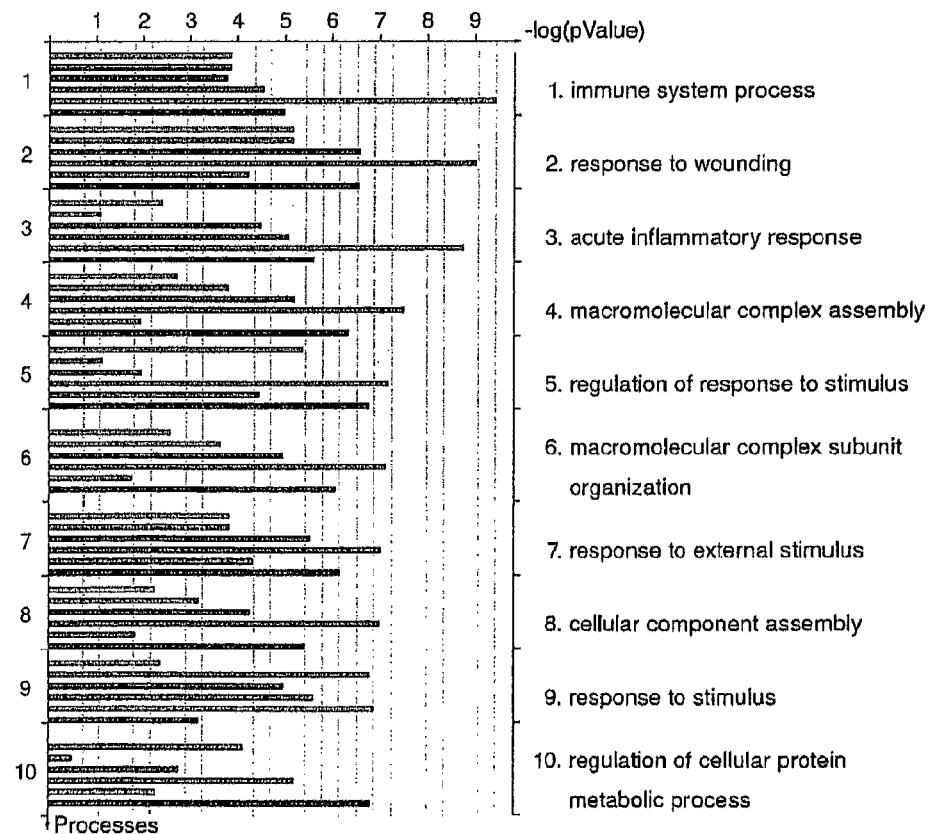

1. immune system process
2. response to wounding
3. acute inflammatory response
4. macromolecular complex assembly
5. regulation of response to stimulus
6. macromolecular complex subunit organization
7. response to external stimulus
8. cellular component assembly
9. response to stimulus
10. regulation of cellular protein metabolic process Processes

Figure 16
Direct carbonylation
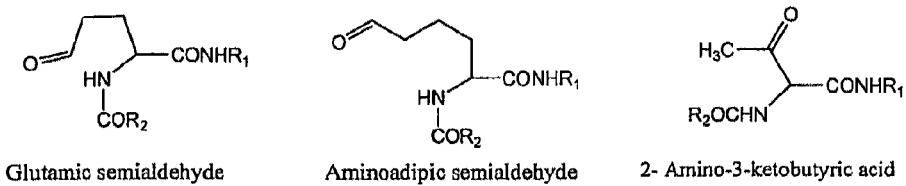
Glutamic semialdehyde    Aminoadipic semialdehyde    2- Amino-3-ketobutyric acid
Glycation and advanced glycation end products (AGEs) adducts
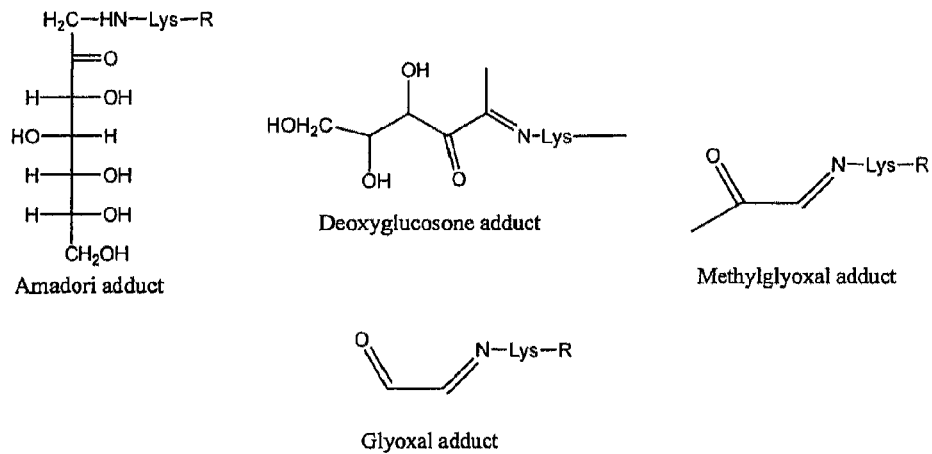
Amadori adduct    Deoxyglucosone adduct    Methylglyoxal adduct
Glyoxal adduct
Advanced lipid peroxidation end products (ALEs) adducts
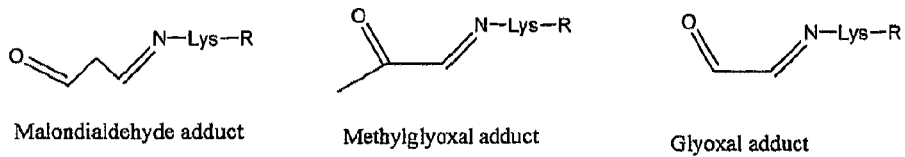
Malondialdehyde adduct    Methylglyoxal adduct    Glyoxal adduct

Figure 33

Direct carbonylation

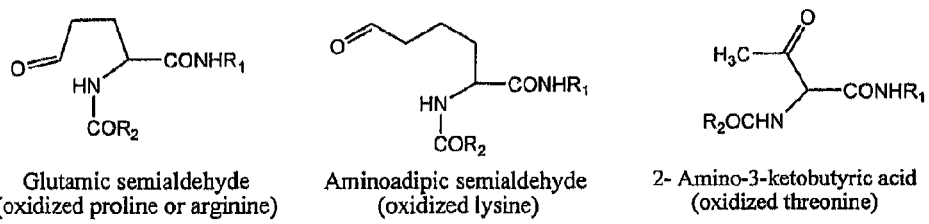

Glutamic semialdehyde  
(oxidized proline or arginine)

Aminoadipic semialdehyde  
(oxidized lysine)

2- Amino-3-ketobutyric acid  
(oxidized threonine)

Glycation and advanced glycation end products (AGEs) adducts

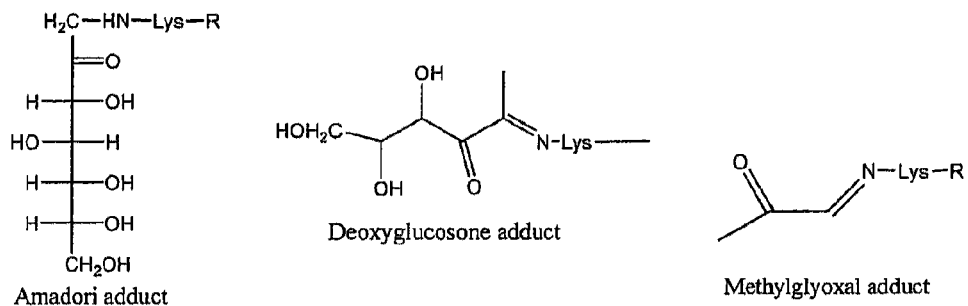

Amadori adduct

Deoxyglucosone adduct

Methylglyoxal adduct

Advanced lipid peroxidation end products (ALEs) adducts

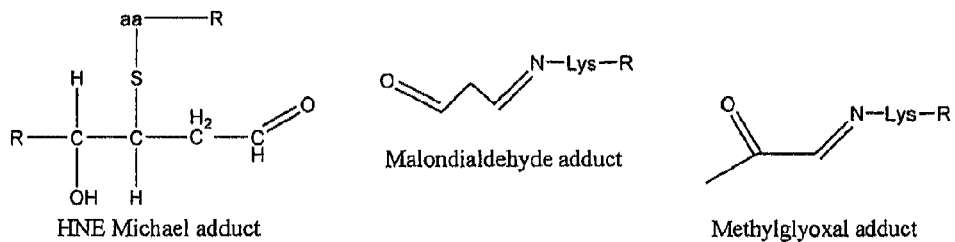

HNE Michael adduct

Malondialdehyde adduct

Methylglyoxal adduct

DETECTION OF OXIDIZED POLYPEPTIDES

CROSS-REFERENCE TO RELATED APPLICATION

This application is a §371 National Phase entry of International Application No. PCT/US2010/059828, filed Dec. 10, 2010, which claims the benefit of U.S. Provisional Patent Application Ser. No. 61/285,830, filed Dec. 11, 2009, each of which is incorporated by reference herein in its entirety.

GOVERNMENT FUNDING

This invention was made with government support under Grant No. 1U24CA126480-01, awarded by the National Institutes of Health, and under Grant No. 5R01AG025362-02, awarded by the National Institutes of Health. The Government has certain rights in the invention.

BACKGROUND

Oxygen-containing free radicals including, for example, hydrogen peroxide, singlet oxygen, peroxynitrite, and superoxide can occur in cells as part of the normal metabolism of nutrients. These reactive oxygen species can cause oxidative damage to sensitive cellular components. Their potential to damage cells is controlled in part by antioxidants and enzymes such as catalase, selenium-dependent glutathione, superoxide dismutase, and thioredoxin hyperoxidase, which are involved in either destroying the reactive oxygen species or repairing oxidative damage (Butterfield et al., *Amino Acids*, 2003, 25(3-4):419-425). Thioreductases also can be involved in repair of oxidative damage by converting disulfides, formed during an episode of oxidative stress, to thiols. When redox signaling and control systems fail or are disrupted, reactive oxygen species can accumulate, causing oxidative stress (Jones, D. P., *Antioxid Redox Signal*, 2006, 8(9-10):1865-1879).

Oxidative damage to DNA, RNA, and/or proteins can threaten the survival of a biological system (Butterfield et al., *Amino Acids*, 2003, 25(3-4):419-425). High concentrations of reactive oxygen species have been implicated in varied conditions such as, for example, Alzheimer's disease, Parkinson's disease, and amyotrophic lateral sclerosis (ALS), atherosclerosis, diabetes mellitus, chronic renal failure, chronic lung disease, cancer, and many inflammatory diseases mellitus, chronic renal failure, chronic lung disease, cancer, and many inflammatory diseases (Haulica et al., *Rom J Physiol*, 2002, 37(1-4):15-27; Butterfield, D., *Brain Res*, 2004, 1000 (1-2):1-7; Dalle-Donne et al., *Trends in Mol. Med.*, 2003, 9(4):169-176; Levine et al., *Free Radic Biol Med*, 2002, 32(9):790-796). One way that a protein may be irreversibly oxidized is though carbonylation (Dalle-Donne et al., *Clin Chim Acta*, 2003, 329(1-2):23-38).

The introduction of carbonyl groups into proteins can occur by i) cleavage of an amino acid side chain, ii) scission of the protein backbone, addition of lipid oxidation products, or iv) oxidation at a glycation site. Under severe oxidative stress, multiple carbonyl groups can be formed on a single protein.

There are many ways that carbonyl groups may be directly introduced into a protein. One way is through oxidation of a side chain of a proline, arginine, lysine, or threonine amino acid residue (Amici et al., *J Biol Chem*, 1989, 264(6):3341-3346). Metal-catalyzed oxidation can produce unique products such as glutamate semialdehyde or aminoadipic semialdehyde (Requena et al., *PNAS*, 2001, 98(1):69-74). Carbonyl groups also can be directly introduced into proteins by cleavage of the protein backbone. Another way that carbonyl groups can be directly introduced into proteins is via α-amidation or diamide pathways. Still another way is by oxidation of glutamyl or aspartyl amino acid side chains, in which case the product generated is N-acylated with a pyruvyl group (Stadtman et al., *Amino Acids*, 2003, 25(3-4):207-218).

There are also many ways that carbonyl groups may be indirectly introduced into a protein. One way is by addition of a carbonyl-containing side chain functional group such as, for example, 4-hydroxy-2-noneal, 2-propenal, or malondialdehyde at a cysteine, histidine, or lysine amino acid residue (*Redox Proteomics*, Dalle-Donne, I., Scalone, A. and Butterfield, D. eds., John Wiley & Sons, Inc., Hoboken, N.J., 2006, pp. 487-525). A second route by which carbonyl groups may be indirectly introduced into a protein is oxidation of advanced glycation end (AGE) products. This route is initiated by non-enzymatic addition of glucose to lysine residues to form a Schiff base that undergoes Amadori rearrangement. Subsequent oxidation of these glycated proteins results in the formation of carbonylated proteins (Dalle-Donne et al., *Clin Chim Acta*, 2003, 329 (1-2):23-38).

SUMMARY OF THE INVENTION

In one aspect, the invention provides a method for monitoring the health of a subject. Generally, the method can includes comparing a plurality of test peptides in a sample obtained from the subject, each test peptide having a detectable oxidation state, with a plurality of reference peptides, each reference peptide having a detectable oxidation state; and detecting a difference in oxidation state between at least one test peptide and the oxidation state of a corresponding reference peptide, wherein the difference in oxidation state is indicative of the health status of the subject.

In another aspect, the invention provides a method for monitoring the health of a subject. Generally, the method can include comparing the value of a parameter associated with the oxidation state of at least one test peptide obtained from the subject with a reference value for the parameter; and detecting a difference in the value of a parameter associated with the oxidation state of the test peptide with the reference value for the parameter, wherein the difference is indicative of the health status of the subject.

In another aspect, the invention provides a method for monitoring the health of a subject. Generally, the method can include obtaining, receiving, providing, or preparing a test oxidized peptidic profile from a subject; obtaining, receiving, providing, or preparing a reference oxidized peptidic profile; comparing the test oxidized peptidic profile with the reference oxidized peptidic profile; and detecting a difference between the test oxidized peptidic profile and the reference oxidized peptidic profile, where a difference between the test oxidized peptidic profile and the reference oxidized peptidic profile is indicative of the health status of the subject.

In another aspect, the invention provides a method for monitoring the health of a subject. Generally, the method can include obtaining, receiving, or providing a sample comprising a plurality of peptides obtained from a subject; and detecting or quantifying at least one oxidized peptide in the sample, wherein the oxidized peptide comprises at least one marker of oxidative stress selected from: 2-amino-3-oxo-butanoic acid; 2-amino-3-oxo-butanoic acid; a hydroxylation; glutamate semialdehyde; sulfonic acid; sulfinic acid; sulfenic acid; formylkynurenin; kynurenin; hydroxykynurenin; 2,4,5,6,7 hydroxylation of tryptophan; oxolactone; 4-hydroxy glutamate; conversion of histidine to asparagine; conversion of histidine to aspartate; 2-oxo-histidine, aminoadipic semialdehyde; an Amadori adduct; a 3-deoxyglucosone adduct; a glyoxal adduct; a methylglyoxal adduct; conversion of proline to pyroglutamic acid; conversion of proline to pyrrolidinone; a 4-hydroxynonenal (4-HNE) adduct; a malondialdehyde adduct; and any other oxidative modification.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 13. Cellular location of the proteins that changed more than 50% in the plasma of breast cancer patients compared to their controls.

FIG. 14. Disease distribution of the proteins that changed more than 50% in the plasma of breast cancer patients compared to their controls. GeneGo™ histogram is ordered based on the most statistically significant diseases. Each bar within the numbered groupings represents a single donor.

FIG. 15. Gene ontology by processes for the proteins that changed more than 50%. The GeneGo™ histogram is ordered based on the most statistically significant processes. Each bar within the numbered groupings represents a single donor.

FIG. 16. The structures of the carbonylation products detected in this study. R refers to a polypeptide sequence. Glutamic semialdehyde is the oxidation product of proline and arginine. Aminoadipic semialdehyde is the oxidation product of lysine. 2-Amino-3-ketobutyric acid is the oxidation product of threonine. All other oxidation adducts are formed by the addition of glycation and advanced glycation end products (AGEs) or Advanced lipid peroxidation end products (ALEs) to the lysine residues.

(Bottom) Both methionine residues (M17 and M26) are oxidized to methionine sulfoxide according to the Mascot identification. The difference between the masses of y2 (after the neutral loss of one $CH_3SOH$ group, mass=63.998 Da) and y1 equals 83 Da. The difference between the masses of y11 (after the neutral loss of two $CH_3SOH$ groups, total mass=127.996 Da) and y10 (after the neutral loss of one $CH_3SOH$ group, mass=63.998 Da) equals 83.06 Da. Addition of the neutral loss mass to the 83 Da value obtained for y2-y1 and y11-y10 yields the mass of methionine sulfoxide.

Figure 22:
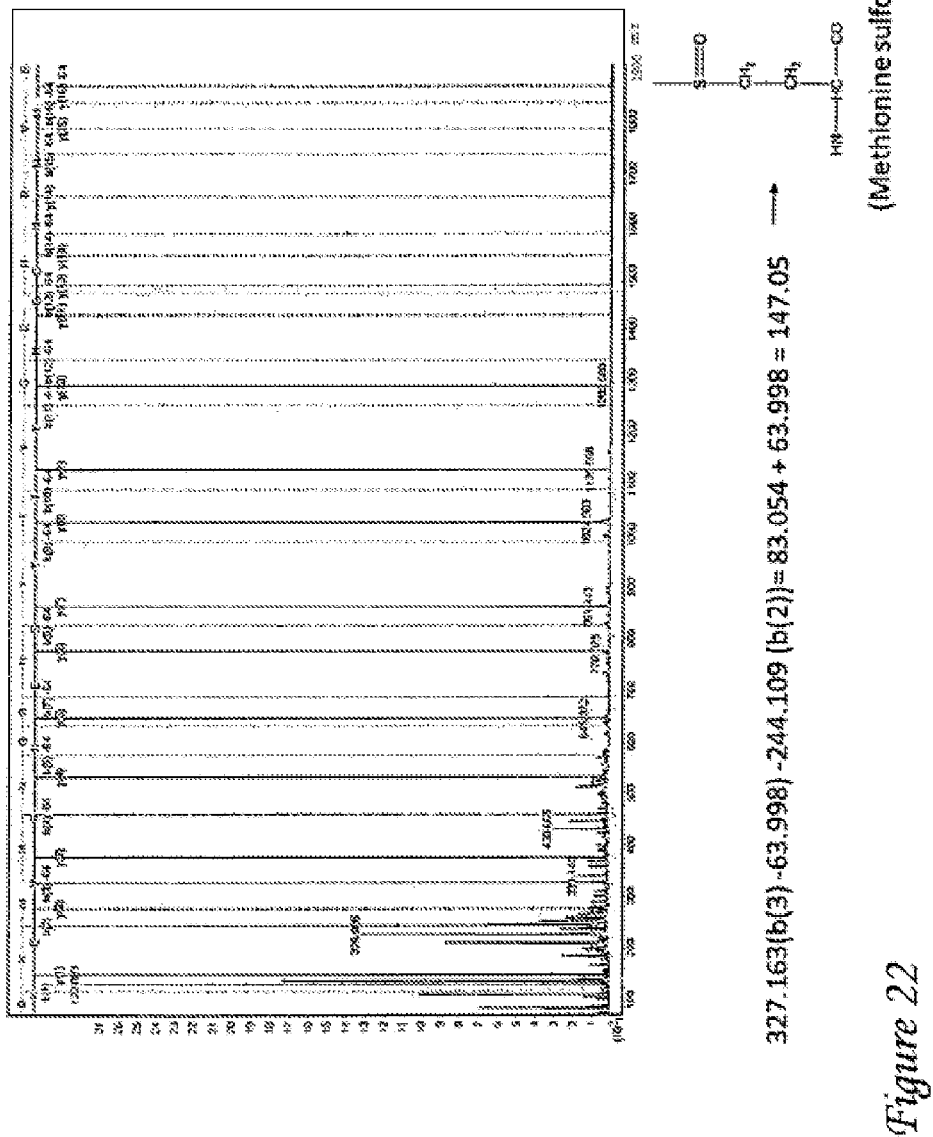

FIG. 22 MS/MS analysis of peptide $^{131}$DKMMNGGMY-TYSENKVEK$^{148}$ (SEQ ID NO:5) in wild-type DJ-1 oxidized with a 500-fold molar excess of $H_2O_2$. (Top) MS/MS spectrum with all of the y and b ions assigned. The y and b ion map is superimposed on the peptide sequence. (Bottom) M133 is oxidized to methionine sulfoxide according to the Mascot identification. The difference between the masses of b3 (after the neutral loss of one $CH_3SOH$ group, mass=63.998 Da) and b2 equals 83.054 Da. The sum of this value and the neutral loss mass equals the mass of methionine sulfoxide.

Figure 23:
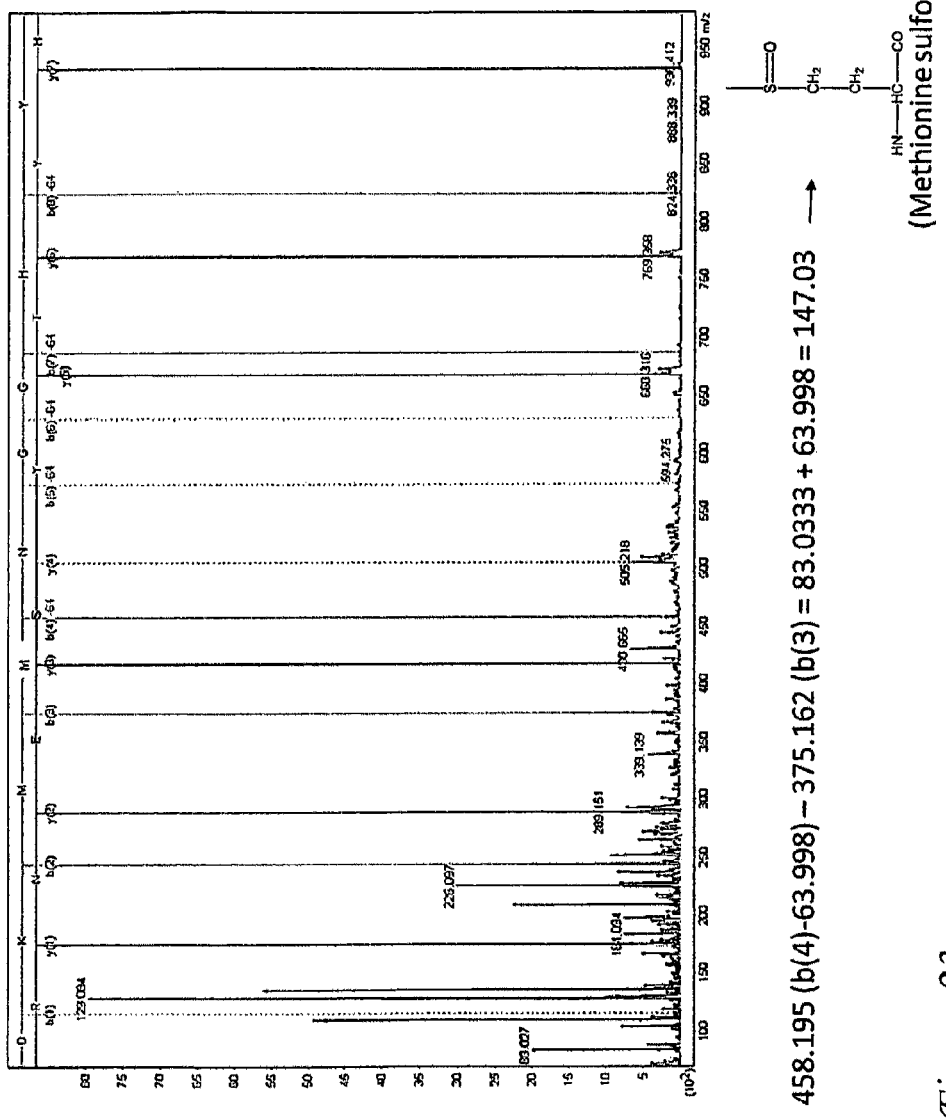

FIG. 23. MS/MS analysis of peptide $^{131}$DKMIMNGGMY-TYSENRVEK$^{148}$ (SEQ ID NO:5) in wild-type DJ-1 oxidized with a 500-fold molar excess of $H_2O_2$. (Top) MS/MS spectrum with all of the y and b ions assigned. The y and b ion map is superimposed on the peptide sequence. (Bottom) M134 is oxidized to methionine sulfoxide according to the Mascot identification. The difference between the masses of b4 (after the neutral loss of one $CH_3SOH$ group, mass=63.998 Da) and b3 equals 83.033 Da. The sum of this value and the neutral loss mass equals the mass of methionine sulfoxide.

Figure 24:
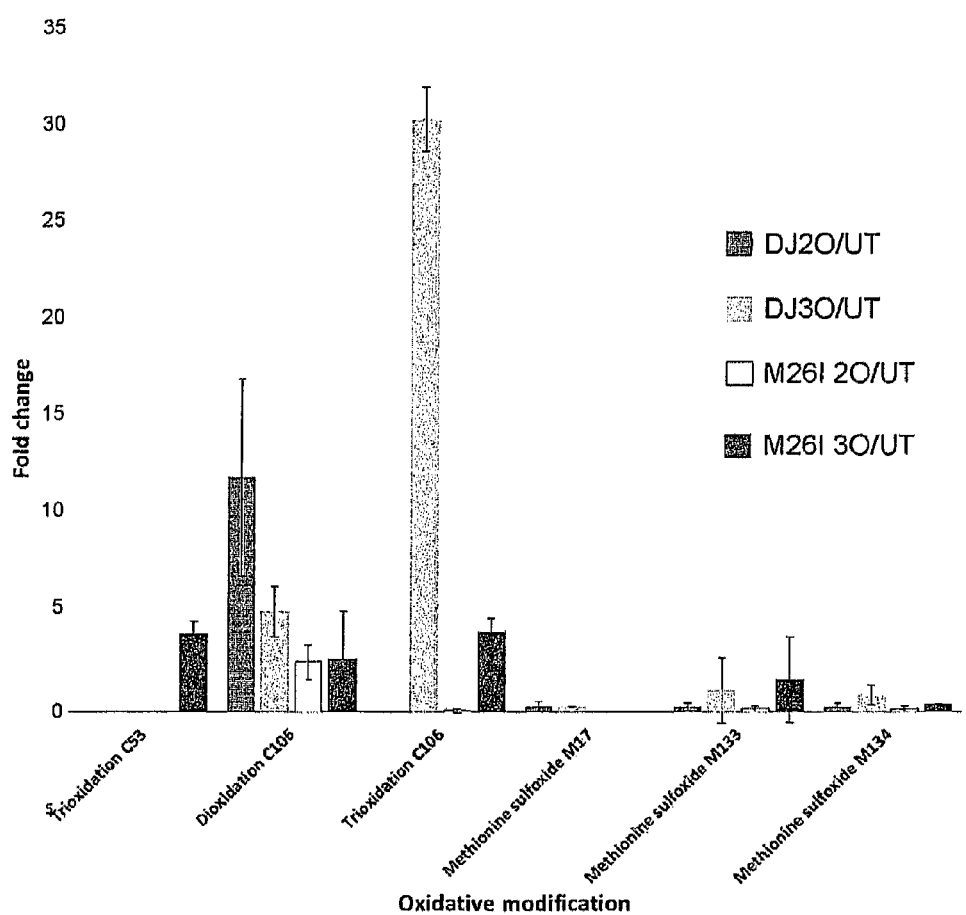

FIG. 24. Relative quantitation of DJ-1 modifications following exposure to different degrees of oxidative stress. DJ2O/UT: fold intensity change for WT DJ-1 oxidized by a 10-fold molar excess of $H_2O_2$ relative to untreated WT DJ-1. DJ3O/UT: fold change for WT DJ-1 oxidized by a 500-fold molar excess of $H_2O_2$ relative to untreated WT DJ-1. M26I2O/UT: fold change for M26I oxidized by a 10-fold molar excess of $H_2O_2$ relative to untreated M26I. M26I3O/UT: fold change for M26I oxidized by a 500-fold molar excess of $H_2O_2$ relative to untreated M26I. Mean±SEM, N=3.

Figure 25A:
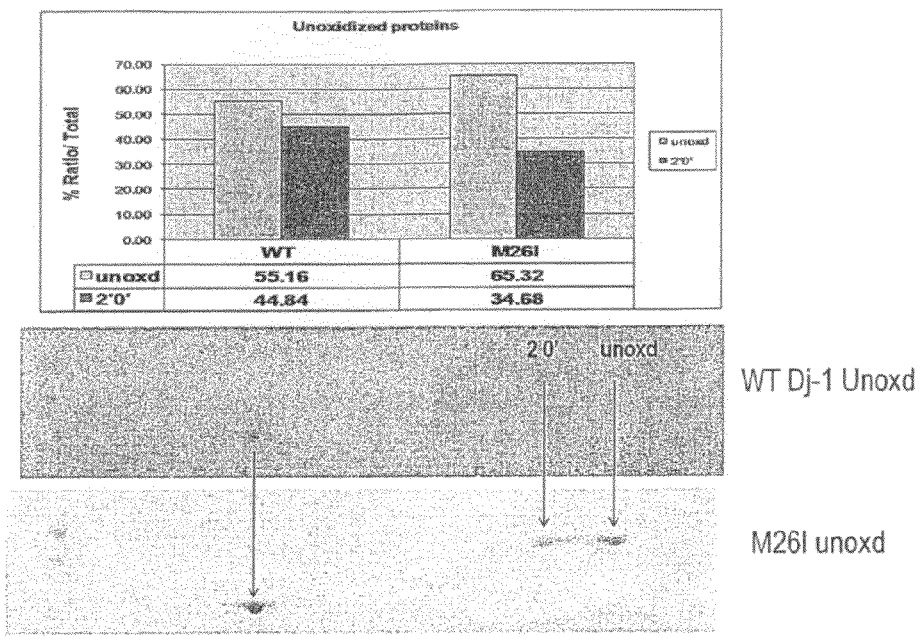
Figure 25B:
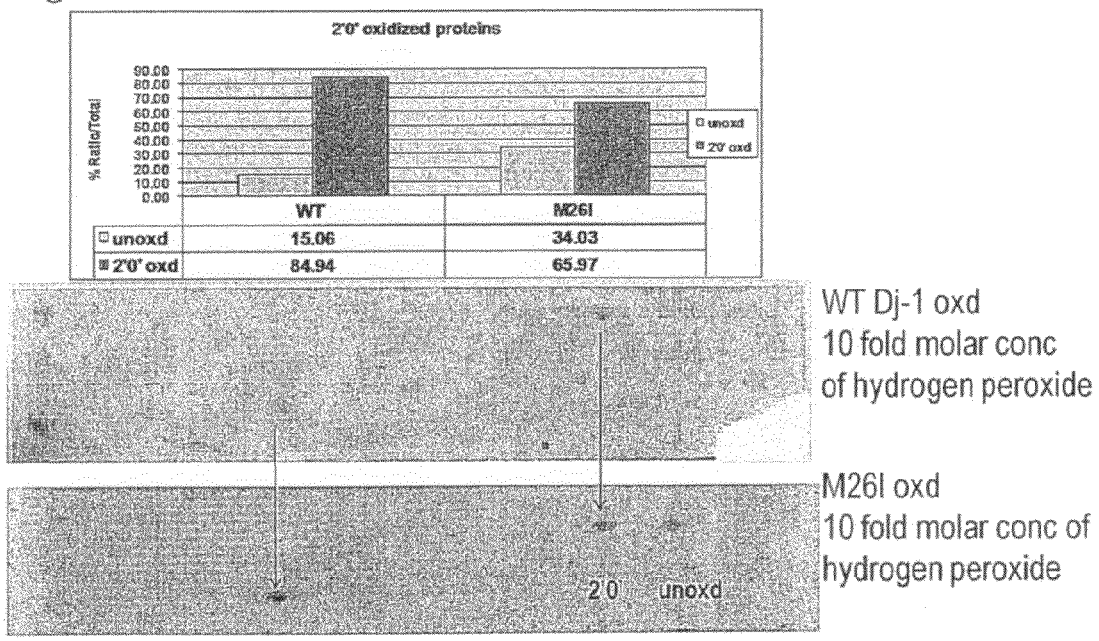

FIG. 25. 2D-PAGE showing the decreased propensity of the C106 of the DJ-1 M26I mutant to oxidize to the 2O form.

Figure 26:
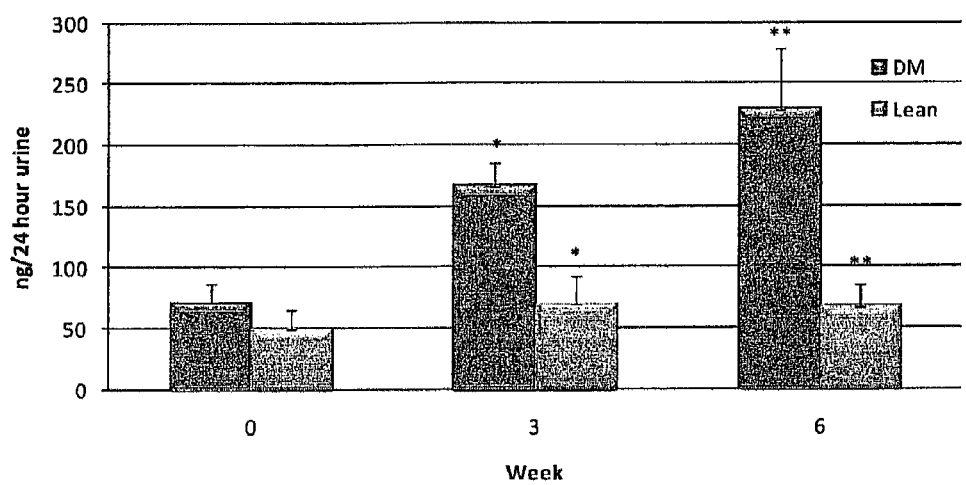

FIG. 26. Urinary isoprostanes (ng/24 hours) measured at baseline, 3, and 6 weeks in diabetic (DM) and control (lean) rats. The difference in isoprostane concentration between diabetic and controls at 3 and 6 weeks was significant to the level of $p<0.05$.

Figure 27:
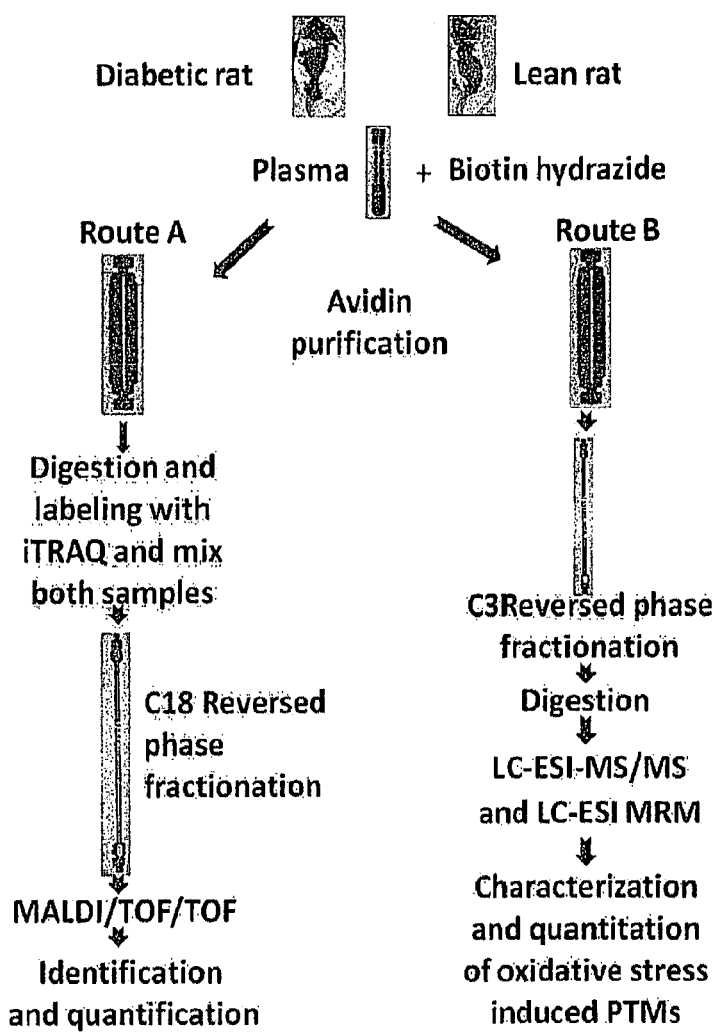

FIG. 27. A schematic illustration of the strategy used for the identification, quantification, and characterization of carbonylated proteins and their oxidation sites in the plasma of diabetic and lean Zucker rats. For protein identification and quantification, the samples were run individually, digested and then labeled with the iTRAQ™ reagent. Characterization and quantification of oxidative post-translational modifications was achieved using pooled samples.

Figure 28:
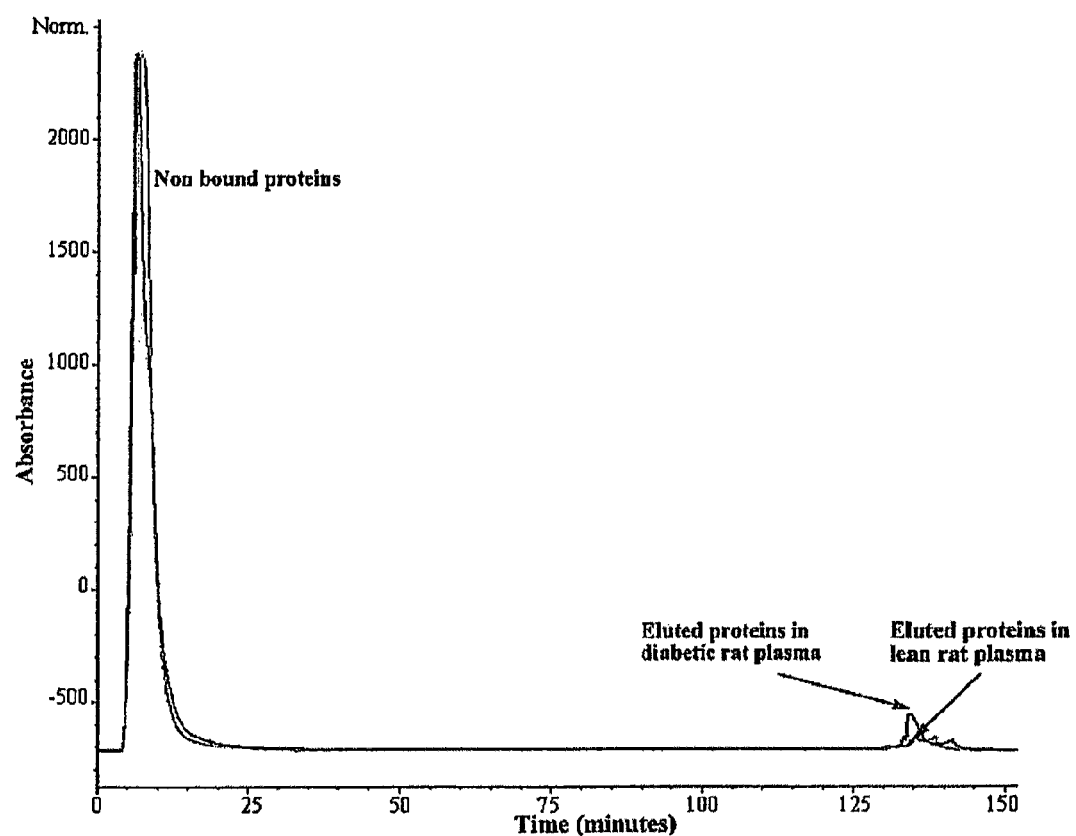

FIG. 28. Avidin affinity chromatogram of a Zucker diabetic rat plasma sample overlayed on that of a lean rat plasma sample. Plasma samples (each of 5 mg total proteins content) were applied directly to a 4.6×100 mm column packed with UltraLink Biosupport™ to which avidin had been immobilized. The column was eluted initially with 0.15 M phosphate buffered saline, (pH 7.4) at 0.5 mL/min for 120 min then switched to a mobile phase containing 0.1M dimethylglycine/HCl (pH 2.5) for an additional 40 min at the same flow rate. Absorbance was monitored at 280 nm. Based on absorbance-based quantification an average of 1% of the total protein from five lean rat plasma samples was captured by avidin affinity chromatography (SD=0.0014). The corresponding amount captured from five diabetic rat plasma samples was 1.7% (SD=0.46).

Figure 29:
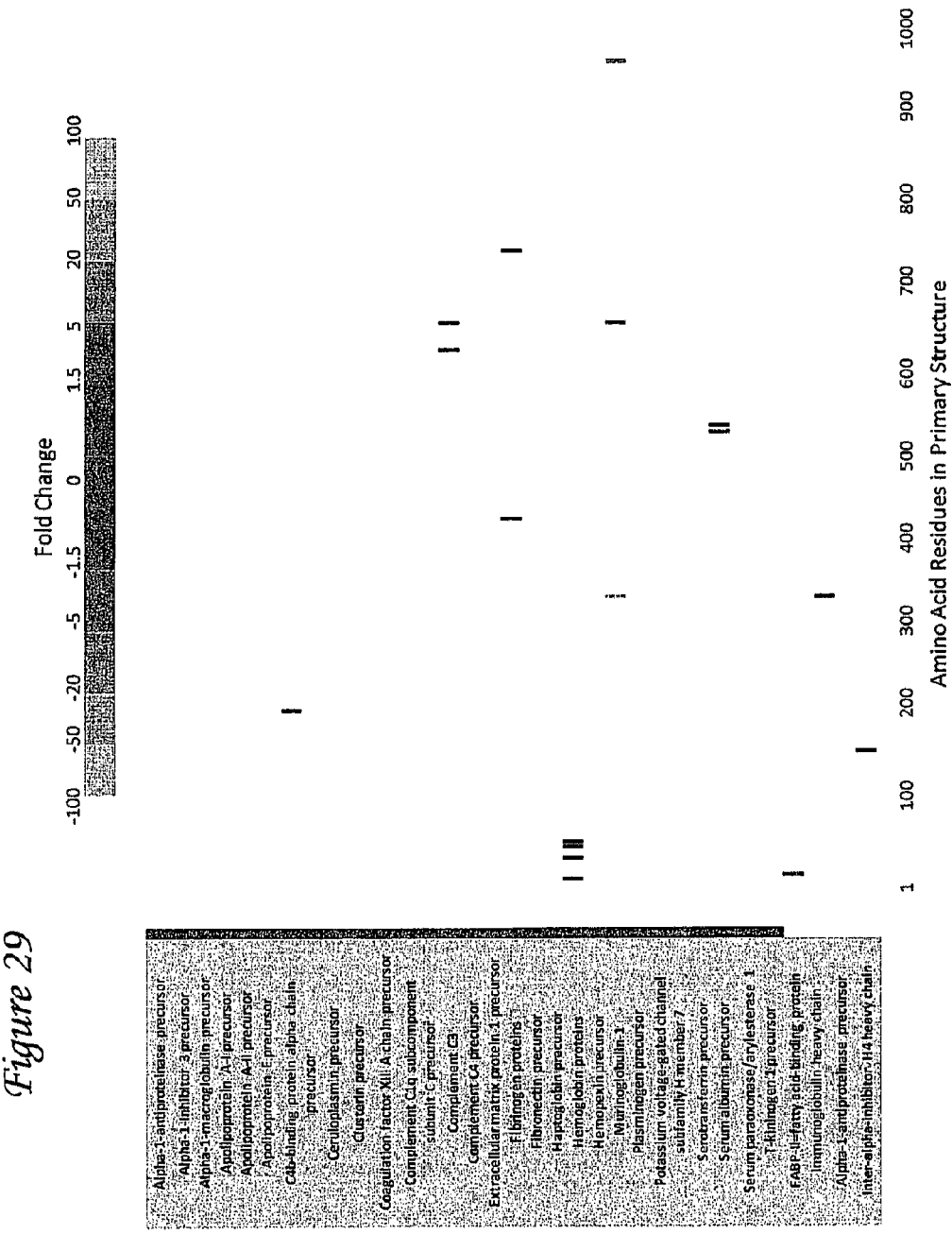

FIG. 29. A heat map of the quantitation of the oxidized proteins and their oxidation sites. The first column shows the proteins detected. The first element of this map is the fold change of these proteins in the diabetic rat plasma versus their lean controls as quantitated by iTRAQ™ labeling strategy. The second element of this map is shown the fold change of the oxidation sites in the diabetic rat plasma versus their lean controls.

Figure 30:
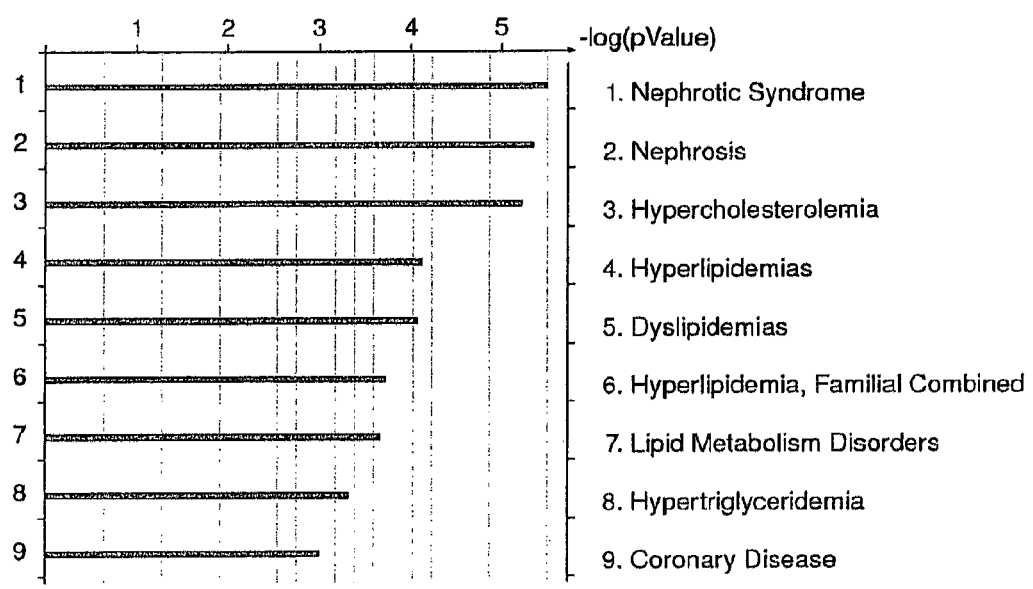

FIG. 30. Disease pathways that were identified by GeneGo™ analyses using oxidized protein data from these studies.

Figure 31:
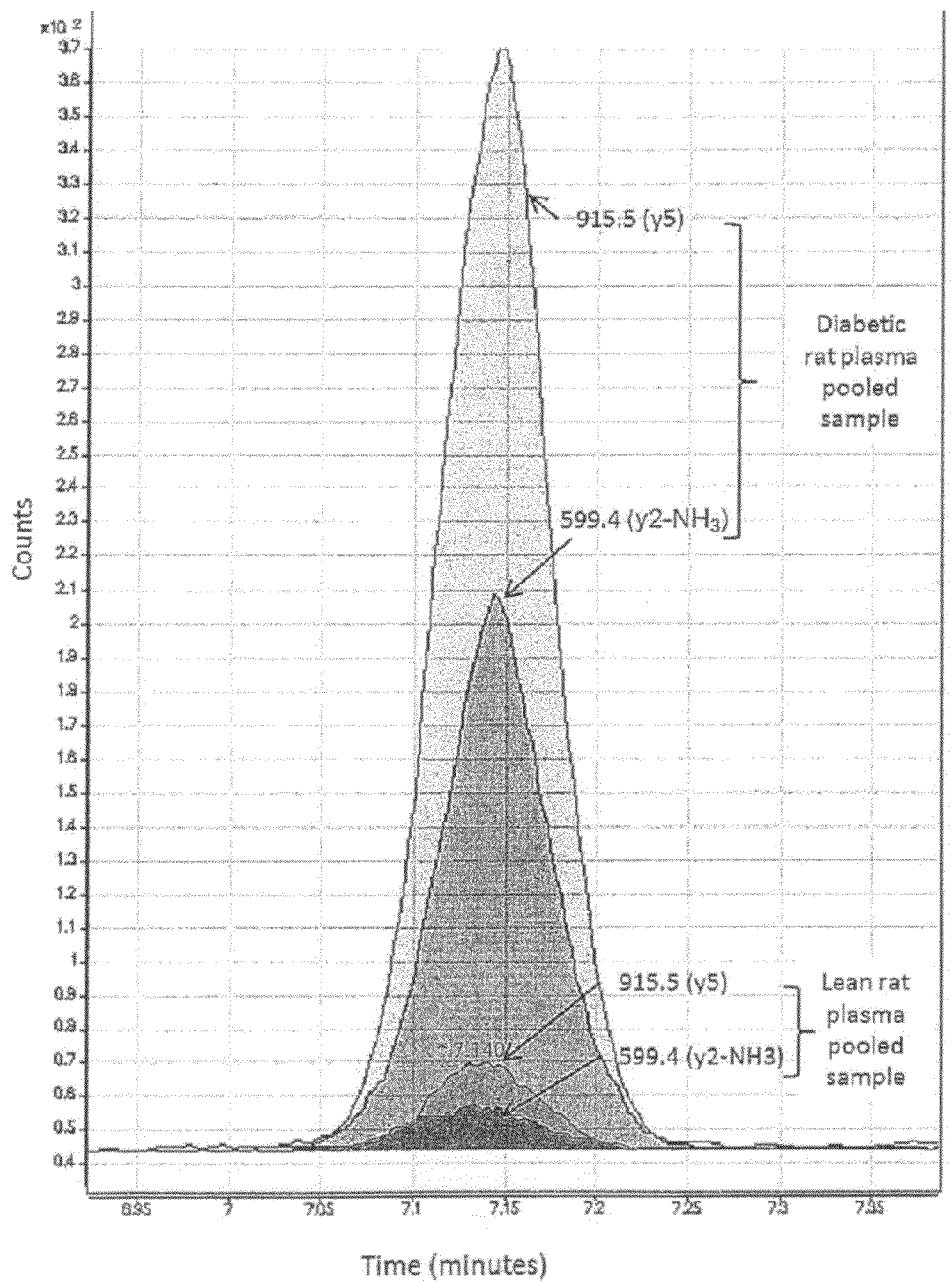

FIG. 31. Relative quantification of the carbonylated peptide KVADALAK (SEQ ID NO: 6) using selective reaction monitoring (SRM). During the analytical work flow, the parent protein beating this HNE modified peptide was biotinylated with biotin hydrazide and after avidin affinity selection of the parent this biotinylated peptide was released by trypsin digestion. Quantification was based on two CID transitions, the fragment ion at m/z=915.5 (y5) and m/z=599.4 (y2-NH3). As shown in the Figure, the levels of these two fragments were elevated 20-fold in the diabetic rat plasma pooled sample compared to their control lean rat plasma pooled sample.

Figure 32:
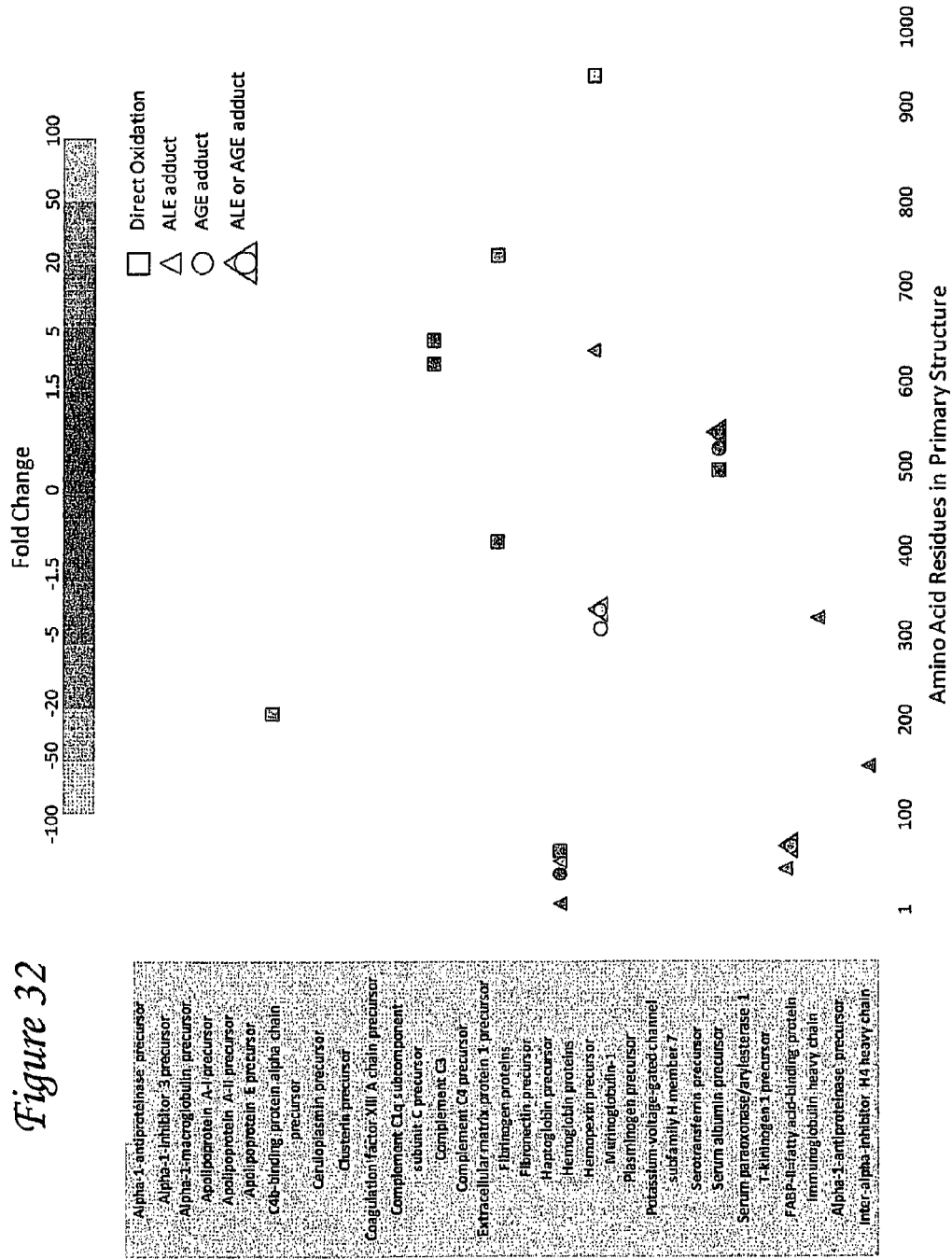

FIG. 32. A heat map of types of oxidation sites detected in this study. The first column shows the proteins detected. These oxidation sites can be either a product of: direct oxidation, Advanced Lipidperoxidation End products (ALE) adducts or Advanced Glycation End products (AGE) adducts. Methylglyoxal and glyoxal can be considered AGE or ALE.

FIG. 33. Structures of carbonylation products detected in this study. R refers to the sequence of polypeptides, aa refers to lysine, histidine or cysteine that can form Michael adducts with 4-HNE.

Figure 34:
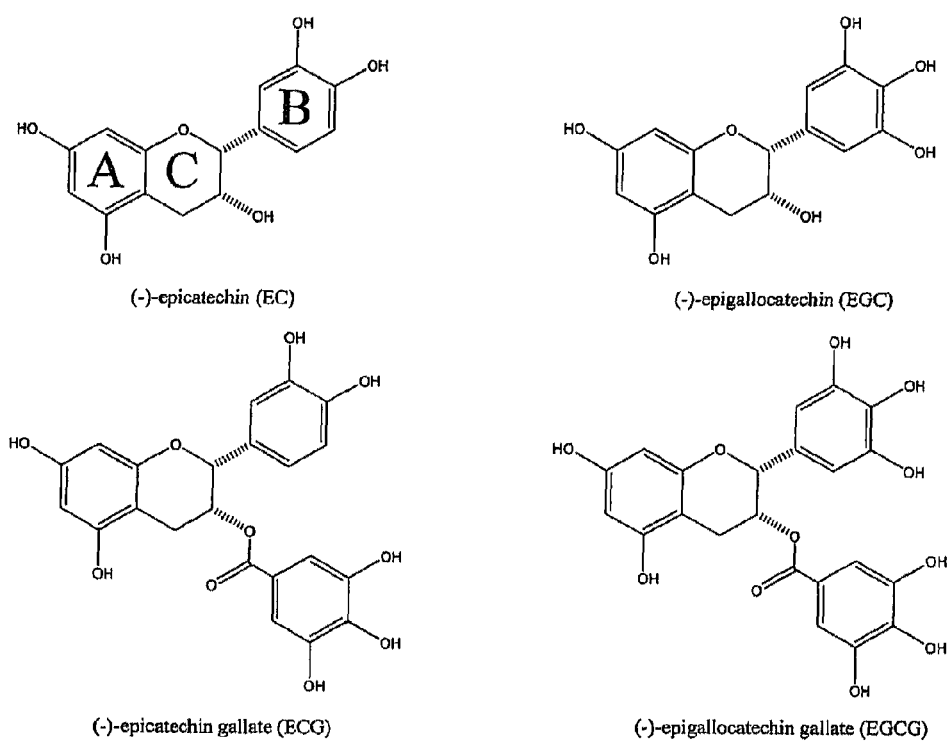

FIG. 34. Structures of green tea polyphenols.

Figure 35:
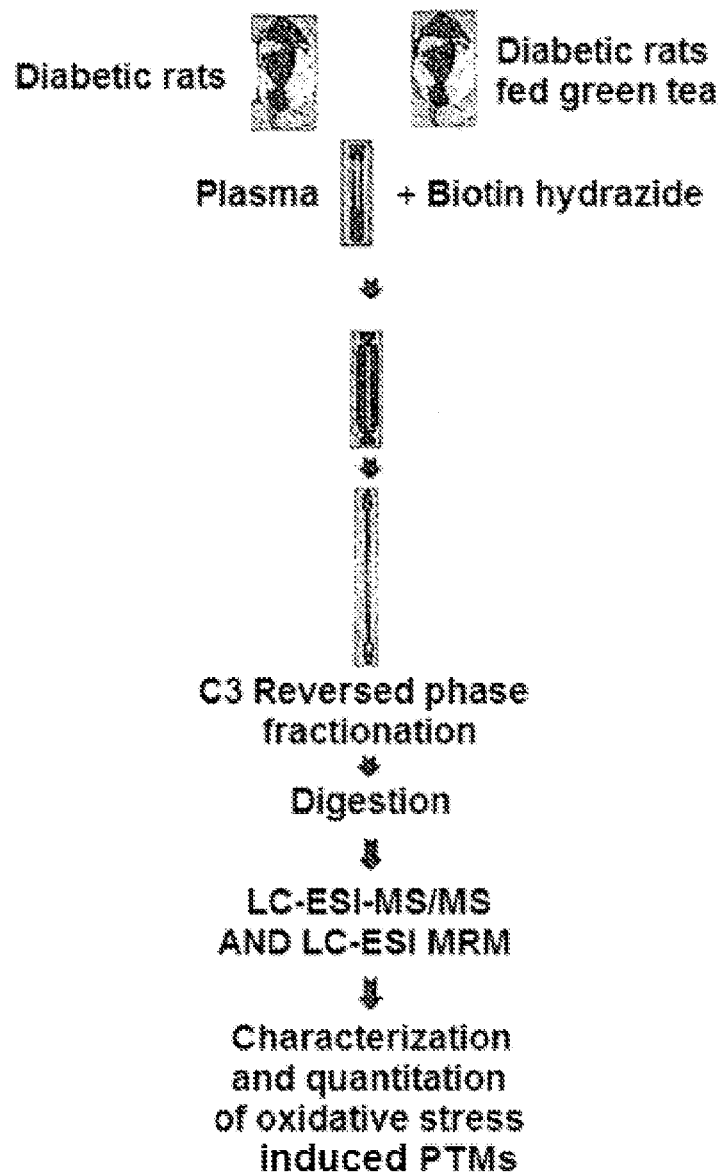

FIG. 35. Schematic illustration for the strategy used for the identification, quantitation and characterization of carbonylated proteins and their oxidation sites in the plasma of green tea fed diabetic and their control diabetic rats. Five samples from each of the green tea fed diabetic and their control diabetic rats were pooled together and the oxidation sites were characterized using LC-ESI-MS/MS and quantitated using selective reaction monitoring (SRM).

Figure 36:
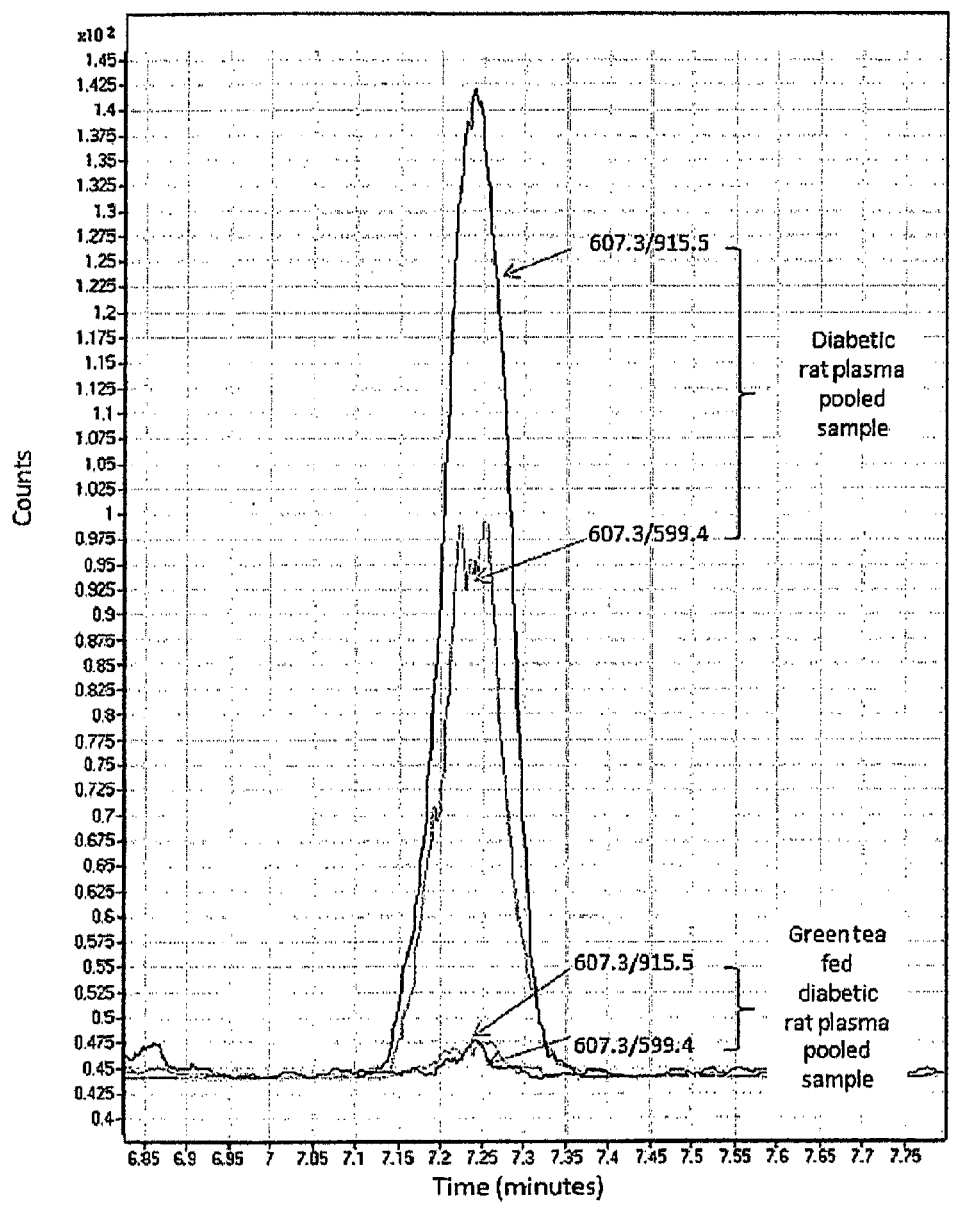

FIG. 36. Relative quantitation of carbonylated peptides using selective reaction monitoring (SRM). The peptide was quantitated based on two transitions, 915.5 (y5) and 599.4 (y2-NH$_3$). As shown in the figure, the levels of these two transitions were significantly reduced (0.04%) in the green tea fed diabetic rat plasma pooled sample compared to their control diabetic rat plasma pooled sample.

Figure 37:
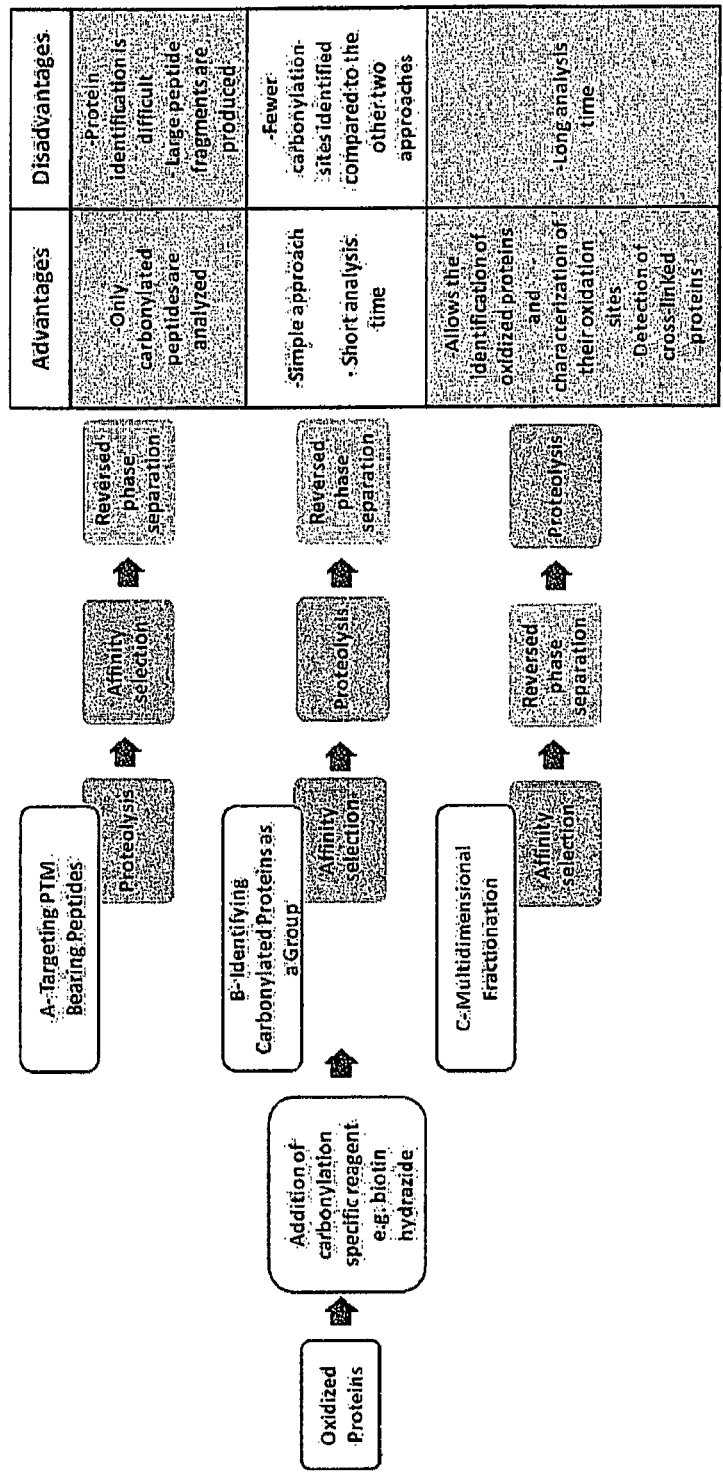

FIG. 37. A diagram comparing three approaches for the identification of carbonylated proteins and their carbonylation sites.

Figure 38:
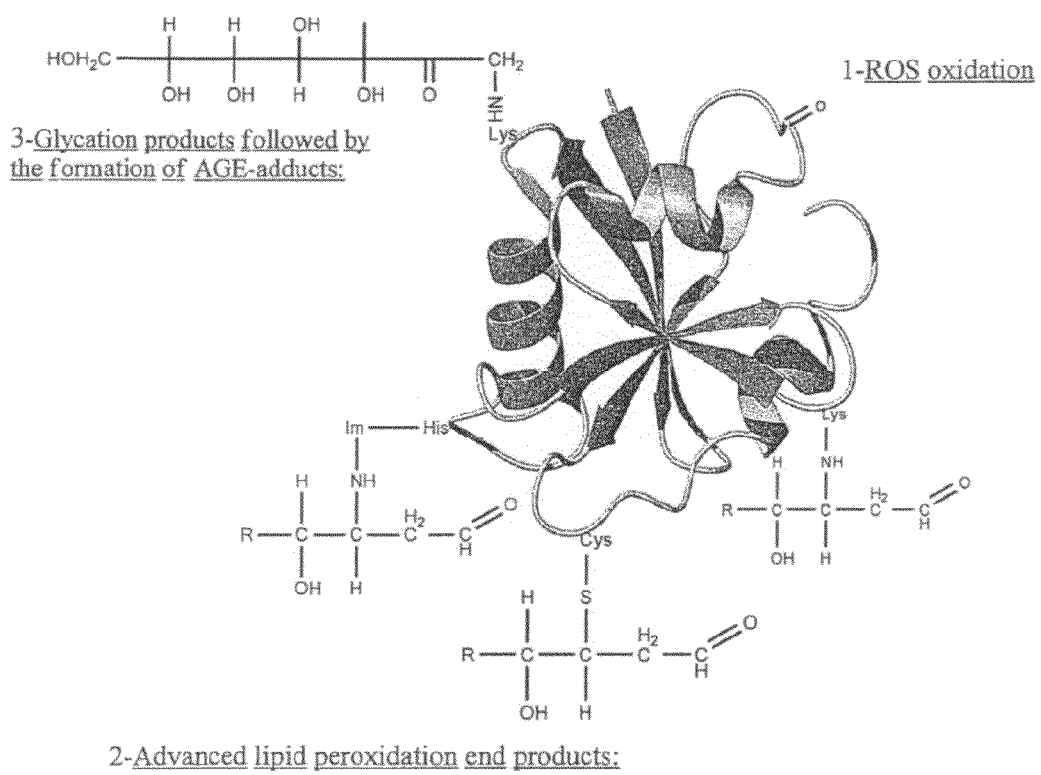

FIG. 38. A general scheme for the different routes of protein carbonylation.

DETAILED DESCRIPTION OF ILLUSTRATIVE EMBODIMENTS

The invention described herein involves the detection of oxidized peptides in the plasma and are used to diagnose or monitor disease states in an individual. These oxidative modifications of peptides are referred to below as an oxidative stress induced post-translational modification (OSi~PTM).

The oxidized peptides being detected are not natively plasma peptides, but instead are peptides, or are derived from peptides, that may originate in cells found in non-blood tissues (e.g., organs or tumors) or are generated at sites of inflammation in the circulatory system.

In some cases, the oxidized peptides may be derived by digesting oxidized peptides selected from plasma. Sites of oxidation often may be more easily detected in digested peptide fragments than in an undigested parent peptide.

Peptide oxidation can be a marker for many different disease states. Peptides can contain multiple sites that were oxidized in, for example, an undigested parent peptide. Moreover, a single peptide may bear multiple types of oxidation. The site and type of oxidation may be disease-specific and, therefore, useful for diagnosis and/or monitoring of a disease. For example, the relative degree (i.e., the level) of oxidation at a particular site can vary with, and be used as a marker for, disease progression. The degree and type of oxidation at any particular site on a peptide may be independent of the oxidation status at other sites on the peptide or on other peptides derived from the same protein parent. Of all the potential oxidation sites on a peptide, only a small number may actually be oxidatively modified by carbonylation through oxidative stress. Carbonylation generally increases in biological systems with increasing oxidative stress, but not necessarily in direct proportion at any particular site.

Additionally, oxidative stress experienced by an organ can be observed by analyzing the oxidative status of organ-specific peptides through, for example, oxidized peptide fragments. Oxidation patterns can be compared between normal and stressed individuals in, for example, a diagnostic method. Alternatively, oxidation patterns can be compared from a single individual at different points in time in, for example, a method that monitors the progression of disease, the efficacy of treatment, or the recurrence of disease.

Oxidative stress itself and therapeutic agents that control oxidative stress can be monitored as well. Some types of carbonylation can be reduced by antioxidants of both natural and synthetic origin that have been administered to biological systems, the purpose being to protect cells against oxidative stress. In some cases, for example, antioxidant concentration can alter some types of protein oxidation and the resulting oxidative signatures. Thus, monitoring protein oxidization can be used to monitor the presence and efficacy of antioxidants.

Throughout this disclosure, each of the following terms shall have the indicated meaning.

"Corresponding oxidation site" refers to a site of peptide oxidation common among a plurality of individual molecules of the same peptide—i.e., molecules having the same amino acid sequence.

"Non-blood peptide" refers to a peptide present in the blood, plasma, or a blood product because the peptide is shed or released into the circulatory system as a result of oxidative stress-induced cell death—whether apoptosis, necrosis, or some other mechanism—as opposed to having a typical blood-related function such as, for example, nutrient transport, oxygen transport, endocrine function, immunological function, maintaining osmolarity, and the like. In contrast, "blood peptide" refers to a peptide modified by oxidative stress at some extracellular location, generally in the circulatory system.

"Normal," in the context of an individual, refers to an individual who does not exhibit any symptoms or clinical signs of a particular disease. In the context of a sample, "normal" refers to sample obtained from an individual who does not exhibit any symptoms or clinical signs of a particular disease.

"Peptide" refers to a sequence of amino acid residues without regard to the length of the sequence. Therefore, the term "peptide" refers to any amino acid sequence having at least two amino acids and therefore includes a full-length protein, any fragment of a full-length protein, any amino acid sequence that possesses an addition, a deletion, and/or a substitution of one or more amino acid residues compared to a reference protein, and any synthetically-produced amino acid sequence that includes at least two amino acid residues.

"Protein" refers to a sequence of amino acid residues as natively expressed by a cell.

"Sign" or "clinical sign" refers to an objective physical finding relating to a particular disease capable of being found by one other than the patient.

"Symptom" refers to any subjective evidence of disease or of a patient's condition.

PTM refers to a post-translational modification.

OSi~PTM refers to an oxidative stress induced post-translational modification.

DNPH refers to dinitrophenylhydrazine.

AGE refers to advanced glycation end products.

ETD refers to electron transfer dissociation.

ECD refers to electron capture dissociation.

CID refers to collision-induced dissociation.

ROS refers to reactive oxygen species.

OS refers to oxidative stress.

RPC refers to reversed-phase chromatography.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Excessive oxidative stress leaves a carbonylation fingerprint on peptides in biological systems. Carbonylation is a post-translational modification that often leads to the loss of protein function and can be a component of multiple diseases. Protein carbonyl groups can be generated directly or indirectly. Direct carbonylation can occur by, e.g., amino acids oxidation or the α-amidation pathway. Indirect carbonylation can occur by, e.g, forming adducts with lipid peroxidation products or glycation and advanced glycation end products. Studies of oxidative stress have historically been complicated by the low concentration of oxidation products and wide array of routes by which proteins are carbonylated. Methods described herein, which generally can include new selection and enrichment techniques, coupled with advances in mass spectrometry, allow one to identify hundreds of new carbonylated protein products from a broad range of proteins located at many sites in biological systems.

Redox regulation is a subject of broad interest in regulatory biology. Oxidation and reduction of amino acid side chains in proteins is a normal part of redox regulation in cells where slight surges in reactive oxygen species are generally dealt with by oxidation of sulfhydryl groups to mixed disulfides. After an oxidative stress episode has passed, these disulfides are reduced back to sulfhydryls and the normal redox potential of the cell is restored. An array of enzymes has evolved in aerobic organisms specifically for repairing oxidative modifications produced in proteins during such events. Proteins that are too seriously damaged for repair are destroyed by proteasomes and lysosomes.

There are, however, cases where these coping mechanisms are exceeded. Excessive levels of reactive oxygen species from either the environment or aberrations in electron transport can produce such high levels of oxidative stress that large amounts of irreparably damaged proteins are generated. In the process, proteasomes and lysosomes themselves can be altered to the point that their ability to degrade proteins is compromised (Brownlee, M., *Diabetes*, 2005, 54(6):1615-1625). Under chronic oxidative stress, damaged proteins can accumulate to toxic levels, often causing cell death and, potentially, oxidative stress-related diseases (Stadtman et al., *Ann. N. Y. Acad. Sci.*, 2000, 928:22-38; Davies et al. *Neurology*, 2006, 66(2, Suppl. 1):S93-S96). Pathological levels of oxidative stress have been implicated in a plethora of diseases ranging from diabetes mellitus (Brownlee, M., *Diabetes*, 2005, 54(6):1615-1625) and neurodegenerative diseases (Uttara et al., *Curr. Neuropharmacol.*, 2009, 7(1): 65-74) to inflammatory diseases (Naito et al., *Curr. Drug Targets: Inflammation Allergy*, 2005, 4(4):511-515), atherosclerosis (Victor et al. *Curr. Pharm. Des.*, 2009, 15(26):2988-3002), cancer (Tas et al. *Med. Oncol.*, 2005, 22(1):11-15), and even aging (Stadtman et al., *Ann. N. Y. Acad. Sci.*, 2000, 928:22-38; Perez et al. *PNAS*, 2009, 106(9):3059-3064). Although all of these diseases have been widely studied, understanding of the protein chemistry involved is relatively primitive. Until very recently protein carbonylation from pathological oxidative stress has been accessed with the dinitrophenylhydrazine (DNPH) colorimetric test for carbonyl groups. The proteins involved, potential changes in their structure and function, sites of oxidation, mechanisms of oxidation, repair or degradation, the long-term fate of oxidized proteins that precipitate in cells, and how oxidized proteins cause cell death are issues that need more study to understand how oxidative stress diseases threaten health.

Collectively, proteins can be oxidized in more than 35 ways (Table 1). All of these post-translational modifications occur in three basic ways that are distinguishable by mass spectrometry. One involves oxidative cleavages in either the protein backbone or amino acid side chains in which Pro, Arg, Lys, Thr, Glu or Asp residues are most likely to undergo oxidative cleavage. A second mechanism is by indirect addition of lipid oxidation products such as 4-hydroxy-2-noneal, 2-propenal, or malondialdehyde to proteins. Mass increases with this type of modification and is unique to the appended group. Finally, carbonyl groups may be generated in proteins by oxidation of what have come to be known as advance glycation end (AGE) products. AGE products are common in long-lived proteins such as hemoglobin, especially in the case where glucose levels and oxidative stress are elevated, as in diabetes mellitus. Structures of some carbonylated oxidation products are seen in Table 2. All of these forms of oxidation can be reflected independently in proteins of an individual at one time.

TABLE 1

Types of oxidative protein modifications

| Amino acid | oxidative modification |
|---|---|
| T | 2-amino-3-oxo-butanoic acid |
| Y | hydroxylation |
| R | glutamic semialdehyde |
| C | cysteic acid (sulfonic acid) |
| C | sulfunic acid |
| C | sulfenic acid |
| W | formylkynurenin |
| W | kynurenin |
| W | hydroxykynurenin |
| W | 2,4,5,6,7 hydroxylation of tryptophan |
| W | oxolactone |
| H | 4-hydroxy glutamate |
| H | asparagine |
| H | aspartate |
| H | 2-oxo-histidine |
| D | hyroxylation |
| M | oxidation (sulfoxide) |
| M | sulfone |
| L | hydroxy Leucine |
| K | Aminoadipic-semialdehyde |
| K | Amadori adduct |
| K | 3-deoxyglucosone adduct |
| K | glyoxal adduct |
| K | methylglyoxal adduct |
| N | hyroxylation |
| P | hyroxylation |
| P | glutamic semialdehyde |
| P | pyroglutamic |
| P | pyrrolidinone |
| F | hyroxylation |
| F | dihydroxy phenylalanine |
| K | hyroxylation |
| C/H/K | hydroxynonenal (HNE) Michael adduct |
| K | malondialdehyde |

TABLE 2

Amino acids and corresponding carbonylation products.

| Amino Acid | Carbonylation product |
|---|---|
| 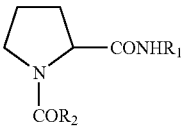<br>Prolyl | 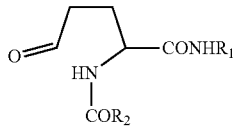<br>Glutamic semialdehyde |
| | 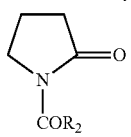<br>2-Pyrrolidinone |

TABLE 2-continued

Amino acids and corresponding carbonylation products.

| Amino Acid | Carbonylation product |
|---|---|
| Arginyl | Glutamic semialdehyde |
| Lysyl | Aminoadipic semialdehyde |
| Threonyl | 2-Amino-3-ketobutyric acid |
| Glutamyl | Pyruvyl |
| Aspartyl | Pyruvyl |
| Peptide or protein | α-amidation pathway |

TABLE 2-continued

Amino acids and corresponding carbonylation products.

| Amino Acid | Carbonylation product |
|---|---|
| P-Lys-NH2 | H₂C—HN-Lys-P<br>║<br>O<br>H——OH<br>HO——H<br>H——OH<br>H——OH<br>CH₂OH<br><br>Amadori product (followed by the formation of AGE-adducts) |
| | Lys-P<br>\|<br>H   NH<br>\|   \|   H₂<br>R—C—C—C—C=O<br>\|   \|       H<br>OH  H<br><br>Advanced lipidation end product (Michael adduct) |
| P-His-IM-NH | Lm-His-P<br>\|<br>H   NH<br>\|   \|   H₂<br>R—C—C—C—C=O<br>\|   \|       H<br>OH  H<br><br>Advanced lipidation end product (Michael adduct) |
| P-Cys-SH | Cys-P<br>\|<br>H   S<br>\|   \|   H₂<br>R—C—C—C—C=O<br>\|   \|       H<br>OH  H<br><br>Advanced lipidation end product ((Michael adduct) |

One analytical problem involves recognizing oxidized proteins and differentiating between the various types of oxidative modifications. Methods described herein address this analytical problem and provide a platform for practical applications of such analyses.

Isolating Carbonylated Proteins

Biological fluids such as blood plasma contain thousands of proteins that vary $10^{10}$-fold or more in concentration, a small portion of which will be oxidatively modified. Current proteomics tools require much simpler mixtures and concentrations of 1 ng/mL or more for large-scale protein identification. As a means of dealing with these problems multiple methods have been described for selection and recognition of carbonylated proteins, all of which exploit the relatively unique property of carbonyl groups to form Schiff bases. Through derivatization of carbonyl groups with a reagent such as dinitrophenylhydrazine or biotin hydrazide (Table 3), affinity chromatography can be used to select oxidized proteins derivatized with these groups, greatly enriching them or their proteolytic fragments in the process.

TABLE 3

Reagents and corresponding enrichment chemistry

| Chemical Reagent | Enrichment chemistry |
|---|---|
| 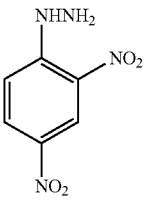<br>Dinitrophenylhydrazine (DNPH) | The hydrazide group reacts with carbonyl groups on oxidized proteins forming hydrazones, which can be then isolated with DNPH-specific antibiodies. |
| 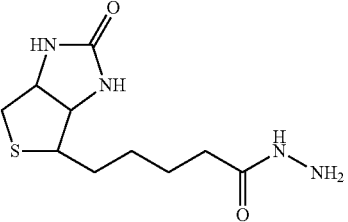<br>Biotin hydrazide | The hydrazide group reacts with carbonyl groups on oxidized proteins forming hydrazones, which can be then isolated with avidin. |
| 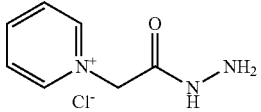<br>Girard's P reagent | The hydrazide group reacts with the carbonyl groups on oxidized proteins forming hydrazones. The quaternary amine can be selected by strong cation exchange (SCX) at pH 6.0. |
| 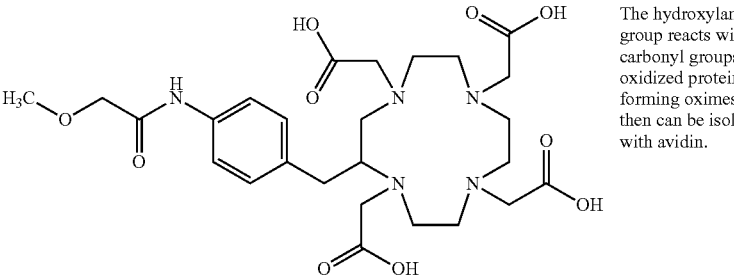<br>tetraazacyclododecane-N,N′,N″,N‴-tetraacetic acid | The hydroxylamine group reacts with carbonyl groups on oxidized proteins forming oximes, which then can be isolated with avidin. |
| 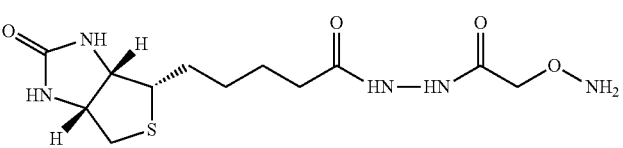<br>N′-aminooxymethylcarbonylhydrazino D-biotin | The hydroxylamine group reacts with carbonyl groups on oxidized proteins forming oximes, which then can be isolated with avidin. |
| 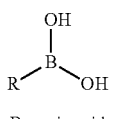<br>Boronic acid | Forms a reversible covalent ester with 1,2- and 1,3-diols in aqueous media that captures glycated peptides and proteins. |

Dinitrophenylhydrazine

Derivatization of carbonyl groups with dinitrophenylhydrazine (DNPH) has been used for more than half a century as a qualitative analytical method in organic chemistry. With slight modification of this old method, DNPH derivatization was adapted to enhance the isolation, identification, and quantification of carbonylated proteins through selection of derivatized proteins with DNPH targeting antibodies. Tryptic digestion of protein mixtures derivatized in this manner and selected followed by reversed-phase chromatography coupled with tandem mass spectrometry (RPC-MS/MS) or ion exchange and reversed-phase chromatography coupled to tandem mass spectrometry (IEC/RPC-MS/MS) has proven successful in identification and quantification of carbonylated proteins.

Biotin Hydrazide

Biotin hydrazide (BHZ) and biocytin hydrazide have been used in a similar fashion. BHZ reacts readily with carbonyl groups, allowing carbonyl groups to be derivatized and the parent proteins to be selected with an immobilized avidin or streptavidin sorbent. Streptavidin and avidin bind biotin with comparable affinity Isolation and identification of carbonylated proteins through biotin derivatization has been achieved with a multiple step chromatographic process in which carbonyl groups are first derivatized with BHZ to form a Schiff base. The Schiff base is then reduced with sodium cyanoborohydride to prevent reversal of derivatization. Excess BHZ is removed before avidin affinity chromatography by either dialysis or precipitation with trichloroacetic acid (TCA). Because the interaction of biotin with native tetrameric avidin affinity chromatography columns is very difficult to disrupt, monomeric avidin columns are frequently used in affinity chromatography. The binding of biotin to monomeric avidin is still highly specific, but much weaker. Monomeric avidin is also easily immobilized and has been used to select oxidized proteins. Elution of biotinylated proteins from monomeric avidin can be affected with 2 mM biotin or 0.1 M glycine. Biocytin hydrazide is similar to biotin hydrazide in structure and reactivity and has been used with streptavidin to isolated and identify carbonylated proteins from aged mice. The BHZ approach has know been used to study oxidized proteins in yeast, rats, and humans.

Additionally, 2-D gel electrophoresis (2DGE) and SDS-PAGE has been used to separate biotinylated proteins after which they were detected with labeled avidin. The limit of detection in gels using avidin FITC (fluorescein isothiocyanate) has been reported to be 10 ng. Detection of biotinylated proteins in gels using streptavidin-conjugated peroxidase for amplification is even more sensitive.

Avidin capture of a protein from a biotinylated does not prove the protein is oxidized. Affinity columns can bind protein complexes. This, when an avidin affinity column captures a biotinylated member of a complex, non-biotinylated, non-oxidized members of the complex can be captured as well. These non-oxidized members of the complex may show up during subsequent shotgun proteomic analyses. Non-oxidized proteins can also bind non-specifically to the chromatographic support matrix or avidin. Proof that a protein is oxidized comes from identification of the oxidation site.

Girard's P Reagent

Derivatization with Girard's P reagent (GPR, (1-(2-hydrazino-2-oxoethyl)pyridinium chloride)) provides another route for the selection of carbonylated peptides. GPR contains i) a hydrazide group that reacts readily with carbonyl groups to form hydrazones and ii) a quaternary amine that can be selected by strong cation exchange (SCX) resin at pH 6.0. Following trypsin digestion of proteins derivatized with GRP, quaternary amine-containing peptides are selected from mixtures with a SCX column and then further fractionated and identified by RPC-MS/MS. Two features of this approach are, first, that excess derivatizing reagent does not have to be removed before chromatographic analysis and, second, derivatization with GPR enhances peptide ionization through quaternization.

Oxidation-Dependent Element Coded Affinity Tags (O-ECAT)

Isolation, identification, and quantification of carbonylation sites also has been achieved with ((S)-2-(4-(2-aminooxy)-acetamido)-benzyl)-1,4,7,10-tetraazacyclododecane-N,N',N'',N'''-tetraacetic acid (O-ECAT). After derivatization of carbonyl groups in a sample, the O-ECAT moiety is used to chelate a rare earth metal such as Tb (158.92 Da) or Ho (164.93 Da). Treating samples with different rare earth metals according to sample origin allows differential coding of samples. Native and oxidized human serum albumin samples may be allowed to react with this reagent and after coding and mixing were tryptic digested. Coded peptide fragments can be selected with an immunosorbent column targeting the derivatizing agent. Peptides selected in this manner can be analyzed by nanoRPC-FTICR mass spectrometry.

Identification Strategies

Affinity chromatography, coupled with modern proteomics methods, is now widely used to study many types of post-translational modifications including, for example, carbonylation. Proteomic analysis of carbonylated proteins has been achieved in three ways (FIG. 37).

Targeting PTM-Bearing Peptides

One route of identification involves immediately digesting biotinylated samples with, for example, trypsin or glu-C and selecting only the carbonylated and biotinylated peptides from samples by avidin affinity chromatography. Carbonylated peptide mixtures thus selected may be then analyzed by RPC-MS/MS. Because arginine and lysine residues can be oxidized, trypsin cleavage at these sites can be blocked, resulting in some fragment that may be larger than theoretically expected based on an expectation that all trypsin digestion sites will be available for digestion.

Identifying Carbonylated Proteins as a Group.

A second approach is to target native proteins. With this method carbonylated proteins are first biotinylated and then selected by avidin affinity chromatography. Following proteolysis, unoxidized peptide fragments from these proteins can be identified by RPC-MS/MS methods common to shotgun proteomics. There are several advantages with this approach. One is that both unmodified and PTM-bearing peptides are available for identification. When ionization of a carbonylated peptide is suppressed or a PTM-bearing peptide does not ionize at all, other peptides from the protein are available for identification. Another advantage is that many carbonylated proteins have also undergone additional types of protein oxidation such as, for example, methionine oxidation, sulfhydryl oxidation, and tyrosine nitrosylation. The fact that addition types of oxidation are co-selected with carbonylation may be fortuitous. One disadvantage of this strategy is that modification sites may not be identified if PTM-bearing peptides are not seen and sequenced. Non-specifically bound proteins could also be mistakenly identified as bearing the PTM if the PTM site is not identified.

Multidimensional Fractionation

A third strategy involves further fractioning affinity-selected proteins by liquid chromatography before proteolysis and identification of peptide fragments by RPC-MS/MS. Beyond affinity selection in the first dimension of chromatography, fractionation is generally achieved by reversed-phase chromatography (RPC) in the second dimension. Protein fractions collected from the RPC column may be trypsin digested and the peptide fragments identified by RPC-MS/MS. Carbonylation sites from 87 yeast proteins have been identified in this manner. Again, oxidatively modified and unmodified tryptic peptides from a protein may appear together, facilitating protein identification based on peptide sequence analysis. The unmodified peptides may be used to identify the protein parent while labeled carbonylated peptides may be used to identify oxidation sites.

Proteins sometimes appear in multiple peaks during RPC fractionation. These peaks can arise from in viva cleavage, protein:protein cross-linking, and/or protein:RNA cross-linking. Isoforms of a protein will generally be missed by the other two procedures described above. Advantages of this approach include the ability to identify isoforms of a protein and the ability to identify the most oxidized proteins. A disadvantage is that it is more laborious than other approaches.

Analysis of Oxidation Mechanisms

Carbonylation of a protein can occur in at least three ways; by direct oxidation with reactive oxygen species (ROS), through Michael addition of lipid peroxidation products, and through formation of advanced glycation end products (FIG. 38).

ROS Oxidation.

Cleavage of amino acid side chains is generally associated with oxidation by reactive oxygen species. Some of these cleavage products are listed in Table 2. Each is linked to a unique change in mass that can be programmed into most peptide/protein identification software. But even so, the molecular weight of the modified peptide can be very similar to that of an unmodified peptide in the proteome. This may be addressed by acquiring data with a high mass accuracy analyzer capable of differentiating PTM-bearing peptides from unmodified peptides on the basis of mass alone. Through hydrogen peroxide-induced oxidative stress in yeast cultures and biotin hydrazide derivatization to select carbonylated proteins, 415 proteins have been identified along with specific sites of oxidation in 87 instances (Mirzaei et al., *J. Proteome Res.*, 2006, 5(9):2159-2168). Thirty-two cases were seen in which proteins appear in multiple, non-adjacent peaks during reversed-phase chromatography. This generally indicates differences in post-translational modification, fragmented forms of the protein, or some type of cross-linking. Typically gel electrophoresis has been used to study protein fragmentation, but RPC works equally well.

Cross-linking is often seen in ROS-induced protein oxidation, occurring in at least six different ways include, for example, a) forming disulphide bonds between proteins through cysteine oxidation, b) Schiff base formation between a carbonyl group on an oxidized amino acid side chain of one protein and a lysine residue on another, c) Schiff base formation between the carbonyl group on an HNE adduct of one protein and a lysine residue on another, d) Schiff base formation between the carbonyl group on a malondialdehyde adduct of one protein and a lysine residue on another, e) Schiff base formation between a carbonylated AGE product and another protein, or f) by free radical cross-linking involving carbon-centered radicals.

Co-elution in multiple separation systems is a good way to recognize cross-linked proteins. This approach has been exploited in recognizing cross-linking of ribosomal proteins to rRNA (Mirzaei et al., *J Chromatogr A*, 2007, 1141(1):22-31). Proteins from $H_2O_2$-stressed yeast were biotinylated, avidin selected, and then further fractionated by RPC. Ribosomal proteins were noted to elute in three different peaks during RPC under strongly denaturing conditions. The ribosomal proteins were subjected to tryptic digestion and further chromatography of the peptides on a borate affinity column that selected species bearing a vicinal diol present in RNA bases. Mass spectral analysis of captured peptides indicated that the peptides had covalently appended nucleotide bases, and b) identified the specific bases involved (Mirzaei et al., *J Proteome Res*, 2006, 5(12):3249-3259). This procedure was used to identify 37 ribosomal proteins from yeast that were cross-linked to rRNA, along with sites in the proteins and on rRNA at which cross-linking occurred.

Although protein oxidation is non-enzymatic and may be expected to be random, it is not. Oxidation occurred at very specific sites. Many of these new, non-genetically-coded oxidation sites conveyed a new biological activity to the oxidized protein and have been named "allotypic active sites" (Mirzaei et al., *J. Proteome Res.*, 2006, 5(9):2159-2168). The type of oxidizing agent may influence the site of protein oxidation. While metal-catalyzed oxidation of human serum albumin in vitro has resulted in carbonylation at Lys-97 and Lys-186, oxidation with hypochlorous acid has resulted in carbonylation at five sites: Lys-130, Lys-257, Lys-438, Lys-499, and Lys-598 (Temple et al., *J. Am. Soc. Mass Spectrom.*, 2006, 17(8):1172-1180).

A substantial amount of work on oxidative stress has been done in model systems. Protein oxidation in vitro, however, may not always be the same as in vivo. Metals have long been known to influence oxidation by reactive oxygen species, often leading to primary structure cleavage. When the oxidation of human serum albumin was catalyzed with FeEDTA, in vitro cleavage was more extensive than that seen in vivo (Lee et al., *J. Proteome Res.*, 2006, 5(3):539-547). This may be because fewer proteins are in the in vitro mixture and reactive oxygen species are not depleted as quickly.

Lipid Peroxidation Adducts.

Examining the Protein-Aldehyde Adducts.

The first direct proof of lipid conjugation to proteins was in oxidized low density lipoproteins (LDL). LDL is composed of a single apolipoprotein B-100 (Apo B-100) with adsorbed fatty acids that together are water-soluble. Oxidizing LDL makes it susceptible to uptake by scavenger receptors inside the endothelium and can lead to the formation of "foam cells." Accumulation of foam cells is the first stage of atherosclerotic plaque formation. One of the degradation products resulting from lipid oxidation is 4-hydroxynonenal-lysine (HNE). HNE can become attached to proteins through either Michael addition or Schiff base formation.

Oxidized LDL has been reduced with $NaBH_4$ (to stabilize the Michael adduct formed between HNE and histidine), de-lipidated to remove non-covalently linked lipid, and digested with trypsin to generate peptides for RPC-MS/MS analysis. Mass spectra of all peptides containing the HNE moiety showed an m/z 268 product ion corresponding to the histidine immonium ion modified by HNE. Product ion scanning of all second dimension mass spectra for this m/z 268 ion was used to locate peptides in the RPC eluent carrying HNE. Peptide sequence and the location of HNE in the peptide were extracted from the spectra of these peptides. Modified residues were found to be located on the surface of LDL.

Michael addition also can occur on lysine and cysteine residues. Moreover, direct addition of carbonyl groups from malondialdehyde (MDA) and 4-hydroxynonenal (HNE) onto lysine is possible.

A recent in vitro study with hemoglobin and β-lactoglobulin under near physiological conditions has shown it is possible to differentiate between Michael addition and Schiff base formation through mass spectrometry. Michael addition of HNE adds 158 Da of mass to the peptide while Schiff base addition of HNE adds 138 Da. Based on mass spectral analysis, Michael adduct formation dominates Schiff base formation by a 99:1 ratio (Bruenner et al., *Chem. Res. Toxicol.*, 1995, 8(4):552-559). When HNE was adducted to apomyoglobin, addition occurred predominantly at histidine residues (Bolgar et al., *Anal. Chem.*, 1996, 68(14):2325-2330). Product ion scanning of immonium ions showed that 3-10 histidine residues were derivatized. In contrast, the adduct ratio of HNE to human serum albumin (HSA) was dependent on the molar ratio of HNE to HSA. Moreover, cysteine, histidine, and lysine were all modified (Aldini et al., *J. Mass Spectrom.*, 2006, 41(9):1149-1161). Cytochrome c forms adducts with histidine, lysine, and arginine. The importance of this is that cytochrome C binds to complexes III and IV in the electron transport chain through lysine residues. Thus, HNE-Lys adduct formation could impact electron transport. In another study amyloid peptide was shown to form one or more HNE adducts in the residue 6-16 region of the primary structure (Magni et al., *Rapid Commun Mass Spectrom*, 2002, 16(15):1485-1493). Addition of reducing agents (e.g., $NaCNBH_3$ or $NaBH_4$) can affect the type of adduct formed as well at the site of modification. Interestingly, if $NaCNBH_3$ is added early in the incubation process, Schiff base formation can be more prominent than Michael addition. In addition, the N-terminal amino acid rather than a histidine residue would be modified. On the other hand, addition of $NaBH_4$ at the end of the reaction between the protein and HNE resulted in the reduction of the Michael adduct formed.

Polypeptide structure can also affect lipid peroxidation product modification. The degree of HNE and 4-oxo-2-nonenal modification in apomyoglobin, which possesses a more open structure, was greater than with myoglobin, which possesses a less open structure.

A variety of mass spectrometers have been used in the analysis of protein oxidation. One of the more important issues is the mass accuracy of the instrument. FTICR-MS was used to characterize HNE modifications in apomyoglobin where it was found that three to nine Michael adducts were formed. Schiff base adducts were observed as well, but with less intensity as expected from the discussion above. An advantage of high mass accuracy and resolving power is that it allows the resolution of fragment ions of very similar mass. Because peptide sequencing by collision-induced dissociation (CID) results in neutral loss and only partial sequence coverage, electron transfer dissociation (ETD) has been used as an alternative and shown to be superior in the characterization of modification sites due to the production of c and z ions. FTICR-MS has also be used to characterize HNE adducts of creatine kinase isoforms in brain were it was shown that cysteine and histidine residues were most likely to be derivatized. A new method for the characterization of HNE-protein adducts has also been developed using a hybrid linear ion trap-FTICR mass spectrometer (LTQ-FT). In this method, both the usual data-dependent mode of acquisition and a neutral loss driven $MS^3$ ($NL-MS^3$) data dependent acquisition mode were utilized. The later depended on the isolation and fragmentation of any ion showing a difference of m/z 78, 52 or 39 from the precursor ion. Twenty four HNE modification sites were observed on fifteen mitochondrial proteins of which six were seen using $NL-MS^3$ data dependent acquisition.

Affinity Purification of the Adducts.

It has been shown above that monitoring immonium product ions contain HNE is a powerful tool for recognizing HNE bearing peptides. Unfortunately, cysteine and lysine do not produce intense HNE bearing immonium product ions. Several new methods have been developed with the aim of enriching these adducts to circumvent this problem. The first is based on the use of an anti-HNE immunosorbent in which the antibody was immobilized on CNBr-activated Sepharose. This immunosorbent has been employed to enrich adducts formed between HNE and peptides from either a tryptic digest of apomyoglobin or a model peptide (residues 87-99) of myelin basic protein. A unique feature of the antibody chosen for HNE selection was that it was specific for Michael adducts only. Anti-dinitrophenyl antibodies have been used as well to select HNE Michael and malondialdehyde Schiff base adducts derivatized with dinitrophenyl hydrazine (DNP). Enrichment and recovery of DNP derivatized peptides was virtually quantitative.

As noted above, enrichment of biotin adducts through avidin affinity purification is another route. Biotinylated hydroxylamine can react with Michael adducts and has been used for enrichment through avidin affinity chromatography. Forming an oxime rather than hydrazone eliminates the need for the reduction step while still allowing determination of the sites of modification (Table 3). Another way to isolate these adducts is by using biotin hydrazide. This allows enrichment of HNE-modified peptides in HNE-spiked yeast lysate. Mapping the HNE modification sites showed that sixty-seven proteins were modified, generally on histidine. The first step in identifying HNE-modified proteins from adipose tissues was incubating biotin hydrazide with adipose tissue from obese mice. Proteins thus biotinylated were captured by avidin affinity chromatography, digested with trypsin, and identified by RPC-MS/MS with online database searches to identify peptides. Among the proteins identified was HNE-modified adipocyte fatty acid-binding protein, which is involved in insulin resistance. Additionally, treating yeast lysates in vitro with HNE resulted in the identification of 67 different proteins carrying 125 HNE modification sites. HNE adducts seen in the in vitro study were not observed in the in vivo study of yeast.

Oxidation of Advanced Glycation End Products

Reducing sugars add to amines in proteins through the Maillard reaction. Addition products thus formed often undergo an Amadori rearrangement and, in the course of doing so, form an isomeric mixture of products with long-term stability known as advance glycation end (AGE) products. An increase in the concentration of AGEs and their oxidation products is associated with OS-associated damage in, for example, diabetes, renal failure, and aging. A series of methods have been developed to assess the nature of these adducts.

Advanced glycation end products of proteins formed by sugar addition are highly complex (Lapolla et al., *Journal of Mass Spectrometry*, 2001, 36(4):370-378). One concern with glycation is that it may modify the biological activity of a protein. With glutathione peroxidase, for example, methylglyoxal can irreversibly modify residues R184 and R185 and inactivate the enzyme. Loss of this oxidative repair enzyme can lead to rising levels of reactive oxygen species.

Glycation also can modify the susceptibility of proteins to proteolysis. This might have biological significance by increasing the half-life of a glycated protein. As seen with human serum albumin, glycation reduces the number of tryptic peptides formed. The same is true with digestion by endoproteinase Lys-C. Proteinase K is better able to digest glycated proteins and more nearly mimics the AGE-protein degrading enzymes occurring in vivo.

One promising advance for analyzing glycated proteins is electron transfer dissociation (ETD)-based analysis in addition to collision-induced dissociation (CID) in ESI-MS instruments. With ETD, a nearly full series of c and z type ions are produced with glycated peptides, allowing easier peptide sequencing. CID, in contrast, produces lower intensity b and y ions and the spectra are filled with ions corresponding to neutral loss of water and furylium ions. Actually, both forms of fragment ion generation have unique applications. Scanning for CID neutral loss of −162 amu is a powerful tool for recognizing glycated peptides. Using an electrospray inlet on a Q-TOF instrument operated at both low and high collision energies has permitted the identification of 31 out of 59 lysine residues in HSA that were glycated. The mode of ionization is also important in glycated- and glycosylated-peptide analysis. In addition to the ESI instrumentation described above, MALDI coupled to tandem TOF/TOF mass spectrometers has proven to be a powerful tool in structure analysis. MALDI-MS of glycosylated peptides is more successful when 2,5-dihydroxybenzoic acid is used as the matrix to initiate laser induced ionization.

Methods for the isolation of AGE products are important as well. Affinity chromatography with meta-amino phenyl boronic acid (mAPBA) (Table 3) columns has proven to be a valuable tool in the isolation of diol species. mAPBA forms a reversible covalent ester with 1,2- and 1,3-diols in aqueous media that captures glycated peptides and proteins, among a variety of other diol-containing species. Glycated peptides have been isolated in this manner and analyzed by tandem mass spectrometry using ETD and CID fragmentation. Five times as many peptides were identified by ETD as with CID. Using mAPBA to isolate glycated proteins and peptides from the human plasma and erythrocytes and ETD in sequencing has shown that individuals with impaired glucose tolerance or type 2 diabetes were likely to have slightly more glycated peptides than normal subjects (Zhang et al. *Journal Proteome Res,* 2008, 7(5):2025-2032). AGE studies have also been carried out using mAPBA on MALDI chips with minimal interference from nonspecific binding.

Quantification
Stable Isotope Coding in Comparative Proteomics.

Most quantification studies to date have involved relative comparisons of concentration between samples involving both staining and stable isotope coding methods. The advantage of stable isotope coding is the relative error in quantification is 6-8%, irrespective of the number of steps involved in the analytical process. Multiple isotopomers of dinitrophenyl hydrazine, GRP, and O-ECAT have been prepared and used in relative quantification studies of protein carbonylation. Advantages of in vitro coding strategy include, for example, that it can be used with small quantities of sample, quantification can be achieved with any biological system after the in vivo component of an experiment is completed, and multiple samples can be examined simultaneously. An oxidized sample was split into equal parts and after differential derivatization according to sample origin with $d_0$-GRP and $d_5$-GRP, the samples were mixed in a 1:1 ratio and examined by RPC-MS/MS. Carbonylated peptides appeared as doublet clusters of ions separated by 5 Da, or a multiple thereof according to the number of carbonyls in the peptide. The possibility of false positive identification was minimized by performing both RPC-MS/MS and MALDI-MS/MS along with parameter filtering including tag number, retention time, resolution, and the correct concentration ratio (Mirzaei et al., *Journal of Chromatography, A,* 2006, 1134(1-2):122-133). A limitation of this strategy is that derivatization may not be quantitative with low abundance proteins.

($^{13}C_6$)-DNPH was used to differentially code OS samples and the unlabeled form of DNPH to code control samples to evaluate stable isotope coding for relative quantification. After differential derivatization of samples with the DNPH isotopomers according to sample origin, samples were mixed and examined by shotgun proteomics using reversed-phase chromatography to separate peptide fragments and electrospray ionization tandem mass spectrometry (ESI-MS/MS) for peptide identification.

Another modification of the biotin hydrazide tag called hydrazide functionalized isotope-coded affinity tag (HICAT) was used to achieve relative quantification of the oxylipid-protein conjugates in the heart mitochondrial proteins. In this method an ENE-peptide adduct is synthesized and derivatized in vitro with a $^{13}C$-label ($^{13}C_4$-HICAT). HNE-peptide adducts from the tryptic digest of a sample are then coded with an isotopically light version of HICAT. The light and heavy isotopomers of HICAT vary by 4 amu due to the presence of four $^{13}C$ atoms in the heavy form. After mixing the differentially labeled isoforms, HNE-peptide adducts are enriched and further fractionated by RPC before analysis by MALDI-MS/MS analysis. Because proteins can be oxidatively modified at multiple sites, quantification of a single-site oxidative modification can involve multiple isoforms of a protein. It is likely that more than a hundred oxidatively modified isoforms of some proteins may occur in vivo.

MRM Methods

Absolute quantification can evaluate the absolute load of oxidized proteins being generated in a cell and/or the fraction of any particular protein being oxidized in a particular pathway. For many years, absolute quantification has been achieved through the addition of heavy isotope labeled internal standards. With proteins the internal standard can either be a heavy isotope labeled isotopomer of a protein generated biosynthetically or a synthetic $^{13}C$-labeled peptide that matches a proteolytic fragment derived from the protein. Use of $^{13}C$-labeled peptides precludes the possibility that peptide isotopomers will be separated by chromatographic or electrophoretic methods before quantification in the mass spectrometer. The internal standard method is often referred to as "multiple reaction monitoring" (MRM) when multiple analytes are being quantified in a single analysis. Triple quadrupole mass spectrometers with special MRM compatible software are capable of quantifying more than 100 pairs of peptide isotopomers in a single analysis. MRM methods can be used to study OS proteomics in several ways. One way is to determine the concentration of several non-oxidized peptides from each protein being targeted for absolute quantification. After affinity selection the oxidized protein fraction should be tryptic digested, $^{13}C$-labeled internal standard peptides added in known amounts, and the mixture analyzed by RPC-MS/MS to determine the isotope ratio of the targeted peptides. Isotope ratio measurements can then be used to compute the absolute concentration of specific proteins.

Internal standards also can be used to determine the concentration of protein isoforms that are oxidized at a particular site. For example, one can determine the absolute quantity of HNE adducts on cysteine- and histidine-containing peptides. Such a method was validated using H-Tyr-His-OH as an internal standard for absolute quantification of HNE adducts on glutathione (GSH), carnosine (CAR), and anserine (ANS) using the MRM approach. The method can be implemented to quantify HNE-Michael adducts in rat skeletal muscle. CAR-HNE was shown to be elevated in the case of lipid peroxidation of excitable tissues.

Biological Consequences of Protein Oxidation

Despite the availability of methods such as those described above, the consequences of oxidative stress have not been widely studied. When identification of carbonylation sites is an objective, studies have frequently been done in vitro, often on model proteins with hydrogen peroxide, and metal catalysis, or through HNE addition. HNE addition in vitro to glyceraldehyde-3-phosphate dehydrogenase (GAPDH) was shown to occur in a sequential manner, first at His-164 and Cys-281, then on Cys-244, and finally at His-327 and Lys-331. All of these residues are located on the surface of the enzyme and easily accessible to HNE and reactive oxygen species. The sequential nature of site modifications in GAPDH suggests a cascade of conformational changes may be necessary for later stage additions. The chaperon activity of Rat Hsp90 is lost after HNE modification of a single cysteine residue at Cys-572, again suggesting HNE addition can cause a conformational change. Carbonylation in adipose tissue of obese insulin-resistant mice produced a 10-fold reduction in the affinity of fatty acid-binding protein for fatty acids. Fatty acid-binding protein was modified by HNE at Cys-117 in vitro. Few carbonylation sites were detected in vivo. For example, carbonylation of Hsp 70-1 in the cornu Anunonis of the macaque monkey occurred at a single site (Arg469) after transient whole-brain ischemia and reperfusion. In another example, ADP/ATP translocase 1 is found in cardiac mitochondrial to be carbonylated by HNE and acrolein at Cys-256.

Detecting smaller numbers of carbonylation sites in vivo could occur for several reasons. One could be that there are so many isoforms that none occurs in a detectable amount. A further complication could be that isoforms are separated in preliminary fractionation and are difficult to locate. Insufficient recovery from gels for mass spectral identification could be another reason. Many of the studies on protein carbonylation have been done with 2-D gel electrophoresis. Difficulty identifying carbonylated peptides that are biotinylated could be another problem. Fragmentation of biotin can cause the introduction of noise peaks, which lowers identification scores. Another problem is that fragmentation of some peptides during CID sequencing is hard to interpret. Use of electron capture dissociation (ECD) might reduce this problem. The CID and ETD modes of fragmentation are complimentary, facilitating the location of modification sites when combined with the hydrazide purification techniques described above.

How protein oxidation impacts biological systems is a major issue. Much of the discussion encompassing this subject has focused on bulk phenomena such as the propensity of oxidized proteins to cross-link and precipitate, difficulties in their degradation, and their cellular toxicity. Alterations in the activity of specific enzymes following oxidation are important as well. It is clear from the discussion above that i) some proteins are more likely to be oxidized than others and ii) oxidative modifications can alter biological activity. Enzymes whose activity may be attenuated by OS-associated oxidation include, for example, GAPDH (discussed above), creatine kinase, and carbonic anhydrase. Carbonylation of creatine kinase and carbonic anhydrase under oxidative stress in the vestus lateralis muscle of patients with COPD leads to a reduction in their activity. Sepsis induced by injecting $E.$ $coli$ lipopolysaccharides into the diaphragm of rats produced other examples: enolase 3b, triosphosphate isomerase 1, aldolase, creatine kinase, aconitase 2, dihydrolipoamide dehydrogenase, carbonic anhydrase III and electron transfer flavoprotein all underwent elevation of HNE addition during treatment. In vitro incubation of the enolase with HNE following the in vivo experiment showed a significant reduction of its activity. Oxidized proteins also can be immunogenic, as has been seen in systemic lupus erythematosus.

Detecting, defining, and/or quantifying oxidative stress biomarkers can permit diagnosis and monitoring of oxidative stress-related diseases. Defining these biomarkers also can permit evaluation of the efficacy of dietary antioxidants, enable validation of new therapeutic approaches for controlling oxidative stress, and establish relationships between the oxidative patterns of biomarker proteins and pathological hallmarks of certain diseases. Despite the connection between oxidative stress and certain diseases, the detection of oxidative stress biomarkers is not used to diagnose these diseases.

Some proteins may be more prone to carbonylation than others. Moreover, the level of protein oxidation can vary between species. The total amount of oxidized proteins in rat plasma, for example, may be substantially higher than in swine (Madian, A. G., unpublished data, 2008). As another example, albumin and $\alpha$1-macroglobulin have been reported to have the highest level of AGE-related carbonylation in mouse plasma; albumin and transferrin have been reported as the major oxidized proteins in rat plasma; and only albumin has reported as carbonylated by this route in Rhesus monkey plasma (Jana et al., $Arch.$ $Biochem.$ $Biophys.$, 2002, 397(2): 433-439; Dalle-Donne et al., $J$ $Cell$ $Mol$ $Med$, 2006, 10(2): 389-406).

We have developed methods involving biotin labeling of carbonyl groups in oxidized peptides—which, in many cases may be derived from carbonylated parent peptides (e.g., full-length proteins), then affinity selecting the biotin-labeled oxidized peptides from complex peptide mixtures. The affinity selection permits significant enrichment of the oxidized peptides prior to analysis. The methods described herein permit spectral analysis of oxidized peptides, reduce the presence—in some cases, even eliminates the presence—of non-oxidized peptides except those that exist in complexes with oxidized peptides, identify the sites of oxidation in peptides, and can permit identifying the mechanism by which a peptide is oxidized.

The methods described herein can therefore provide more sensitive and/or specific tests for certain diseases than current tests based on the presence of a single peptide in the plasma or the activity of enzymes in the plasma that are related to a disease of interest.

Generally, the methods described herein can be used to determine, depending upon the particular biomarker or biomarkers being detected, the presence or absence of a disease in an individual. The methods may be employed to ascertain one or more of the following: (i) the disease status of the individual from whom a sample is obtained, (ii) the stage of the disease at the time the sample was obtained, (iii) response of the individual to the disease, (iv) response of the disease to treatment, (v) the general health of the individual, (vi) the biological age of an organ, and (vii) the extent to which the disease is recurring in an individual.

Through analysis of appropriate biomarkers, the presence or absence of an oxidative stress-associated condition such as, for example, aging or a disease such as, for example, diabetes mellitus, breast cancer, Parkinson's disease, or other oxidative stress-associated condition can be monitored. In certain circumstances, the monitoring for a disease may involve an initial diagnosis by, for example, comparing a sample obtained from an individual with a reference that reflects the presence of the disease or a reference that reflects the absence of disease. In other circumstances, the monitoring may involve comparing an analysis performed on samples taken from the same individual at different times so that a time course of the progression, regression, and/or recurrence of the disease may become evident.

In another aspect, methods described herein may be used to detect and/or measure a specified set of oxidized peptides in a sample obtained from an individual. The oxidation state of a particular peptide may relate to the presence of at least one marker of oxidative stress such as, for example, 2-amino-3-oxo-butanoic acid; 2-amino-3-oxo-butanoic acid; hydroxylation; glutamate semialdehyde; cysteic acid (sulfonic acid); sulfinic acid; sulfenic acid; formylkynurenin; kynurenin; hydroxykynurenin; 2,4,5,6,7 hydroxylation of tryptophan; oxolactone; 4-hydroxy glutamate; conversion of histidine to asparagine; conversion of histidine to aspartate; 2-oxo-histidine; aminoadipic semialdehyde; an Amadori adduct; a 3-deoxyglucosone adduct; a glyoxal adduct; a methylglyoxal adduct; conversion of proline to pyroglutamic acid; conversion of proline to pyrrolidinone; a 4-HNE (4-hydroxynonenal) adduct; and malondialdehyde adducts and any other oxidative modification.

In some embodiments, the oxidized peptides may be labeled. The oxidized peptides may be labeled using any suitable method known to those of ordinary skill in the art. The labeling may be performed in vitro or in vivo, as appropriate for the given method. Suitable methods for labeling oxidized peptides include, for example, isotope coded affinity tagging, stable isotope labeling of amino acids in cell culture (SILAC), isobaric tagging for relative and absolute quantification (iTRAQ™), ICAT labeling, labeling using fluorinated affinity tags, amino-terminal sulphonation, dimethyl labeling, global internal standard technology (GIST), 160/180 labeling, or labeling using any combination of such methods.

Some of these labeling methods and other methods of sample preparation and analysis that are suitable for use in one or more aspects or embodiments of the methods described herein are further described in U.S. Pat. No. 6,864,099, U.S. Pat. No. 6,872,575, U.S. Patent Publication No. 2003/0129769, U.S. Patent Publication No. 2008/0145863, International Patent Application Publication No. WO 2001/86306, U.S. Pat. No. 7,449,170, U.S. Patent Publication No. 2009/0148952, International Patent Application Publication No. WO 2003/027682, and International Patent Application Publication No. WO 2009/134439.

In some embodiments, the oxidized peptides may be isolated or purified to some extent from a sample having additional components. Oxidized peptides may be isolated or purified from a sample by, for example, affinity chromatography. In some cases, oxidized peptides, previously biotinylated, can be isolated using avidin.

In another aspect, methods described herein can involve detecting changes in an oxidized peptidic and/or an oxidized proteomic profile that is associated with the presence of a particular disease, absence of a particular disease, or a certain change in status of a particular disease. As used herein, an "oxidized peptidic profile" refers to at least two oxidized peptides and/or oxidized proteins that are obtained from an individual and that can be used to identify the presence, absence, or status of a particular disease in the individual. For example, a particular combination of a plurality of specific oxidized peptides and/or oxidized proteins—i.e., an "oxidized peptidic profile" or, simply, a "profile"—in an individual's sample may identify the absence of a particular disease, while another profile of the particular oxidized peptides and/or oxidized proteins may indicate a disease state, while a further profile of the particular oxidized peptides and/or oxidized proteins may identify a patient's response to therapy and/or the severity, recurrence, or progression of the disease. An "oxidized peptidic profile" can include the identity of oxidized peptides, particular oxidation sites that are oxidized, the particular oxidation at each oxidation site, and/or the frequency or ratio of any of these characteristics in a population of molecules of a particular peptide. Thus, one may compare the oxidation status of a particular oxidation of a particular peptide with the corresponding oxidation site on other molecules of the same peptide—i.e., other molecules having the same amino acid sequence to determine, for example, whether a particular oxidation site of a particular peptide may have been subject to complete or incomplete oxidation and/or which form or forms of oxidation occur at a particular oxidation site in a sample. Any one or any combination of these characteristics can be sufficient, in certain analyses, to provide information regarding a patient's response to therapy and/or the severity, recurrence, or progression of the disease, or of the patient's general health. Thus, various oxidized peptide profiles may correlate with various states of the disease.

In another aspect, the methods described herein can provide for tailored treatment of a disease in an individual. By analyzing oxidized peptides and/or oxidized proteins from samples obtained from the individual in the non-diseased state and the diseased state, the individual can serve as an appropriate control for monitoring oxidized peptide profiles taken at different times.

Example 1 and FIGS. 1-6 report proteomic-based identification and characterization of oxidized proteins in human plasma. The study was conducted by isolating carbonylated proteins from the plasma of male subjects (age 32-36) with avidin affinity chromatography subsequent to biotinylation of carbonyl groups with biotin hydrazide and sodium cyanoborohydride reduction of the resulting Schiff's bases. Avidin-selected proteins were digested with trypsin and the peptide fragments separated by C18 reversed-phase chromatography, identified and characterized by both electrospray ionization and matrix assisted laser desorption ionization mass spectrometry. Approximately 0.2% of the total protein in plasma was selected with this method. Sixty-five high, medium, and low abundance proteins were identified, the majority appearing in all subjects. One feature of the oxidized proteins isolated was that in addition to carbonylation they often bore other types of oxidative modification referred to as an OSi~PTM. Twenty-four oxidative modifications were mapped in fourteen proteins. Fifteen carbonylation sites carried on seven proteins were detected. Methionine oxidation was the most frequent single type of oxidative modification, i.e., OSi~PTM, followed by tryptophan oxidation. Apolipoprotein B-100 had 20 oxidative modifications, the largest number for any protein observed in this study. Among the organs contributing oxidized proteins to plasma, kidney, liver, and soft tissues were the most frequent donors. One outcome of this work was that mass spectral analysis allowed differentiation between different biological mechanisms of oxidation in individual proteins. For the first time, oxidation products arising from direct reactive oxygen species (ROS) oxidation of amino acid side chains in proteins, formation of advanced glycation end products (AGEs) adducts, and formation of adducts with lipid peroxidation products were simultaneously recognized and assigned to specific sites in proteins.

Blood proteins have been widely used in the assessment of human health, primarily in single protein assays (Jacobs et al. *J. Proteome Res.*, 2005, 4(4):1073-85; Issaq et al., *Chem Rev,* 2007, 107(8):3601-20). We show that new proteomics methods can be used to identify and assess groups of proteins that change in either structure or concentration in association with disease progression. These disease-specific molecular signatures can be more diagnostic than single proteins. Moreover, in many cases, the disease-specific molecular signatures include one or more peptides analyzed from a blood sample that are non-blood peptides. As used herein, a "non-blood peptide" is a peptide that is typically localized in a non-blood tissue such as, for example, the liver, kidney, neural tissue, or another soft tissue. A non-blood peptide may be present in the blood, plasma, or a blood product because the peptide is shed or released into the circulatory system as a result of OS-induced cell death—whether apoptosis, necrosis, or some other mechanism—as opposed to having a typical blood-related function such as, for example, nutrient transport, oxygen transport, endocrine function, immunological function, maintaining osmolarity, and the like.

One class of diseases amenable to this type of analysis is oxidative stress-associated diseases. Oxidative stress is a phenomenon in which reactive oxygen species can accumulate in cells, organs, or extracellular sites in the circulatory system to a level that proteins, DNA, RNA, and lipids are irreversibly damaged by oxidation. Oxidative stress has been implicated in multiple ailments ranging from neurological diseases such as Alzheimer's disease, Parkinson's disease, and amyotrophic lateral sclerosis to a variety of diseases ranging from atherosclerosis, diabetes mellitus, chronic renal failure, and chronic lung disease, to cancer. Antioxidants and cellular catalysts such as catalase, selenium-dependent glutathione, superoxide dismutase, and thioredoxin hydroperoxidase are sufficiently abundant in most subjects that reactive oxygen species (e.g., hydrogen peroxide, singlet oxygen, peroxynitrite, or superoxide) are destroyed before causing irreversible protein oxidation. However, when the capacity of cells to destroy reactive oxygen species is exceeded, the system may become "oxidatively stressed." This can lead to protein carbonylation and oxidative injury to cells. However, as a prerequisite to the identification of disease markers that correlate with oxidative stress-related diseases, it is necessary to understand the "normal" distribution of oxidized proteins in plasma. Prior to this disclosure, there is almost no data on oxidized proteins in human blood.

One possible reason for the paucity of data on oxidized proteins in plasma may be the difficulty of finding oxidized proteins in complex matrices, the multiplicity of possible oxidative modifications, and low abundance (Barelli et al., *Proteomics: Clin. Appl.*, 2007, 2(2):142-157). Methods described herein circumvent some of these problems.

Methods described herein involve assessing human oxidative stress through detection and analysis of carbonylation in the plasma proteome. Plasma samples taken from normal, undedicated, non-smoking male subjects from 32-36 years of age were obtained, prepared, and analyzed as described in Example 1. MS/MS analyses were carried out in both the matrix assisted laser desorption and electrospray ionization modes. Oxidative stress is thought to be influenced by factors ranging from aging, gender, and diet to smoking, diseases, and medications. Thus, donors were of the same gender (males), non-smoking, had no diagnosed diseases, were not receiving medications, and were age matched (32-36 years of age).

The analytical protocol used in these studies (FIG. 1) is a modified version of a method first described for the analysis of the yeast proteome (Mirzaei et al., *Anal. Chem.*, 2005, 77(8):2386-2392). A fresh plasma sample (6 ml) was drawn from a donor and carbonyl groups biotinylated with biotin hydrazide and the resulting Schiff bases reduced. Samples thus derivatized were dialyzed to remove excess biotin hydrazide along with low molecular weight biotinylated species including small polypeptides. Following dialysis only high molecular weight species remained, most of which were proteins. Avidin affinity chromatography was then used to select and enrich carbonylated species for identification of oxidized proteins, sites of oxidation, and the particular types of oxidation involved.

Oxidized proteins were identified in two ways. One was by RPC fractionation of the avidin-selected fraction followed by proteolysis of RPC fractions and MS-based identification with MALDI-MS/MS. A second approach was to tryptic digest the affinity-selected fraction and proceed directly to RPC- and MS-based identification. Because the second method is simpler and provided similar numbers of identifications to the first, the second method was used in this work. Avidin-selected proteins were digested with trypsin, the peptide cleavage fragments fractionated with a C18 RPC column, and the peptides from RPC identified by MALDI-MS/MS (4800 plus, Applied Biosystems, Inc., Foster City, Calif.) and then further characterized with an LTQ Orbitrap XL. Protein Pilot and Mascot were used for the analysis of the mass spectra respectively as described in Example 1.

In order to isolate and analyze carbonylated proteins from the plasma proteome, one must consider that carbonyl groups react readily with free amine groups on proteins as they sit on the bench or are stored, thereby forming Schiff's bases and making the carbonyl groups inaccessible to biotin hydrazide derivatization. Thus, we added a large excess of biotin hydrazide to plasma samples within a few minutes of the time they are drawn. Once biotin hydrazide has been added, samples can be frozen and stored indefinitely. Further, we added a protease inhibitor cocktail to the samples to inhibit the activity of intrinsic cysteine and serine proteases and preserve the samples.

An avidin affinity column was used in our procedure. Plasma samples were applied directly onto the affinity column without abundant protein removal. The column was used in processing approximately 50 samples over six months without significant loss of capacity, based on the binding of standard biotinylated bovine serum albumin at periodic intervals.

Although abundant protein removal is widely used in discovery proteomics studies, that approach was not used in this work for several reasons. One reason is that oxidized proteins could be associated non-covalently with abundant proteins and be removed. Recent studies in which 129 low abundance proteins were found to be associated with abundant proteins gives credibility to this abundant protein "sponge effect" hypothesis (Issaq et al., *Chem Rev,* 2007, 107(8):3601-20; Gong et al, *J. Proteome Res.* 2006, 5(6):1379-1387). A second reason is that peptides from abundant proteins did not interfere with oxidized protein identification. In fact, there was no relationship between the presence of peptides from abundant proteins and their concentration in affinity selected fractions. A third reason is that washing affinity columns with 15 or more column volumes of loading buffers can elute most proteins bound to columns with low affinity. In our procedure, sixty column volumes of loading buffer were pumped through the affinity column after loading. During this washing step, eluent absorbance returned to zero (FIG. 2), as expected.

The avidin affinity column captured approximately 0.2% of the protein in plasma, based on absorbance at 280 nm (Table 4). It should be noted that naturally biotinylated proteins, proteins naturally complexed with or cross-linked to the biotinylated proteins, and non-specifically bound proteins are included in this affinity-selected fraction as well. The relative standard deviation of peak areas among the four human plasma samples was 0.057%.

TABLE 4

The relative amounts of the affinity-purified protein from normal human plasma samples selected by avidin affinity chromatography

| Donor number | % affinity-purified proteins (based on the 280 nm absorbance) |
| --- | --- |
| Donor number 1 | 0.20% |
| Donor number 2 | 0.23% |
| Donor number 3 | 0.14% |
| Donor number 4 | 0.28% |
| Average | 0.21% |
| Standard deviation | 0.057 |

Figure 1:
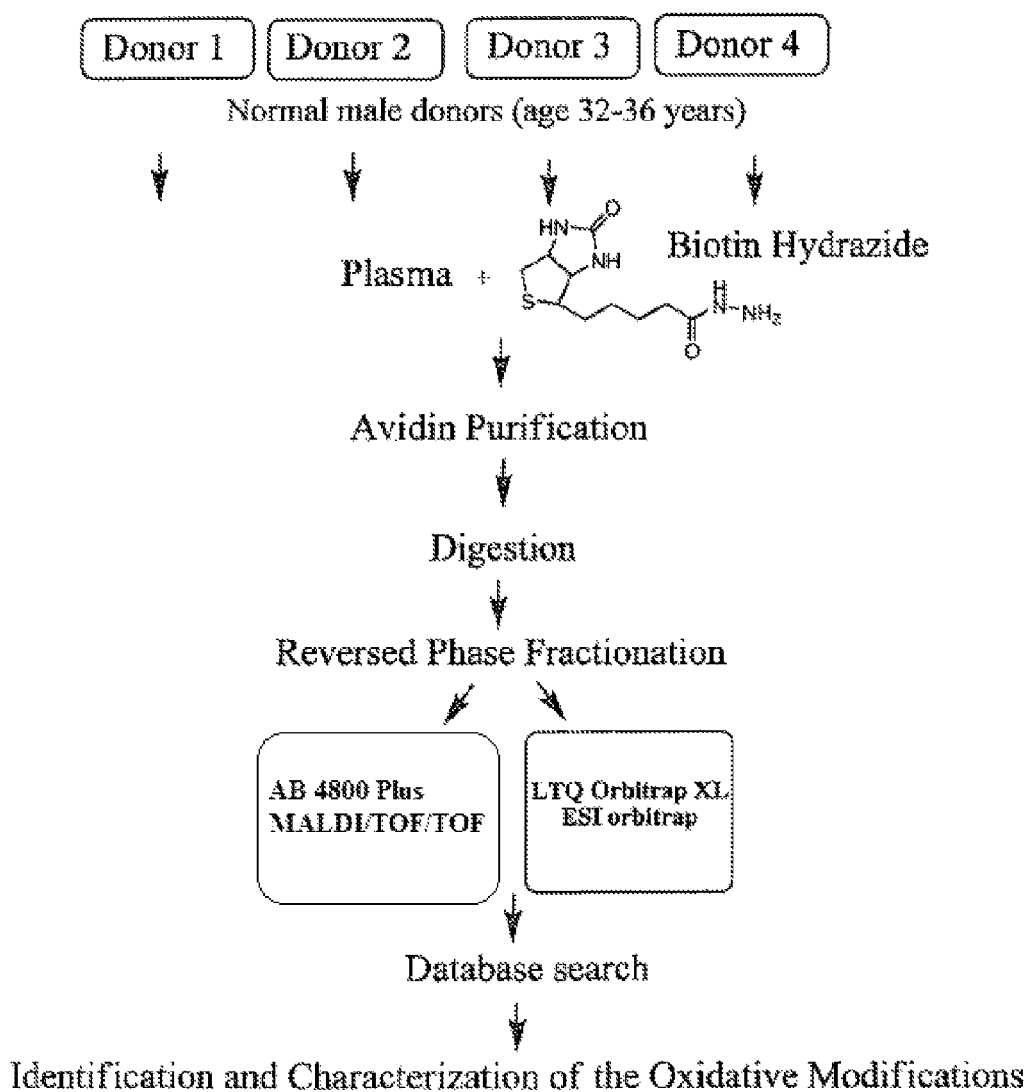
FIG. 1. Schematic illustration of the strategy used for the identification of oxidized proteins and their oxidation sites in normal human plasma. Samples were examined individually to facilitate protein identification. Those with oxidative modifications were then enriched by pooling the samples.
Figure 2:
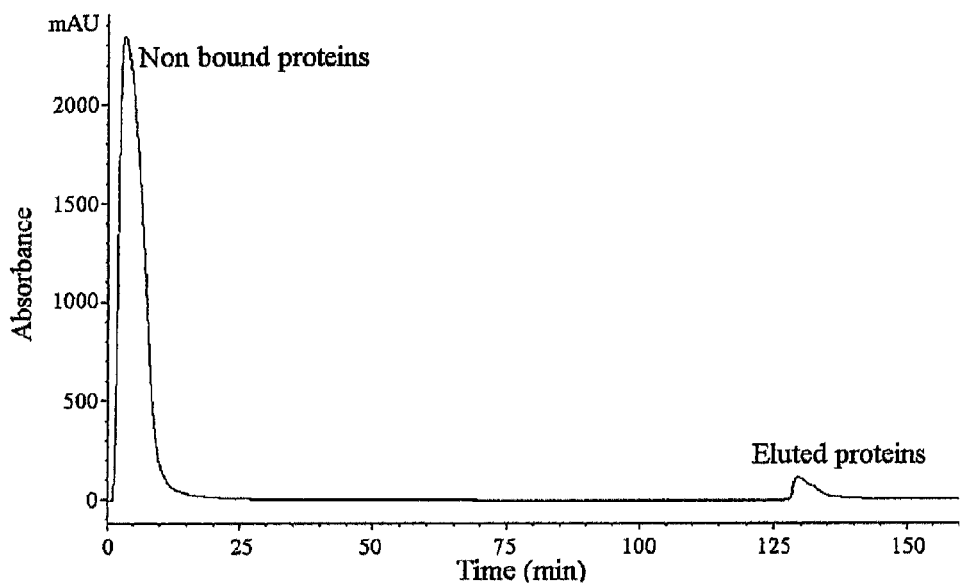
FIG. 2. Chromatogram from avidin affinity chromatography of a normal human plasma sample. A sample of the plasma (15 mg of total protein) was applied directly to a 4.6 mm×100 mm column packed with Agarose to which avidin had been immobilized. The column was eluted initially with 0.15 M phosphate buffered saline, (pH 7.4) at 0.5 mL/min for 120 minutes then switched to a mobile phase containing 0.1M glycine/HCl (pH 2.5) for an additional 40 minutes at the same flow rate. Absorbance was monitored at 280 nm.
Figure 3:
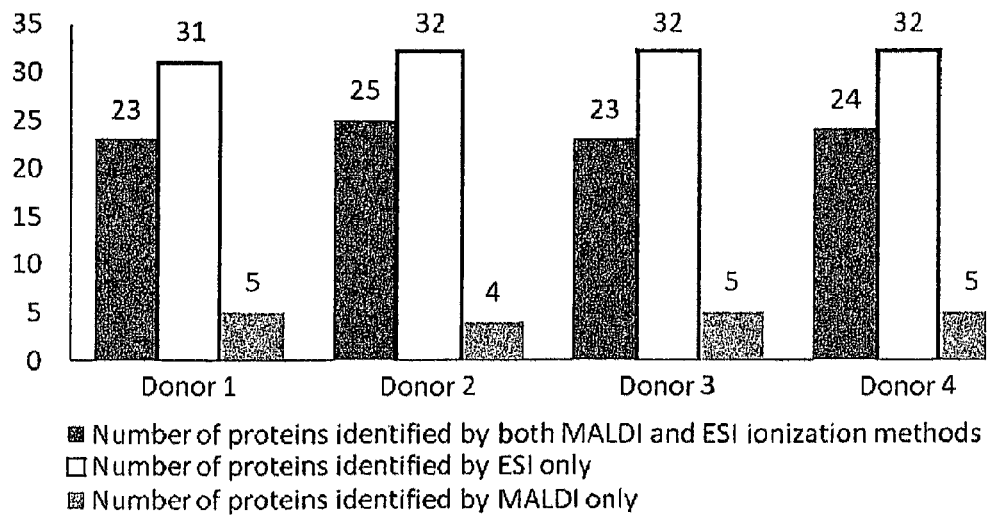
FIG. 3. Relative numbers of proteins identified by MALDI only, ESI only, and using both MALDI and ESI ionizing methods.
Figure 5:
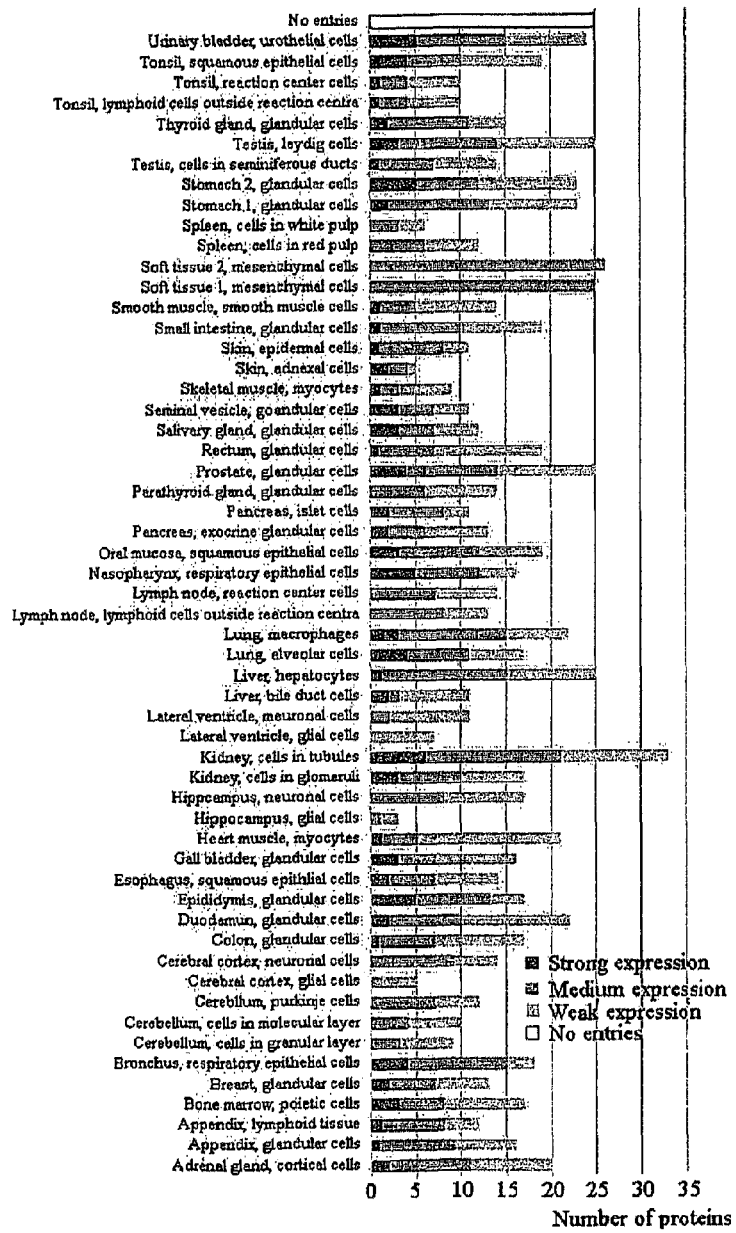
FIG. 5. Annotation of proteins identified according to their tissues of origin. Proteins were searched in the human protein atlas database and their degree of expression (low, medium, strong) was plotted against tissue of origin.

Because MALDI-MS/MS and ESI-MS/MS used together often can identify more proteins than either method alone, both types of ionization were used in these studies. Analysis of affinity-selected proteins from the four plasma samples generated an average of 7724 spectra in the ESI-MS mode as opposed to 601 spectra in the MALDI-MS mode. An average of sixty-five proteins were identified based on 525 unique peptides identified by ESI-MS/MS and 225 by MALDI-MS/MS. Twenty-four proteins were identified by both MALDI-MS and the ESI-MS. Thirty-two proteins were identified by ESI-MS alone and five proteins were identified by MALDI-MS only (FIG. 3). The data showed good reproducibility. Fifty-eight proteins were identified in all the four donors, two proteins were identified in three donors only and five proteins were identified in two donors only The list of proteins identified (Table 5 and Table 6) includes highly abundant proteins (e.g., alpha-1-antitrypsin precursor, alpha-2-macroglobulin precursor, apolipoprotein A-I precursor, apolipoprotein B-100 precursor), some of moderate abundance (e.g., hempexin and kininogen-1 precursor) and several low abundance proteins (e.g., tetranectin precursor and transthyretin precursor). Tissue origin of the proteins found in this study was obtained from the Human Protein Atlas (version 4.0). This is a database containing approximately five million immunohistochemical-based images produced using 6120 antibodies against 5067 protein coding human genes. Kidney (cells in the tubules), soft tissues and liver (hepatocytes) contributed the largest numbers of proteins found in this study (FIG. 5).

TABLE 5

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score |
| A1AT_HUMAN | Alpha-1-antitrypsin precursor (*Homo sapiens* (Human)) | 20.1 | 7 | 342 | 25 | 15 | 353 | 53.1 | 39 | 1801 | 49 | 15 | 1203 |
| A2AP_HUMAN | Alpha-2-antiplasmin precursor *Homo sapiens* (Human) | 3.5 | 1 | 23 | 13 | 2 | 128 | 11.4 | 12 | 106 | 7.9 | 2 | 125 |
| FETUA_HUMAN | Alpha-2-HS-glycoprotein precursor (Fetuin-A)-*Homo sapiens* (Human) | ND | ND | ND | 14 | 4 | 218 | 22.9 | 7 | 506 | 32 | 6 | 488 |
| ANT3_HUMAN | Antithrombin-III Precursor (ATIII)-*Homo sapiens* (Human) | ND | ND | ND | 13 | 3 | 214 | 7.8 | 14 | 75 | 16 | 4 | 224 |
| APOA1_HUMAN | Apolipoprotein A-I precursor (Apo-AI) *Homo sapiens* (Human) | 51.3 | 17 | 1953 | 60 | 20 | 3570 | 60.7 | 6 | 2835 | 52 | 18 | 2639 |
| APOA2_HUMAN | Apolipoprotein A-II precursor (Apo AII) (*Homo sapiens* (Human)) | 43 | 4 | 691 | 59 | 5 | 1246 | 28 | 3 | 382 | 25 | 2 | 373 |
| APOA4_HUMAN | Apolipoprotein A-IV precursor (Apo-AIV) (*Homo sapiens* (Human)) | 30.8 | 10 | 527 | 27 | 8 | 678 | 10.6 | 22 | 136 | 25 | 6 | 360 |
| APOB_HUMAN | Apolipoprotein B-100 precursor (Apo B-100) *Homo sapiens* (Human) | 18.7 | 63 | 3123 | 21 | 69 | 4342 | ND | ND | ND | 0.6 | 6 | 33 |
| APOC1_HUMAN | Apolipoprotein C-I precursor (Apo-CI) *Homo sapiens* (Human) | 26.5 | 4 | 685 | 13 | 3 | 240 | 45.8 | 5 | 891 | 27 | 3 | 642 |
| APOC3_HUMAN | Apolipoprotein C-III precursor (Apo-CIII) *Homo sapiens* (Human) | 27.3 | 2 | 477 | 27 | 2 | 189 | 62.6 | 4 | 1419 | 30 | 4 | 669 |

TABLE 5-continued

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Mascot score | Number of unique peptides assigned to the protein | Sequence coverage | Mascot score | Number of unique peptides assigned to the protein | Sequence coverage | Mascot score | Number of unique peptides assigned to the protein | Sequence coverage | Mascot score | Number of unique peptides assigned to the protein |
| APOD_HUMAN | Apolipoprotein D precursor (Apo D) Homo sapiens (Human) | 26.5 | 497 | 6 | 19 | 235 | 3 | 20.1 | 273 | 5 | 20 | 351 | 3 |
| APOE_HUMAN | Apolipoprotein E precursor (Apo-E)- Homo sapiens (Human) | 12.9 | 148 | 4 | 27 | 523 | 7 | 10.1 | 89 | 10 | 9.5 | 117 | 2 |
| APOM_HUMAN | Apolipoprotein M (Apo-M) Homo sapiens (Human) | 39.9 | 253 | 6 | 26 | 174 | 3 | 29.3 | 272 | 2 | 33 | 191 | 2 |
| APOH_HUMAN | Beta-2-glycoprotein 1 precursor (Beta-2-glycoprotein I) (Apolipoprotein H) (Homo sapiens (Human) | 19.1 | 65 | 3 | 22 | 229 | 4 | 40.6 | 875 | 32 | 33 | 594 | 10 |
| C4BP_HUMAN | C4b-binding protein alpha chain precursor (C4bp) Homo sapiens (Human) | 48.1 | 8900 | 24 | 58 | 9153 | 25 | 17.6 | 573 | 8 | 12 | 419 | 4 |
| C4BB_HUMAN | C4b-binding protein beta chain precursor- Homo sapiens (Human) | 34.9 | 1014 | 6 | 26 | 563 | 4 | 12.3 | 55 | 6 | 12 | 114 | 2 |
| CADH5_HUMAN | Cadherin-5 precursor (Vascular endothelial-cadherin) (VE-cadherin) Homo sapiens (Human) | ND | ND | ND | ND | ND | ND | 5.2 | 86 | 7 | 5.2 | 63 | 6 |
| CD5L_HUMAN | CD5 antigen-like precursor (SP-alpha) Homo sapiens (Human) | 20.7 | 297 | 5 | 40 | 612 | 11 | ND | ND | ND | ND | ND | ND |
| CLUS_HUMAN | Clusterin precursor Homo sapiens (Human) | 20.3 | 462 | 8 | 23 | 611 | 6 | 22.9 | 729 | 3 | 27 | 918 | 8 |
| FA5_HUMAN | Coagulation factor V precursor Homo sapiens (Human) | 0.7 | 29 | 3 | 0.6 | 39 | 2 | 4.1 | 181 | 4 | 3.9 | 436 | 8 |

TABLE 5-continued

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score |
| C1QB_HUMAN | Complement C1q subcomponent subunit B precursor-*Homo sapiens* (Human) | 20.7 | 3 | 279 | 21 | 4 | 232 | ND | ND | ND | ND | ND | ND |
| C1QC_HUMAN | Complement C1q subcomponent subunit C precursor-*Homo sapiens* (Human) | 16.3 | 2 | 307 | 17 | 3 | 175 | ND | ND | ND | ND | ND | ND |
| CO3_HUMAN | Complement C3 precursor-*Homo sapiens* (Human) | 5.5 | 6 | 1474 | 15 | 10 | 1083 | 5 | 6 | 608 | 2.6 | 0 | 610 |
| CO4B_HUMAN | Complement C4-B precursor *Homo sapiens* (Human) | 4.6 | 4 | 571 | 4.6 | 4 | 651 | ND | ND | ND | ND | ND | ND |
| CFAH_HUMAN | Complement factor H precursor (H factor 1)-*Homo sapiens* (Human) | 4.5 | 3 | 146 | 7.1 | 8 | 397 | 1.5 | 5 | 61 | 1.9 | 1 | 141 |
| FIBA_HUMAN | Fibrinogen alpha chain precursor *Homo sapiens* (Human) | 31.1 | 16 | 5885 | 27 | 22 | 6213 | 32.3 | 32 | 9346 | 26 | 16 | 7145 |
| FIBB_HUMAN | Fibrinogen beta chain precursor *Homo sapiens* (Human) | 30.3 | 11 | 428 | 42 | 13 | 782 | 27.3 | 3 | 387 | 20 | 10 | 617 |
| FIBG_HUMAN | Fibrinogen gamma chain precursor-*Homo sapiens* (Human) | 24.1 | 5 | 263 | 37 | 10 | 782 | 28 | 5 | 342 | 26 | 5 | 601 |
| FINC_HUMAN | Fibronectin precursor (FN) *Homo sapiens* (Human) | 1.5 | 3 | 61 | 3.5 | 7 | 262 | ND | ND | ND | ND | ND | ND |
| HPTR_HUMAN | Haptoglobin-related protein precursor-*Homo sapiens* (Human) | 12.1 | 3 | 164 | 16 | 3 | 100 | 14.1 | 1 | 226 | 14 | 1 | 314 |
| HBA_HUMAN | Hemoglobin subunit alpha *Homo sapiens* (Human) | 25.4 | 3 | 261 | 15 | 1 | 59 | 48.6 | 2 | 158 | 42 | 2 | 143 |
| HBB_HUMAN | Hemoglobin subunit beta *Homo sapiens* (Human) | 21.8 | 3 | 353 | 22 | 3 | 254 | 6.8 | 8 | 33 | 16 | 2 | 95 |

TABLE 5-continued

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score |
| HEMO_HUMAN | Hemopexin precursor Homo sapiens (Human) | 1.7 | 3 | 40 | 6.3 | 3 | 105 | 18.4 | 6 | 219 | 17 | 4 | 251 |
| HRG_HUMAN | Histidine-rich glycoprotein precursor (HPRG)- Homo sapiens (Human) | 10.5 | 2 | 131 | 5.7 | 2 | 91 | 20.8 | 26 | 444 | 21 | 6 | 465 |
| IGHA1_HUMAN | Ig alpha-1 chain C region-Homo sapiens (Human) | 45.3 | 8 | 2006 | 48 | 10 | 1732 | 47.3 | 2 | 1318 | 48 | 9 | 2094 |
| IGHG1_HUMAN | Ig gamma-1 chain C region-Homo sapiens (Human) | 59.4 | 15 | 3676 | 58 | 13 | 4293 | 50.9 | 4 | 2693 | 52 | 13 | 2288 |
| IGHG2_HUMAN | Ig gamma-2 chain C region-Homo sapiens (Human) | 40.8 | 7 | 1629 | 41 | 7 | 1985 | 41.1 | 5 | 1241 | 42 | 8 | 1191 |
| IGHG3_HUMAN | Ig gamma-3 chain C region Homo sapiens (Human) | 29.7 | 5 | 655 | 29 | 2 | 1056 | 22.8 | 4 | 681 | 20 | 2 | 520 |
| IGHG4_HUMAN | Ig gamma-4 chain C region-Homo sapiens (Human) | 44.6 | 3 | 1459 | 44 | 2 | 1373 | 31.8 | 2 | 937 | 37 | 2 | 912 |
| KAC_HUMAN | Ig kappa chain C region-Homo sapiens (Human) | 86.8 | 7 | 7925 | 82 | 7 | 6495 | 86.8 | 4 | 3469 | 91 | 9 | 2345 |
| LAC_HUMAN | Ig lambda chain C regions-Homo sapiens (Human) | 70.5 | 4 | 2437 | 71 | 5 | 2016 | 46.7 | 3 | 574 | 47 | 3 | 842 |
| MUC_HUMAN | Ig mu chain C region-Homo sapiens (Human) | 58.6 | 17 | 6770 | 63 | 25 | 7084 | 36.3 | 4 | 1348 | 31 | 8 | 507 |
| K1C10_HUMAN | Keratin, type I cytoskeletal 10 (Cytokeratin-10)-Homo sapiens (Human) | 20.7 | 6 | 463 | 28 | 8 | 577 | 35.6 | 4 | 2523 | 40 | 19 | 2575 |
| K1C9_HUMAN | Keratin, type I cytoskeletal 9 (Cytokeratin-9)-Homo sapiens (Human) | 14 | 4 | 349 | 17 | 4 | 412 | 34.8 | 6 | 1794 | 41 | 15 | 1875 |

TABLE 5-continued

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score |
| K2C1_HUMAN | Keratin, type II cytoskeletal 1 (Cytokeratin-1) *Homo sapiens* (Human) | 18.3 | 8 | 1062 | 11 | 7 | 689 | 28.7 | 1 | 2608 | 27 | 14 | 2994 |
| K22E_HUMAN | Keratin, type II cytoskeletal 2 epidermal (Cytokeratin-2e) (*Homo sapiens* (Human) | 7.1 | 3 | 238 | 5.6 | 6 | 404 | 25.4 | 2 | 1207 | 25 | 10 | 1171 |
| K2C5_HUMAN | Keratin, type II cytoskeletal 5 (Cytokeratin-5) *Homo sapiens* (Human) | ND | ND | ND | ND | ND | ND | 5.9 | 3 | 298 | 9 | 2 | 411 |
| KNG1_HUMAN | Kininogen-1 precursor (Alpha-2-thiol proteinase inhibitor) *Homo sapiens* (Human) | ND | ND | ND | 7.5 | 4 | 115 | 23.3 | 5 | 861 | 21 | 10 | 452 |
| LBP_HUMAN | Lipopolysaccharide-binding protein precursor (LBP)- *Homo sapiens* (Human) | 6 | 2 | 87 | 10 | 3 | 228 | 14.6 | 10 | 724 | 15 | 5 | 322 |
| LYSC_HUMAN | Lysozyme C precursor (EC 3.2.1.17) *Homo sapiens* (Human) | 26.4 | 3 | 209 | 39 | 4 | 614 | 20.3 | 2 | 288 | 20 | 3 | 385 |
| PHLD1_HUMAN | Phosphatidylinositol-glycan-specific phospholipase D 1 precursor *Homo sapiens* (Human) | 8.8 | 5 | 245 | 10 | 4 | 218 | 2.6 | 1 | 82 | 8.7 | 7 | 243 |
| PCOC1_HUMAN | Procollagen C-endopeptidase enhancer 1 precursor *Homo sapiens* (Human) | 12.7 | 5 | 450 | 23 | 5 | 299 | 36.5 | 2 | 729 | 28 | 7 | 324 |
| PRG4_HUMAN | Proteoglycan-4 precursor (Lubricin) (Human) | 9.2 | 17 | 889 | 9.7 | 20 | 725 | 9.2 | 8 | 608 | 11 | 11 | 790 |
| TRFE_HUMAN | Serotransferrin precursor (Transferrin) (Human) | ND | ND | ND | 8.5 | 5 | 123 | 8 | 2 | 229 | 6.3 | 3 | 120 |

TABLE 5-continued

Proteins identified using the LTQ Orbitrap XL.

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score | Sequence coverage | Number of unique peptides assigned to the protein | Mascot score |
| ALBU_HUMAN | Serum albumin precursor-*Homo sapiens* (Human) | 32.2 | 12 | 784 | 38 | 14 | 1204 | 24.8 | 3 | 1446 | 25 | 12 | 1070 |
| PON1_HUMAN | Serum paraoxonase/arylesterase 1-*Homo sapiens* (Human) | 37.5 | 8 | 1493 | 46 | 10 | 1730 | 47.3 | 1 | 882 | 53 | 10 | 1246 |
| PON3_HUMAN | Serum paraoxonase/lactonase 3 *Homo sapiens* (Human) | 2.5 | 1 | 59 | 2.5 | 9 | 122 | 2.5 | 4 | 56 | 2.5 | 1 | 128 |
| TETN_HUMAN | Tetranectin precursor (TN) 4-binding protein)-*Homo sapiens* (Human) | ND | ND | ND | ND | ND | ND | 5.9 | 3 | 63 | 23 | 4 | 197 |
| PROS_HUMAN | Vitamin K-dependent protein S precursor-*Homo sapiens* (Human) | 24.7 | 13 | 1189 | 23 | 12 | 1348 | 22.9 | 2 | 569 | 23 | 12 | 866 |
| VTNC_HUMAN | Vitronectin precursor (Serum-spreading factor) *Homo sapiens* (Human) | 14.4 | 5 | 419 | 22 | 5 | 787 | 23 | 2 | 988 | 20 | 6 | 1053 |
| TTHY_HUMAN | Transthyretin precursor *Homo sapiens* (Human) | 15 | 2 | 76 | ND | ND | ND | 23.8 | 11 | 180 | 15 | 1 | 130 |

TABLE 6

| | | Proteins identified using MALDI-MS/MS (ABI 4800 plus) | | | | | | | | | | |
|---|---|---|---|---|---|---|---|---|---|---|---|---|
| | | Donor 1 | | | Donor 2 | | | Donor 3 | | | Donor 4 | | |
| Accessions | Name | Sequence coverage | Number of unique peptides assigned to the protein | ProteinPilot score | Sequence coverage | Number of unique peptides assigned to the protein | ProteinPilot score | Sequence coverage | Number of unique peptides assigned to the protein | ProteinPilot score | Sequence coverage | Number of unique peptides assigned to the protein | ProteinPilot score |
| P01009|A1AT_HUMAN | Alpha-1-antitrypsin precursor *Homo sapiens* (Human) | 11.72 | 1 | 2 | 3.349 | 1 | 2 | 10.5 | 2 | 4 | 3.35 | 2 | 2 |
| P01023|A2MG_HUMAN | Alpha-2-macroglobulin precursor (Alpha-2-M)-*Homo sapiens* (Human) | 8.005 | 4 | 8 | 17.3 | 9 | 18 | 19.3 | 14 | 29.02 | 10 | 4 | 7.5 |
| P01008|ANT3_HUMAN | Antithrombin-III precursor (ATIII)-*Homo sapiens* (Human) | 23.71 | 3 | 6.24 | 13.15 | 3 | 6 | 20.5 | 3 | 6 | 12.5 | 2 | 4 |
| P02647|APOA1_HUMAN | Apolipoprotein A-I precursor (Apo-AI) *Homo sapiens* (Human) | 44.57 | 5 | 10 | 52.06 | 6 | 11.7 | 62.5 | 7 | 14.33 | 50.9 | 6 | 12 |
| P04114|APOB_HUMAN | Apolipoprotein B-100 precursor (Apo B-100) *Homo sapiens* (Human) | 10.96 | 3 | 7.73 | 7.364 | 1 | 2 | 12.5 | 3 | 6.48 | 13 | 4 | 8 |
| P02654|APOC1_HUMAN | Apolipoprotein C-I precursor (Apo-CI) (ApoC-I)-*Homo sapiens* (Human) | 24.1 | 3 | 4 | 13.25 | 2 | 4 | 13.3 | 2 | 4 | 32.5 | 3 | 4 |
| P02649|APOE_HUMAN | Apolipoprotein E precursor (Apo-E)-*Homo sapiens* (Human) | 27.44 | 2 | 4.37 | 44.48 | 2 | 5.36 | 45.1 | 6 | 12 | 28.7 | 2 | 4 |
| P04003|C4BP_HUMAN | C4b-binding protein alpha chain precursor (C4bp) *Homo sapiens* (Human) | 21.27 | 4 | 9.61 | 26.97 | 6 | 12.9 | 23.3 | 5 | 10.35 | 33.8 | 7 | 15 |
| P00450|CERU_HUMAN | Ceruloplasmin precursor*Homo sapiens* (Human) | 5.446 | 2 | 4.44 | 10.99 | 2 | 4.08 | 14.3 | 3 | 5.7 | 13.9 | 2 | 4 |
| P10909|CLUS_HUMAN | Clusterin precursor *Homo sapiens* (Human) | 21.38 | 6 | 14.9 | 21.38 | 4 | 11 | 30.5 | 4 | 11.35 | 24.3 | 4 | 11 |

TABLE 6-continued

Proteins identified using MALDI-MS/MS (ABI 4800 plus)

| Accessions | Name | Donor 1 | | | Donor 2 | | | Donor 3 | | | Donor 4 | | |
|---|---|---|---|---|---|---|---|---|---|---|---|---|---|
| | | Sequence coverage | Number of unique peptides assigned to the protein | ProteinPilot score | Sequence coverage | Number of unique peptides assigned to the protein | ProteinPilot score | Sequence coverage | Number of unique peptides assigned to the protein | ProteinPilot score | Sequence coverage | Number of unique peptides assigned to the protein | ProteinPilot score |
| P00736\|C1R_HUMAN | Complement C1r subcomponent precursor *Homo sapiens* (Human) | 17.73 | 3 | 6 | 23.55 | 6 | 10.8 | 19.4 | 4 | 8.2 | 27.2 | 5 | 12 |
| P01024\|CO3_HUMAN | Complement C3 precursor-*Homo sapiens* (Human) | 17.14 | 7 | 14.7 | 21.89 | 8 | 19.7 | 25.2 | 11 | 25.16 | 19.7 | 12 | 21 |
| P0C0L5\|CO4B_HUMAN; P0C0L4\|CO4A_HUMAN | Complement C4-B precursor *Homo sapiens* (Human) | 12.67 | 3 | 6.98 | 18.86 | 3 | 6.88 | 17.2 | 4 | 8.13 | 20.1 | 3 | 6.3 |
| P02671\|FIBA_HUMAN | Fibrinogen alpha chain precursor *Homo sapiens* (Human) | 40.88 | 23 | 44.4 | 41.8 | 23 | 50.4 | 49.1 | 37 | 85.8 | 39.1 | 20 | 45 |
| P02675\|FIBB_HUMAN | Fibrinogen beta chain precursor *Homo sapiens* (Human) | 58.04 | 20 | 55.7 | 63.75 | 27 | 66 | 70.9 | 28 | 74.05 | 62.7 | 29 | 69 |
| P02679\|FIBG_HUMAN | Fibrinogen gamma chain precursor-*Homo sapiens* (Human) | 55.63 | 12 | 26.3 | 64.9 | 15 | 30 | 77.9 | 20 | 43.09 | 63.8 | 14 | 30 |
| P02751\|FINC_HUMAN | Fibronectin precursor (FN) *Homo sapiens* (Human) | 33.91 | 22 | 52.6 | 47.49 | 47 | 103 | 28 | 49 | 105.6 | 40.6 | 47 | 100 |
| P68871\|HBB_HUMAN | Hemoglobin subunit beta *Homo sapiens* (Human) | 51.7 | 4 | 7.82 | 27.21 | 2 | 5.22 | 27.2 | 2 | 4 | ND | ND | ND |
| P02790\|HEMO_HUMAN | Hemopexin precursor-*Homo sapiens* (Human) | 22.94 | 5 | 10.9 | 37.66 | 9 | 17.5 | 29.9 | 4 | 9.22 | 32.5 | 7 | 13 |
| P01876\|IGHA1_HUMAN | Ig alpha-1 chain C region-*Homo sapiens* (Human) | ND | ND | ND | ND | ND | ND | 20.4 | 2 | 4.16 | 33.4 | 5 | 9.7 |
| P01877\|IGHA2_HUMAN; P01876\|IGHA1_HUMAN | Ig alpha-2 chain C region-*Homo sapiens* (Human); *Homo sapiens* (Human) | 10 | 3 | 6 | 7.941 | 2 | 3.52 | ND | ND | ND | 35.3 | 6 | 9.7 |
| P01857\|IGHG1_HUMAN | Ig gamma-1 chain C region-*Homo sapiens* (Human) | 39.7 | 6 | 12 | 44.24 | 5 | 10 | 44.2 | 7 | 15.38 | 50 | 8 | 15 |
| P01859\|IGHG2-HUMAN | Ig gamma-2 chain C region-*Homo sapiens* (Human) | 36.2 | 5 | 10 | 32.82 | 4 | 8.02 | ND | ND | ND | 38.7 | 9 | 17 |

TABLE 6-continued

| | | Proteins identified using MALDI-MS/MS (ABI 4800 plus) | | | | | | | | | | | |
|---|---|---|---|---|---|---|---|---|---|---|---|---|
| | | Donor 1 | | | Donor 2 | | | Donor 3 | | | Donor 4 | | |
| Accessions | Name | Sequence coverage | ProteinPilot score | Number of unique peptides assigned to the protein | Sequence coverage | ProteinPilot score | Number of unique peptides assigned to the protein | Sequence coverage | ProteinPilot score | Number of unique peptides assigned to the protein | Sequence coverage | Number of unique peptides assigned to the protein | ProteinPilot score |
| P01861\|IGHG4_HUMAN | Ig gamma-4 chain C region-*Homo sapiens* (Human) | ND | ND | ND | ND | ND | ND | 37 | 12 | 5 | 47.7 | 6 | 15 |
| P01842\|LAC_HUMAN | Ig lambda chain C regions-*Homo sapiens* (Human) | 14.29 | 2 | 1 | 14.29 | 2 | 1 | 33.3 | 4 | 2 | 14.3 | 6 | 2 |
| P01871\|MUC_HUMAN | Ig mu chain C region-*Homo sapiens* (Human) | 22.69 | 12 | 6 | 19.16 | 12 | 6 | 39.9 | 15.53 | 7 | 27.3 | 5 | 11 |
| P02787\|TRFE_HUMAN | Serotransferrin precursor (Transferrin) *Homo sapiens* (Human) | ND | ND | ND | 10.74 | 5.53 | 3 | 14.6 | 4 | 2 | 21.5 | 2 | 4 |
| P02768\|ALBU_HUMAN | Serum albumin precursor-*Homo sapiens* (Human) | 30.54 | 12.4 | 6 | 27.42 | 14.2 | 8 | 32.8 | 27.75 | 13 | 48.4 | 10 | 20 |
| P27169\|PON1_HUMAN | Serum paraoxonase/arylesterase 1 *Homo sapiens* (Human) | 28.45 | 8 | 4 | 25.63 | 8 | 4 | 21.7 | 6 | 4 | 35.2 | 5 | 10 |
| P07225\|PROS_HUMAN | Vitamin K-dependent protein S precursor-*Homo sapiens* (Human) | 6.657 | 5.15 | 2 | 20.71 | 10 | 5 | 7.84 | 6.33 | 3 | 16.1 | 3 | 6.4 |
| P04004\|VTNC_HUMAN | Vitronectin precursor (Serum-spreading factor) *Homo sapiens* (Human) | 23.85 | 11.7 | 5 | 26.57 | 12.3 | 6 | 26.8 | 21.44 | 10 | 27.6 | 7 | 16 |

Figure 6:
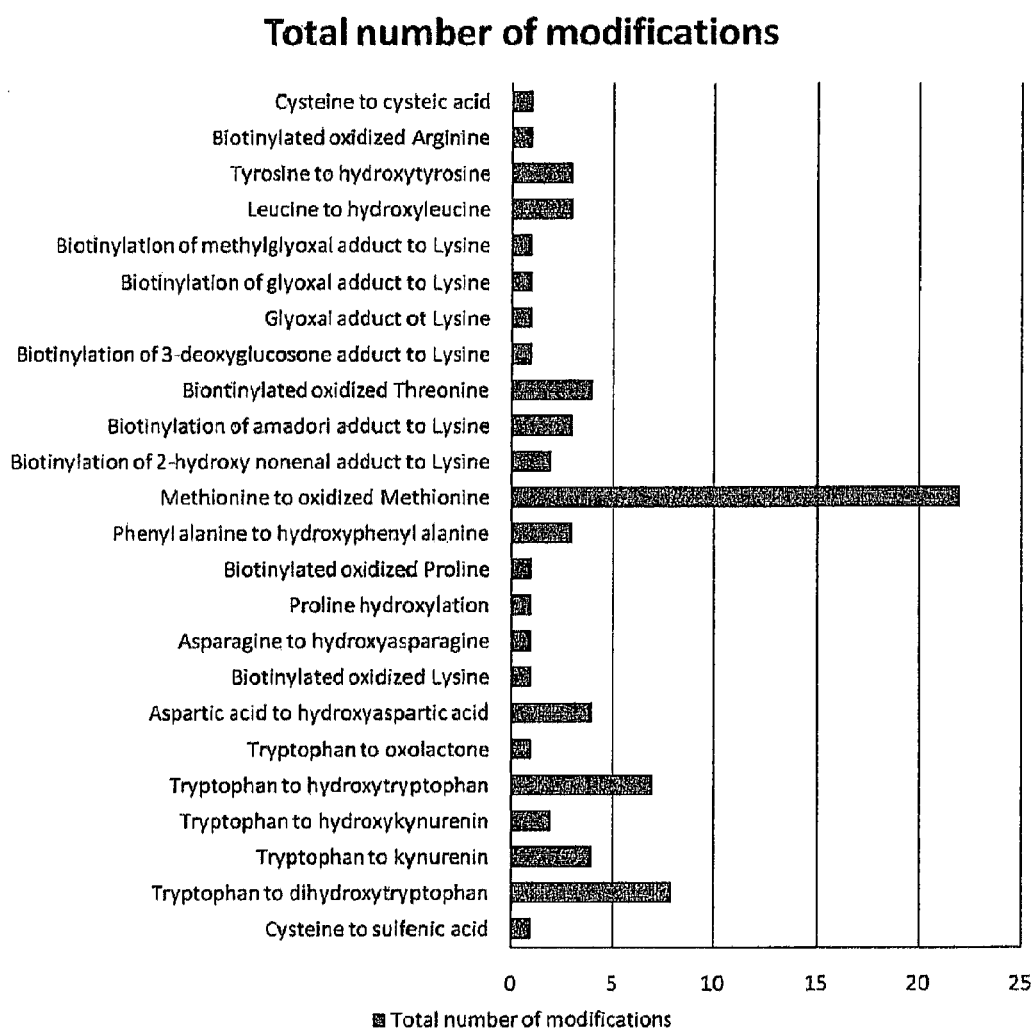
FIG. 6. Total number of modifications identified and the corresponding oxidative modifications.

Seventy-four oxidative stress-induced post-translational modifications (OSi~PTM) were mapped to these proteins (FIG. 6). Among the sites identified, oxidation of methionine-to-methionine sulphoxide appeared more frequently than any other OSi~PTM. Twenty-two proteins with a methionine sulphoxide OSi~PTM were mapped. The oxidation of tryptophan to dihydroxytryptophan, kynurenin, hydroxykynurenin, or hydroxytryptophan came second in frequency of oxidation. The high frequency of methionine oxidation agrees with literature reports that sulfur amino acids (methionine and cysteine) are more sensitive to oxidation by reactive oxygen species than other amino acids (Stadtman et al., *Biochim. Biophys. Acta, Proteins Proteomics*, 2005, 1703 (2):135-140). That only one cysteine oxidation product was detected is not surprising for several reasons. One reason is that disulfide and sulfenic acid reduction occurs naturally in biological systems. Another reason is that detecting the oxidation of sulfhydryls to disulfides can be precluded by the reduction of disulfide bonds with dithiothreitol and iodoacetamide alkylation during sample preparation.

Carbonyl groups generated directly (e.g., by oxidation of threonine, arginine, lysine, and proline) and those formed indirectly (e.g., by the formation of Amadori, glyoxal, methylglyoxal, 3-doxyglucosone, and 2-hydroxy-nonenal adducts) could be isolated with the same procedure. Thus, it is possible to simultaneously identify oxidation products involving direct ROS oxidation of amino acid side chains residues, oxidation of adducts from AGE product addition, and adducts from lipid peroxidation products.

Fourteen proteins were shown to have at least one oxidation site as seen in Table 7. Apolipoprotein B-100 in contrast was found to undergo 20 oxidative modifications; the largest number of OSi~PTMs of any protein observed. Interestingly, this protein was carbonylated due to the formation of both glycation/AGEs (3-deoxyglucosone and methylglyoxal) and lipid peroxidation (2-hydroxy-nonenal) adducts. Fifteen carbonylation sites carried on seven proteins were detected. These proteins are: alpha-2-HS-glycoprotein precursor (fetuin-A), antithrombin-III precursor (ATIII), apolipoprotein B-100 precursor (Apo B-100), apolipoprotein E precursor (Apo-E), C4b-binding protein alpha chain precursor, clusterin precursor and coagulation factor V precursor.

TABLE 7

Proteins identified in the pooled sample with at least one oxidation site

| Protein description | Oxidative modifications |
|---|---|
| Alpha-1-antitrypsin precursor - *Homo sapiens* (Human) | $^{16}$M398, $^{16}$M382 $^{15}$F376 |
| Alpha-2-HS-glycoprotein precursor (Fetuin-A) *Homo sapiens* (Human) | $^{16}$M321, $^{15}$F320, $^{1}$T158, $^{3}$R159 |
| Antithrombin-III precursor (ATIII) - *Homo sapiens* (Human) | $^{23}$K182 |
| Apolipoprotein A-I precursor (Apo-AI) - *Homo sapiens* (Human) | $^{16}$M110, $^{6}$W74, $^{6}$W96, $^{9}$W96, $^{16}$M136, $^{9}$W74, $^{12}$N73, $^{11}$D97, $^{15}$F95 |
| Apolipoprotein A-II precursor (Apo-AII) - *Homo sapiens* (Human) | $^{22}$L48, $^{2}$Y44 |
| Apolipoprotein B-100 precursor (Apo B-100) *Homo sapiens* (Human) | $^{16}$M3280, $^{13}$P3281, $^{16}$M1266, $^{21}$K3229, $^{18}$K3234, $^{16}$M1881, $^{11}$D1880, $^{16}$M1189, $^{16}$M2526, $^{22}$L1060, $^{16}$M901, $^{16}$M2597, $^{16}$M812, $^{16}$M495, $^{16}$M499, $^{18}$K305, $^{19}$K314, $^{16}$M2042, $^{18}$K766, $^{23}$K2147 |
| Apolipoprotein C-I precursor (Apo-CI) (ApoC-I) - *Homo sapiens* (Human) | $^{7}$W67, $^{6}$W67, $^{9}$W67, $^{16}$M64, $^{8}$W67, $^{15}$F68 |
| Apolipoprotein C-III precursor (Apo-CIII) (ApoC-III) - *Homo sapiens* (Human) | $^{7}$W85, $^{6}$W85, $^{7}$W62, $^{8}$W62, $^{9}$W62, $^{10}$W62, $^{6}$W62, $^{6}$W74, $^{9}$W62, $^{11}$D65, $^{2}$Y73, $^{9}$W74 |
| Apolipoprotein E precursor (Apo-E) - *Homo sapiens* (Human) | $^{14}$P30 |
| C4b-binding protein alpha chain precursor (C4bp) - *Homo sapiens* (Human) | $^{16}$M249, $^{6}$W163, $^{11}$D243, $^{22}$L555, $^{4}$C468, $^{22}$L466, $^{5}$C468, $^{2}$Y470, $^{9}$W163, $^{1}$T592, $^{1}$T419 |
| Cadherin-5 precursor - *Homo sapiens* (Human) | $^{16}$M396 |
| Clusterin precursor *Homo sapiens* (Human) | $^{1}$T93, $^{17}$K94 |
| Coagulation factor V precursor (Activated protein C cofactor) *Homo sapiens* (Human) | $^{20}$K2132 |

TABLE 7-continued

Proteins identified in the pooled sample with at least one oxidation site

| Protein description | Oxidative modifications |
| --- | --- |
| Complement C1q subcomponent subunit B precursor - *Homo sapiens* (Human) | [16]M147 |

[1]Biotinylated oxidized threonine;
[2]Tyrosine hydroxylation;
[3]Biotinylated oxidized Arginine;
[4]Cysteic acid (sulfonic acid);
[5]Sulfenic acid;
[6]Dihydroxytryptophan;
[7]Kynurenin;
[8]Hydroxykynurenin;
[9]2,4,5,6,7 hydroxylation of tryptophan;
[10]Oxolactone;
[11]Aspartic acid hydroxylation;
[12]Asparagines hydroxylation;
[13]Proline hydroxylation;
[14]Biotinylated oxidized proline;
[15]Phenylalanine hydroxylation;
[16]Methionine oxidation (sulphoxide);
[17]Biotinylated oxidized Lysine;
[18]Biotinylation of Amadori adduct;
[19]Biotinylation of 3 deoxyglucosone adduct;
[20]Biotinylation of glyoxal adduct;
[21]Biotinylation of methylglyoxal adduct;
[22]hydroxy Leucine;
[23]Biotinylation of 2-Hydroxynonenal adduct.

Avidin affinity-selected proteins with no detectable carbonyls also were seen. This could be because they were cross-linked or complexed with carbonylated proteins. It could also be the result of non-specific binding to the avidin-agarose affinity system. Still another possibility is that two other unoxidized peptides from the proteins were not found as specified in our identification criteria. This strict evaluation criterion eliminated a large number of ambiguous carbonylation sites not confirmed by manual interpretation of the mass spectra.

In vivo oxidation of human plasma proteins has been most widely studied with colorimetric methods as in the cases of risk assessment with breast cancer and smoking (Rossner et al., *J Cell Mol Med*, 2007, 11(5):1138-1148; Yeh et al., *Environ. Res.*, 2008, 106(2):219-225). These studies, however, do not identify the proteins being oxidized. In contrast, the methods described herein exploit biotin labeling of carbonyl groups and avidin affinity chromatography selection of the biotinylated species to isolate heavily oxidized proteins from the plasma proteome, identify the oxidized proteins, and characterize the sites and types of oxidation. Approximately 0.2% of the total protein in plasma was isolated by avidin affinity chromatography in these 32- to 36-year-old male subjects. Eleven different amino acids were found to be involved in at least 23 different types of OSi~PTM. Sixty-five proteins were identified from the male subjects. With this degree of complexity it is possible that a peptide with an OSi~PTM can be of very similar mass to an unmodified peptide, making it difficult to differentiate between them. Differentiation was most specifically achieved by going to high mass accuracy instrumentation such as the LTQ-Oribitrap XL mass analyzer with a mass accuracy approaching 1 ppm.

Oxidized proteins were found in these normal male subjects, indicating that irreversible oxidative stress with accompanying permanent alterations of protein structure is a part of normal metabolic processes. Thus, protein oxidation can be analyzed in an individual who is not exhibiting any signs or symptoms of a disease. The methods described herein can, therefore, be performed on samples obtained from normal individuals to establish a personal baseline against which analyses of samples obtained from the individual can be compared.

The presence of a conjugated metal in a protein increases the probability it will be carbonylated, presumably by internal metal catalysis. As expected, serotransferrin, ceruplasmin, hemoglobin, hemopexin, and fibrinogen were identified in our study. Fibrinogen is i) more likely to be oxidized than serum albumin, ii) the most susceptible protein to oxidation in plasma under intravenous administration of iron gluconate, iii) one of the best indicators of oxidative stress in coronary heart disease, and iv) readily oxidized to the level that it causes atherosclerosis and thrombosis along with changes in blood rheology. At least in the case of atherosclerosis, some of the same metalloproteins associated with the disease state are also seen in normal male subjects, albeit not at the same concentration.

Unsequestered metals play a major role in protein oxidation through the Fenton reaction as well, especially in diseases that reduce the concentration of proteins that chelate metals. Friedreich's Ataxia is one example in which production of the mitochondrial protein frataxin declines with disease progression. The function of frataxin is to sequester $Fe^{+2}$ in mitochondria. As its concentration declines with disease progression, $Fe^{+2}$ concentration increases in mitochondria and ROS production rises sharply as a result of the Fenton reaction, causing serious neurological problems similar to muscular dystrophy.

A series of other variables contribute to the presence of oxidized proteins in the plasma proteome as well. One is the mechanism by which proteins from organs and cells enter the plasma proteome and the location at which oxidation occurs. There is no evidence that oxidized proteins enter plasma by excretion from cells. Instead, cells die and lyse. As cells die and lyse, their soluble proteins may be released into the circulatory system. Thus, protein oxidation can occur in a biological compartment (organ, tissues, cells, or sites along the vascular endothelium) other than plasma and the oxidized proteins can be released into and diffuse throughout the plasma proteome, where they may be easily recovered, isolated, identified, and analyzed. Analyzing oxidized proteins can be a powerful tool in the study, diagnosis, and/or monitoring of diseases that involve sufficiently high incidence of cell death that the oxidized proteins resulting from that cell death may be recovered from the plasma proteome.

The location of a protein relative to sources of oxidative stress can influence the frequency and/or extent to which a protein may be oxidized. For example, membrane proteins are necessarily in relatively close proximity to fatty acids in the plasma membrane. Lysine, cysteine, or histidine residues on proteins can be subjected to addition, through a Michael addition mechanism, of fatty acid fragments that can result from lipid peroxidation. Integral membrane proteins and proteins in close proximity to membranes are the most likely to undergo this type of adduct formation. Proximity to sources of oxidation also may influence the oxidation of proteins in the circulatory system. The largest number of oxidative modifications in a plasma protein was found on apolipoprotein B-100, which is involved in oxidative modification of LDL and atherosclerosis (Obama et al., *Proteomics,* 2007, 7(13): 2132-2141). α-1-Antitrypsin was also readily oxidized and is a component of LDL. This protein is another part of the complex that accumulates on arterial walls and contributes to early stage atherosclerosis. (Mashiba et al., *Arterioscler., Thromb., Vasc. Biol.,* 2001, 21(11):1801-1808.) The results of Example 1 show that proteins associated with heart disease are being produced in high abundance in normal individuals in the 32- to 36-year age group.

Advanced glycation end (AGE) products were found in this study of normal individuals. Since glycation of a protein seems to have relatively little impact on biological activity, it is interesting that glycated proteins are being oxidized. The resulting carbonylated proteins would seem to be more dangerous to cells than the glycated starting material. Protein glycation along with the subsequent AGE oxidation is an issue in diabetes. The analytical protocol described here for the analysis of AGE oxidation products may be of value in the study of OS in diabetes.

Tracing oxidized proteins back to their tissue of origin using the Human Protein Atlas showed that kidney, liver, and soft tissues contributed more proteins than other organs. This observation is supported by literature showing that high levels of oxidative stress occur in the liver and kidney (Dhahbi et al., *Biology of Aging and Its Modulation,* 2003, 3:271-291; Nistala et al., *Antioxid. Redox Signaling,* 2008, 10(12):2047-2090). This may allow the identification of organs experiencing high oxidative stress through the analysis of blood.

Example 1 and FIGS. 1-6 show that approximately 0.2% of the protein in the plasma of normal, 32- to 36-year-old human male subjects can be selected by avidin affinity chromatography after biotinylation of carbonyl groups with biotin hydrazide and that this protein fraction has a series of characteristic, OS-related features. One feature is that roughly 25 different types of OS-induced post-translational modifications (OSi-PTMs) are present in normal plasma. Multiple forms of OSi-PTM were observed with the same amino acid species in addition to the same OSi-PTM occurring on multiple amino acids. A second feature is that more than half of the amino acid species used in protein synthesis were modified by some type of post-translational modification and that these modifications did not appear to have involved enzymatic catalysis. A third feature was that a protein could be oxidized at multiple sites in an unrelated, non-stoichiometric pattern, thus creating multiple oxidized isoforms of a protein.

A further observation is that some of the proteins reported to be a factor in several oxidative stress related diseases are present in the plasma of normal male subjects. Whether these individuals will later develop these disease is unknown. If they do, oxidized proteins might be useful as early indicators of impending health problems.

Finally, the probability that a plasma protein will be oxidized can depend on a series of variables. Among these variables are i) structural features such as the presence of conjugated metals and the position of specific amino acids in the structure of the protein, ii) the degree of oxidative stress in the compartment where the protein originated before being released into the circulatory system, iii) the extent of AGE generation in cells and plasma, and iv) the concentration of ROS at locations in the circulatory system such as with atherosclerosis. The fact that plasma proteins can be used to assess localized oxidative stress might make them useful as clinical diagnostic agents.

The methods described in Example 1 establish the technical foundation on which the remaining methods described herein are based. Examples 3-6, discussed in more detail below, reflect methods that exploit the technical platform described in Example 1. Examples 3-6 describe methods that isolate, detect, quantify, characterize the degree of oxidation, and/or identify oxidized peptides associated with particular conditions: breast cancer (Example 3), Parkinson's disease (Example 4), and diabetes mellitus (Example 5 and Example 6). The Examples, below, establish the universal utility of the methods described herein and permit one to practice the methods in order to isolate, detect, quantify, characterize the degree of oxidation, and/or identify oxidized peptides associated with any other condition of interest such as, for example, other cancers, neurodegenerative diseases, inflammatory diseases, atherosclerosis, aging, etc.

Moreover, Examples 3-6 demonstrate how the technical platform described in Example 1 can be employed as a diagnostic tool, to establish an OS profile of proteins for a disease (e.g., breast cancer (Example 3) and diabetes mellitus (Example 5)), and how to use data from samples collected from an individual at different times to assess the time-dependent course of a disease such as, for example, before and after a set duration of treatment (Example 6).

Breast Cancer

Example 3 demonstrates the utility of methods described herein for analyzing the oxidation of peptides to monitor cancers such as, for example, breast cancer. There is growing evidence that redox regulation is disrupted in various cancers, resulting in overproduction of reactive oxygen species (ROS). Indeed, 8-isoprostane, a widely used ROS indicator, was of significantly higher concentration in the plasma of breast cancer patients relative to controls. One outcome of ROS overproduction is the oxidation of proteins through, for example, the production of carbonyl groups. We detected differences in levels of carbonylated plasma proteins between breast cancer patients and undiagnosed controls.

Carbonyl groups in proteins from freshly drawn blood were prepared and analyzed as described in Example 3. Four hundred sixty proteins were identified and quantified in breast cancer patients, 98 of which exhibited an increase in concentration of at least 1.5-fold relative to the controls. Carbonylation was found to occur at a small number of specific sites in proteins. Other forms of oxidation also were found in the selected proteins. Nearly one fourth of the affinity-selected proteins were of cytoplasmic, nuclear, or of membrane origin.

Analysis of the data by unbiased knowledge assembly indicated the most likely disease associated with the proteins was breast neoplasm. Pathway analysis showed that oxidized proteins are strongly associated with breast cancer (e.g., Brca1, the breast cancer type-1 susceptibility protein). Exemplary molecular functions of the oxidized proteins included defense and immunity, nucleic acid binding, DNA helicase activity, serine protease inhibition, microtubule binding, and RNA helicase activity.

Reactive oxygen species appear to be involved in breast cancer pathogenesis (Chua et al., *Experimental Biology and Medicine*, 2009, 234:1086-1094; Sener et al., *Cell Biochemistry and Function*, 2007, 25:377-382). Overproduction of ROS and the oxidative stress associated with overproduction of ROS can occur in several ways. One way is by enhanced expression of enzymes such as, for example, thymidine phosphorylase and lactoperoxidase that elevate ROS production from within the tumor (Brown et al, *Breast Cancer Research [online computer file]* 2001, 3:323-327). Another way is by extracellular production of ROS through macrophage recruitment.

Extracellular ROS entering tumor cells can oxidatively damage mitochondria, nuclear DNA, ribosomal RNA, intercellular proteins, and lipids. This damage can further stimulate uncontrolled growth, ischemia, and glucose deprivation, which can result in reduced neovascularization and a further increase in oxidative stress.

Metabolites associated with oxidative stress have been associated with breast cancer. For example, elevated urinary levels of 15-F2t-isoprostane (15-F2t-IsoP) have been linked to breast cancer risk (Rossner et al., *Cancer Epidemiology, Biomarkers & Prevention*, 2006, 15:639-644). Also, urinary 8-oxo-2-deoxyguanosine and plasma malondialdehyde are elevated in breast cancer patients compared to normal controls (Sener et al., *Cell Biochemistry and Function*, 2007, 25:377-382; Gonenc et al., *Journal of Clinical Pharmacy and Therapeutics*, 2001, 26:141-144; Kuo et al., *Mutation Research, Genetic Toxicology and Environmental Mutagenesis*, 2007, 631:62-68). Two recent studies have shown that the total concentration of carbonylated plasma proteins is strongly connected to breast cancer risk (Rossner et al., *J Cell Mol Med*, 2007, 11:1138-1148; Zipprich et al., *Cancer Res* 2009, 69:2966-2972).

The methods described herein permit one to isolate carbonylated proteins from the plasma of breast cancer patients, identify the oxidized proteins, locate oxidation sites, and establish the mechanism by which oxidation occurred at various sites within a protein. Moreover, one can analyze proteins carrying OSi~PTMs from oxidatively stressed tissue that are shed or released into blood and can provide an oxidative stress signature of the organ or tumor from which the oxidized proteins originated. Thus, the methods allow one to construct a profile of oxidative stress proteins associated with breast cancer. Such a profile can be used as a diagnostic tool for other individuals.

Breast cancer patients and cancer-free subjects were compared to determine whether the elevated levels of oxidative stress that occurs in the tumor influenced proteins that can be detected in the plasma. We detected qualitative and quantitative differences between oxidized proteins found in the plasma of six breast cancer patients and matched controls.

Figure 9:
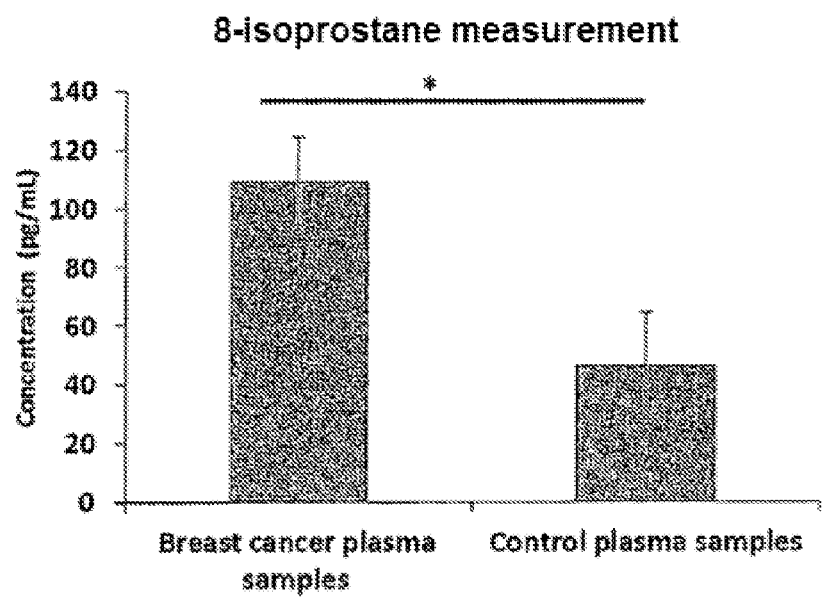
FIG. 9. Plasma 8-isoprostane levels were significantly higher in breast cancer patients compared to their controls. Concentrations of the samples were expressed as averages with standard errors of control independent samples (n=6) and cancer patient samples (n=6). Comparison of control and cancer patients was made using the Student t-test. A p-value of 0.02 on a 2-tailed test was obtained which was considered statistically significant.

We first validated that breast cancer patients experienced elevated oxidative stress by measuring 8-isoprostane in their plasma. 8-Isoprostane is formed specifically as a consequence of free radical induced lipid peroxidation and is considered to be one of the most reliable indicators of in vivo oxidative stress. FIG. 9 shows that the level of 8-isoprostane was significantly higher in cancer patient plasma than in the controls. This result is consistent with a study in which isoprostanes were elevated in the urine of patients with invasive breast cancer.

Figure 7:
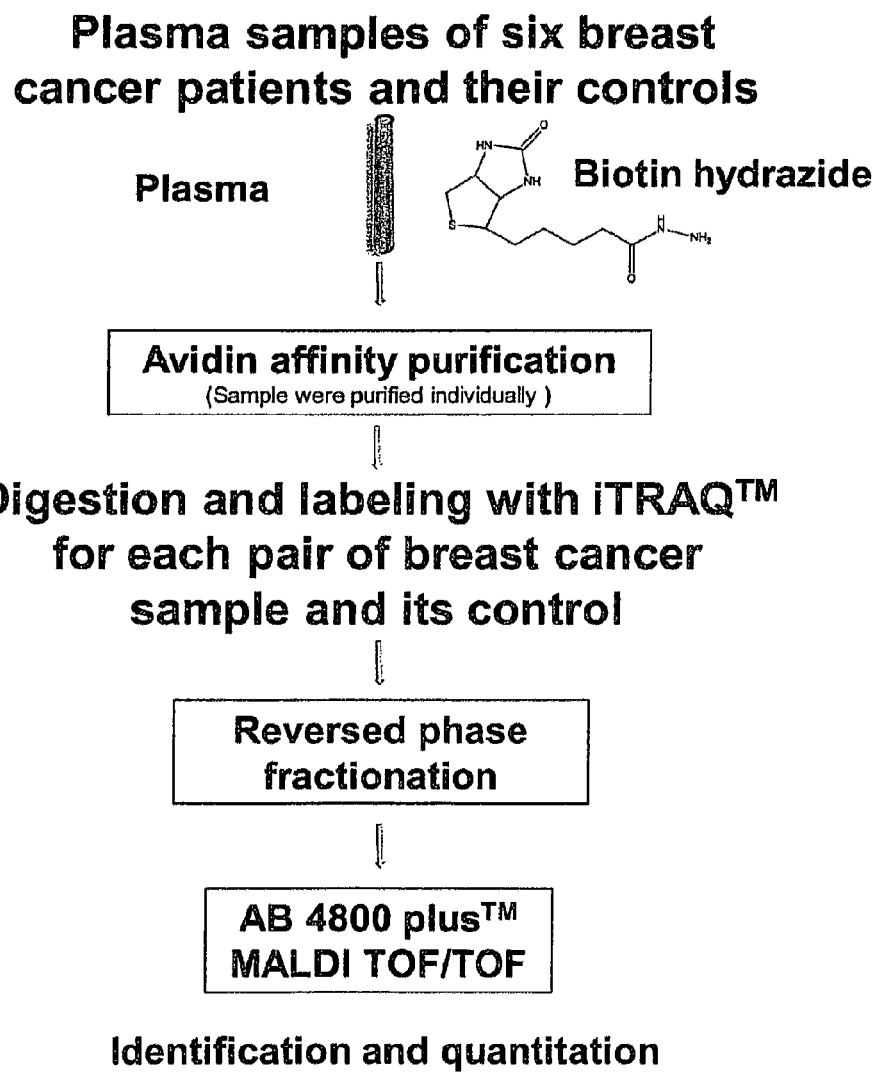
FIG. 7. Schematic illustration for the strategy for the identification and quantitation of oxidized proteins in the plasma of breast cancer patients compared to their controls. The samples were purified individually using avidin. Each pair of purified samples from breast cancer patient and their controls were then labeled with iTRAQ™ and identified and quantified using AB 4800 MALDI/TOF/TOF.
Figure 8:
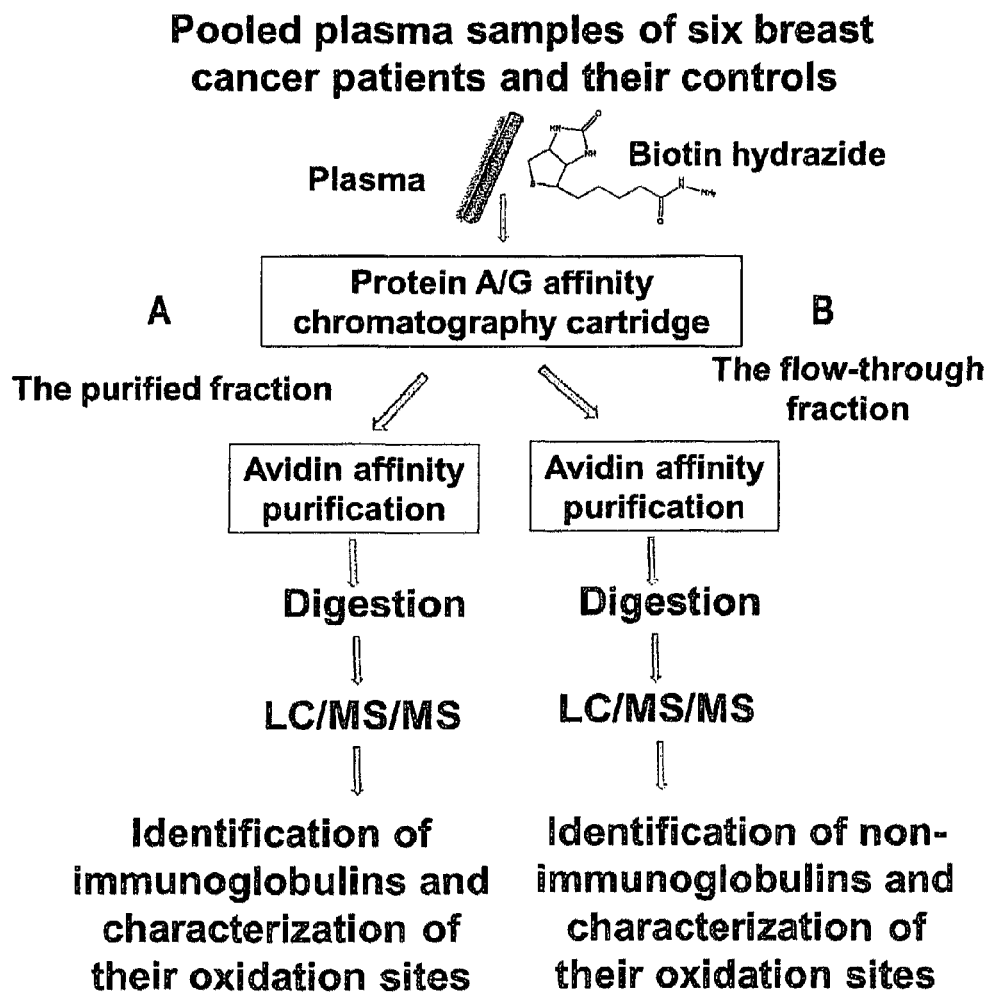
FIG. 8. Schematic illustration for the strategy for the detection of the oxidation sites of immunoglobulins and non-immunoglobulins.

The general protocols used in Example 3 are illustrated in FIG. 7 and FIG. 8. Initial analysis of the data (to be discussed later) indicated that a major portion of the biotinylated protein fraction was most likely immunoglobulins. This observation was further confirmed through a second approach in which biotinylated plasma samples were subjected to tandem affinity chromatography. The first of the tandem dimensions employed a protein A/G column to select immunoglobulins from the blood proteome while an avidin affinity column was used in the second dimension to select oxidized forms of immunoglobulins that had been biotinylated. Protein A/G was immobilized on a cross-linked agarose column. Following trypsin digestion of the tandem affinity-selected fraction, the total hydrolysate was subjected to RPC-MS/MS analysis in an effort to identify these immunoglobulins and characterize their oxidation sites (FIG. 8A). The large amount of oxidized immunoglobulins in the plasma of breast cancer patients suppressed the ionization of some of the non-immunoglobulins. Therefore, the immunoglobulin-stripped flow through fraction from the protein A/G column was used for avidin affinity selection in the second dimension. The eluted fraction from the avidin column was then digested with trypsin and the peptides were subjected to RPC-MS/MS analysis to characterize the oxidation sites of non-immunoglobulins (FIG. 8B).

By using this protocol, one finds that 1) multiple sites of oxidation are often found in a single protein, 2) oxidation can be non-stoichiometric across these sites, and 3) multiple forms of oxidation involving many amino acids can be found in a biotinylated protein. Thus, a single protein can exist in many different oxidized forms. The protocol does not necessarily capture nor recognize all oxidized forms of a given protein; only oxidation sites that are co-resident on a protein with a free carbonyl group are captured and analyzed. Although it is likely that all types of oxidation occurring in a biological system are seen with this method, not all forms of oxidation are quantitatively selected.

The initial phase of this study described immediately above generated an average of 3540 spectra. A total of 460 proteins were identified and quantified in the six breast cancer patients and their controls. Among these proteins, 98 proteins exhibited at least a 1.5-fold increase in concentration in cancer patients relative to controls (Table 8).

TABLE 8

Proteins that changed more than 50% in the plasma of in any of the breast cancer patients compared to their controls. The ratios were calculated as fold change

| Protein number | Unused | Total | % Cov | Accession # | Name | Species | Number of peptides used in the identification | Breast cancer/ control (fold change) |
|---|---|---|---|---|---|---|---|---|
| 1 | 2.02 | 3.78 | 5.3 | O60318\|MCM3A_HUMAN | 80 kDa MCM3-associated protein | HUMAN | 12 | −2.1 |
| 2 | 4.79 | 4.79 | 13.4 | P01009\|A1AT_HUMAN | Alpha-1-antitrypsin precursor[a] | HUMAN | 7 | −1.8 |

TABLE 8-continued

Proteins that changed more than 50% in the plasma of in any of the breast cancer patients compared to their controls. The ratios were calculated as fold change

| Protein number | Unused | Total | % Cov | Accession # | Name | Species | Number of peptides used in the identification | Breast cancer/ control (fold change) |
|---|---|---|---|---|---|---|---|---|
| 2 | 4.21 | 4.21 | 15.8 | P01009\|A1AT_HUMAN | Alpha-1-antitrypsin precursor[a] | HUMAN | 7 | 1.8 |
| 3 | 2.19 | 2.21 | 6.9 | P01023\|A2MG_HUMAN | Alpha-2-macroglobulin precursor | HUMAN | 13 | 2.5 |
| 4 | 2.48 | 2.48 | 19 | P02652\|APOA2_HUMAN | Apolipoprotein A-II precursor | HUMAN | 3 | 1.9 |
| 5 | 2 | 2 | 12.4 | P06727\|APOA4_HUMAN | Apolipoprotein A-IV precursor[a] | HUMAN | 5 | −2.0 |
| 5 | 4 | 4.01 | 12.6 | P06727\|APOA4_HUMAN | Apolipoprotein A-IV precursor[a] | HUMAN | 6 | −2.0 |
| 5 | 31.28 | 31.28 | 54.5 | P06727\|APOA4_HUMAN | Apolipoprotein A-IV precursor[a] | HUMAN | 20 | −1.7 |
| 6 | 3.54 | 3.54 | 5 | P04114\|APOB_HUMAN | Apolipoprotein B-100 precursor | HUMAN | 22 | 1.8 |
| 7 | 4.29 | 4.29 | 30.1 | P02654\|APOC1_HUMAN | Apolipoprotein C-I precursor | HUMAN | 3 | −2.0 |
| 8 | 2 | 2 | 19.2 | P02656\|APOC3_HUMAN | Apolipoprotein C-III precursor[a] | HUMAN | 2 | −6.4 |
| 8 | 2 | 2 | 21.2 | P02656\|APOC3_HUMAN | Apolipoprotein C-III precursor[a] | HUMAN | 2 | −8.1 |
| 9 | 2 | 2 | 18.1 | P55056\|APOC4_HUMAN | Apolipoprotein C-IV precursor | HUMAN | 2 | 2.2 |
| 10 | 10.3 | 10.3 | 18.9 | P02649\|APOE_HUMAN | Apolipoprotein E precursor[a] | HUMAN | 6 | 1.9 |
| 10 | 11.12 | 11.12 | 48.3 | P02649\|APOE_HUMAN | Apolipoprotein E precursor[a] | HUMAN | 5 | −1.6 |
| 10 | 22.21 | 22.21 | 57.7 | P02649\|APOE_HUMAN | Apolipoprotein E precursor[a] | HUMAN | 17 | 2.4 |
| 11 | 2 | 2 | 3.8 | O14791\|APOL1_HUMAN | Apolipoprotein-L1 precursor | HUMAN | 1[b] | 5.0 |
| 12 | 2.07 | 3.29 | 7 | O94833\|BPAEA_HUMAN | Bulious pemphigoid antigen 1, isoforms | HUMAN | 50 | −2.5 |
| 13 | 8.64 | 8.68 | 15.2 | P04003\|C4BP_HUMAN | C4b-binding protein alpha chain precursor | HUMAN | 11 | 1.7 |
| 14 | 6 | 6 | 13 | O43866\|CD5L_HUMAN | CD5 antigen-like precursor | HUMAN | 4 | 2.0 |
| 15 | 2.84 | 3.11 | 4.2 | P49454\|CENPF_HUMAN | Centromere protein F | HUMAN | 12 | −5.5 |
| 16 | 6.93 | 6.93 | 10.8 | P00450\|CERU_HUMAN | Ceruloplasmin precursor[a] | HUMAN | 12 | −2.1 |
| 16 | 5.72 | 5.73 | 10 | P00450\|CERU_HUMAN | Ceruloplasmin precursor[a] | HUMAN | 11 | 1.5 |
| 16 | 11.71 | 11.74 | 15.6 | P00450\|CERU_HUMAN | Ceruloplasmin precursor[a] | HUMAN | 17 | 1.6 |
| 17 | 6 | 6 | 8.5 | P05160\|F13B_HUMAN | Coagulation factor XIII B chain precursor[a] | HUMAN | 3 | −2.4 |
| 17 | 6 | 6 | 11.6 | P05160\|F13B_HUMAN | Coagulation factor XIII B chain precursor[a] | HUMAN | 8 | −1.6 |
| 17 | 12.59 | 12.59 | 25 | P05160\|F13B_HUMAN | Coagulation factor XIII B chain precursor[a] | HUMAN | 7 | 1.5 |
| 18 | 2.14 | 2.14 | 12.2 | P02745\|C1QA_HUMAN | Complement C1q subcomponent subunit A precursor | HUMAN | 3 | 2.0 |
| 19 | 4 | 4 | 14.7 | P02747\|C1QC_HUMAN | Complement C1q subcomponent subunit C precursor | HUMAN | 3 | 1.9 |
| 20 | 63.46 | 63.46 | 43.4 | P01024\|CO3_HUMAN | Complement C3 precursor | HUMAN | 37 | −1.6 |
| 21 | 17.23 | 17.26 | 18.2 | P0C0L5\|CO4B_HUMAN | Complement C4-B precursor | HUMAN | 8 | 1.5 |
| 22 | 4.83 | 4.84 | 9.6 | P08603\|CFAH_HUMAN | Complement factor H precursor[a] | HUMAN | 11 | 2.0 |
| 22 | 2 | 4.04 | 17.6 | P08603\|CFAH_HUMAN | Complement factor H precursor[a] | HUMAN | 8 | 2.0 |
| 23 | 45.86 | 45.86 | 33.3 | P02671\|FIBA_HUMAN | Fibrinogen alpha chain precursor[a] | HUMAN | 47 | 2.1 |
| 23 | 51.54 | 51.54 | 41.7 | P02671\|FIBA_HUMAN | Fibrinogen alpha chain precursor[a] | HUMAN | 50 | −1.8 |
| 23 | 93.83 | 93.85 | 60.7 | P02671\|FIBA_HUMAN | Fibrinogen alpha chain precursor[a] | HUMAN | 123 | −2.1 |
| 23 | 96.2 | 96.2 | 63.6 | P02671\|FIBA_HUMAN | Fibrinogen alpha chain precursor[a] | HUMAN | 114 | 2.5 |

TABLE 8-continued

Proteins that changed more than 50% in the plasma of in any of the breast cancer patients compared to their controls. The ratios were calculated as fold change

| Protein number | Unused | Total | % Cov | Accession # | Name | Species | Number of peptides used in the identification | Breast cancer/ control (fold change) |
|---|---|---|---|---|---|---|---|---|
| 24 | 77.51 | 77.53 | 66.2 | P02675\|FIBB_HUMAN | Fibrinogen beta chain precursor[a] | HUMAN | 115 | 2.0 |
| 24 | 44.93 | 44.93 | 49.7 | P02675\|FIBB_HUMAN | Fibrinogen beta chain precursor[a] | HUMAN | 35 | 1.9 |
| 24 | 88.89 | 88.91 | 76.4 | P02675\|FIBB_HUMAN | Fibrinogen beta chain precursor[a] | HUMAN | 125 | −1.8 |
| 25 | 14.99 | 14.99 | 30.9 | P02679\|FIBG_HUMAN | Fibrinogen gamma chain precursor[a] | HUMAN | 7 | 1.7 |
| 25 | 22.18 | 22.33 | 46.1 | P02679\|FIBG_HUMAN | Fibrinogen gamma chain precursor[a] | HUMAN | 15 | −1.7 |
| 25 | 40.56 | 40.57 | 52.5 | P02679\|FIBG_HUMAN | Fibrinogen gamma chain precursor[a] | HUMAN | 37 | 2.0 |
| 25 | 43.53 | 43.53 | 68.9 | P02679\|FIBG_HUMAN | Fibrinogen gamma chain precursor[a] | HUMAN | 38 | −1.8 |
| 26 | 79.06 | 79.06 | 33.9 | P02751\|FINC_HUMAN | Fibronectin precursor[a] | HUMAN | 46 | 1.7 |
| 26 | 143.08 | 143.1 | 45.2 | P02751\|FINC_HUMAN | Fibronectin precursor[a] | HUMAN | 107 | −2.1 |
| 26 | 183.52 | 183.5 | 50.8 | P02751\|FINC_HUMAN | Fibronectin precursor[a] | HUMAN | 172 | −2.0 |
| 27 | 4 | 4 | 9.2 | Q08380\|LG3BP_HUMAN | Galectin-3-binding protein precursor a | HUMAN | 4 | 9.0 |
| 28 | 5.35 | 5.35 | 20.7 | P00738\|HPT_HUMAN | Haptoglobin precursor | HUMAN | 7 | 2.2 |
| 29 | 2.34 | 2.34 | 15.6 | P68871\|HBB_HUMAN | Hemoglobin subunit beta[a] | HUMAN | 2 | −3.0 |
| 29 | 4 | 4 | 23.8 | P68871\|HBB_HUMAN | Hemoglobin subunit beta[a] | HUMAN | 3 | 1.9 |
| 29 | 10 | 10 | 45.6 | P68871\|HBB_HUMAN | Hemoglobin subunit beta[a] | HUMAN | 6 | 1.6 |
| 30 | 6 | 6 | 27.2 | P02042\|HBD_HUMAN | Hemoglobin subunit delta | HUMAN | 4 | −2.2 |
| 31 | 6.96 | 6.96 | 18.4 | P02790\|HEMO_HUMAN | Hemopexin precursor[a] | HUMAN | 9 | 1.5 |
| 31 | 14.57 | 14.57 | 27.9 | P02790\|HEMO_HUMAN | Hemopexin precursor[a] | HUMAN | 12 | 2.6 |
| 32 | 8.01 | 8.01 | 17.3 | P04196\|HRG_HUMAN | Histidine-rich glycoprotein precursor[a] | HUMAN | 11 | 1.7 |
| 32 | 1.7 | 1.7 | 12 | P04196\|HRG_HUMAN | Histidine-rich glycoprotein precursor[a] | HUMAN | 7 | −1.6 |
| 33 | 6.01 | 6.01 | 28.5 | P13747\|HLAE_HUMAN | HLA class I histocompatibility antigen, alpha chain E precursor | HUMAN | 9 | −2.7 |
| 34 | 2.12 | 2.12 | 3.9 | Q96ED9\|HOOK2_HUMAN | Hook homolog 2 | HUMAN | 4 | 2.6 |
| 35 | 2 | 2 | 2.9 | Q14520\|HABP2_HUMAN | Hyaluronan-binding protein 2 precursor | HUMAN | 2 | 1.6 |
| 36 | 12.48 | 12.48 | 18.4 | P01876\|IGHA1_HUMAN | Ig alpha-1 chain C region[a] | HUMAN | 14 | 2.6 |
| 36 | 8.21 | 8.21 | 18.1 | P01876\|IGHA1_HUMAN | Ig alpha-1 chain C region[a] | HUMAN | 8 | 1.8 |
| 37 | 5.1 | 5.1 | 17.4 | P01877\|IGHA2_HUMAN | Ig alpha-2 chain C region | HUMAN | 8 | 1.6 |
| 38 | 20.36 | 20.36 | 54.8 | P01857\|IGHG1_HUMAN | Ig gamma-1 chain C region[a] | HUMAN | 22 | −1.6 |
| 38 | 25.19 | 25.19 | 58.5 | P01857\|IGHG1_HUMAN | Ig gamma-1 chain C region[a] | HUMAN | 21 | 1.6 |
| 38 | 39.84 | 39.85 | 75.2 | P01857\|IGHG1_HUMAN | Ig gamma-1 chain C region[a] | HUMAN | 27 | −1.6 |
| 38 | 4.48 | 19.81 | 62.4 | P01857\|IGHG1_HUMAN | Ig gamma-1 chain C region[a] | HUMAN | 13 | 3.2 |
| 39 | 6.65 | 13.78 | 51.2 | P01859\|IGHG2_HUMAN | Ig gamma-2 chain C region | HUMAN | 22 | 1.9 |
| 40 | 2 | 9.92 | 64.8 | P01860\|IGHG3_HUMAN | Ig gamma-3 chain C region | HUMAN | 6 | 2.4 |
| 41 | 3.2 | 10.06 | 31.8 | P01861\|IGHG4_HUMAN | Ig gamma-4 chain C region | HUMAN | 5 | −2.8 |
| 42 | 4.03 | 4.03 | 20.5 | P23083\|HV103_HUMAN | Ig heavy chain V-I region V35 precursor | HUMAN | 7 | 1.5 |
| 43 | 2.16 | 3.52 | 37.1 | P01781\|HV320_HUMAN | Ig heavy chain V-III region GAL | HUMAN | 5 | 1.9 |
| 44 | 2 | 3.27 | 20.6 | P01772\|HV311_HUMAN | Ig heavy chain V-III region KOL | HUMAN | 3 | 1.7 |
| 45 | 3.51 | 3.6 | 30.3 | P01777\|HV316_HUMAN | Ig heavy chain V-III region TEI | HUMAN | 4 | 6.5 |

TABLE 8-continued

Proteins that changed more than 50% in the plasma of in any of the breast cancer patients compared to their controls. The ratios were calculated as fold change

| Protein number | Unused | Total | % Cov | Accession # | Name | Species | Number of peptides used in the identification | Breast cancer/ control (fold change) |
|---|---|---|---|---|---|---|---|---|
| 46 | 2 | 2.42 | 26.2 | P01762\|HV301_HUMAN | Ig heavy chain V-III region TRO | HUMAN | 4 | 2.1 |
| 47 | 10.04 | 10.04 | 70.8 | P01834\|KAC_HUMAN | Ig kappa chain C region$^a$ | HUMAN | 11 | −2.0 |
| 47 | 23.45 | 23.46 | 84 | P01834\|KAC_HUMAN | Ig kappa chain C region$^a$ | HUMAN | 25 | 2.3 |
| 48 | 4.74 | 4.74 | 24.8 | P04432\|KV124_HUMAN | Ig kappa chain V-I region Daudi precursor | HUMAN | 4 | 2.4 |
| 49 | 2 | 2 | 31.5 | P01610\|KV118_HUMAN | Ig kappa chain V-I region WEA | HUMAN | 2 | 1.6 |
| 50 | 2.59 | 5.52 | 28.7 | P01610\|KV118_HUMAN | Ig kappa chain V-I region WEA | HUMAN | 3 | 1.7 |
| 51 | 2.36 | 4.37 | 42.7 | P06309\|KV205_HUMAN | Ig kappa chain V-II region GM607 precursor | HUMAN | 5 | −2.8 |
| 52 | 4.18 | 4.19 | 41.1 | P04207\|KV308_HUMAN | Ig kappa chain V-III region CLL precursor | HUMAN | 6 | 2.0 |
| 53 | 3.2 | 5.21 | 55.8 | P18135\|KV312_HUMAN | Ig kappa chain V-III region HAH precursor | HUMAN | 9 | 2.2 |
| 54 | 4.98 | 4.98 | 49.6 | P18136\|KV313_HUMAN | Ig kappa chain V-III region HIC precursor | HUMAN | 6 | 2.2 |
| 55 | 6.06 | 6.07 | 49.3 | P06314\|KV404_HUMAN | Ig kappa chain V-IV region B17 precursor | HUMAN | 7 | 2.0 |
| 56 | 2 | 2.02 | 33.1 | P06313\|KV403_HUMAN | Ig kappa chain V-IV region JI precursor | HUMAN | 6 | 1.7 |
| 57 | 14.03 | 14.04 | 67.6 | P01842\|LAC_HUMAN | Ig lambda chain C regions$^a$ | HUMAN | 10 | 1.8 |
| 57 | 11.72 | 11.76 | 63.8 | P01842\|LAC_HUMAN | Ig lambda chain C regions$^a$ | HUMAN | 8 | −1.8 |
| 58 | 3.71 | 3.71 | 34.2 | P01701\|LV103_HUMAN | Ig lambda chain V-I region NEW | HUMAN | 3 | 1.7 |
| 59 | 2 | 2 | 28 | P01717\|LV403_HUMAN | Ig lambda chain V-IV region Hil$^a$ | HUMAN | 2 | 1.7 |
| 59 | 4 | 4 | 28 | P01717\|LV403_HUMAN | Ig lambda chain V-IV region Hil$^a$ | HUMAN | 3 | 1.6 |
| 59 | 2 | 2 | 17.8 | P01717\|LV403_HUMAN | Ig lambda chain V-IV region Hil$^a$ | HUMAN | 2 | 1.5 |
| 60 | 48.88 | 48.89 | 62.6 | P01871\|MUC_HUMAN | Ig mu chain C region$^a$ | HUMAN | 41 | 2.7 |
| 60 | 31.42 | 31.42 | 44.9 | P01871\|MUC_HUMAN | Ig mu chain C region$^a$ | HUMAN | 19 | −1.5 |
| 61 | 1.4 | 22.78 | 45 | P04220\|MUCB_HUMAN | Ig mu heavy chain disease protein | HUMAN | 13 | −2.3 |
| 62 | 4 | 4 | 17.5 | P01591\|IGJ_HUMAN | Immunoglobulin J chain | HUMAN | 3 | 1.6 |
| 63 | 4.01 | 4.01 | 3.7 | P19827\|ITIH1_HUMAN | Inter-alpha-trypsin inhibitor heavy chain H1 precursor | HUMAN | 3 | −6.3 |
| 64 | 1.31 | 1.31 | 6.6 | Q9BVA0\|KTNB1_HUMAN | Katanin p80 WD40-containing subunit B1 | HUMAN | 6 | −3.4 |
| 65 | 1.4 | 1.47 | 7.7 | Q9C0H6\|KLHL4_HUMAN | Kelch-like protein 4 | HUMAN | 10 | −3.5 |
| 66 | 1.7 | 1.7 | 3.9 | Q8IXQ5\|KLHL7_HUMAN | Kelch-like protein 7 | HUMAN | 2 | −4.7 |
| 67 | 1.7 | 1.71 | 7.4 | Q96L93\|SNX23_HUMAN | Kinesin-like motor protein C20orf23 | HUMAN | 14 | −2.3 |
| 68 | 3.58 | 3.58 | 18.3 | P01042\|KNG1_HUMAN | Kininogen-1 precursor | HUMAN | 8 | 1.9 |
| 69 | 1.57 | 1.57 | 4.6 | Q13753\|LAMC2_HUMAN | Laminin subunit gamma-2 precursor | HUMAN | 6 | −11.6 |
| 70 | 2 | 2 | 3.2 | Q8IUZ0\|LRC49_HUMAN | Leucine-rich repeat-containing protein 49 | HUMAN | 2 | −2.2 |
| 71 | 2 | 2 | 2.3 | O00187\|MASP2_HUMAN | Mannan-binding lectin serine protease 2 precursor | HUMAN | 2 | 9.0 |
| 72 | 2.02 | 2.02 | 4.9 | P27816\|MAP4_HUMAN | Microtubule-associated protein 4 | HUMAN | 5 | −3.0 |
| 73 | 2 | 2.01 | 2.5 | Q8NEV4\|MYO3A_HUMAN | Myosin IIIA | HUMAN | 7 | −1.6 |
| 74 | 2.04 | 2.81 | 6.9 | Q9ULV0\|MYO5B_HUMAN | Myosin-5B | HUMAN | 20 | −1.5 |
| 75 | 2.07 | 2.09 | 7.5 | Q86WG5\|MTMRD_HUMAN | Myotubularin-related protein 13 | HUMAN | 20 | 4.7 |
| 76 | 2.1 | 2.93 | 5 | Q8NF91\|SYNE1_HUMAN | Nesprin-1 | HUMAN | 56 | −2.8 |
| 77 | 1.52 | 2.23 | 7.6 | O43929\|ORC4_HUMAN | Origin recognition complex subunit 4 | HUMAN | 4 | −1.6 |

TABLE 8-continued

Proteins that changed more than 50% in the plasma of in any of the breast cancer patients compared to their controls. The ratios were calculated as fold change

| Protein number | Unused | Total | % Cov | Accession # | Name | Species | Number of peptides used in the identification | Breast cancer/ control (fold change) |
|---|---|---|---|---|---|---|---|---|
| 78 | 1.53 | 1.66 | 5.3 | P56715\|RP1_HUMAN | Oxygen-regulated protein 1 | HUMAN | 18 | −3.0 |
| 79 | 4 | 4 | 23.2 | P32119\|PRDX2_HUMAN | Peroxiredoxin-2 | HUMAN | 3 | −9.2 |
| 80 | 2 | 2.06 | 4.9 | O60486\|PLXC1_HUMAN | Plexin-C1 precursor | HUMAN | 12 | −5.1 |
| 81 | 2.02 | 2.83 | 5.3 | Q92954\|PRG4_HUMAN | Proteoglycan-4 precursor | HUMAN | 15 | −1.5 |
| 82 | 2.35 | 2.35 | 13.3 | P00734\|THRB_HUMAN | Prothrombin precursor | HUMAN | 11 | −1.9 |
| 83 | 2 | 2.06 | 5.2 | Q9UHD2\|TBK1_HUMAN | Serine/threonine-protein kinase TBK1 | HUMAN | 5 | −1.6 |
| 84 | 4 | 4 | 12 | P02787\|TRFE_HUMAN | Serotransferrin precursor | HUMAN | 8 | 2.4 |
| 85 | 49.75 | 49.75 | 50.7 | P02768\|ALBU_HUMAN | Serum albumin precursor | HUMAN | 41 | 2.7 |
| 86 | 10.05 | 10.05 | 17.7 | P27169\|PON1_HUMAN | Serum paraoxonase/arylesterase 1 | HUMAN | 8 | 1.6 |
| 87 | 1.7 | 1.7 | 2.5 | Q9Y5W8\|SNX13_HUMAN | Sorting nexin-13 | HUMAN | 2 | −3.4 |
| 88 | 1.46 | 1.55 | 6.4 | P02549\|SPTA1_HUMAN | Spectrin alpha chain, erythrocyte | HUMAN | 25 | −4.1 |
| 89 | 1.45 | 1.47 | 13.7 | P23246\|SFPQ_HUMAN | Splicing factor, proline- and glutamine-rich | HUMAN | 10 | −1.5 |
| 90 | 4.04 | 4.74 | 7.8 | Q8WZ42\|TITIN_HUMAN | Titin | HUMAN | 201 | −1.7 |
| 91 | 4 | 4 | 24.5 | P02766\|TTHY_HUMAN | Transthyretin precursor | HUMAN | 2 | −3.0 |
| 92 | 1.4 | 1.4 | 14.7 | Q9Y333\|LSM2_HUMAN | U6 snRNA-associated Sm-like protein LSm2 | HUMAN | 2 | −3.6 |
| 93 | 2.34 | 2.35 | 7.5 | Q70EL4\|UBP43_HUMAN | Ubiquitin carboxyl-terminal hydrolases 43 | HUMAN | 12 | 2.2 |
| 94 | 2.02 | 2.08 | 3.4 | O75445\|USH2A_HUMAN | Usherin precursor | HUMAN | 27 | −2.5 |
| 95 | 1.4 | 1.51 | 5.3 | Q5THJ4\|VP13D_HUMAN | Vacuolar protein sorting-associated protein 13D[a] | HUMAN | 29 | −2.4 |
| 95 | 2.04 | 2.08 | 3.4 | Q5THJ4\|VP13D_HUMAN | Vacuolar protein sorting-associated protein 13D[a] | HUMAN | 22 | −2.5 |
| 96 | 33.26 | 33.26 | 49.4 | P04004\|VTNC_HUMAN | Vitronectin precursor | HUMAN | 44 | −1.6 |
| 97 | 1.7 | 1.7 | 1.6 | Q96FK6\|WDR89_HUMAN | WD repeat protein 89 | HUMAN | 1[b] | −4.5 |
| 98 | 1.7 | 1.7 | 1.6 | Q9Y493\|ZAN_HUMAN | Zonadhesin precursor | HUMAN | 4 | −7.8 |

[a]These proteins were identified in multiple donors
[b]The mass spectra for any peptide associated with single hit proteins were further manually inspected.

Four biotinylated proteins: intestinal alkaline phosphatase, horseradish peroxidase, protein A, and protein G were mixed together and applied on the avidin purification system four times. The four purified fractions were, reduced, alicylated, digested and labeled with the 114, 115, 116, or 117-dalton iTRAQ™ labeling reagents. Then each two of these fractions were mixed with an expected ratio of 1:1. The greatest variability was seen with horseradish peroxidase in the sample labeled with an error of 0.16, which indicate that a change of 50% is almost 3-fold greater than error due to the iTRAQ™ labeling (Table 9).

TABLE 9 iTRAQ™ ratios for proteins from each of the four analyzed aliquots of a biotinylated proteins mixture[a]

| Accession no. | Protein ID | No. pept. | Unused | % Cov. | Ratio 116:115 | Ratio 117:114 |
|---|---|---|---|---|---|---|
| sp\|P19111\| | Intestinal alkaline phosphatase | 87 | 78.6 | 68.9 | 1.04 | 0.95 |
| sp\|P02976\| | Protein A | 32 | 57.1 | 76.4 | 1.09 | 0.89 |
| sp\|P00433\| | Peroxidase | 17 | 17.9 | 36 | 1.16 | 0.94 |
| sp\|P19909\| | Protein G | 3 | 7.8 | 23.1 | 0.93 | 0.96 |

[a]To evaluate the variability of iTRAQ™ induced by the avidin affinity purification. Four aliquots of biotinylated proteins mixture (each of total protein concentration of 400ug) were analyzed in parallel. The theoretical ratios for all of the four proteins are 1:1.

Knowledge Assembly Analysis

Knowledge assembly is a term used here to describe the process of assembling new knowledge based on integration of findings reported in the literature and new experimental findings. An objective of this work was to examine whether organs or tissue undergoing elevated oxidative stress are shedding proteins into the circulatory system with oxidative stress induced oxidative modifications and providing a protein signature. Although a series of proteins were found to have undergone concentration changes exceeding 1.5-fold in cancer patient plasma relative to controls, they may not necessarily have come from a tumor. This issue was addressed by using pathway analysis software such as GeneGo™ and DAVID to determine whether an un-biased analysis of the scientific literature connects these proteins to cancer. GeneGo™ (St. Joseph, Mich.) is a comprehensive set of databases for pathway analysis that uses more than 50,000 signaling interactions based on 4.5 million reports collected from the literature over the last five years. The Database for Annotation, Visualization, and Integrated Discovery (DAVID), which is a tool available at no cost from NIAID, provides 40 annotation categories such as protein-protein interactions, disease associations, bio-pathways, gene function, and tissue expression using the most relevant gene ontology (GO) associated with genes. The degree to which these two differing data analysis suites gave the same interpretation of the data was a strong factor in evaluating the validity of the analyses.

DAVID GO by Molecular Function

Figure 10:
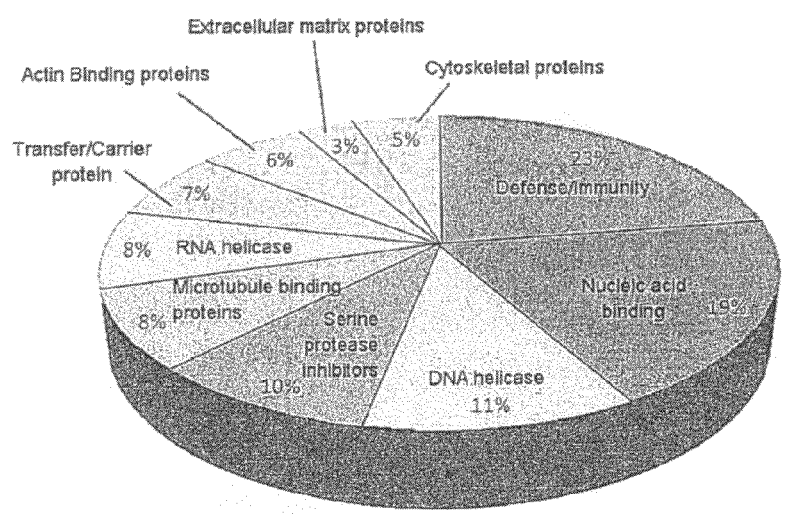
FIG. 10. A DAVID Gene Ontology (GO) analysis by molecular function of proteins that changed more than 50% in the plasma of BC patients compared to their controls.

Gene ontology (GO) analysis of the molecular function (FIG. 10) of the proteins identified showed that 23% function in defense and immunity (e.g., immunoglobulin heavy constant gamma). Nineteen percent are involved in nucleic acid binding (e.g., mitosin and splicing factor proline/glutamine-rich protein) while another 11% were related to DNA helicase (e.g., transthyretin and laminin gamma). Other molecular functions include 10% being serine protease inhibitors (e.g., set binding factor 2), 8% are functioning as microtubule binding proteins (e.g., chromosome 20 open reading frame 23), 8% are related to RNA helicase activity (e.g., proteoglycan 4), 8% serve as transfer (carrier) proteins (e.g., apolipoprotein e), 7% act as actin binding proteins (e.g., titin), 3% are extracellular matrix proteins (e.g., coagulation factor) and 5% are cytoskeletal proteins (e.g., titin).

DAVID GO by Biological Processes

GO analysis of the biological processes involving these proteins shows (FIG. 11) that 34% function in response to stimulus (e.g., complement factor h), 20% are involved in immune system processes (e.g., immunoglobulin kappa constant), 17% are part of protein transport (e.g., transferrin), 10% are used in positive regulation of biological process (e.g., katanin p80), 7% are part of acute inflammatory responses (e.g., complement component), 6% function in cell adhesion (e.g., zonadhesin), and 6% are involved in cytoskeleton organization and biogenesis (e.g., titin).

Network Analysis

Figure 12:
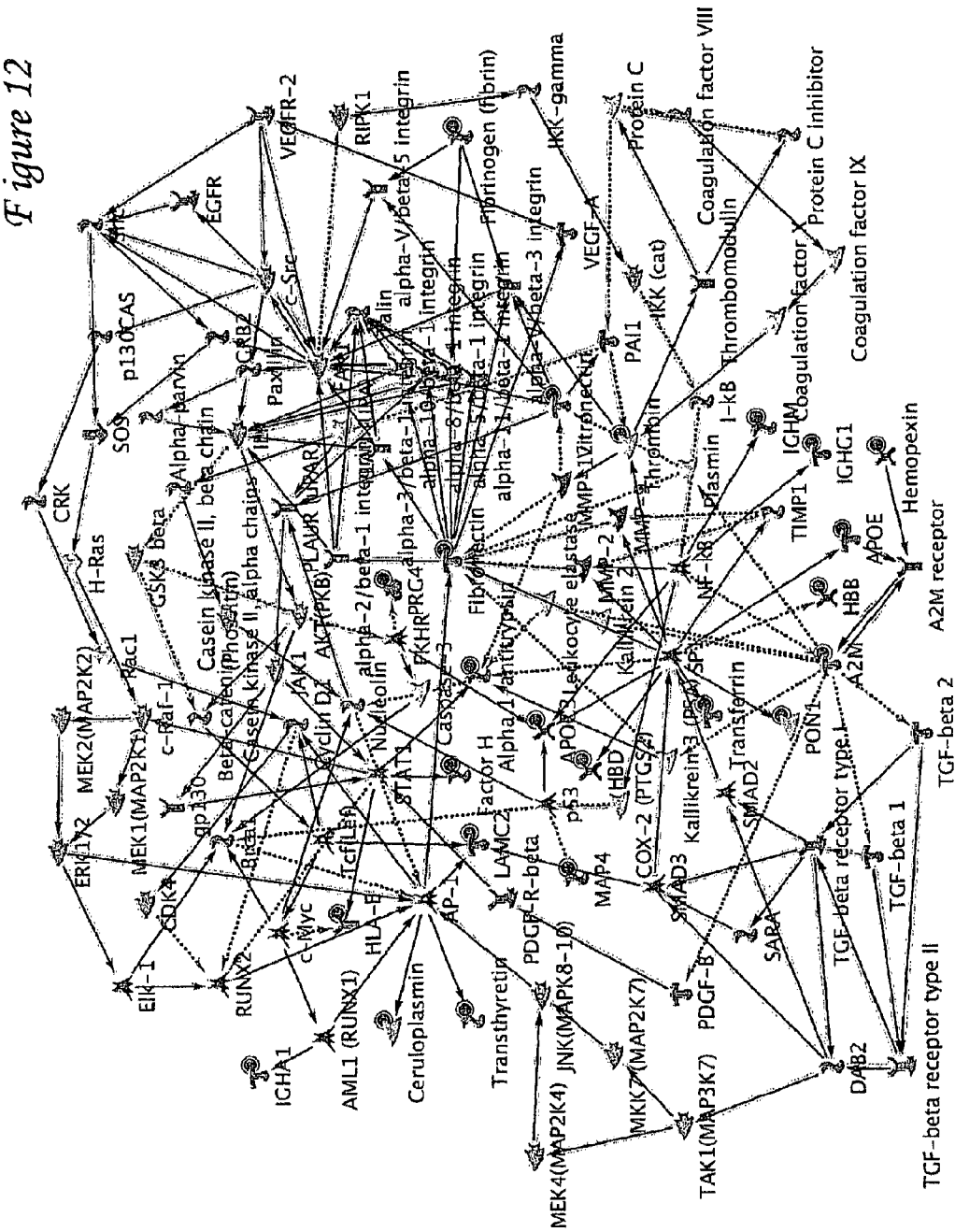
FIG. 12. A network analysis of transcription factors showing positive regulation of biological processes. Arrows with solid lines indicate activation, arrows with dashed lines indicate inhibition, and canonical pathways (either activating or inhibiting) are highlighted. This network is statistically significant to a P-Value of $3.47e^{-42}$.

The Build Network tool from GeneGo™ was used to identify protein-protein interactions and biological pathways shared by the proteins with an OSi~PTMs found in this work as shown in FIG. 12. We built the network by allowing GeneGo™ to find the shortest path between our data set and transcription factors using the Analyze Network by Transcription Factors. This is because many of the proteins identified were involved in DNA binding (see GO by Molecular function), immune system regulation, and biological process regulation (see GO by Biological process). From the list of networks obtained, the most statistically significant was a network involved in "positive regulation of biological processes" with a P-val of $3.47e^{42}$ that correlated with results obtained by DAVID. This network includes proteins such as Brca1 (the breast cancer type-1 susceptibility protein), TGFR-beta types I and II (transforming growth factor receptor beta), and proteins from the MAPKK pathway, all of which are involved in cancer.

Cellular Location

FIG. 13 shows the cellular locations of proteins that changed in concentration more than 50%. Three were located in the nucleus, 19 in the cytoplasm, two in membranes and the rest were in the extracellular compartment. The detection of nuclear, cytoplasmic, and the membrane proteins in the blood is an important piece of information in that it indicates these oxidized proteins were released by apoptosis and necrosis. They were not excreted. Excessive protein oxidation has been strongly associated with cell death in the literature.

Disease Distribution

Searching disease connections with GeneGo™ (FIG. 14), we found that breast neoplasm was the most likely disease associated with the proteins identified as having changed more than 50% in concentration. Atherosclerosis was the second most likely disease. Based on the fact that the "breast cancer patient" samples were known to have come from subjects diagnosed to have breast cancer and all of the blood donors were approximately 55 years of age, it is reasonable that GeneGo™ would associate these samples with breast neoplasia and atherosclerosis. The bars in FIG. 14 represent breast cancer donors compared to controls.

GeneGo™ GO Processes

The bars in FIG. 15 represent each of the six patients and indicate that the most commonly shared function of the oxidized proteins identified in the six patients involves immune system processes.

Amino acid side chain modifications identified in Example 3 are shown in FIG. 16. Oxidized proteins were recognized in data analysis by the identification of a peptide bearing an OSi~PTM, the site of the modification, and/or the structure of the modification. Before an oxidation site or type of oxidation was considered to have been identified, the presence of the OSi~PTM-bearing peptide and at least two unoxidized peptides from the same protein were required. No attempt was made to identify cross-linking sites. Mascot was used for the analysis of the mass spectra as described under Example 3. False positive identifications of OSi~PTM-bearing peptides was eliminated by using instrumentation such as the LTQ-Orbitrap XL™ with a mass accuracy approaching 1 ppm.

Based on GeneGo™ and DAVID analysis, the largest fraction of proteins associated with cancer was connected to immunity, both in terms of molecular function and biological processes involved. As a consequence, it was decided that identification of the participating oxidized immunoglobulins might shed light on this process. Biotin hydrazide-derivatized samples were analyzed using a two-dimensional fractionation scheme. The total immunoglobulin fraction of plasma samples was selected in a first separation dimension by affinity chromatography using an immobilized protein A/G column. The affinity selected immunoglobulin fraction was then subjected to avidin affinity chromatography in which biotinylated immunoglobulins were selected in a second separation dimension. Oxidized immunoglobulins thus selected were tryptic digested and identified as before.

Oxidation sites were characterized by pooling the six breast cancer patient samples and control samples, respectively, and biotinylated immunoglobulins from the two pooled samples were isolated and analyzed using the two-dimensional affinity chromatography approach described immediately above. Peptide identification was achieved using the LTQ Orbitrap XL™ mass spectrometer (Table 10). Twelve immunoglobulins were identified in the pooled breast cancer plasma sample while only eight were identified in the pooled normal plasma sample. Carbonylation sites were detected in five of these immunoglobulins (Table 11). A total of seven carbonylation sites were detected representing the three routes of carbonylation. Direct carbonylation was seen at T55 from arginine oxidation in the immunoglobulin heavy chain region while the glyoxal adduct at K97 in IGHG1 was from reaction with an advance lipid peroxidation end product and the deoxyglucosone adduct at K75 in immunoglobulin lambda light chain VU region was from advanced glycation end product formation.

TABLE 11-continued

Oxidation sites detected in the immunoglobulins in the breast cancer plasma (analyzed LTQOrbitrap XL)

| Accession number | Protein name | Oxidation site | Modification |
|---|---|---|---|
| gi\|11119125 | immunoglobulin heavy chain | T55 | Biotinylated 2-amino 3-ketobutyric acid |
| gi\|392717 | immunoglobulin heavy chain variable region | T90, R97 and P99 | T: Biotinylated 2-amino 3-ketobutyric acid, P and R: Biotinylated glutamic semialdehyde |

In order to characterize the oxidation sites of non-immunoglobulin proteins, the two-dimensional fractionation process described above was modified. The total immunoglobulin fraction of biotinylated samples was removed in the first

TABLE 10

Oxidized immunoglobulins detected in the normal and breast cancer plasma, respectively (analyzed LTQOrbitrap XL ™)

| | Normal plasma | | | | Breast cancer plasma | | | | |
|---|---|---|---|---|---|---|---|---|---|
| Protein accession number | Protein name | Protein score | Number of peptides used in the identification | percent coverage | Protein accession number | Protein name | Protein score | Number of peptides used in the identification | percent coverage |
| gi\|229601 | Ig G1 H Nle | 503 | 7 | 18.8 | gi\|229601 | Ig G1 H Nle | 551 | 6 | 20.5 |
| gi\|11275302 | anti TNF-alpha antibody light-chain Fab fragment | 372 | 4 | 28.5 | gi\|11275302 | anti TNF-alpha antibody light-chain Fab fragment | 320 | 4 | 28.5 |
| gi\|442920 | Chain B, Fab Fragment Of Humanized Antibody 4d5, Version 4 | 243 | 2 | 13.9 | gi\|442920 | Chain B, Fab Fragment Of Humanized Antibody 4d5, Version 4 | 268 | 2 | 13.9 |
| gi\|54778900 | immunoglobulin mu heavy chain | 153 | 2 | 13.7 | gi\|54778900 | immunoglobulin mu heavy chain | 182 | 4 | 22.5 |
| gi\|46254112 | immunoglobulin heavy chain | 156 | 2 | 14.3 | gi\|37777926 | immunoglobulin heavy chain variable region | 176 | 2 | 20.1 |
| gi\|12054078 | immunoglobulin heavy chain constant region gamma 4 | 246 | 2 | 11.9 | gi\|21669609 | immunoglobulin lambda light chain VLI region | 137 | 3 | 8 |
| gi\|185927 | immunoglobulin kappa-chain VK-1 | 404 | 4 | 34.1 | gi\|10334541 | immunoglobulin heavy chain | 130 | 3 | 11.9 |
| gi\|60688640 | IGHG1 protein | 288 | 4 | 13.3 | gi\|54780728 | immunoglobulin mu heavy chain | 90 | 4 | 13.3 |
| | | | | | gi\|2765425 | immunoglobulin lambda heavy chain | 362 | 5 | 12.4 |
| | | | | | gi\|9857759 | recombinant IgG4 heavy chain | 40 | 1 | 4.1 |
| | | | | | gi\|127514 | ig mu chain C region | 181 | 6 | 15.6 |
| | | | | | gi\|15779222 | IGHG1 protein [Homo sapiens] | 379 | 12 | 34 |

TABLE 11

Oxidation sites detected in the immunoglobulins in the breast cancer plasma (analyzed LTQOrbitrap XL)

| Accession number | Protein name | Oxidation site | Modification |
|---|---|---|---|
| gi\|15779222 | IGHG1 protein | K97 | Biotinylated glyoxal adduct |
| gi\|21669609 | immunoglobulin lambda light chain VLJ region | K75 | Biotinylated deoxyglucosone adduct |
| gi\|21669399 | immunoglobulin kappa light chain VLJ region | T220 | Biotinylated 2-amino 3-ketobutyric acid | dimension with a protein A/G affinity column as before. The immunoglobulin-stripped flow through fraction from the protein A/G column was used for avidin affinity selection in the second dimension. The eluted fraction from the avidin purification was then digested and analyzed by RPC-MS using the LTQ-Orbitrap XL™ as describe above. This resulted in the detection of 67 non-immunoglobulins while only 32 non-immunoglobulins were detected when immunoglobulins were not removed.

Twenty-six proteins were shown to have at least one oxidation site (Table 12). A total of 21 carbonyls carried on eleven proteins were detected. Fifteen of them were direct carbonylation products (oxidized proline, arginine, threonine, or lysine). Six were formed by indirect carbonylation (glyoxal, methyl glyoxal, malondialdehyde, or Amadori adducts). Proteoglycan-4 precursor carried four carbonylation sites, the largest number of carbonylation sites observed for any single protein in this study. Each of the four sites present in proteoglycan-4 precursor was a site of direct ROS oxidation of an arginine, proline, or threonine residue. In the other proteins, direct oxidation sites included twenty-nine methionine sulfoxides, one methionine sulfone, two hydroxyl leucines, one hydroxyproline, one hydroxyphenylalanine, one oxo-histidine, and one cysteine sulfenic acid.

TABLE 12

Oxidation sites detected in the non-immunoglobulin proteins in the breast cancer plasma (analyzed LTQOrbitrap XL ™)

| Accession | Protein name | Oxidation site | Modification |
|---|---|---|---|
| CO3_HUMAN | Complement component C3 | K678 | Biotinylated oxidized lysine (aminoadipic semialdehyde) |
| | | M42, M201, M990 | Methionine sulfoxide |
| | | P366 | Hydroxyproline |
| FINC_HUMAN | Fibronectin precursor (FN) | P1759 | Biotinylated oxidized proline (glutamic semialdehyde) |
| | | K1586 | Biotinylated amadori adduct |
| | | M926, M1548 | Methionine sulfoxide |
| A1AT_HUMAN | Alpha-1-antitrypsin precursor (Alpha-1 protease inhibitor) | K246, | Biotinylated oxidized lysine (aminoadipic semialdehyde) |
| | | R247 | Biotinylated oxidized arginine (glutamic semialdehyde) |
| | | L377 | Hydroxyleucine |
| CLUS_HUMAN | Clusterin precursor | T63 | Biotinylated oxidized threonine (2-amino-3-ketobutyric acid) |
| C4BP_HUMAN | C4b-binding protein alpha chain precursor (C4bp) | K14, K16 | Biotinylated oxidized lysine (aminoadipic semialdehyde) |
| CFAH_HUMAN | Complement factor H precursor (H factor 1) | R1149 | Biotinylated oxidized arginine (glutamic semialdehyde) |
| | | T1151 | Biotinylated oxidized threonine (2-amino-3-ketobutyric acid) |
| | | P1160 | Biotinylated oxidized proline (glutamic semialdehyde) |
| PRG4_HUMAN | Proteoglycan-4 precursor (Lubricin) (Megakaryocyte stimulating factor) | K1048 | Biotinylated oxidized lysine (aminoadipic semialdehyde) |
| | | T1156 | Biotinylated oxidized threonine (2-amino-3-ketobutyric acid) |
| | | T1391 | Biotinylated oxidized threonine (2-amino-3-ketobutyric acid) |
| | | R1392 | Biotinylated oxidized arginine (glutamic semialdehyde) |
| HBA_HUMAN | Hemoglobin subunit alpha | P6 | Biotinylated oxidized proline (glutamic semialdehyde) |
| | | T10 | Biotinylated oxidized threonine (2-amino-3-ketobutyric acid) |
| APOB_HUMAN | Apolipoprotein B-100 precursor | K293 | Biotinylated methyl glyoxal adduct |
| | | K2425 | Biotinylated glyoxal adduct |
| | | M812, M901, M1234, M2042, M2597, M3267 | Methionine sulfoxide |
| | | M564 | Methionine sulfone |
| ITIH2_HUMAN | Inter-alpha-trypsin inhibitor heavy chain H2 precursor | K902 | Biotinylated methyl glyoxal adduct |
| CFAB_HUMAN | Complement factor B precursor | K648 | Biotinylated malondialdehyde adduct |
| | | K652 | Biotinylated Amadori adduct |
| ALBU_HUMAN | Serum albumin precursor | C148 | Sulfenic acid |
| | | M353 | Methionine sulfoxide |
| A2MG_HUMAN | Alpha-2-macroglobulin precursor | F155 | Hydroxyphenylalanine |
| | | M713, M1378 | Methionine sulfoxide |
| APOA1_HUMAN | Apolipoprotein A-I precursor | M136 | Methionine sulfoxide |
| VTNC_HUMAN | Vitronectin precursor | M350, M359 | Methionine sulfoxide |
| CLUS_HUMAN | Clusterin precursor | H171 | 2-Oxo-histidine |
| | | M431 | Methionine sulfoxide |
| FIBB_HUMAN | Fibrinogen beta chain precursor | M468 | Methionine sulfoxide |
| APOE_HUMAN | Apolipoprotein E precursor | M153 | Methionine sulfoxide |
| FIBA_HUMAN | Fibrinogen alpha chain precursor | M537 | Methionine sulfoxide |
| C4BP_HUMAN | C4b-binding protein alpha chain precursor | M248 | Methionine sulfoxide |
| PON1_HUMAN | Serum paraoxonase/arylesterase 1 | L14 | Hydroxyleucine |
| | | M12 | Methionine sulfoxide |
| C1R_HUMAN | Complement C1r subcomponent precursor | M472 | Methionine sulfoxide |
| | | M394 | Methionine sulfoxide |
| CFAH_HUMAN | Complement factor H precursor | M162 | Methionine sulfoxide |

TABLE 12-continued

Oxidation sites detected in the non-immunoglobulin proteins in the breast cancer plasma (analyzed LTQOrbitrap XL ™)

| Accession | Protein name | Oxidation site | Modification |
|---|---|---|---|
| TRFE_HUMAN | Serotransferrin precursor | M275 | Methionine sulfoxide |
| APOA4_HUMAN | Apolipoprotein A-IV precursor | M322 | Methionine sulfoxide |
| FETUA_HUMAN | Alpha-2-HS-glycoprotein precursor | M321 | Methionine sulfoxide |

We show that the elevated concentration of oxidized proteins in plasma that correlates with breast cancer is the result of increased oxidation of a small group of proteins at specific sites. Based on affinity chromatographic selection of oxidized proteins and proteins with which they are conjugated, a total of 460 proteins were identified. Among these proteins, 98 changed in concentration by more than 50%. These proteins appear to be oxidized at a small number of specific sites.

Despite isolating the oxidized proteins from plasma samples, at least some of the oxidized proteins are of tumor origin and not native to the circulation. Network analysis with GeneGo™ showed a clear involvement of the tumor suppressor breast cancer type 1 (BRCA1) gene pathway. This pathway is responsible for maintaining the integrity of genes in response to DNA damage induced by several factors including, for example, oxidative stress. To perform this function, BRCA1 interacts with various repair proteins. Additionally, the loss or reduction of BRCA1 alters TGF-β growth inhibiting activity during cellular response to oxidative stress. Moreover, oxidative stress activates the migration of poorly invasive cancer cells through the activation of Erk signaling. Comparative network analysis of the age and oxidant-estrogen+ER52 gene signatures reveals two such pathways, the tumor necrosis factor (TNF) and transforming growth factor-β (TGF-β) signaling pathways, which are common to both oxidatively stressed and early-onset ER-positive breast cancers. Thus, some portion of the oxidized proteins in the plasma of breast cancer patients arose from tumor cells.

This conclusion is supported by gene ontology analyses in which the molecular function of the oxidized, elevated proteins was found to be broadly in the areas of immunity, nucleic acid binding, DNA helicase, serine protease inhibitors, microtubule binding proteins, RNA helicase, carrier proteins, actin binding proteins, and extracellular matrix proteins. An unbiased in silico analysis of biological function revealed that the oxidized proteins were associated with responses to immune system processes, protein transport, positive regulation of biological processes, acute inflammatory response, cell adhesion, cytoskeleton organization, and biogenesis. All of these processes are components of the Brca1 (Breast cancer type-1 susceptibility protein) pathway.

Figure 11:
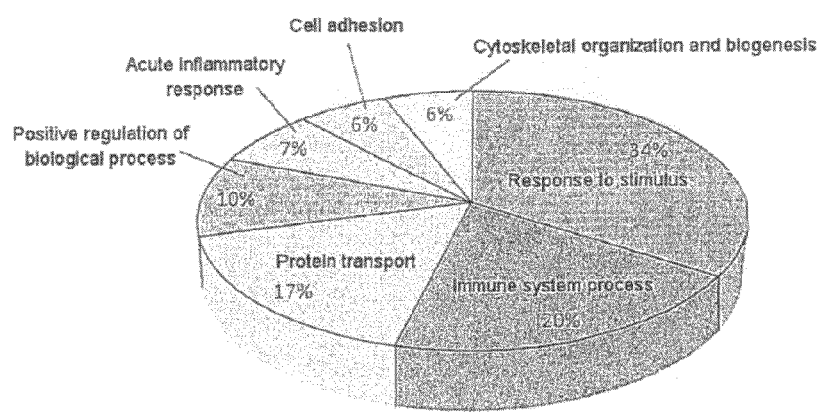
FIG. 11. DAVID gene ontology (GO) by biological process of proteins that changed more than 50% in the plasma of BC patients compared to their controls.

Moreover, the proteins and their oxidation sites may represent a peptidic breast cancer signature or profile. The complete list of proteins that changed more than 1.5-fold strongly correlated with breast neoplasia based on their role in signaling pathways related to breast cancer. The plasma concentrations of these oxidized proteins changed by more than 50%, relative to controls, in the six breast cancer patients, despite the variability observed between patients (FIG. 11).

Parkinson's Disease

Example 4 describes using the methods described herein to analyze oxidized peptides associated with Parkinson's disease. Mutations in the gene encoding DJ-1 have been identified in patients with familial Parkinson's disease (PD) and are thought to inactivate a neuroprotective function. The oxidation of a cysteine residue, C106, to the sulfinic acid can enhance the protein's neuroprotective activity, whereas "over-oxidation" to the sulfonic acid may be detrimental. Some familial mutations may disrupt DJ-1 activity by interfering with the conversion of C106 to the sulfinic acid. Methods described in Example 4 may be used to measure the degree of oxidation at specific sites in mutant DJ-1 as compared to the wild-type protein.

Recombinant wild-type DJ-1 and M26I, a mutant involved in familial PD, were treated with different amounts of $H_2O_2$ and compared with untreated samples using a method involving trypsin digestion, $^{18}O$ labeling, and tandem mass spectrometry. Seven sites of oxidative modification involving cysteine, methionine, and histidine residues were identified, and in each case the degree of oxidation was quantified. Treatment of wild-type DJ-1 with a 10-fold molar excess of $H_2O_2$ resulted in a robust oxidation of C106 to cysteine sulfuric acid, whereas this modification was approximately sevenfold less abundant in a sample of M26I exposed to identical conditions. These results were validated by 2D-PAGE data, which showed that the M26I mutant was oxidized less readily at C106 than the wild-type protein. These findings suggest that the M26I substitution (and potentially other DJ-1 mutations identified in familial PD patients) disrupts DJ-1 function by interfering with a site-specific oxidative modification required for optimal neuroprotective activity.

Parkinson's disease (PD) is a neurodegenerative disorder characterized by muscular rigidity, slowness of voluntary movement, poor balance, and tremor at rest. These symptoms are caused by the death of neurons in a region of the midbrain called the substantia nigra. The neurons that survive in this region exhibit a defect in complex I of the mitochondrial electron transport chain and show signs of oxidative damage. In addition, surviving neurons contain characteristic cytosolic inclusions named "Lewy bodies" that are enriched with aggregated forms of the presynaptic protein α-synuclein (aSyn). Reactive oxygen species may accumulate as a result of mitochondrial impairment and contribute to neurodegeneration by causing the oxidation of lipid, proteins, and DNA. A buildup of reactive oxygen species may promote the formation of harmful aSyn aggregates in the brains of PD patients. ROS accumulation is thought to occur preferentially in nigral dopaminergic neurons because of the catabolism and auto-oxidation of dopamine, reactions that result in the generation of $H_2O_2$.

Some patients with familial, early-onset, recessive PD have been found to harbor homozygous loss-of-function mutations (e.g., M26I, E64D, A104T, D149A, E163K, L166P) in the gene encoding DJ-1, a homodimeric protein (subunit molecular weight=20 kDa) that is abundant throughout the central nervous system. Dysfunction of wild-type DJ-1 as a result of destabilizing oxidative modifications is also thought to play a role in more common sporadic forms of PD. DJ-1 may suppress neurodegeneration in cellular and animal models by activating antioxidant responses, upregulating or carrying out a molecular chaperone function, and/or inducing pro-survival signaling responses. Cysteine 106 (C106) in the DJ-1 sequence may be readily oxidized to the sulfinic acid (or "2O") form under oxidizing conditions.

Structural data indicate that C106 is located in a pocket at the subunit interface lined with polar residues from both subunits, and these residues facilitate the oxidation of C106 to the sulfinic acid. The design of this pocket suggests that controlled oxidation of DJ-1 at position 106 is advantageous for optimal DJ-1 function. Consistent with this idea, the oxidation of C106 to the 2O form is apparently critical for the ability of DJ-1 to translocate to mitochondria or suppress fibril formation by recombinant α-synuclein. In contrast, overoxidation of DJ-1, leading to the conversion of C106 to the sulfonic acid ("3O") form may result in thermodynamically instability and a loss of chaperone activity.

The L166P mutant has a pronounced protein-folding defect, resulting in impaired homodimer formation, rapid protein turnover, and a high propensity to form large protein complexes. In contrast, other substitutions destabilize the protein to a lesser extent, and it is unclear why they disrupt DJ-1 function. As one possibility, some of these mutants may have a lower ability to undergo oxidation at position 106 to yield the 2O form. Thus, we examined the impact of the M26I familial substitution on the propensity of DJ-1 to become oxidized at position 106 and other sites on the polypeptide chain. Using a novel mass spectrometry approach, we quantified site-specific oxidative modifications of M26I as compared to wild-type DJ-1 after treatment with different amounts of $H_2O_2$. Our results indicate that the M26I substitution has a profound disruptive effect on the ability of DJ-1 to undergo oxidation at C106.

Figure 17:
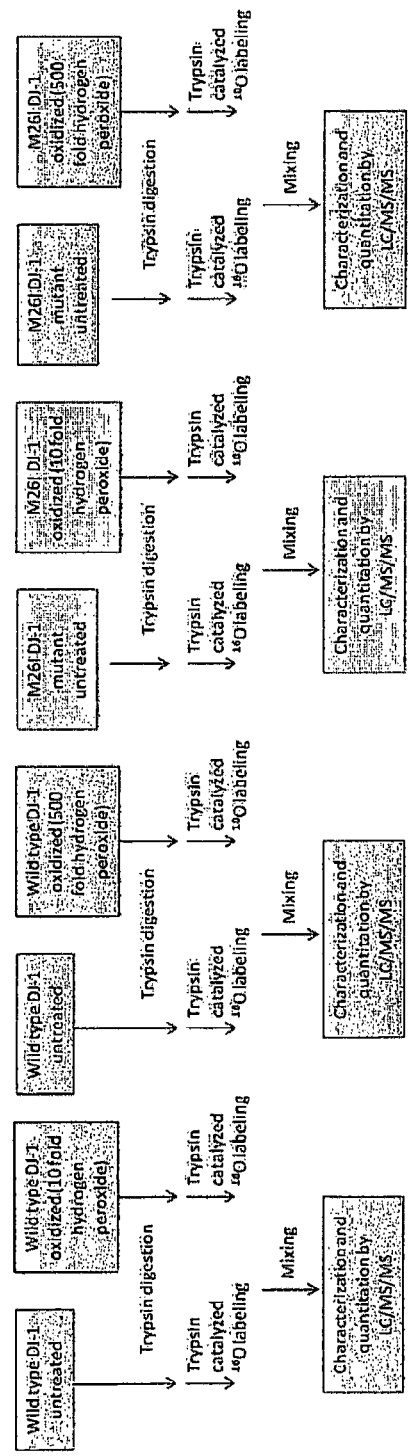
FIG. 17. Schematic overview of the strategy used to quantitate oxidative modifications of DJ-1. Wild-type DJ-1 and M26I were untreated or exposed to a 10- or 500-fold molar excess of $H_2O_2$. The proteins were digested with trypsin, and the tryptic peptides were labeled by trypsin-catalyzed $^{16}O/^{18}O$ labeling. The $^{16}O$- and $^{18}O$-labeled peptides were mixed and analyzed by nanoscale LC/MS/MS.

Example 4 describes an analytical strategy that combines affinity purification, $^{18}O$ labeling, and LC-MS analysis (FIG. 17). Recombinant wild-type DJ-1 and M26I isolated from *E. coli* were untreated or treated with a 10- or 500-fold molar excess of $H_2O_2$. After tryptic digestion, the proteins were labeled at the C-terminus with either $^{16}O$ (untreated DJ-1) or $^{18}O$ ($H_2O_2$-treated DJ-1) by incubation with trypsin in either $H_2^{16}O$ or $H_2^{18}O$, respectively. The $^{16}O$- and $^{18}O$-labeled peptides were mixed and analyzed by nanoscale LC/MS/MS. Sequence-specific oxidative modifications were then quantitated by measuring the ratio of $^{18}O$- to $^{16}O$-labeled peptides. Next, the mass spectrometry data were validated by characterizing wild-type DJ-1 and M26I in terms of their propensities to undergo C106 oxidation via 2D-PAGE. Finally, to better understand why wild-type DJ-1 and M26I exhibit different degrees of oxidation, the two proteins were compared in terms of thermodynamic stability and quaternary structure.

Approximately 6400 spectra were obtained for each analysis. The following post-translational modifications were identified and quantified: (i) oxidation of two cysteine residues (C53 and C106) to the sulfuric or sulfonic acid; and (ii) oxidation of four methionine residues (M17, M26, M133, and M134), to the sulfoxide or sulfone.

Figure 18:
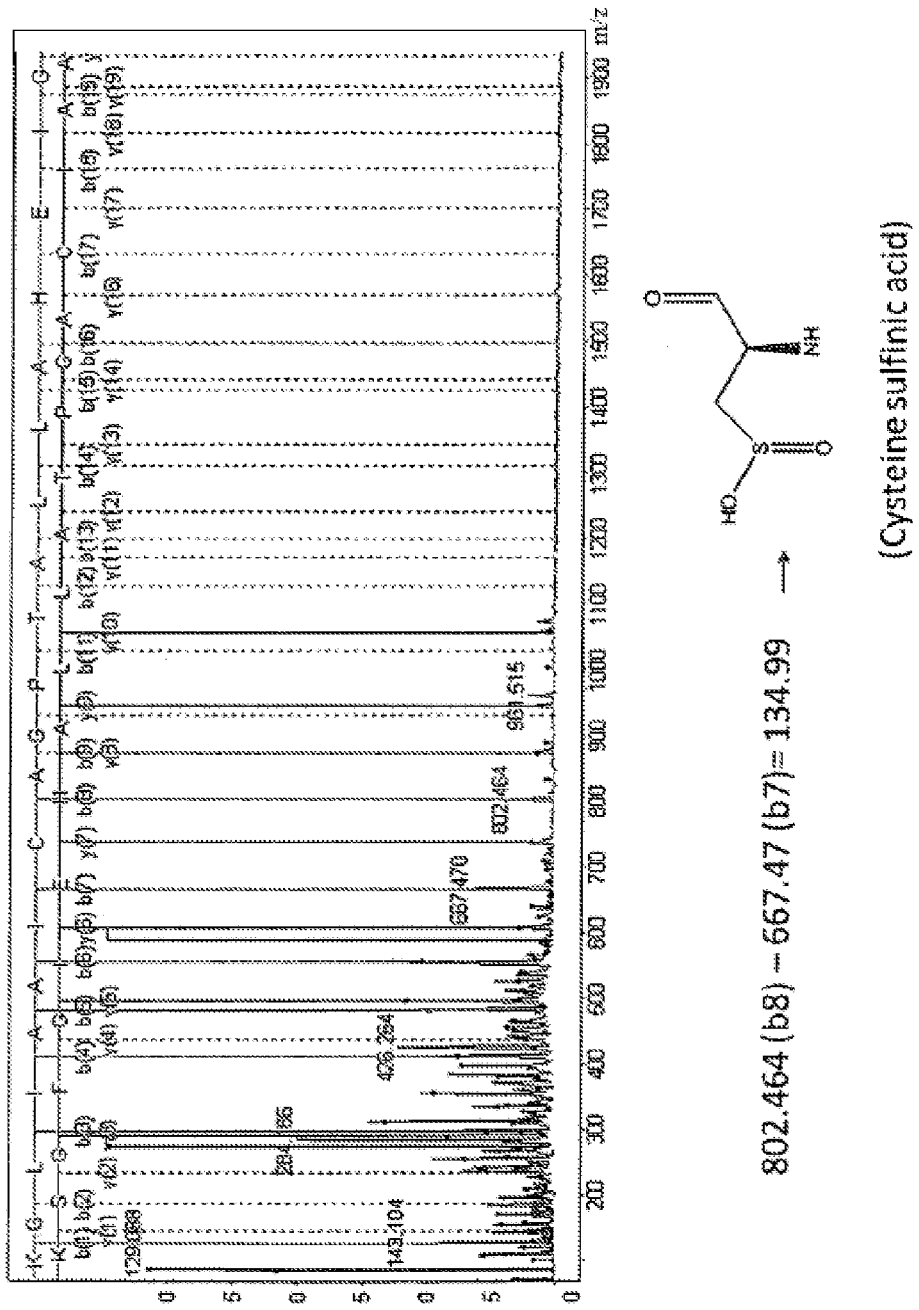
FIG. 18. MS/MS analysis of peptide $^{99}$KGLIAAICAGP-TALLABEIGFGSK$^{122}$ (SEQ ID NO:1) in wild-type DJ-1 oxidized with a 10-fold molar excess of $H_2O_2$. (Top) MS/MS spectrum with all of the y and b ions assigned. The y and b ion map is superimposed on the peptide sequence. (Bottom) C106 is oxidized to cysteine sulfinic acid ("2O" form) according to the Mascot identification. The difference between the masses of the b8 and b7 ions equals the mass of cysteine sulfinic acid.
Figure 19:
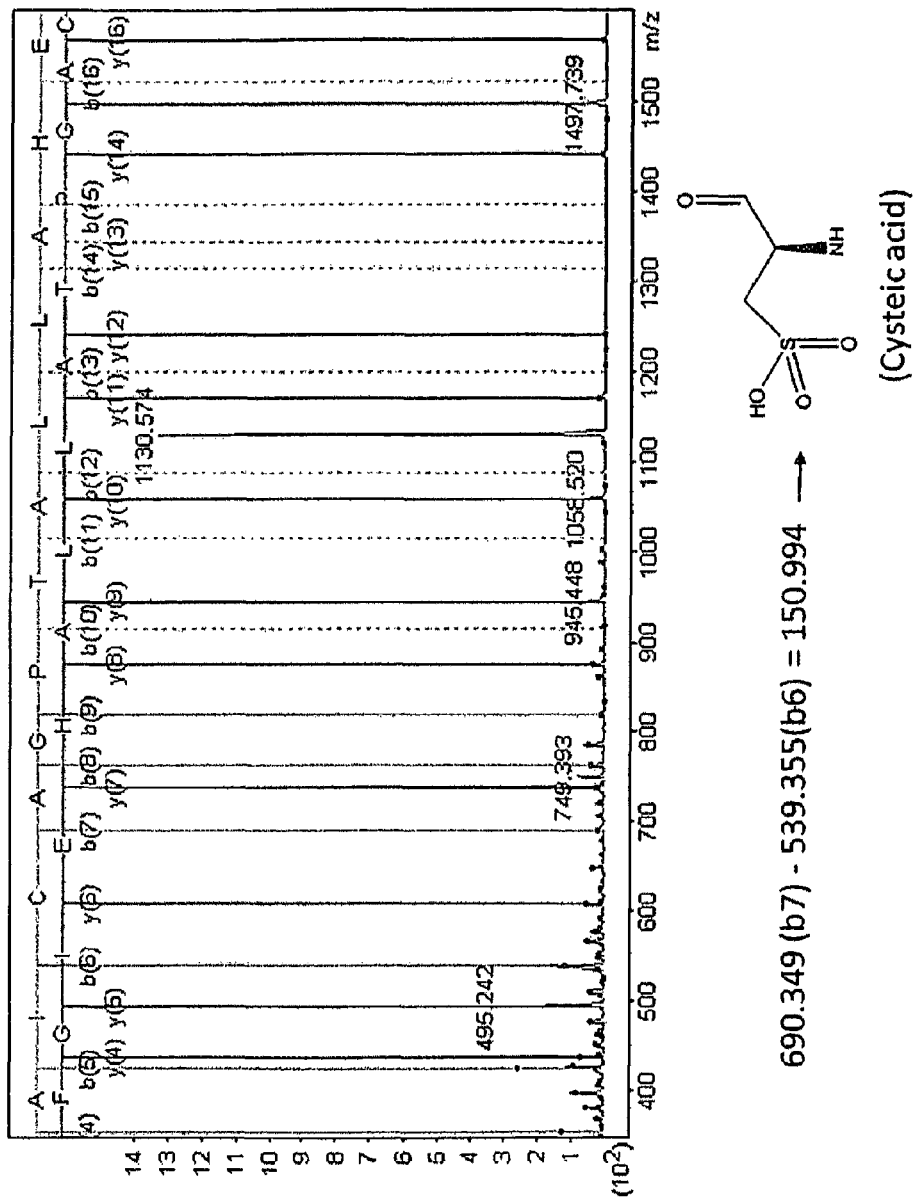
FIG. 19. MS/MS analysis of peptide $^{100}$GLIAAICAGP-TALLAHEIGFGSK$^{122}$ (SEQ ID NO:2) in wild-type DJ-1 oxidized with a 500-fold molar excess of $H_2O_2$. (Top) MS/MS spectrum with all of the y and b ions assigned. The y and b ion map is superimposed on the peptide sequence. (Bottom) C106 is oxidized to cysteic acid ("3O" form) according to the Mascot identification. The difference between the masses of the b7 and b6 ions equals the mass of cysteic acid.
Figure 20:
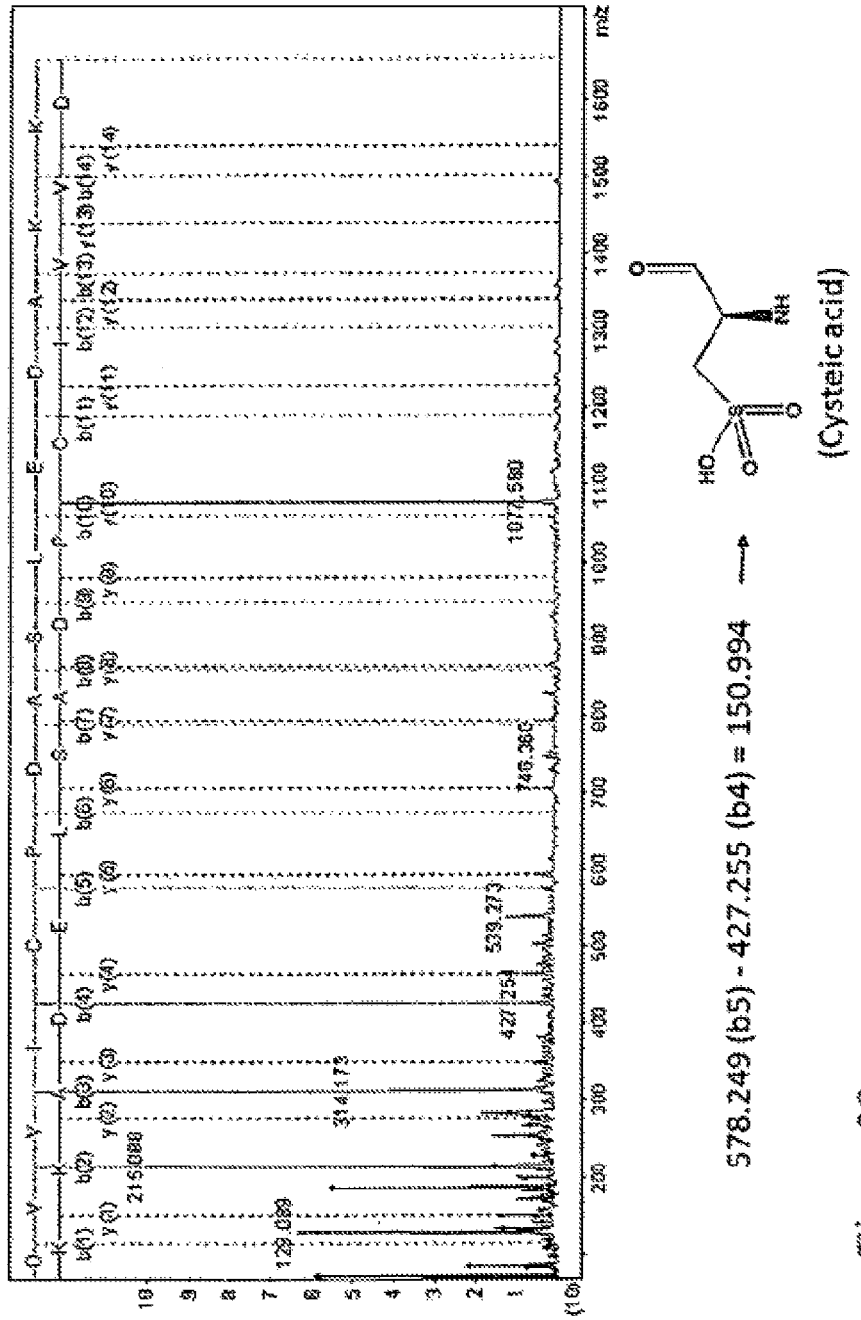
FIG. 20. MS/MS analysis of peptide $^{49}$DVVICP-DASLEDAKK$^{63}$ (SEQ ID NO:3) in the M26I mutant DJ-1 protein oxidized with 500-fold molar excess of $H_2O_2$. (Top). MS/MS spectrum with all of the y and b ions assigned. The y and b ion map is superimposed on the peptide sequence. (Bottom) C53 is oxidized to cysteic acid ('3O' form) according to the Mascot identification. The difference between the masses of the b5 and b4 ions equals the mass of cysteic acid.

Treatment of DJ-1 with $H_2O_2$ resulted in a dose-dependent oxidation of the protein's cysteine residues to the sulfinic or sulfonic acid form. FIG. 18 shows the MS/MS spectrum of peptide $^{99}$KGLIAAICAGPTALLAHEIGFGSK$^{122}$ (SEQ ID NO:1) derived from wild-type DJ-1 following oxidation with a 10-fold molar excess of $H_2O_2$. The "y" and "b" ion peaks in the spectrum were assigned labels corresponding to their m/z values. The mass difference between the b(8) ion (m/z=802.464 Da) and the b(7) ion (m/z=667.47 Da) was equal to the mass of a cysteine sulfinic acid (134.99 Da), suggesting that residue C106 had undergone oxidation to the form under these conditions. FIG. 19 shows the MS/MS spectrum of peptide $^{100}$GLIAAICAGPTALLAHEIGFGSK$^{122}$ (SEQ ID NO:2) derived from wild-type DJ-1 after oxidation with a 500-fold molar excess of $H_2O_2$. In this case the mass difference between b(7) (m/z=690.349 Da) and b(6) (m/z=539.355 Da) was equal to the mass of cysteine sulfonic acid (150.994 Da), suggesting that C106 was converted to the 3O form under the more stringent oxidizing conditions. Similarly, the MS/MS spectrum of peptide $^{49}$DVVICPDASLEDAKK$^{63}$ (SEQ ID NO:3) derived from M26I following exposure with a 500-fold molar excess of $H_2O_2$ clearly revealed a difference between b(5) (m/z=578.249 Da) and b(4) (m/z=427.255 Da) equal to the mass of cysteine sulfonic acid (FIG. 20), suggesting that C53 was oxidized to the 3O form upon exposure to the high dose of peroxide.

Figure 21:
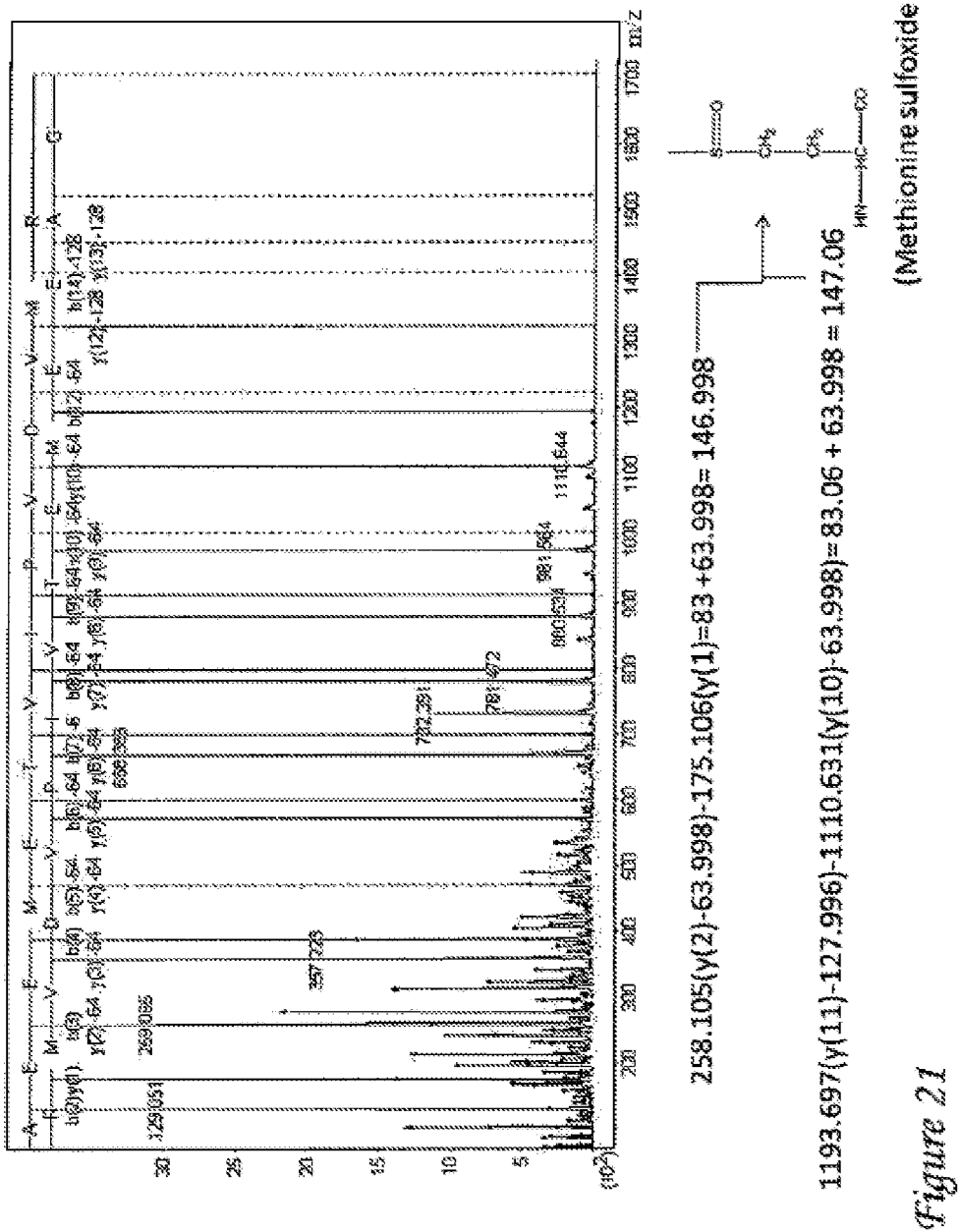
FIG. 21. MS/MS analysis of peptide $^{13}$GAEEMETVIPVDVMR$^{27}$ (SEQ ID NO:4) in wild-type DJ-1 oxidized with a 500-fold molar excess of $H_2O_2$. (Top) MS/MS spectrum with all of the y and b ions assigned. The y and b ion map is superimposed on the peptide sequence.

The identification of oxidized methionine residues is more complex because methionine sulfoxide (MetSO) undergoes a characteristic neutral loss of methanesulfenic acid ($CH_3SOH$, 63.998 Da) during collision-induced dissociation. The Mascot search engine accounts for this neutral loss when assigning peaks in the MS/MS spectrum. FIG. 21 shows the MS/MS spectrum of peptide $^{13}$GAEENEETVIPVDVMR$^{27}$ (SEQ ID NO:4) derived from wild-type DJ-1 following oxidation with a 500-fold molar excess of $H_2O_2$. The mass difference between y(11) (m/z=1193.697 Da after the neutral loss of two $CH_3SOH$ groups) and y(10) (m/z=1110.631 Da after the neutral loss of one $CH_3SOH$ group) was equal to the mass of methionine sulfoxide minus the neutral loss mass (83 Da=147 Da−64 Da). Additionally, the mass difference between y(2) (m/z=258.105 Da after the neutral loss of $CH_3SOH$) and y(1) (m/z=175.106 Da) was equal to the mass of methionine sulfoxide minus the neutral loss mass (83 Da). These results indicate that both methionine residues in the parent peptide (M17 and M26) were oxidized to methionine sulfoxide under these $H_2O_2$ treatment conditions. Additional MS/MS data revealed the presence of methionine sulfoxide at positions 133 (FIG. 22) and 134 (FIG. 23) of peptide $^{131}$DKMNINGGMYTYSENRVEK$^{148}$ (SEQ ID NO:5) derived from wild-type DJ-1 oxidized with a 500-fold molar excess of $H_2O_2$.

Next we determined relative levels of post-translationally modified DJ-1 peptides generated in the presence of a low or high concentration of $H_2O_2$ via quantitative analysis of the MS peak intensities. The method involved dividing the peak intensity of each $^{18}O$-labeled peptide from $H_2O_2$-treated wild-type DJ-1 or M26I by the peak intensity of the identical $^{16}O$-labeled peptide derived from the untreated protein. Reproducible data from three independent experiments revealed remarkable differences in relative levels of cysteine-modified peptides when comparing wild-type DJ-1 and M26I exposed to a 10- or 500-fold molar excess of $H_2O_2$ (FIG. 24, Table 13). These differences include: (i) wild-type DJ-1 exhibited markedly higher relative levels of C106 sulfinic acid compared to M26I following incubation with a 10-fold molar excess of $H_2O_2$; (ii) the wild-type protein (but not M26I) exhibited higher relative levels of C106 sulfinic acid after exposure to a 10-fold molar excess of $H_2O_2$ compared to a 500-fold molar excess of the peroxide; (iii) wild-type DJ-1 exhibited dramatically higher relative levels of C106 sulfonic acid compared to M26I after incubation with a 500-fold molar excess of $H_2O_2$ whereas the "3O" form of C106 was essentially undetectable in samples of wild-type DJ-1 or M26I exposed to a 10-fold molar excess of the peroxide); (iv) M26I (but not wild-type DJ-1) exhibited an increase in relative levels of C53 sulfonic acid following exposure to a 500-fold molar excess of $H_2O_2$ (whereas this modification didn't appear in any other forms of the protein). In contrast to the pronounced differences in relative levels of cysteine oxidation products outlined above, the relative abundance of peptides containing methionine sulfoxide varied little between wild-type DJ-1 and M26I following exposure of the proteins to a 10-fold or 500-fold molar excess of $H_2O_2$ (FIG. 24, Table 13).

TABLE 13

Quantitation of oxidative modifications in wild-type DJ-1 and M26I[a]

| | Mass spectral ratio[a] | | | |
|---|---|---|---|---|
| oxidative | 10-fold molar excess $H_2O_2$ | | 500-fold molar excess $H_2O_2$ | |
| modification | wild-type DJ-1 | M26I | wild-type DJ-1 | M26I |
| C53 sulfonic acid | ND[b] | ND[b] | ND[b] | 4.0 ± 0.4 |
| C106 sulfinic acid | 12 ± 3 | 2.8 ± 0.8 | 5.1 ± 0.7 | 4.0 ± 0.6 |
| C106 sulfonic acid | ND[b] | ND[b] | 30.3 ± 0.9 | 4.1 ± 0.4 |
| H115 asparagine | 1.95 ± 0.03 | ND[b] | 2.1 ± 0.7 | ND[b] |
| M17 sulfoxide | 0.3 ± 0.2 | ND[b] | 0.26 ± 0.01 | ND[b] |
| M133 sulfoxide | 0.2$_5$ ± 0.2$_2$ | 0.2 ± 0.1 | 1 ± 2 | 2 ± 2 |
| M134 sulfoxide | 0.2 ± 0.2 | 0.2 ± 0.1 | 0.9 ± 0.5 | 0.39 ± 0.02 |

[a]Mass spectral ratios were determined by dividing the peak intensity of each $^{18}O$-labeled peptide derived from $H_2O_2$-treated DJ-1 by the peak intensity of the identical $^{16}O$-labeled peptide derived from untreated (control) protein. Mean ± SEM, N = 3.
[b]ND, not detected.

Structural and functional data suggest that the oxidation of DJ-1 to the 2O form enhances the protein's protective function. M26I, a pathogenic mutation to DJ-1, causes significant changes in the degree of oxidation of various residues inside the protein. The oxidation sites quantitated were: dioxidation of C106, trioxidation of C106, trioxidation of C46, oxidation of methionines M17, M133, M134, and the oxidation of histidine 115 to asparagine. The most dramatic changes in the degree of oxidation were in the C106 oxidation that is involved in the function of DJ-1. The M26I mutation reduced oxidation C106 to sulfuric acid more than 6-fold. In the wild-type DJ-1, oxidation of C106 to sulfinic acid is involved in the inhibition of the α-synuclein fibrillation. The reduced of this oxidation by the M26I mutation may reduce the anti-aggregation activity against α-synuclein.

These changes can be attributed to the change in the geometry of the protein. M26I is located in the core of the protein dimer. Although the M26I mutation occurs in the helical region near the dimer interface, it is involved in the formation of the dimer. The replacement of the bulky methionine with the smaller isoleucine, in this mutation, causes a packing defect in the interior of the protein. CD and X-ray crystallographic data of the reduced M26I DJ-1 indicated that the protein maintained its secondary structure in solution and in crystal. On the other hand, under oxidative stress conditions, M26I DJ-1 has a reduced secondary structure, low stability, and tends to aggregate. These slight conformational changes may have caused the change in the degree of oxidation reported in our study. Additionally, NMR data suggest that residues near M26 had chemical shifts that may indicate alterations that could influence C106 oxidation.

Another modification in the M26I mutant is the trioxidation of C106 to cysteic acid. This modification is reduced more than 7-fold in the M26I mutant. The presence of both cysteine sulfinic acid and cysteic acid residues at C106 in both the wild-type DJ-1 and M26I DJ-1 proteins exposed to 500 molar-fold of hydrogen peroxide may indicate that the oxidation of C106 to cysteic acid passes first by the conversion to sulfinic acid then to cysteic acid.

Also, trioxidation of the C46 residue appeared in the M26I mutant, but only when oxidized with 500 mM hydrogen peroxide. To our knowledge, this is the first time that trioxidation of C46 in the M26I mutant has been reported. C46 is partially buried within the dimer interface. The C46 residue modulates the C106-dependent binding of DJ-1 to ASK1. This binding depends on the oxidation of C106 to disulphide bond. Therefore, the increased oxidation at C46 in the M26I mutant may have modulated the function of the C106 residue.

Changes in the degree of methionine oxidation at positions 17, 133, and 134 were also analyzed.

The data presented here, together with observations that oxidation of DJ-1 to the 2O form is necessary for inhibition of aSyn aggregation, suggest that M26I may have a reduced ability to suppress aSyn fibrillation than the wild-type protein. In addition, the oxidation of DJ-1 at position 106 is necessary for protection against toxicity related to complex I inhibition. Accordingly, the decreased propensity of M26I to undergo conversion to the 2O form as shown in Example 4 may result in various functional defects in familial PD patients, including a reduced ability of the protein to carry out a chaperone function in cytosolic and/or mitochondrial compartments.

Finally, this study exploited the unique power of mass spec-based proteomic techniques for the quantitation of the effect of the M26I mutation on the level of oxidation of different residues in the DJ1 protein. While mass spectrometry has been used before to identify DJ-1 post-translation modifications, mass spectrometry has not been used to quantitate post-translation modifications under the effect of the pathogenic mutations.

Diabetes Mellitus

Example 5 describes using methods described herein to identify and analyze proteins associated with diabetes mellitus, by assessing qualitative and quantitative differences in carbonylated proteins shed, under oxidative stress, from organs and into the blood of diabetic and lean rats. Carbonylated proteins were obtained, prepared and analyzed as described in Example 5. The avidin affinity column bound approximately 1.7% of the proteins in the plasma of Zucker diabetic rats as compared to 0.98% in the case of plasma from lean rats.

Thirty proteins were identified and quantified. The concentration of four out of the thirty proteins changed significantly. The most significant changes occurred in the proteins Apo, AII, clusterin, and hemopexin precursor. Eighteen carbonylated peptides were detected and quantified, eleven of these eighteen exhibited significant concentration changes.

The oxidized proteins exhibited three types of carbonylation: direct oxidative cleavage by reactive oxygen species, oxidation of advanced glycation end products, and addition of lipid peroxidation end products. Carbonylation by direct oxidation of amino acid side chains was the most common form of protein oxidation observed. Hemoglobin was the most heavily oxidized protein. Carbonylation sites in proteins generally occurred in a non-stoichiometric ratio.

Finally, the analyses revealed molecular signatures associated with diabetes based on the identity of oxidized proteins in the plasma of a diabetic animal model and the sites of oxidation.

Diabetes is characterized by hyperglycemia, which can lead to oxidative stress that can drive flux increases in multiple pathways (Brownlee, M. *Diabetes*, 2005, 54:1615-1625). Hallmarks of hyperglycemia include flux elevation in the 1) polyol pathway, 2) formation of advanced glycation end products, 3) activation of protein kinase C, and/or 4) flow of metabolites in the hexosamine pathway, all of which can lead to tissue damage in diabetics (Brownlee, M. *Nature*, 2001, 414:813-820). Tissue damage from hyperglycemia may be the result of increased production of reactive oxygen species such as, for example, superoxide anions in mitochondria, which in turn disrupt cell signaling by protein oxidation (Evans et al., *Diabetes*, 2003, 52:1-8; Evans et al., *Endocrine Reviews*, 2002, 23:599-622; Brownlee, M. *Diabetes*, 2005, 54:1615-1625; Vincent et al., *Endocrine Reviews*, 2004, 25:612-628).

Oxidative stress in involved in diabetes-associated damage to the kidney, eyes, and the nervous system (Brownlee, M. *Nature*, 2001, 414:813-820). This diabetes-associated, oxidative stress-initiated organ damage is cumulative and is manifested in several organs. For example, short-term hyperglycemia in diabetic monkeys can induce the oxidation of arterial wall proteins by hydroxyl-like species (Pennathur et al., *J Clin Invest*, 2001, 107:853-860). Additionally, analysis of the diabetic Otsuka Long-Evans Tokushima Fatty (OLETF) rats showed elevated levels of multiple carbonylated proteins including desmin, actin, and myosin (Oh-Ishi et al., *Free Radical Biology & Medicine*, 2002, 34:11-22). Moreover, there was a 2- to 3-fold increase in total adipose protein carbonylation in obese, insulin-resistant mice compared to lean insulin sensitive mice (Grimsrud et al., *Mol Cell Proteomics*, 2007, 6:624-637).

Example 5 describes methods that exploit the observation that oxidized proteins released from damaged organs are shed into blood and can be used as indicators of organ damage and long-term consequences of chronic disease processes. These methods involve assessing qualitative and quantitative differences in the carbonylation of proteins that are shed into the blood of diabetic and lean rats.

Zucker diabetic rats develop metabolic disturbances characteristic of diabetes in which the animals become hyperglycemic by seven weeks of age on diet of PURINA 5008 CHOW. Hyperinsulinemia occurs during the development of diabetes in this animal and then decreases by nineteen weeks. As shown in Table 14, mean fasting glucose was significantly higher in the diabetic animal (449.3 mg/dl) than in a lean non-diabetic animal (93.4 mg/dl).

TABLE 14

The mean fasting glucose level for five diabetic rats and control lean rats at 16 weeks.

| Sample | Mean fasting glucose level at 16 weeks |
|---|---|
| Lean plasma | 93.4 mg/dl (SD = 11.3) |
| Diabetic rat plasma | 449.3 mg/dl (SD = 110.4) |

Oxidative stress was demonstrated by urinary isoprostanes using competitive ELISA (Oxford Biomedical Research, Oxford, Mich.). Isoprostane is formed specifically as a consequence of free radical induced lipid peroxidation and is considered to be one of the most reliable indicators of in vivo oxidative stress. At weeks 3 and 6, 24-hour isoprostanes were significantly greater ($p<0.05$) in the diabetic than the controls rats (FIG. 26).

FIG. 27 shows the analytical strategy employed in these studies. Five diabetic Zucker rats were sacrificed and 6 mL of plasma withdrawn from each. The same procedure was used with non-diabetic control animals. After centrifugation, carbonylated proteins in plasma samples were biotinylated with biotin hydrazide (BH), Schiff base products of the reaction were reduced with sodium cyanoborohydride, and the samples were dialyzed to remove excess BH. Biotinylated proteins were subsequently selected from samples with avidin affinity chromatography and following proteolysis identified and quantified by LC-MS/MS.

Two analytical protocols were used. Samples from individual animals were examined in Protocol A; pooled samples were used in Protocol B. Following selection of biotinylated proteins from individual samples by avidin affinity chromatography in Protocol A, the selected proteins were digested with trypsin, labeled with iTRAQ™ coding agents, and further fractionated by C18 reversed-phase chromatography (RPC). Tryptic peptides in fractions collected from the RPC column were identified and quantified with an ABI 4800 plus MALDI/TOF/TOF mass spectrometer. Protein Pilot was used for the analysis of the mass spectra as described in Example 5.

Samples from diabetic and lean rats, respectively, were pooled in Protocol B for oxidation site identification. Five mg of pooled protein from either the diabetic or lean group of animals were applied to the avidin affinity column. Proteins thus selected were further fractionated on a C3 RPC column and collected for trypsin digestion. Following proteolysis, digested fractions were examined by the LC-MS/MS using a Waters nano-UPLC coupled to a QSTAR Pulsar mass spectrometer. Relative changes of the levels of the peptides carrying the carbonylation sites were quantitated with selective reaction monitoring (SRM) using an Agilent Triple Quad 6410 LC/MS.

After selecting the biotinylated proteins, avidin affinity columns were washed with approximately 60 column volumes of mobile phase. Elution of nonspecifically bound proteins was assessed by the degree to which absorbance had returned to zero after sample application (FIG. 28).

Using absorbance at 280 nm and assuming that affinity selected and unbound proteins have the same extinction coefficient, approximately 1.7% (SD=0.0014) of the protein in Zucker diabetic rat plasma was bound to the avidin affinity column compared to 0.98% (SD=0.46) from lean rat plasma (FIG. 28). This affinity-selected fraction includes naturally biotinylated proteins, proteins naturally complexed with or cross-linked to the biotinylated proteins, and non-specifically bound proteins.

Protocol A produced an average of 2604 mass spectra from the plasma samples. Thirty proteins were identified and quantified based on two peptides found in two or more pairs of diabetic or lean animals with a confidence level higher than 95% (FIG. 29 and Table 15). The procedure identified proteins oxidized in high abundance (e.g., fibrinogen alpha chain precursor), medium abundance (e.g., fibronectin) and low abundance (e.g., extracellular matrix protein 1 precursor) were found. Fourteen of these proteins were detected and quantified in five diabetic and lean pairs. Four proteins appeared in four diabetic and lean pairs, six proteins appeared in three diabetic and lean pairs, and another six proteins appeared in two diabetic and lean pairs. Apolipoprotein AII (Apo AII) precursor, clusterin precursor, and hemopexin precursor were elevated more than 1.5-fold in the diabetic animals. The protein from potassium voltage-gated channel subfamily H member 7 decreased more than 1.5-fold.

TABLE 15

Carbonylation sites quantitated using SRM

| Accession number | Protein name | Oxidative modification | Site | Ratio (diabetic plasma pooled sample/lean plasma pooled sample) replicate 1 | Ratio (diabetic plasma pooled sample/lean plasma pooled sample) replicate 2 | Average |
|---|---|---|---|---|---|---|
| gi\|60678292 | hemoglobin alpha 2 chain | Biotinylated HNE adduct | 69 | 25.88 | 14.54 | 20.21 |
| gi\|204352 | hemoglobin beta-chain | Biotinylated deoxyglucosone adduct | 49 | 0.79 | 1.25 | 1.02 |
| gi\|60678292 | hemoglobin alpha 2 chain | Biotinylated malodialdehyde | 12 | 1.94 | 2.06 | 2.00 |
| gi\|60678292 | hemoglobin alpha 2 chain | Biotinylated glyoxal | 17 | 0.52 | 0.87 | 0.69 |
| gi\|204570 | major beta-hemoglobin | Biotinylated oxidized lysine | 77 | 7.19 | 2.21 | 4.70 |
| gi\|56797757 | fibrinogen, alpha polypeptide isoform 1 | Biotinylated oxidized arginine | 770 | 6.05 | 6.00 | 6.03 |
| gi\|56797757 | fibrinogen, alpha polypeptide isoform 1 | Biotinylated oxidized arginine | 419 | 2.46 | 1.51 | 1.98 |
| gi\|404382 | FABP-II = fatty acid-binding protein {N-terminal} | K8: Biotinylated malondialdehyde adduct, K17: Biotinylated methyl glyoxal adduct | 8, 17 | 17.35 | 2.36 | 9.85 |
| gi\|2493792 | C4b-binding protein alpha chain precursor (C4bp) | K224: Biotinylated oxidized lysine, R: 228 Biotinylated oxidized arginine | 224, 228 | 0.15 | 0.11 | 0.13 |
| gi\|55391508 | Albumin [Rattus norvegicus] | Biotinylated oxidized proline | 543 | 1.20 | 1.00 | 1.10 |
| gi\|243866 | immunoglobulin heavy chain | Biotinylated malodialdehyde | 345 | 1.69 | 3.63 | 2.66 |
| gi\|2292988 | Inter-alpha-inhibitor H4 heavy chain | Biotinylated malodialdehyde | 161 | 1.25 | 0.66 | 0.95 |
| gi\|8393024 | complement component 3 | Biotinylated oxidized arginine | 688 | 2.71 | 2.57 | 2.64 |
| gi\|8393024 | complement component 3 | Biotinylated oxidized arginine | 656 | 1.62 | 1.09 | 1.35 |
| gi\|12831225 | Murinoglobulin 1 homolog | Biotinylated oxidized lysine | 973 | 0.02 | 0.02 | 0.02 |
| gi\|12831225 | Murinoglobulin 1 homolog | K347: biotinylated deoxyglucosone adduct, K352: biotinylated methylglyoxal | 347, 352 | 0.01 | 0.01 | 0.01 |
| gi\|12831225 | Murinoglobulin 1 homolog | Biotinylated malodialdehyde | 682 | 0.86 | 0.98 | 0.92 |
| gi\|55391508 | Albumin | K548: Biotinylated methylglyoxal adduct, K549: biotinylated Amadori adduct | 548, 549 | 1.18 | 1.34 | 1.26 |

The highest sequence coverage for the proteins identified and quantified came from fibrinogen beta chain precursor (92.3% coverage), fibrinogen gamma chain precursor (84% coverage), and fibronectin precursor (70.8% coverage).

We investigated the relationship between certain oxidized proteins and disease using GeneGo™ (FIG. 30). GeneGo™ analysis of disease ontology revealed that the group of proteins oxidized 50% or more than in the control correlated with nephrotic syndrome and other kidney pathologies in the diabetic rats. In addition, oxidized proteins correlated with lipid-related disorders. These findings are consistent with kidney diseases and coronary heart disease being complications of diabetes.

Carbonylation sites were identified through Protocol B in which samples from multiple diabetic or lean animals were pooled to enrich the sample for oxidized proteins. After avidin affinity chromatography, the selected proteins were further resolved by RPC on a column with a C3 alkyl silane stationary phase. Fractions collected from the RPC column were trypsin digested and the resulting peptides identified by LC-MS/MS using a QSTAR ESI/MS/MS. Quantification was achieved by selective reaction monitoring. Unmodified peptides were used to identify the protein parent while biotin-modified peptides were used to identify oxidation sites An average of 10625 spectra was obtained per analysis. As shown in FIG. 29 and Table 15, eighteen carbonylation sites were detected using the QSTAR ESI/MS/MS. Carbonylation sites were characterized and quantified with the Agilent 6410 QqQ ESI/MS/MS using an SRM approach.

SRM analysis allowed precise, reliable, and highly sensitive quantitation of peptides below the detection limit of conventional LC/MS/MS methods. SRM analysis also allowed detection of carbonylated peptides fragment that were not seen in the initial product ion scan by conventional LC/MS/MS. In all cases, the peptide quantified with SRM should reside in the same fraction (i.e., after the separation of the purified proteins with C3-RPC and digestion) as the carbonylated peptide characterized initially by QSTAR/MS/MS. This appears to be the first use of SRM-MS to quantify carbonylated peptides (FIG. 29 and Table 15). An example of the transition used to quantify carbonylated peptides is shown in FIG. 31.

In all cases, QSTAR/MS/MS experiments were used to predict the major charge state of the precursor ion. As shown in FIG. 29, eighteen carbonylated peptides were quantitated using this strategy. The concentrations of eight of these peptides were significantly higher (at least 2-fold) in the diabetic pooled plasma compared to the lean pooled plasma. The concentrations of three proteins decreased significantly. Finally, a total of seven carbonylated peptides didn't show any significant change. The presence of a number of carbonylated peptides without any significant changes suggests that the changes at other carbonylation sites are not random.

All three mechanisms by which protein carbonylation occurs are represented in the proteins exhibiting increased oxidation levels in the diabetic rat plasma. Among the significantly changed modifications (i.e., either increased or decreased), seven originated from direct oxidation of an amino acid side chain (e.g., oxidation of arginine), four involved the formation of advanced lipid peroxidation product adducts (e.g., malondialdehyde adducts), one involved glycation and advanced glycation end product adducts (e.g., a deoxyglucosone adduct), two sites arose as a result of methylglyoxal adducts, arising from either advance glycation or advance lipid peroxidation end products (FIG. 32).

Among the identified oxidized proteins, hemoglobin and murinoglobulin 1 homolog had the largest number of carbonylation sites, possessing sites derived from all three types of carbonylation: direct carbonylation (e.g., oxidized lysine), glycoxidation of advanced glycation end products (AGE) (e.g., 3-deoxyglucosone adducts), and advanced lipid peroxidation end products (ALE) adducts (e.g., malondialdehyde adducts). The diabetic:lean ratio at carbonylation sites was surprisingly diverse. Whereas the deoxyglucosone adduct ratio was unchanged at 1.02, the HNE adduct, oxidized lysine, and malondialdehyde had ratios of 20, 4.7 and 2.00, respectively, favoring diabetic animals. Similar results were observed with murinoglobulin 1 homolog. The oxidized lysine, deoxyglucosone adduct, and methylglyoxal adduct had a ratio of nearly 0.01, favoring lean animals. The malondialdehyde adduct remained unchanged. Fibrinogen alpha polypeptide isoform 1 provided a similar example. The ratio of arginine oxidation between diabetic and lean animals at sites 419 and 770 was 1.98 and 6.03, respectively. A last example is the complement component 3 protein which had two sites of arginine oxidation. One was unchanged while the other increased more than two-fold in diabetic animals.

The oxidative stress environment inside cells is one factor that determines the degree of oxidation. Diabetes is a complex disease that involves oxidative stress, hyperlipidemia, and hyperglycemia. Thus, direct carbonylation is a common oxidation mechanism in diabetes. Hyperglycemia increases the superoxide anion in mitochondria. The superoxide anion may then leak out, causing the oxidation of other proteins. Additionally, the formation of ALE and AGE adducts is a result of increase reactive oxygen species levels. Diabetic liver mitochondria and microsomes, however, are unable to consume exogenous HNE to the same extent as the non-diabetic organelles. This may be due to the decreased activity of the enzymes that metabolize HNE in the liver, which may itself be a result of oxidative stress. On the other hand, high levels of reducing sugars, primarily glucose, in cells and plasma lead to Schiff base formation between the sugar and lysine residues on proteins. Following Amadori rearrangement a stable glycated protein product may be formed. Over time, oxidative degradation of the Amadori adducts leads to the formation of a reactive carbonyl or dicarbonyl functional group at the site. These compounds can be also produced by the autoxidation of glucose. A list of adducts that can be detected by the methodology described here is shown in FIG. 33.

The structure of proteins seems to play an important role in the propensity of particular sites to be oxidized. Half-life is important as well. Hemoglobin (Hb) is one of the most heavily oxidized proteins reported in this study. The half-life of red blood cells is 120 days. This makes them susceptible to the formation of adducts with AGEs and ALEs. The presence of iron in hemoglobin structure increases its potential for oxidation. The susceptibility of metal-containing proteins to be oxidation is reflected in the oxidation of serotransferrin, ceruplasmin, hemopexin, and fibrinogen as well.

The location of a protein relative to the source of reactive oxygen species may influence the probability that the protein will be oxidized, as seen with intestinal fatty acid binding protein (I-FABP). This protein is involved in the transport of fatty acids to the mitochondrion and their subsequent β-oxidation. The close proximity of I-FABP to mitochondria and the fatty acids might explain how malondialdehyde and methylglyoxal adducts were formed in diabetic rat plasma.

The effects of oxidative stress observed in Example 5 reflect diabetes-induced changes in multiple pathways, sometimes within a single protein as seen with hemoglobin, fibrinogen alpha polypeptide isoform 1, complement component 3, and murinoglobulin homolog 1. Multiple oxidation sites were observed in these proteins, each of which was oxidized to a different extent in diabetic rats.

Monitoring Antioxidant Treatment of Diabetes Mellitus

Example 6 describes the use of methods described herein to monitor the effect of therapy on the status of a disease. As noted above, chronic oxidative stress diseases can be associated with elevated levels of free radicals that can destroy cells and organs over time. Thus, the pathological effects associated with multiple oxidative stress diseases may be ameliorated with antioxidants. However, methods for elucidating the mechanisms by which antioxidants may reduce oxidative stress-related protein damage are lacking. Methods described herein report a novel method that can permit one to evaluate the efficacy of dietary antioxidant supplementation on the protection of protein oxidative damages in diabetic animals. We evaluated the efficacy of green tea, as an exemplary source of dietary antioxidants, for the ability to protect against oxidative stress-related oxidized peptide signatures in the plasma of diabetic Zucker rats. The mechanism of antioxidant protection was examined through the types and extent of OSi~PTMs in oxidized proteins. Oxidative stress from advanced glycation end-product (AGE) oxidation was differentiated from lipid peroxidation- and reactive oxygen species (ROS)-initiated oxidation through the type of oxidation at particular sites in proteins.

Carbonylated proteins in freshly drawn blood samples were prepared and analyzed as described in Example 6. Eighteen carbonylated peptides were detected and quantified. Eight of the peptides changed significantly: eight decreased significantly while one increased significantly. Green tea changed the three routes for carbonylation: direct oxidative cleavage from reactive oxygen species, glycation and addition of advanced glycation end products (AGEs), and addition of lipid peroxidation products (ALEs). The major effect of green tea was on the AGEs followed by ALEs followed by direct carbonylation.

Existing in vitro assays for measuring antioxidant activity include, for example, the 1,1-diphenyl-2-picrylhydrazyl (DPPH) assay (Cos et al., *Free Radical Res.,* 2002, 36(6):711-716) and horseradish peroxidase-luminol-hydrogen peroxide assay (Georgetti et al., *AAPS PharmSci* 2003, 5(2):E20). These assays, however, correlate poorly with actual in vivo efficacy of antioxidant compounds. The physiological environment, interactions with other food components in vivo, the in vivo degradation of the antioxidants, the bioavailability (absorption, distribution, metabolism and excretion) of the antioxidants, and the location of the antioxidants relative to the reactive oxygen species are some reasons for the poor correlation between the assays and the actual in vivo protective activity of antioxidants.

Existing in vivo assays for measuring antioxidant activity include, for example, assays that test the efficacy of antioxidant on oxidative lipid damage (e.g., thiobarbituric acid test, (Hermans et al., *J. Chromatogr., B: Anal. Technol. Biomed Life Sci.,* 2005, 822(1-2):33-39)) and oxidative DNA damage (e.g., 8-hydroxy-2'-deoxyguanosine test, (Podmore et al., *Nature,* 1998, 392(6676):559)).

Assessing the utility of antioxidants in preventing the oxidative damage of proteins, however, has not been well explored, primarily due to the lack of evaluation tools. Measuring antioxidant efficacy protecting against oxidative protein damage has focused mainly on the determination of the total protein carbonyl content (PCC) by a colorimetric reaction (Levine et al., *Methods Enzymol.,* 1990, 186(Oxygen Radicals Biol. Syst., Pt. B):464-478). This assay, however, doesn't provide the specific mechanism of oxidative stress (Hermans et al., *Curr. Med. Chem.,* 2007, 14(4):417-430). Also, this assay doesn't provide information about the proteins involved in the protection process. Another test is the measurement of the total 3-nitrotyrosine released after the acid treatment or enzymatic digestion of the proteins (Salman-Tabcheh et al., *Free Radical Biol. Med.,* 1995, 19(5): 695-698). This assay only gives information about the efficacy of antioxidants in the prevention of the nitration of the proteins. Also, it doesn't give information about the proteins carrying the nitrated tyrosine residues. Finally, a recent method tested the efficacy of antioxidants on the protein expression levels (Weinreb, O. et al. *Free Radical Biol. Med.,* 2007, 43(4):546-556; Santos-Gonzalez et al., *Exp. Gerontol.,* 2007, 42(8):798-806; and Li et al, *Chin. Med. J. (Engl. Ed),* 2008, 121(24):2544-2552). This assay doesn't indicate whether these proteins are damaged, nor does it account for the fact that oxidative stress causes the degradation of these proteins making the results obtained about the expression of these proteins unreliable.

Generally, none the previous assays account for the enormous complexity by which oxidative damage occurs and the efficacy of antioxidants in mitigating the various forms of oxidative damage.

The methods described herein provide a new approach to directly measure the efficacy of antioxidants on the different kinds of oxidative damages of proteins. This measurement allows the elucidation of antioxidant protection mechanisms in vivo. The methods described herein can be used to assess the efficacy of antioxidants on the nature and/or extent of individual protein oxidation. The methods also may be used to identify the probable source of oxidation as having resulted from i) direct ROS-initiated oxidation of amino acids (e.g., Pro, Arg, Lys and Thr), ii) indirect oxidation through forming advanced glycation end products adducts (e.g., deoxyglucosone), or indirect oxidation through adding lipid peroxidation products (e.g., 4-hydroxy-2-noneal, 2-propenal, or malondialdehyde).

We analyzed the effects of Green tea (*Camellia sinensis*) on the Oxidative Stress-induced Post-translational Modifications (OSi~PTMs) that are profiled for type II diabetes mellitus Example 5. Diabetes was chosen because pathological changes that are associated with the disease—e.g., renal failure, neuropathy, cardiovascular disease, and blindness—can be the result of four OS-induced pathways that commence at disease onset, when hyperglycemia and depletion of antioxidant defenses begin (Brownlee, M., *Diabetes,* 2005, 54(6): 1615-1625). In Example 5, we characterize the oxidative stress signature for type II diabetes mellitus in the plasma of diabetic Zucker rats.

Green tea was selected because its content of epigallocatechin-3-gallate (EGCG) showed strong antioxidant efficacy. Its mechanism depends on the chelation of iron and copper and scavenging reactive oxygen and nitrogen species as well as the inhibition "pro-oxidant" enzymes and redox-sensitive transcription factors (Camargo et al., *Nutr. Res.,* 2006, 26(12): 626-631; Ounjaijean et al., *Med. Chem.,* 2008, 4(4):365-370). This study is based on the assessment of the qualitative and quantitative differences in the proteins carbonylation sites shed in the blood of the green tea fed diabetic and control diabetic rats. This assessment involves labeling the proteins carbonyl groups with biotin hydrazide. The resultant Schiff's bases were reduced using sodium cyanoborohydride. The proteins thus biotinylated were dialyzed and enriched with avidin purification followed by separation, digestion, identification of the proteins, characterization and quantitation of their OSi~PTMs.

Example 5 describes identifying and quantifying the effect of type II diabetes on the oxidation sites of proteins released into the plasma. Example 6 describes testing the effect of the administration of an antioxidant (green tea) on the oxidation sites characterized in Example 5. Thus, Example 6 describes a new method for determining the efficacy of antioxidants by testing their ability to affect the disease-related oxidative stress-induced PTMs. More broadly, example 6 describes a method for monitoring the effect of treatment. Example 6 uses a control population of diabetic rats as a baseline against which antioxidant-treated rats can be compared. In other embodiments, the control may be a sample obtained earlier from the individual receiving treatment. The previously obtained sample may be obtained prior to the initiation of treatment or at a time during the course of treatment.

The analytical protocol used in Example 6 is similar to the protocol used in Example 5 for the detection of OSi~PTMs (FIG. 35). In Example 6, roughly 6 mLs of fresh plasma were withdrawn from each of five green tea-fed Zucker diabetic rats and each of their control Zucker diabetic rats. Biotin hydrazide was added to biotinylate the carbonylated proteins in the plasma, the samples were then dialyzed to remove excess reagent.

The OSi~PTMs were first enriched by pooling the samples, either from green tea-fed diabetic rats or the control diabetic rats, respectively, and enriching the carbonylated proteins with avidin affinity purification. The desorbed proteins were further separated by a C3 reversed-phase column. The proteins separated were then digested and analyzed by the LC/MS/MS (nano-UPLC coupled to QSTAR Pulsar i mass spectrometer). The relative changes of the levels of the peptides carrying the carbonylation sites were then quantitated using selective reaction monitoring (SRM) using Agilent Triple Quad 6410 LC/MS.

Samples purified with avidin were further fractionated at the protein level using C3 reversed-phase chromatography.

These fractions were then digested with trypsin and carbonylation sites were detected with QSTAR ESI/MS/MS and quantified with ESI/SRM. The separation was done at the protein level rather than at the peptide level as this allows the detection of the unmodified peptides, which are used for the identification of the protein; the modified peptides allows detection of the oxidation site. Generally, the use of SRM offered two advantages: a) increased sensitivity for the detection of carbonylated peptides present at levels below the detection limit for the conventional LC/ESI/MS/MS., and b) validation of the carbonylation sites detected by using product ions as transitions that weren't detected in the conventional LC/ESI/MS/MS analysis. As a practical matter, peptides quantitated using SRM must reside in the same fraction as those detected initially in the LC/ESI/MS/MS analyses. Two transitions were used for each peptide and they co-eluted perfectly at the same time.

An average of 10625 spectra were obtained for these analyses. As shown in Table 16, eighteen carbonylation sites were detected and quantified.

Plasma samples of green tea-fed animals had significantly reduced levels of seven of these peptides. On the other hand, it has significantly increased levels of one peptide.

Six carbonylated peptides didn't significantly change between the diabetic and lean samples. Of these six, green tea significantly reduced the level of five of them. The only carbonylated peptide that wasn't affected by green tea, in this category, was the peptide carrying oxidized proline residue at position 543 in albumin. Eight carbonylated peptides exhibited significantly increased concentrations in the diabetic plasma samples compared to plasma samples from lean rats. Of these eight, two proteins returned to the normal values using green tea: the peptides that form 1) an HNE adduct with the lysine residue at position 69 in the hemoglobin alpha 2 chain, and 2) a deoxyglucosone adduct with the lysine residue at position 49 in the hemoglobin beta chain.

On the other hand, the concentrations of the oxidized peptide forming adducts with malondialdehyde and methyl glyoxal at the lysine residues at positions 8 and 17, respectively, in the intestinal fatty acid binding protein were increased by

TABLE 16

Carbonylation sites quantitated using SRM

| Accession number | Protein name | Oxidative modification | Site | Average (diabetic/lean rat plasma pooled sample) | Average (green tea/diabetic rat plasma pooled sample) | SD (green tea/diabetic rat plasma) |
|---|---|---|---|---|---|---|
| gi\|60678292 | hemoglobin alpha 2 chain | Biotinylated HNE adduct | 69 | 20.21 | 0.03 | 0.01 |
| Gi\|204352 | hemoglobin beta-chain | Biotinylated deoxyglucosone adduct | 49 | 1.02 | 0.13 | 0.03 |
| gi\|60678292 | hemoglobin alpha 2 chain | Biotinylated malodialdehyde | 12 | 2.00 | 1.28 | 0.13 |
| gi\|60678292 | hemoglobin alpha 2 chain | Biotinylated glyoxal | 17 | 0.52 | 0.87 | 0.03 |
| Gi\|204570 | major beta-hemoglobin | Biotinylated oxidized lysine | 77 | 4.70 | 0.73 | 0.06 |
| gi\|56797757 | fibrinogen, alpha polypeptide isoform 1 | Biotinylated oxidized arginine | 770 | 6.03 | 0.24 | 0.02 |
| gi\|56797757 | fibrinogen, alpha polypeptide isoform 1 | Biotinylated oxidized arginine | 419 | 1.98 | 1.03 | 0.24 |
| Gi\|404382 | FABP-II = fatty acid-binding protein {N-terminal} | K8: Biotinylated malondialdehyde adduct, K17: Biotinylated methyl glyoxal adduct | 8, 17 | 9.85 | 3.17 | 0.08 |
| gi\|2493792 | C4b-binding protein alpha chain precursor (C4bp) | K224: Biotinylated oxidized lysine, R: 228 Biotinylated oxidized arginine | 224, 228 | 0.13 | 0.66 | 0.05 |
| gi\|55391508 | Albumin | Biotinylated oxidized proline | 543 | 1.10 | 0.66 | 0.04 |
| Gi\|243866 | immunoglobulin heavy chain | Biotinylated malodialdehyde | 345 | 2.66 | 1.20 | 0.39 |
| gi\|2292988 | Inter-alpha-inhibitor H4 heavy chain | Biotinylated malodialdehyde | 161 | 0.95 | 0.32 | 0.26 |
| gi\|8393024 | complement component 3 | Biotinylated oxidized arginine | 688 | 2.64 | 1.10 | 0.09 |
| gi\|8393024 | complement component 3 | Biotinylated oxidized arginine | 656 | 1.35 | 0.18 | 0.18 |
| gi\|12831225 | Murinoglobulin 1 homolog | Biotinylated oxidized lysine | 973 | 0.02 | 1.01 | 0.02 |
| gi\|12831225 | Murinoglobulin 1 homolog | K347: biotinylated deoxyglucosone adduct, K352: biotinylated methylglyoxal | 347, 352 | 0.01 | 1.03 | 0.03 |
| gi\|12831225 | Murinoglobulin 1 homolog | Biotinylated malodialdehyde | 682 | 0.92 | 0.08 | 0.04 |
| gi\|55391508 | Albumin | K548: Biotinylated methylglyoxal adduct, K549: biotinylated Amadori adduct | 548, 549 | 1.26 | 0.50 | 0.02 | more than three-fold in the green tea-fed diabetic rats plasma samples compared their control diabetic rats samples. Among the three carbonylated peptides that decreased significantly in the diabetic rat plasma samples compared to the lean rat plasma samples, green tea didn't have any significant change on these peptides.

Among a total of eight direct carbonylation sites, green tea was able to significantly reduce two of them. These are the oxidized arginines at positions 770 and 656 in fibrinogen alpha polypeptide isoform 1 and complement component 3, respectively. Although arginine was oxidized at another two positions on the same proteins, at positions 419 in fibrinogen alpha polypeptide isoform 1 and 688 in the complement component 3, green tea didn't have a significant effect on either of these other sites. Moreover, among the five advanced lipid peroxidation ALE adducts, green tea significantly reduced three of them and increased the levels of a peptide carrying an ALE modification (malondialdehyde adduct with lysine at position 8 in the intestinal fatty acid binding protein). Additionally, among the three AGE adducts, green tea significantly reduced two of them. Finally, methyl glyoxal adducts can be of either ALE or AGE origin. Among the three peptides carrying methyl glyoxals, green tea reduced one of them (at lysine 548 in albumin) and increased the level of another one (at lysine 17 in intestinal fatty acid binding protein). This indicates that green tea reduced the effect of three routes involved in carbonylation. AGE adducts were the most affected by the green tea, followed by the ALE adducts, followed by the direct carbonylation.

Generally, the most dramatic decreases in the levels of carbonylated peptides induced by green tea were the reduction of the HNE adduct at the lysine residue 69 in the hemoglobin alpha 2 chain. The second most dramatic decrease of the carbonylated peptides by the green tea was the reduction of the malondialdehyde adduct with the lysine residue at position 682 in the murinoglobulin 1 homolog.

Thus, Example 6 provides an analytical methodology for determining how dietary antioxidant supplementation impacts oxidative stress (OS) signatures in proteins. The assessment of the impact of antioxidant supplementation on OS in vivo was based on the site, extent, and type of OS-initiated post-translational modification (OSi~PTM) in plasma proteins. By examining changes in OS signatures in association with supplementation it is possible to predict whether a given supplement may be beneficial in interrupting a specific disease process.

More broadly, Example 6 describes a general analytical methodology for monitoring the status of a disease over time, e.g., prior to and then after some event such as, for example, a course of treatment or a dietary change. The methodology can be used to identify changes in the population and/or extent of oxidized peptides to determine whether a disease has progressed, regressed, recurred, is responding to treatment, etc. The method may be employed simply to monitor the efficacy of a course of treatment. In other cases, the method may be used to screen potential treatments for efficacy. In either case, the method may be used to assist a health professional in determining the course of treatment most likely to be effective for a particular individual under a particular set of circumstances.

The method exploits several observations. Among these observations are i) carbonylation is a universal indicator of oxidative stress, ii) carbonylated proteins are easily selected from a proteome, iii) carbonylated proteins carry multiple forms of OSi~PTMs, iv) specific sites and types of oxidative modification can be identified for an individual protein that is a component of a complex mixture of oxidized proteins, v) there are apparent differences in protein oxidation based on the level of OS and antioxidant treatment, vi) carbonylated signature proteins appear reproducibly in plasma, vi) oxidized proteins shed from organs can be readily identified in plasma, and vii) there seem to be no inherent differences in the way low and high abundance proteins are oxidized, suggesting that high abundance oxidation products are equally valid for testing the efficacy of antioxidants.

As part of the differential analysis of OSi~PTMs, the sites of oxidation, the types of oxidative modifications, and the extent of oxidative modifications within individual proteins were examined. Carbonylation sites were identified using MS/MS and the sensitivity and selectivity of SRM was used to quantitate these sites. Using this methodology, we found that green tea significantly reduced seven of these sites while it increased one of them. This can be attributed to the fact that green tea is rich in polyphenolic compounds. One third of its dry weight is composed mainly of flavonols known as catechins. These include: epicatechin, epigallocatechin, epicatechin gallate, and epigallocatechin gallate (FIG. 34). Generally, these constituents showed large antioxidant activity. For example, the administration of green tea increased the antioxidant potential in the serum of normal and dyslipidemic subjects. Also, there is increasing evidence that green tea ameliorates oxidative stress in diabetes.

TABLE 17

SRM transitions used for the quantitation of the carbonylated peptides

| Accession number | Protein name | Oxidative modification | Site | Q1 | Q3 | z (+) | Ion | CE | Frag-mentor | Dwell time | R.T. |
|---|---|---|---|---|---|---|---|---|---|---|---|
| gi\|60678292 | hemoglobin alpha 2 chain | Biotinylated HNE adduct | 69 | 607.3 | 915.5 | 1 | y5 | 22 | 140 | 50 | 7.25 |
| gi\|60678292 | hemoglobin alpha 2 chain | Biotinylated HNE adduct | 69 | 607.3 | 599.4 | 1 | y2-NH$_3$ | 22 | 140 | 50 | 7.25 |
| gi\|60678292 | hemoglobin alpha 2 chain | Biotinylated glyoxal | 17 | 430.2 | 674.3 | 1 | y3 | 11 | 130 | 100 | 8.28 |
| gi\|60678292 | hemoglobin alpha 2 chain | Biotinylated glyoxal | 17 | 430.2 | 745.4 | 1 | y3 | 11 | 130 | 100 | 8.28 |
| gi\|204352 | hemoglobin beta-chain | Biotinylated deoxyglucosone adduct | 49 | 762.9 | 327.2 | 1 | b4 | 24 | 130 | 50 | 6.6 |
| gi\|204352 | hemoglobin beta-chain | Biotinylated deoxyglucosone adduct | 49 | 762.9 | 598.4 | 1 | b7 | 16 | 130 | 50 | 6.6 |
| gi\|60678292 | hemoglobin alpha 2 chain | Biotinylated malodialdehyde | 12 | 794.5 | 500.3 | 2 | y6 | 16 | 130 | 100 | 10.1 |

TABLE 17-continued

SRM transitions used for the quantitation of the carbonylated peptides

| Accession number | Protein name | Oxidative modification | Site | Q1 | Q3 | z (+) | Ion | CE | Fragmentor | Dwell time | R.T. |
|---|---|---|---|---|---|---|---|---|---|---|---|
| gi\|60678292 | hemoglobin alpha 2 chain | Biotinylated malondialdehyde | 12 | 794.5 | 428.3 | 1 | y1 | 32 | 130 | 100 | 10.1 |
| gi\|204570 | major beta-hemoglobin | Biotinylated oxidized lysine | 77 | 730.4 | 251.2 | 2 | y2 | 25 | 140 | 100 | 8.3 |
| gi\|204570 | major beta-hemoglobin | Biotinylated oxidized lysine | 77 | 730.4 | 129 | 1 | b1 | 25 | 140 | 100 | 8.3 |
| gi\|56797757 | fibrinogen, alpha polypeptide isoform 1 | Biotinylated oxidized arginine | 770 | 490.73 | 187.3 | 2 | y1 | 27 | 130 | 100 | 6.4 |
| gi\|56797757 | fibrinogen, alpha polypeptide isoform 1 | Biotinylated oxidized arginine | 770 | 490.74 | 244.1 | 2 | y2 | 11 | 130 | 100 | 6.4 |
| gi\|56797757 | fibrinogen, alpha polypeptide isoform 1 | Biotinylated oxidized arginine | 419 | 805.9 | 399.2 | 2 | b8-$NH_3$ | 20 | 130 | 100 | 9.1 |
| gi\|56797757 | fibrinogen, alpha polypeptide isoform 1 | Biotinylated oxidized arginine | 419 | 805.9 | 584.3 | 2 | y9 | 20 | 130 | 100 | 9.1 |
| gi\|404382 | FABP-II = fatty acid-binding protein {N-terminal} | K8: Biotinylated malondialdehyde adduct, K17: Biotinylated methyl glyoxal adduct | 8, 17 | 767.1 | 283.7 | 2 | b5 | 20 | 140 | 100 | 8.7 |
| gi\|404382 | FABP-II = fatty acid-binding protein {N-terminal} | Biotinylated malondialdehyde adduct, Biotinylated methyl glyoxal adduct | 8, 17 | 767.1 | 851.0 | 2 | b14 | 20 | 140 | 100 | 8.7 |
| gi\|2493792 | C4b-binding protein alpha chain precursor (C4bp) | K224: Biotinylated oxidized lysine, R: 228 Biotinylated oxidized arginine | 224, 228 | 579.60 | 237.1 | 2 | y2 | 12 | 130 | 100 | 8.2 |
| gi\|2493792 | C4b-binding protein alpha chain precursor (C4bp) | K224: Biotinylated oxidized lysine, R: 228 Biotinylated oxidized arginine | 224, 228 | 579.60 | 388.2 | 2 | b5-$NH_3$ | 8 | 130 | 100 | 8.2 |
| gi\|243866 | immunoglobulin heavy chain | Biotinylated malondialdehyde | 345 | 810.89 | 265.12 | 2 | b4 | 28 | 130 | 100 | 11.52 |
| gi\|243866 | immunoglobulin heavy chain | Biotinylated malondialdehyde | 345 | 810.89 | 529.24 | 1 | b3 | 20 | 130 | 100 | 11.52 |
| gi\|55391508 | Albumin [Rattus norvegicus] | Biotinylated oxidized proline | 543 | 714.0 | 416.2 | 2 | y5 | 17 | 130 | 100 | 11.0 |
| gi\|55391508 | Albumin [Rattus norvegicus] | Biotinylated oxidized proline | 543 | 714.0 | 201.1 | 1 | b2 | 25 | 130 | 100 | 11.0 |
| gi\|2292988 | Inter-alpha-inhibitor H4 heavy chain | Biotinylated malondialdehyde | 161 | 766.9 | 654.4 | 1 | y3 | 15 | 130 | 100 | 9.5 |
| gi\|2292988 | Inter-alpha-inhibitor H4 heavy chain | Biotinylated malondialdehyde | 161 | 766.9 | 541.3 | 1 | y2 | 31 | 130 | 100 | 9.5 |
| gi\|8393024 | complement component 3 | Biotinylated oxidized arginine | 688 | 762.38 | 675.3 | 2 | b10 | 23 | 130 | 100 | 9.5 |
| gi\|8393024 | complement component 3 | Biotinylated oxidized arginine | 688 | 762.38 | 459.2 | 2 | b6 | 27 | 130 | 100 | 9.5 |
| gi\|8393024 | complement component 3 | Biotinylated oxidized arginine | 656 | 680.3 | 508.8 | 2 | y7 | 16 | 130 | 100 | 9.6 |
| gi\|8393024 | complement component 3 | Biotinylated oxidized arginine | 656 | 680.3 | 257.6 | 2 | b5 | 28 | 130 | 100 | 9.6 |
| gi\|12831225 | Murinoglobulin 1 homolog | K347: biotinylated deoxyglucosone adduct, K352: biotinylated methylglyoxal | 347, 352 | 618.3 | #### | 1 | b7 | 30 | 130 | 100 | 8.9 |
| gi\|12831225 | Murinoglobulin 1 homolog | K347: biotinylated deoxyglucosone adduct, K352: biotinylated methylglyoxal | 347, 352 | 618.3 | 483.3 | 2 | y5 | 30 | 130 | 100 | 8.9 |
| gi\|12831225 | Murinoglobulin 1 homolog | Biotinylated malondialdehyde | 682 | 754.4 | 655 | 1 | y3 | 18 | 130 | 100 | 8.44 |
| gi\|12831225 | Murinoglobulin 1 homolog | Biotinylated malondialdehyde | 682 | 754.4 | 452 | 2 | y2 | 14 | 130 | 100 | 8.44 |

TABLE 17-continued

SRM transitions used for the quantitation of the carbonylated peptides

| Accession number | Protein name | Oxidative modification | Site | Q1 | Q3 | z (+) | Ion | CE | Frag-mentor | Dwell time | R.T. |
|---|---|---|---|---|---|---|---|---|---|---|---|
| gi\|55391508 | Albumin | K548: Biotinylated methylglyoxal adduct, K549: biotinylated Amadori adduct | 548, 549 | 738.4 | 386 | 1 | b3 | 30 | 130 | 100 | 7.57 |
| gi\|55391509 | Albumin | K548: Biotinylated methylglyoxal adduct, K549: biotinylated Amadori adduct | 548, 549 | 738.4 | 489 | 2 | y2 | 30 | 130 | 100 | 7.57 |
| gi\|12831225 | Murinoglobulin 1 homolog | Biotinylated oxidized lysine | 973 | 458.96 | 587.97 | 3 | y13 | 3 | 130 | 100 | 8.77 |
| gi\|12831225 | Murinoglobulin 1 homolog | Biotinylated oxidized lysine | 973 | 458.96 | 382.2 | 3 | y9 | 11 | 130 | 100 | 8.77 |

For any method disclosed herein that includes discrete steps, the steps may be conducted in any feasible order. And, as appropriate, any combination of two or more steps may be conducted simultaneously.

Exemplary embodiments of the invention include:

1. A method for monitoring the health of a subject comprising:

comparing a plurality of test peptides in a sample obtained from the subject, each test peptide having a detectable oxidation state, with a plurality of reference peptides, each reference peptide having a detectable oxidation state; and detecting a difference in oxidation state between at least one test peptide and the oxidation state of a corresponding reference peptide, wherein the difference in oxidation state is indicative of the health status of the subject.

2. The method of embodiment 1 wherein the plurality of test peptides, the plurality of reference peptides, or both are detectably labeled.

3. The method of embodiment 1 or 2 wherein comparing the plurality of test peptides with the plurality of reference peptides comprises using global internal standard technology.

4. The method of any previous embodiment wherein comparing the plurality of test peptides with the plurality of reference peptides comprises using isotopically labeled internal standard peptides.

5. The method of any previous embodiment wherein comparing the plurality of test peptides with the plurality of reference peptides comprises using global isotopic coding.

6. The method of any previous embodiment wherein the at least a portion of the plurality of test peptides, at least a portion of the reference peptides, or both are labeled using a procedure selected from stable mass isotope coding, radioisotope coding, isotope coded affinity tagging (ICAT), stable isotope labeling of amino acids in cell culture (SILAC), isobaric tagging for relative and absolute quantification (iTRAQ™), labeling using fluorinated affinity tags, amino terminal sulphonation, dimethyl labeling, global internal standard technology (GIST), 16O/18O labeling, or any combination thereof.

7. The method of embodiment 6 wherein the labeling is performed in vivo.

8. The method of embodiment 6 wherein the labeling is performed in vitro.

9. The method of embodiment 1 wherein neither the plurality of test peptides nor the plurality of reference peptides are detectably labeled, and wherein comparing the plurality of test peptides with the reference peptides comprises using a label-free method.

10. The method of any previous embodiment wherein comparing the plurality of test peptides with the plurality of reference peptides comprises using mass spectrometry.

11. The method of any previous embodiment wherein comparing the plurality of test peptides with the plurality of reference peptides comprises using mass spectrometry comprising electron transfer dissociation (ETD), collision-induced dissociation (CED), or both.

12. The method of any previous embodiment wherein comparing the plurality of test peptides with the plurality of reference peptides comprises using liquid chromatography-mass spectrometry (LC/MS).

13. The method of any previous embodiment wherein comparing the plurality of test peptides with the plurality of reference peptides comprises using a mass spectrometry method comprising selected ion monitoring (SIM), selected reaction monitoring (SRM), or multiple reaction monitoring (MRM), or any combination thereof.

14. The method of any previous embodiment wherein comparing the plurality of test peptides with the plurality of reference peptides comprises using interferometry.

15. The method of any previous embodiment wherein comparing the plurality of test peptides with the plurality of reference peptides comprises using fluorescence.

16. The method of any previous embodiment wherein comparing the plurality of test peptides with the plurality of reference peptides comprises:

using liquid chromatography; and absorbance or fluorescence monitoring.

17. The method of any previous embodiment wherein comparing the plurality of test peptides with the plurality of reference peptides comprises performing an immunological assay on the sample obtained from the subject and a sample from at least one disease-free subject to detect biomarkers in the samples.

18. The method of any previous embodiment further comprising using affinity selection to enrich for oxidized peptides.

19. The method of any previous embodiment, wherein at least one of the plurality of test peptides or at least one of the plurality of reference peptides is oxidized, the method further comprising biotinylating at least one oxidized peptide.

20. The method of embodiment 19 comprising affinity selecting the biotinylated peptides using avidin.

21. The method of any previous embodiment wherein the difference in oxidation state between at least one test peptide and the corresponding reference peptide comprises:
   a difference in the concentration of an oxidized test peptide relative to the reference peptide;
   a difference in the level of oxidation of the test peptide relative to the reference peptide;
   a difference in the molecular location of oxidation in the test peptide relative to the reference peptide;
   or any combination thereof.

22. The method of any previous embodiment wherein at least one test peptide or at least one reference peptide is oxidized at more than one site.

23. The method of any previous embodiment wherein different forms of oxidation are present at a corresponding oxidation site in different molecules of at least one test peptide or different forms of oxidation are present at a corresponding oxidation site in different molecules of at least one reference peptide.

24. The method of any previous embodiment wherein the plurality of test peptides, plurality of reference peptides, or both comprise multiple isoforms of a peptide, wherein the isoforms differ in their oxidation pattern.

25. The method of any previous embodiment wherein the sample obtained from the subject is obtained from the blood or a blood product of the subject.

26. The method any previous embodiment wherein the sample obtained from the subject was obtained from the plasma of the subject.

27. The method of any previous embodiment wherein the plurality of test peptides and the plurality of reference peptides comprise non-blood peptides.

28. The method of any previous embodiment wherein detecting a difference in oxidation state between at least one test peptide and the oxidation state of a corresponding reference peptide comprises detecting differences in oxidation state of a test non-blood peptide and a reference non-blood peptide.

29. The method of any previous embodiment wherein comparing the plurality of test peptides with the plurality of reference peptides comprises using oxidative site mapping to identify at least one specific oxidative modification.

30. The method of any previous embodiment wherein at least one test peptide, at least one reference peptide, or both comprises an oxidized peptide comprising a carbonyl group, wherein the carbonyl group is a product of, or is associated with:
   oxidative cleavage of an amino acid side chain;
   cleavage of the primary peptide structure;
   glycation;
   an AGE-peptide adduct; or
   addition of a lipid peroxidation product 31. The method of any previous embodiment wherein at least one test peptide, at least one reference peptide, or both comprises an oxidative stress induced post-translational modification (OSi-PTM).

32. The method of any previous embodiment wherein detecting a difference in oxidation state between at least one test peptide and the oxidation state of a corresponding reference peptide comprises using software to differentiate between a test peptide or reference peptide comprising an oxidative stress induced post-translational modification (OSi-PTM), and a test peptide or reference peptide lacking an OSi-PTM.

33. The method of any previous embodiment further comprising mapping the at least one test peptide to a cell type, organ, tissue, pathogen, or disease.

34. The method of any previous embodiment wherein at least one test peptide is a low abundance peptide.

35. The method of any previous embodiment wherein at least one reference peptide is obtained from the subject.

36. The method of any previous embodiment wherein at least one reference peptide is obtained from the subject at a time different from the time the plurality of test peptides are obtained from the subject.

37. The method of any previous embodiment wherein at least one reference peptide was obtained from a different subject or multiple subjects as a pooled sample.

38. The method of any previous embodiment wherein at least one reference peptide is selected from the following group:
   a peptide of known structure and concentration;
   a peptide obtained from a normal subject, wherein the normal subject is optionally matched with the subject by at least one of age, gender or genetic origin;
   a peptide obtained from or part of a pooled sample obtained from normal subjects, wherein the normal subjects are optionally matched with the subject by at least one of age, gender or genetic origin;
   a peptide obtained from a diseased subject, wherein the diseased subject is optionally matched with the subject by at least one of age, gender or genetic origin; and
   a peptide obtained from or part of a pooled sample obtained from diseased subjects, wherein the diseased subjects are optionally matched with the subject by at least one of age, gender or genetic origin.

39. The method of any previous embodiment wherein at least one test peptide, reference peptide, or both comprise at least one marker of oxidative stress selected from:
   2-amino-3-oxo-butanoic acid; 2-amino-3-oxo-butanoic acid; a hydroxylation; glutamate semialdehyde; sulfonic acid; sulfinic acid; sulfenic acid; formylkynurenin; kynurenin; hydroxykynurenin; 2,4,5,6,7 hydroxylation of tryptophan; oxolactone; 4-hydroxy glutamate; conversion of histidine to asparagine; conversion of histidine to aspartate; 2-oxo-histidine, aminoadipic semialdehyde; an Amadori adduct; a 3-deoxyglucosone adduct; a glyoxal adduct; a methylglyoxal adduct; conversion of proline to pyroglutamic acid; conversion of proline to pyrrolidinone; a 4-hydroxynonenal (4-HNE) adduct; a malondialdehyde adduct; and any other oxidative modification.

40. The method of any previous embodiment wherein a difference in oxidation state is indicative of the status of the subject, the status of the disease, the response of the subject to the disease, the response of disease to treatment, the effect or efficacy of a therapeutic agent, the general health status of subject, or the determination of biological age of an organ, or any combination thereof.

41. A method for monitoring the health of a subject comprising:
   comparing the value of a parameter associated with the oxidation state of at least one test peptide obtained from the subject with a reference value for the parameter; and
   detecting a difference in the value of a parameter associated with the oxidation state of the test peptide with the reference value for the parameter, wherein the difference is indicative of the health status of the subject.

42. The method of embodiment 41 wherein the reference value is derived from analysis of an earlier sample obtained from the subject.

43. The method of embodiment 41 wherein the reference value is not derived from an analysis of an earlier sample obtained from the subject.

44. A method for monitoring the health of a subject, comprising:
obtaining, receiving, providing, or preparing a test oxidized peptidic profile from a subject;
obtaining, receiving, providing, or preparing a reference oxidized peptidic profile;
comparing the test oxidized peptidic profile with the reference oxidized peptidic profile; and
detecting a difference between the test oxidized peptidic profile and the reference oxidized peptidic profile, where a difference between the test oxidized peptidic profile and the reference oxidized peptidic profile is indicative of the health status of the subject.

45. A method for monitoring the health of a subject comprising:
obtaining, receiving, or providing a sample comprising a plurality of peptides obtained from a subject; and
detecting or quantifying at least one oxidized peptide in the sample, wherein the oxidized peptide comprises at least one marker of oxidative stress selected from:
2-amino-3-oxo-butanoic acid; 2-amino-3-oxo-butanoic acid; a hydroxylation; glutamate semialdehyde; sulfonic acid; sulfuric acid; sulfenic acid; formylkynurenin; kynurenin; hydroxykynurenin; 2,4,5,6,7 hydroxylation of tryptophan; oxolactone; 4-hydroxy glutamate; conversion of histidine to asparagine; conversion of histidine to aspartate; 2-oxo-histidine, aminoadipic semialdehyde; an Amadori adduct; a 3-deoxyglucosone adduct; a glyoxal adduct; a methylglyoxal adduct; conversion of proline to pyroglutamic acid; conversion of proline to pyrrolidinone; a 4-hydroxy-nonenal (4-HNE) adduct; a malondialdehyde adduct; and any other oxidative modification.

46. The method of embodiment 45 further comprising mapping the oxidized peptide to a cell type, organ, tissue, pathogen or disease.

47. The method of embodiment 45 or 46 wherein the oxidized peptide is a low abundance peptide.

48. The method of any previous embodiment wherein monitoring the health of the subject comprises detecting the presence, absence, progression, regression, status, or extent of oxidative stress, disease, infection, or a disorder in the subject.

49. The method of any previous embodiment wherein monitoring the health of the subject comprises detecting the presence, absence, progression, regression, status, or extent of oxidative stress, disease, infection, or a disorder in an organ or tissue of the subject.

50. The method of embodiment 49 wherein the subject peptides are organ-specific or tissue-specific peptides.

51. The method of any previous embodiment wherein monitoring the health of the subject comprises detecting the presence, absence, progression, regression, status, or extent of oxidative stress, disease, infection, or a disorder in a subject, wherein the oxidative stress, disease, infection, or disorder of the subject is systemic or otherwise affect multiple organs or tissues of the body.

52. The method of any previous embodiment wherein monitoring the health of the subject comprises monitoring changes in the subject associated with aging.

53. The method of any previous embodiment wherein monitoring the health of the subject comprises monitoring the general wellness of the subject.

54. The method of any previous embodiment wherein the disease is selected from the group consisting of cancer, Type I diabetes, Type II diabetes, a neurodegenerative disease, atherosclerosis, chronic renal failure, chronic lung disease, and an inflammatory disease.

55. The method of embodiment 54 wherein the neurodegenerative disease comprises Alzheimer's disease, Parkinson's disease, or amyotrophic lateral sclerosis.

56. The method of any previous embodiment wherein indicators of the oxidation state of a test peptide is disease-specific.

57. The method of embodiment 56 wherein a pattern of oxidations within hemoglobin is indicative that the subject has diabetes.

58. The method of embodiment 56 wherein a pattern of oxidations within murinoglobin 1 analog is indicative that the subject has diabetes.

59. The method of any previous embodiment used to test the effect or efficacy of a therapeutic agent.

60. The method of embodiment 59 wherein the therapeutic agent comprises an antioxidant.

The present invention is illustrated by the following examples. It is to be understood that the particular examples, materials, amounts, and procedures are to be interpreted broadly in accordance with the scope and spirit of the invention as set forth herein.

EXAMPLES

Example 1

Profiling Carbonylated Proteins in Human Plasma

Materials

As further described in Madian et al., *J Proteome Res*, 2010, 9:1330-1343, Sodium cyanoborohydride Biotin hydrazide, ultralinked immobilized monomeric avidin, D-biotin, and Slide-A-Lyzer dialysis cassettes were purchased from Pierce (Rockford, Ill.). Iodoacetamide, dithiothreitol (DTT), trypsin, Glycine, α-Cyano-4-hydroxy-cinnamic acid (CHCA), proteomics grade N-p-tosyl-phenylalanine chloromethyl ketone (TPCK)-treated trypsin, ammonium bicarbonate, guanidine, dithiothreitol, iodoacetamide acid (IAA), and L-cysteine were obtained from Sigma Chemical Co. (St. Louis, Mo.). Protease inhibitor cocktail was purchased from Roche Diagnostics (Indianapolis, Ind.). The ABI 4700 Proteomics Analyzer Calibration Mixture (4700 Cal Mix, bradykinin, angiotensin I, glu1-fibrinopeptide B, ACTH fragment 1-17, ACTH fragment 18-39, and ACTH fragment 7-38) were purchased from Applied Biosystems, Inc. (Foster. City, Calif.). Trifluoroacetic acid (TFA), and HPLC grade acetonitrile were purchased from Mallinckrodt Chemicals (Phillipsburg, N.J.). Sodium phosphate, sodium chloride were purchased from Mallinkrodt (St. Louis, Mo.). Amicon Ultra-4 centrifugal filter devices were purchased from Millipore (Billerica, Mass.).

Methods

Biotinylation of Normal Human Plasma.

Blood was withdrawn from four drug free, non-smoking male subjects (age 32-36 years). Samples were mixed with EDTA and protease inhibitor, centrifuged at 1500×g for 15 minutes, and the supernatant was removed. After centrifugation again at 2000×g for 15 minutes, 50 mM biotin hydrazide was added to a final concentration of 5 mM and the reaction was allowed to proceed at room temperature for another two hours. Sodium cyanoborohydride was then added to a final concentration of 15 mM and the reaction was permitted to proceed at 0° C. for one hour. Three sequential dialyses were performed in at least 200 volume equivalents of PBS buffer to remove any unreacted biotin hydrazide.

Avidin Selection of Biotinylated Proteins.

For the sake of identification, avidin selection was performed individually on the four samples. Characterization of oxidative stress induced post-translational modifications (OSi~PTM) was achieved however by pooling the four samples and enriching modified proteins. An Agilent series 1100 (Agilent Technologies) HPLC was used for packing immobilized monomeric avidin into affinity columns as well as the purification of biotinylated proteins. Ultralinked immobilized monomeric avidin was self-packed in a PEEK column (4.6 mm×100 mm). After packing, the column was washed with 50 column volumes (CV) of PBS (0.15M pH 7.4) followed by 100 CV of 2 mM biotin to block any non-reversible biotin binding sites. This was followed by a 100 CV wash with regeneration buffer (0.1 M glycine pH 2.5) and 100 CV of PBS re-equilibration phase. Bradford assays were used to estimate the concentration of the protein in the plasma samples. A total of 15 mg of plasma proteins was applied onto the affinity column with PBS mobile phase (0.15 M phosphate buffered saline, pH 7.4) at a flow rate of 0.5 mL/min. To remove any unbound proteins, the column was washed thoroughly with more than 60 CV loading buffer. The bound proteins were then eluted with regeneration buffer (0.1 M glycine pH 2.5). The resulting chromatogram was monitored at 280 nm.

Proteolysis.

Affinity purified proteins were concentrated with an Amicon Ultra-4 centrifugal filter devices. The samples were further dried and reconstituted in 6 M guanidine HCl and 10 mM dithiothreitol. After one-hour incubation at 70° C., iodoacetamide (at a final concentration of 10 mM) was added to the reaction and allowed to incubate for 30 minutes at 4° C. The sample was diluted six-fold in ammonium bicarbonate (0.1 M, pH 8.0) and sequence grade trypsin (2%) was added. Proteolysis was allowed to proceed at 37° C. for at least 18 hours, after which the reaction was stopped by addition of tosyl lysine chloroketone (TLCK) (trypsin:TLCK ratio of 1:1 (w/w)). The resulting tryptic peptide mixture was analyzed with the MALDI-TOF/TOF and LTQ orbitrap XL instruments.

LTQ Orbitrap Based Identification and Characterization.

The digested peptide mixtures resulting from trypsin proteolysis were separated on an Agilent 1100 HPLC system using a 75 µm×120 mm C18 reversed-phase chromatography (RPC) column packed with 5 µm C18 Magic beads. Peptide separations were achieved using a 60 min linear mobile phase gradient from 0.1% formic acid to 0.1% formic acid in acetonitrile at a flow rate of 0.3 µL/rain. The electrospray ionization emitter tip was generated on the pre-packed column with a laser puller (Model P-2000, Sutter Instrument Co.). The HPLC system was coupled directly to the LTQ Orbitrap hybrid mass spectrometer (Thermoelectron, San Jose, Calif.). The LTQ Orbitrap was equipped with a nanoelectrospray ion source (Proxeon Biosystems, Odense, Denmark). The MS was operated in the data-dependent mode, in which a survey full scan MS spectrum (from m/z 300 to 1600) was acquired in the Orbitrap with a resolution of 60,000 at m/z 400. This was then followed by MS/MS scans of the three most abundant ions with +2 to +3 charge states. Target ions already selected for MS/MS were dynamically excluded for 180s. The resulting fragment ions were recorded in the linear ion trap. Proteins are listed in Table 5 according to their Swiss-Prot entry names and accession numbers.

MALDI/TOF/TOF Based Protein Identification.

The tryptic peptides fractions obtained from the digestion of the affinity purified proteins were desalted and fractionated using an Agilent 1100 Series HPLC (Agilent Technologies).

A Pepmap C18 trap column and a Zorbax 300sB-C18, 3.5 µm, 100 µm i.d. RPC column of 15 cm length, (Agilent Technologies, Santa Clara, Calif.) were used. The RPC separation was achieved using a 40 min linear gradient from 98% solvent A: 2% solvent B to 60% solvent A: 40% solvent B at a flow rate of 800 nL/min. Solvent A was composed of 0.1% TFA in deionized water while solvent B was composed of 0.1% TFA in acetonitrile. Peptide fractions from the RPC column were mixed with MALDI matrix (α-cyano-4-hydroxycinnamic acid, 4 mg/mL in 60% ACN/0.1% TFA) continuously using a mixing tee at the end of the RPC column. An Applied Biosystems Inc. model 4800 MALDI/TOF/TOF Proteomics Analyzer equipped with a 200 Hz Nd:Yag laser was used in the positive ion mode for the analysis of peptides spotted on a MALDI plate. The 4000 Explorer software furnished with the ABI 4800 controlled the automated acquisition of MS and MS/MS data. Protein identification based on acquired MS/MS spectra were carried out using Protein Pilot software 2.0 with the Pro Group™ algorithm for protein identification. A 95% confidence level of peptide identification was used as the minimum acceptance criterion. Proteins were identified based on the presence of at least two unmodified peptides from the same protein identified by the Pro Group™ algorithm at the 95% confidence level. Proteins identified in this analysis are listed in Table 6 according to their Swiss-Prot entry names and accession numbers.

Mascot Database Searching.

The MS data files (recorded with the Xcalibur software version 2.0.7, Thermo Fisher Scientific) obtained by LC/MS/MS analysis on the LTQ Orbitrap XL instrument were converted to dta files using the in house online LTQ_dta software. Minimum scans per group parameter were set to 1. The charge of the precursor ions was determined automatically by the software. Files were then sent to an in-house MASCOT server (Version 2.2, Matrix Science (Perkins et al., *Electrophoresis* 1999, 20(18):3551-3567)). The human taxonomy in the Swiss-Prot/Uniprot database was searched. Mascot has the limitation of allowing just nine modifications per search. Therefore, it was searched separately six times for each sample with a maximum of six modifications each time. The variable modifications were as follows. Search one targeted carbamidomethyl (C), oxidation (C, D, F, H, K, L, N, P, R, W, Y) and oxidation (M). The second focused on carbamidomethyl (C), dioxidation (C, F, M, P, R, W) and trioxidation (C). The third was directed to carbamidomethyl (C), biotinylated HNE (H, C, K), biotinylated glyoxal (K), biotinylated Amadori (K), biotinylated 3-deoxyglucosone (K) and biotinylated methyl glyoxal. The fourth search targeted carbamidomethyl (C), biotinylated oxidized arginine, biotinylated oxidized lysine, biotinylated oxidized proline, and biotinylated oxidized threonine. The fifth search was directed toward carbamidomethyl (C), the oxidation of tryptophan to kynurenin, the oxidation of tryptophan to hydroxykynurenin, the oxidation of tryptophan to oxolactone, the oxidation of proline to pyroglutamic acid and the oxidation of proline to pyrrolidinone. In the sixth search, only carbamidomethyl (C) was searched. A decoy method was used to estimate the false discovery rate. The decoy for the four samples was generally less than 1.8%. Four missed cleavages were allowed. The precursor mass tolerance was set to 5 ppm and the fragment mass tolerance was set to 0.6 Da. Only proteins with at least two unmodified peptides were considered as correct matches. Proteins that were identified based on just one peptide or appeared in just one sample were rejected. Strict criteria were used to eliminate false positive identification of any of the modifications identified. For all modifications except biotinylation, the modification had to have an expectation value less than 0.05 and was manually validated in order to be considered as a correct match. The fragmentation of biotin however produces noise in the spectrum that increases the expectation value (Borisov Oleg et al., *Anal. Chem.* 2002, 74(10):2284-92; Han et al., *Anal. Chem.* 2007, 79(9):3342-54; Mirzaei et al., *J. Chromatogr., B: Anal. Technol. Biomed. Life Sci.* 2008, 873(1):8-14). Consequently, the biotinylated modifications were validated manually only.

Annotating the Identified Proteins Based on their Tissue of Origin.

Figure 4:
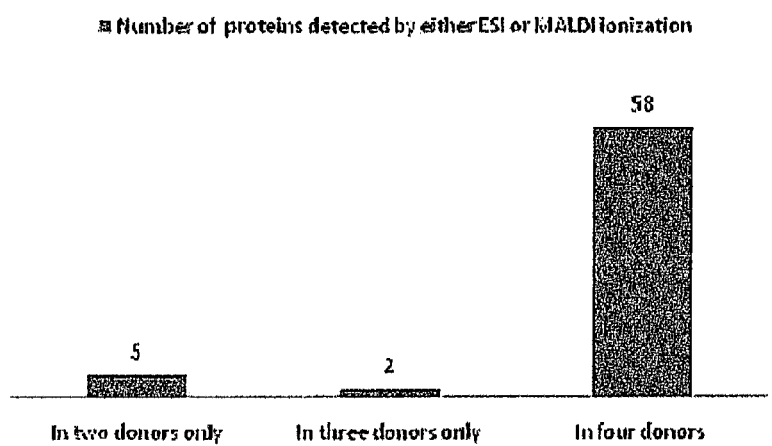
FIG. 4. Comparison between the number of oxidized proteins identified in the four donors' plasma using ESI-MS, MALDI-MS, or both.

The human plasma atlas (version 4.0; Berglund et al., *Mol. Cell. Proteomics* 2008, 7(10):2019-2027) was used to annotate the identified proteins according to their expression in the different tissues inside the body. The degree of their expression can be strong, medium or weak. FIG. 4 shows a distribution of these proteins in the different tissues.

Example 2

Affinity Chromatographic Selection of Carbonylated Proteins Followed by Identification of Oxidation Sites Using Tandem Mass Spectrometry Materials As further described in Mirzaei et al., *Anal. Chem.*, 2005, 77(8):2386-2392, biotin hydrazide, ultralinked immobilized monomeric avidin, D-biotin, sodium cyanoborohydride, trifluoroacetic acid (TFA), Slide-A-Lyzer dialysis cassettes, and Coomassie blue (Bradford) protein assay kits were purchased from Pierce Co. (Rockford, Ill.). Iodoacetic acid (IAA), dithiothreitol (DTT), trypsin, N—R-tosyl-L-lysine chloromethyl ketone (TLCK), and bovine serum albumin (BSA) were obtained from Sigma Chemical Co. (St. Louis, Mo.), Iron(III) chloride, potassium chloride, magnesium chloride, ascorbic acid, urea, and calcium chloride were purchased from Mallinckrodt. (St. Louis, Mo.). Protease inhibitor cocktail was purchased from Roche Diagnostics Corp. (Indianapolis Ind.). A 218TP54 reversed-phase C18 and 208TP54 reversed-phase C8 column was purchased from Vydac™ (W. R. Grace & Co., Columbia, Md.). The affinity selection and reversed-phase chromatography analyses were done on an Integral Micro-analytical Workstation (PE Biosystems, Framingham, Mass.). Mass spectral analyses were done using a Sciex QSTAR hybrid LC/MS/MS quadrupole TOF mass spectrometer. All spectra were obtained in the positive ion mode.

Methods

Protein Oxidation and Concentration Measurements.

Metal-catalyzed oxidation of BSA was accomplished according to Stadman and Oliver (*J. Biol. Chem.* 1991, 266: 2005-2008). BSA was dissolved at a concentration of 10 mg/mL in oxidation buffer (50 mM Hepes buffer, pH 7.4, 100 mM KCl, 10 mM $MgCl_2$) at a total volume of 1 mL. The BSA solution was then dialyzed against the solubilization buffer (3×500 mL) at 4° C. to remove any impurities that might be present in the commercial BSA and could interfere with oxidation reaction. Oxidation was accomplished by incubation with a freshly prepared mixture of neutral ascorbic acid (to a final concentration of 25 mM) and $FeCl_3$ (to a final concentration of 100 µM) at 37° C. overnight in a shaking bath. The reaction was stopped by addition of EDTA (1 mM). This sample was then dialyzed against phosphate buffer saline (PBS) (0.1 M sodium phosphate, 0.15 M NaCl, pH 7.4) (3×500 mL) at 4° C. A control sample was prepared in oxidation buffer supplemented with 1 mM EDTA. The protein concentration was measured using the Coomassie blue protein assay.

Protein Oxidation and Derivatization.

Metal-catalyzed oxidation of BSA was accomplished as described in the previous section. The only difference was addition of biotin hydrazide (5 mM final concentration) prior to addition of a freshly prepared mixture of neutral ascorbic acid and $FeCl_3$. Protein concentration was reduced to 2 mg/mL by addition of PBS. Hydrazone bonds were reduced at 0° C. with addition of an equal volume of 30 mM sodium cyanoborohydride in PBS followed by incubation for an additional 40 minutes at the same temperature (Hermanson, *Bioconjugate techniques*; Academic Press: New York, 1996). Excess reactants were removed by dialysis against PBS. Control samples were prepared in oxidation buffer supplemented with 1 mM EDTA.

Avidin Affinity Selection.

Ultralinked immobilized monomeric avidin was packed into a stainless steel column (4.6 mm i.d.×100 mm, 1.7 mL volume) at 100 psi. The packed column was washed with 10 column volumes of PBS and five column volumes of 2 mM D-biotin in PBS (biotin blocking and elution buffer) to block any nonreversible biotin binding sites on the column. Biotin from reversible biotin binding sites was removed by washing with five column volumes of 0.1 M glycine, pH 2.8 (regeneration buffer). Finally, the column was re-equilibrated with 10 column volumes of PBS. A 500 µL volume of sample (2 mg/mL) was loaded into the column followed by 0.25 mL of PBS. The column was incubated at room temperature for one hour and washed with 10 column volumes of PBS to remove all unbound proteins. Biotinylated proteins were eluted with 10 column volumes of biotin blocking and elution buffer (2 mM D-biotin in PBS), and the column was regenerated with 10 column volumes of regeneration buffer (0.1 M glycine, pH 2.8) followed by 10 column volumes of PBS.

Selectivity Experiment.

Yeast (A-type strain) was grown in synthetic complete medium lacking uracil (the yeast proteome was available from another study) media to an OD of 2-3. Cells were harvested and lysed by a French press. The lysed cells were centrifuged at 150000 g for 90 minutes, and the supernatant was collected. The protein concentration of the cell lysate was measured to be 1.98 mg/mL with the Bradford assay. The oxidized biotinylated BSA as described above was added to the yeast extract at a concentration of 50 µg/mL. A 1-mL sample of the yeast extract was avidin affinity selected, and the captured fraction was further separated by a C8 reversed-phase column.

Proteolysis.

To denature, reduce, and alkylate samples, urea and DTT were added to a final concentration of 6 M and 10 mM, respectively. Mixtures were incubated for one hour at 37° C., IAA was then added to a final concentration of 20 mM, and the reaction was allowed to proceed for an additional 30 minutes at 4° C. Cysteine was then added to a final concentration of 10 mM to quench extra IAA. Samples were diluted six-fold with 50 mM HEPES, pH 8.0, 10 mM $MgCl_2$, and 10 mM $CaCl_2$. Sequence grade trypsin was added (2%) and the reaction mixture incubated at 37° C. for at least 8 hours. Proteolysis was stopped by adding TLCK (trypsin/TLCK ratio of 1:1 (w/w)).

Reversed-Phase Chromatography.

Tryptic digest of the oxidized proteins was fractionated on a Vydac C18 column (4.6 mm×250 mm) using an Integral Micro-analytical Workstation at 1 mL/min. Solvent A contained 0.1% TFA, 0.5% acetonitrile (ACN), and 99.5% deionized $H_2O$ (dI $H_2O$) and solvent B contained 0.1% TFA, 95% ACN, and 5% dI $H_2O$. The peptides from tryptic digest were fractionated by a 60 min gradient from 100% A to 60% B.

Fractions were collected, speed vacuum-dried, and stored at −20° C. for mass spectrometry.

Mass Spectrometry.

Collected fractions from the previous step were redissolved in 50% methanol, 50% dl $H_2O$, and 0.1% acetic acid. Fractions were directly electrosprayed using a direct syringe pump. All MS spectra were acquired on TOF-MS scan mode with ion spray voltage adjusted to 5500 V and curtain gas 25 V. The MS spectra were manually searched, and candidate peptides were identified for MS/MS analysis. All MS/MS spectra were acquired on product ion scan mode with the same electrospray setting. The collision energy for fragmentation of peptides was manually adjusted for each peptide.

Induction of Oxidation by 2-Nitropropane and Extraction of Oxidized Proteins from Rat Liver.

Rats were dosed with 350 mg of 2-nitropropane/kg known to cause oxidative damage to the proteins in vivo. Control rats were dosed with 0.9% NaCl. Rats were sacrificed with $CO_2$. Liver tissue was homogenized in buffer containing 0.1 M sodium phosphate pH 7.4, 0.1 M NaCl, 0.1% SDS, 1 tablet of protease inhibitor cocktail (including broad spectrum of serine, cysteine, and metalloprotease as well as calpains inhibitors), and 5 mM biotin hydrazide. The sample was centrifuged at 6000 g for one hour at 4° C. and the supernatant collected after measuring the protein concentration. Samples were diluted to 2 mg/mL with homogenizing buffer and incubated at room temperature for two hours in darkness. An equal volume of 30 mM sodium cyanoborohydride was then added and the mixture incubated at 0° C. for 40 minutes. Reactants were removed via dialysis against PBS. The dialyzed solution was centrifuged at 14000 g for 20 minutes, and the supernatant was collected.

Example 3

Proteomic Analysis of the Oxidative Stress Profile of Proteins in the Plasma of Breast Cancer Patients Materials Sodium cyanoborohydride, biotin hydrazide (BH), ultralinked immobilized monomeric avidin, D-biotin, protein A/G chromatography cartridges, UltraLink Biosupport™, Slide-A-Lyzer™ dialysis cassettes, biotinylated alkaline phosphatase, biotinylated horseradish peroxidase, biotinylated protein A and biotinylated protein G were purchased from Pierce (Rockford, Ill.). Iodoacetamide, dithiothreitol (DTT), glycine, α-cyano-4-hydroxy-cinnamic acid (CHCA), proteomics grade N-p-tosyl-phenylalanine chloromethyl ketone (TPCK)-treated trypsin, ammonium bicarbonate, guanidine, and L-cysteine were obtained from Sigma Chemical Co. (St. Louis, Mo.). Complete, Mini, EDTA-free, protease inhibitor Cocktail™ tablets were purchased from Roche Diagnostics (Indianapolis, Ind.). The ABI 4700 Proteomics Analyzer Calibration Mixture (4700 Cal Mix, bradykinin, angiotensin I, glu1-fibrinopeptide B, ACTH fragment 1-17, ACTH fragment 18-39, and ACTH fragment 7-38) and iTRAQ™ reagent Multiplex kit were purchased from Applied Biosystems, Inc. (Foster City, Calif.). Trifluoroacetic acid (TFA), and HPLC grade acetonitrile were purchased from Mallinckrodt Chemicals (Phillipsburg, N.J.). OxiSelect™ 8-iso-Prostaglandin F1α Activity Assay Kit was purchased from Cell Biolabs Inc. (San Diego, Calif.). BD Vacutainer™ venous blood collection tubes with EDTA were purchased from Fisher Scientific (Hanover Park, Ill.). Sodium phosphate, sodium chloride and formic acid 88% were purchased from Mallinkrodt (St. Louis, Mo.). Amicon Ultra-4™ centrifugal filter devices were purchased from Millipore (Billerica, Mass.).

Methods

Plasma Samples.

Blood sample collection was carried out as part of the program on Clinical Proteomics Technology Assessment for Cancer (CPTAC) sponsored by NCI using protocols approved by Institutional Review Boards at UCSF and Purdue University. Samples were collected at the UCSF, biotinylated (with 50 mM biotin hydrazide reagent to a final concentration of 5 mM), reduced (with sodium cyanoborohydride to a final concentration of 15 mM), frozen, and transferred in the frozen state to Purdue University. Breast cancer patient plasma samples were derived from newly diagnosed female subjects (four stage I and two stage 11 subjects) before any type of therapeutic intervention. Six breast cancer patients and six normal matched controls of 55 years average age donated blood.

Plasma Sample Preparation.

Carbonylated proteins form Schiff bases with lysine residues on other proteins during storage, even at −80° C. This means that carbonyl content will decline during storage and blood samples must be derivatized with biotin hydrazide (BI-1) before storage or transport. This was precluded by adding biotin hydrazide to plasma samples immediately after initial plasma preparation. A mixture of inhibitors for cysteine and serine proteases was included with biotin hydrazide to prevent formation of new peptides by intrinsic endoproteases as has been recently reported (Shipitsin et al., *Cancer Cell* 2007, 11:259-273). Generally, each tablet of the protease inhibitor cocktail was dissolved in 1 ml of distilled water. Then the protease inhibitor solution was mixed with plasma in ratio of 1:10 (v/v) respectively. Because plasma samples were maintained at neutral pH during biotinylation and affinity selection there was no need to inhibit aspartate protease along with proteases that are only active at acidic pH.

Biotinylation of Plasma Samples.

Freshly drawn blood samples were collected in BD Vacutainer™ venous blood collection tubes coated with EDTA (Fisher Scientific, Hanover Park, Ill.). Protease inhibitor cocktail was then added (as described in the previous section). Plasma was then centrifuged at 1500×g for 15 minutes, the supernatant was removed, and then centrifuged a second time at 2000×g for 15 minutes. Immediately thereafter 50 mM of biotin hydrazide (BH) was added to the plasma to a final concentration of 5 mM and the reaction was allowed to proceed at room temperature for two hours. Sodium cyanoborohydride was then added to a final concentration of 15 mM and the solution incubated at 0° C. for one hour. The samples were then dialyzed three times against at least 200 volumes of PBS buffer to remove unreacted BH.

Affinity Chromatography.

An Agilent series 1100 (Agilent Technologies) system was used for packing the immobilized monomeric avidin columns and the purification of biotinylated proteins. This ultralinked immobilized monomeric avidin (Pierce, Rockford, Ill.) was self-packed in a PEEK column (4.6 mm×100 mm) The column was then washed with PBS (0.15M pH 7.4) followed by 2 mM biotin to block any non-reversible biotin binding sites. This was followed by washing with a regeneration buffer (0.1 M glycine, pH 2.5) and re-equilibration by PBS. The Bradford assay was used to estimate protein concentration in plasma. In the first phase of this study, plasma samples from breast cancer patient and their controls were affinity selected individually. Each time, a total of 5 mg of plasma proteins was applied to the avidin affinity column with PBS mobile phase (0.15 M phosphate buffered saline, pH 7.4) at a flow rate of 0.5 mL/min for 320 column volumes. The bound proteins were then eluted with the regeneration buffer (0.1 M glycine, pH 2.5). The affinity-selected samples were then reduced, alkylated, digested and labeled with the iTRAQ™ reagent as described below (FIG. 17). In the second phase of this study, in order to isolate the oxidized immunoglobulin from pooled breast cancer patients' plasma samples and their pooled controls, protein A/G chromatography cartridge (1.3 3.8 cm) was used before the avidin purification. In that case the immunoglobulin fraction isolated using protein A/G chromatography cartridge (Pierce, Rockford, Ill.) was purified using Amicon Ultra-4™ centrifugal devices (Millipore, Billerica, Mass.) as described by the supplier's guidelines and applied on the avidin column (FIG. 18A). On the other hand, in order to isolate the oxidized non-immunoglobulins, the same system (protein A/G chromatography cartridge connected before immobilized avidin column) was used. But in this case only the flow-through fraction from the protein A/G was directed to the avidin purification (FIG. 18B). In each case, the sample was applied with PBS mobile phase (0.15 M phosphate buffered saline, pH 7.4) at a flow rate of 0.5 mL/min for 320 column volumes. The bound proteins were then eluted from either the protein A/G or avidin column with the regeneration buffer (0.1M glycine, pH 2.5). The purified proteins were then reduced, alkylated and analyzed using LTQ-orbitrap XL™ as described below.

Quantitative Comparison of Protein Abundance with iTRAQ™ and MALDI/TOF/TOF Analysis.

Proteins that were purified using avidin affinity chromatography were digested and labeled with iTRAQ™ reagent. The supplier's guidelines (Applied Biosystems, Inc. Foster City, Calif.) were followed for both trypsin digestion and labeling with iTRAQ™ reagent. The six breast cancer samples and their controls were labeled with the 117-Da and 114-Da iTRAQ™ labeling agents respectively. The labeled peptides were then desalted and fractionated using Agilent 1100 Series HPLC (Agilent Technologies). A Pepmap C18 trap column and a nano-column (Zorbax 300SB-C18, 3.5 µm, 100 µm i.d., 15 cm length, Agilent Technologies, Santa Clara, Calif.) were used. Two solvents were used for the reversed-phase separation, solvent A composed of 0.1% TFA in deionized water and solvent B composed of 0.1% TFA in acetonitrile. The RPC separation was achieved using a 40 min linear gradient from 98% solvent A: 2% solvent B to 60% solvent A: 40% solvent B at a flow rate of 800 mL/min. A mixing tee was used to mix the peptides separated with (α-cyano-4-hydroxy-cinnamic acid, 4 mg/mL in 60% ACN/0.1% TFA) a matrix. A microfraction collector was used to spot the peptides matrix solution on the plate. The spotted peptides were analyzed using ABI 4800 Plus™ (4800 MALDI/TOF/TOF) Proteomics Analyzer equipped with a 200 Hz Nd:Yag laser in the positive ion mode. 4000 Explorer™ software controlled the automated acquisition of MS and MS/MS analysis. Protein identification based on the acquired MS/MS spectra was carried out utilizing Protein Pilot software 2.0 using the Pro-Group™ algorithm (ABI) for protein identification. Protein Pilot™ software 2.0 with the ProGroup™ algorithm performed automated MS/MS data analysis for protein identification and quantification of iTRAQ™ reporter ions. The peaks thus generated in this analysis were searched against *Homo sapiens* species in the UniProt/Swiss-Prot database. One missed cleavage was allowed. Variable modifications used were Cys alkylation using methyl methanethiosulfonate (MMTS) and all the biological modifications which include 126 modifications included in the ProteinPilot™ software. Only proteins with a confidence level of 95% or more were (unused score 1.3) were accepted. The false discovery rate (FDR) was generally less than 5% for the proteins identified.

Testing iTRAQ™ reproducibility. Four mixtures of 100 µg of each of biotinylated alkaline phosphatase, biotinylated horseradish peroxidase, biotinylated protein A and biotinylated protein G (Pierce, Rockford, Ill.) were prepared. Each of these mixtures was purified with avidin as described above. The purified fractions were then reduced, alkylated and digested. The four digested samples were then labeled with 114-Da, 115-DA, 116-Da, or 117-Da iTRAQ™ labeling agents. The 114-Da iTRAQ™ labeled fraction was mixed with the 117-Da iTRAQ™ labeled fractions and the 115-Da iTRAQ™ was mixed with the 116-Da iTRAQ™ labeled fractions. These two samples were then purified, analyzed with MALDI/TOF/TOF as described above.

Proteolysis.

Tryptic digests of oxidized immunoglobulins and non-immunoglobulins were used to identify their oxidation sites. Samples were reconstituted in 6 M guanidine HCl and 10 mM dithiothreitol and incubated for one hour at 70° C. Iodoacetamide was then added to the reaction to a final concentration of 10 mM and allowed to incubate for 30 minutes at 4° C. This was followed by a six-fold dilution of the sample with 0.1 M ammonium bicarbonate (pH 8.0). Sequence grade trypsin (2%) was added and the reaction mixture incubated at 37° C. for at least 18 hours. Proteolysis was stopped by addition of tosyl lysine chloroketone (TLCK). (trypsin:TLCK ratio of 1:1 (w/w)). The tryptic peptides were then used for the characterization of the oxidation sites using a nanoHPLC-LTQ Orbitrap XL™ mass spectrometer.

LTQ Orbitrap-Based Identification and Characterization.

The digested peptide mixtures resulting from trypsin proteolysis were separated on an Agilent 1100 HPLC system using a 75 µm 120 mm C18 reversed-phase chromatography (RPC) column packed with 5 µm C18 Magic beads. Peptide separations were achieved using a 60 min linear mobile phase gradient from 0.1% formic acid to 0.1% formic acid in acetonitrile at a flow rate of 0.3 µL/min. The HPLC system was coupled directly to the LTQ Orbitrap™ hybrid mass spectrometer (Thermoelectron, San Jose, Calif.). The LTQ Orbitrap™ was equipped with a nanoelectrospray ion source (Proxeon Biosystems, Odense, Denmark). The MS was operated in the data-dependent mode, in which a survey full scan MS spectrum (from m/z 300 to 1600) was acquired in the Orbitrap™ with a resolution of 60,000 at m/z 400. This was then followed by MS/MS scans of the three most abundant ions with +2 to +3 charge states. Target ions already selected for MS/MS were dynamically excluded for 180s. The resulting fragment ions were recorded in the linear ion trap.

Mascot Database Searching.

The MS data files (recorded with the Xcalibur™ software version 2.0.7, Thermo Fisher Scientific) obtained by LC/MS/MS analysis on the LTQ Orbitrap XL™ instrument were converted to DTA files using the in house online LTQ_DTA software. Minimum scans per group parameter were set to 1. The charge of the precursor ions was determined automatically by the software. Files were then sent to an in-house MASCOT™ server (Version 2.2, Matrix Science). The human taxonomy in the Swiss-Prot/Uniprot database was searched. Mascot™ has the limitation of allowing only nine modifications per search. Therefore, it was searched separately four times. In all cases the fixed modifications targeted carbamidomethyl (C). The variable modifications were as follows. Search one targeted oxidation (C, D, F, H, K, L, N, P, R, W, Y) and oxidation (M). The second focused on dioxidation (C, F, M, P, R, W) and trioxidation (C). The third was directed to biotinylated HNE (H, C, K), biotinylated glyoxal (K), biotinylated Amadori (K), biotinylated 3-deoxyglucosone (K) and biotinylated methyl glyoxal. The fourth search targeted biotinylated oxidized arginine, biotinylated oxidized lysine, biotinylated oxidized proline, and biotinylated oxidized threonine. A decoy method was used to estimate the false discovery rate. The precursor mass tolerance was set to 5 ppm and the fragment mass tolerance was set to 0.6 Da. The decoy was generally less than 3% for the peptides identified. Strict criteria were used to eliminate false positive identification of any of the modifications identified. For all modifications except biotinylation, the modification had to have an expectation value less than 0.05 and was manually validated in order to be considered as a correct match. The fragmentation of biotin however produces noise in the spectrum that increases the expectation value (Borisov Oleg et al., *Anal. Chem.* 2002, 74:2284-2292; Han et al., *Anal. Chem.* 2007, 79:3342-3354; Mirzaei and Regnier, *J. Chromatog. B* 2008, 873:8-14). Consequently, the biotinylated modifications were validated manually only.

Gene Ontology (GO) and Pathway Analysis.

Only proteins with more than 1.5-fold changes were used in these analyses. To identify the role of these proteins in breast cancer, their Uniprot_Accession and SwissProt identifiers were uploaded into DAVID (Dennis et al., *Genome Biol* 2003, 4:P3; Huang et al., *Nat. Protoc.* 2009, 4:44-57; The Database for Annotation, Visualization, and Integrated Discovery) for gene ontology analysis, and GeneGo™ (GeneGo Inc., Joseph, Mich.) for the pathway analysis respectively. In both cases the background gene population was set to "Human." On DAVID, proteins were analyzed using the functional annotation tool that provides GO by molecular function and GO by biological processes. Pie charts were made based on the output data from the gene ontologies. To study protein interactions and relationship with diseases among our data set, we used the "build network" tool from GeneGo™. We selected the "network analysis" by "transcription factors" because a big portion of our list was involved in DNA binding (see GO by molecular function), immune system regulation and biological process regulation (see GO by Biological process). We also filtered the network by interactions. We selected all types of interactions with positive and negative effects and excluded non-specified interactions, pharmacological effects, toxic effects, and miRNA binding. To determine whether GeneGo™ could correlate our data set with specific diseases we used the GeneGo™ "disease biomarker networks" tool, which contain disease biomarkers as seed nodes for the network. The networks were set to the default value of 0.5 of significant level, which indicates a false positive value of no more than 5% for the list of significant networks. For cellular localization, the protein list was uploaded and analyzed using the Build Network tool from GeneGo™. The output was then filtered by cellular localization to determine where these proteins are normally found in the cell. For GeneGo™ GO distributions, we uploaded the protein list along with their calculated fold changes. All networks and distributions were sorted by the most statistically significant using a P-value of 0.5 as the cutoff.

Testing Non-Specific Binding (NSB) to the Support Material.

Proteins can non-specifically bind to the support material (UltraLink Biosupport™) on which avidin was immobilized. In order to test this, 300 mg of UltraLink Biosupport™ was mixed with 1.0 M Tris, pH 8.0 buffer to block the reactive azalactone groups. This then went through a three cycles of centrifugation at 1,200×g and resuspension. The beads were then resuspended in PBS pH 7.4 (5% Sodium azide). The slurry was then self-packed in a PEEK column (4.6 mm×100 mm). Then a pooled breast cancer sample and a pooled control sample were applied on the column. These samples were applied with PBS mobile phase (0.15 M phosphate buffered saline, pH 7.4) at a flow rate of 0.5 mL/min for 320 column volumes. The bound proteins were then eluted with the regeneration buffer (0.1 M glycine, pH 2.5). The proteins eluted were then digested and identified using MALDI/TOF/TOF as described above.

8-Isoprostane Measurement.

Measurement of both free and esterified 8-iso-Prostaglandin F2α (8-iso-PGF2α) was achieved by treating the six breast cancer patient plasma samples and their controls with 2N NaOH at 45° C. for two hours. The procedure for the enzyme immunoassay (EIA) was executed according to the instructions provided by Cell Biolabs Inc. (San Diego, Calif.). Plasma samples (1304) were assayed twice by measuring absorbance at 450 nm. Concentrations of 8-isoprostanes at pg/ml levels were compared between control and cancer plasma samples using the Student t-test. A P-value of <0.05 on a 2-tailed test with 95% confidence intervals was considered statistically significant.

Example 4

Effect of the M26I Substitution on Oxidative Modifications of the Parkinson's Disease-Related Protein, DJ-1

Materials

Unless otherwise specified, chemicals were obtained from Sigma Chemical Co. (St. Louis, Mo.). Isopropylthiogalactoside (IPTG) was purchased from Gold Biotechnologies (St. Louis, Mo.). PreScission™ Protease was obtained from GE Healthcare (Piscataway, N.J.). The bicinchoninic acid (BCA) protein assay kit was purchased from Pierce Biotechnology (Rockford, Ill.). Immobilized trypsin and tris(2-carboxyethyl) phosphine (TCEP) were purchased as Pierce products from Thermofisher Scientific (Rockford, Ill.). Amicon Ultra-0.5 mL (Ultracel YM-10) and Amicon Ultra-4 (Ultracel-3) centrifugal filters and $H_2O_2$ were purchased from Millipore (Billerica, Mass.). Trifluoroacetic acid (TFA) and HPLC grade $CH_3CN$ were purchased from Mallinckrodt Chemicals (Phillipsburg, N.J.). Materials for 2D PAGE (immobilized pH gradient (IPG) strips, sample rehydration buffer, Criterion XT 12% Bis-Tris pre-cast gels, XT MOPS 2D PAGE running buffer, protein standards) were obtained from Bio-Rad (Hercules, Calif.). Urea was obtained from Mallinckrodt Laboratories (Phillipsburg, N.J.), and agarose was purchased from Invitrogen (Carlsbad, Calif.).

Methods

Preparation of Bacterial Expression Constructs.

Human wild-type DJ-1 and the familial mutant M26I were expressed as N-terminal glutathione-S-transferase (GST) fusions. A construct encoding GST-DJ-1$_{M26I}$ in the pGEX-6P1 vector (courtesy of Dr. Soumya Ray, Brigham and Women's Hospital (Logan et al., *Biochemistry*, 2010, 49(27): 5624-5633)) was converted to a new construct encoding GST-DJ-1$_{WT}$ by PCR using the QuikChange method (Stratagene, Santa Clara, Calif.). The sequence of the DJ-1-encoding insert in each construct was verified using an ABI 3700 DNA sequencer (Applied Biosystems, Inc., Foster City, Calif.).

Purification of Recombinant DJ-1.

Wild-type and mutant DJ-1 were purified as described (Logan et al., *Biochemistry*, 2010, 49(27): 5624-5633). Cells of the BL21(DE3) strain of *Escherichia coli* were transformed with each pGEX-6P-1 GST DJ-1 construct by electroporation. The transformed cells were grown to an OD$_{600}$ of 0.4-0.6 in LB plus ampicillin (100 µg/mL) at 37° C., and IPTG was added to a final concentration of 1 mM. The cells were grown under inducing conditions for 18 hours at 18° C., harvested by centrifugation, and resuspended in buffer G (25 mM $KP_i$, pH 7.0, 200 mM KCl). The cells were lysed by incubation on ice in the presence of lysozyme (1 mg/mL, 30 minutes) followed by passage through a French pressure cell (p.s.i.>1000). After centrifugation (20,000 g, 20 minutes), the supernatant was applied to a GSTPrep FF column (GE Healthcare), from which GST DJ-1 was eluted in 250 mM Tris HCl, pH 8.0, 500 mM NaCl, and 0.3% [w/v] reduced glutathione (GSH). Fractions most highly enriched with GST DJ-1 were identified by SDS PAGE with Coomassie Blue staining and pooled. The pooled fractions were dialyzed against buffer G plus dithiothreitol (DTT) (0.25 mM) to remove excess GSH. The overall protein concentration was determined with a BCA protein assay kit, and the fusion protein was cleaved with PreScission™ Protease (16 hours, 4° C., 1 U protease per 133 µg DJ-1). Untagged DJ-1 was separated from uncleaved GST-DJ-1, free GST, and residual protease (which contains an uncleavable GST tag) by elution from a GSTPrep FF column equilibrated with buffer G. Fractions most highly enriched with DJ-1 were identified by SDS-PAGE with Coomassie Blue staining and pooled. The final protein sample (estimated purity, 95%) was supplemented with glycerol (5%, [v/v]) and DTT (2-3 mM), and aliquots were frozen at −80° C. For all of the analyses outlined below, the concentration of recombinant DJ-1 was estimated using the BCA assay and verified with quantitative amino-acid analysis (Purdue University Proteomics Core).

Controlled Oxidation of DJ-1.

Aliquots of purified DJ-1 (wild-type or M26I) were dialyzed against 10 mM Tris at pH 8.0 to remove reductant, and the protein was treated with a tenfold molar excess of $H_2O_2$ for one hour at 22° C. These conditions were previously found to be suitable to convert DJ-1 to the '2O' form (Zhou et al., *Journal of Molecular Biology*, 2006, 356(4):1036-1048). Excess $H_2O_2$ was removed from each sample by exchanging the protein into fresh buffer (10 mM Tris at pH 8.0) using Amicon Ultra-4 centrifugal filters (molecular weight cutoff, 3 kDa).

Two-Dimensional Polyacrylamide Gel Electrophoresis.

Changes in the isoelectric point (pI) of DJ-1 following oxidation were monitored via two-dimensional polyacrylamide gel electrophoresis (2D-PAGE) (Canet-Aviles et al., *PNAS*, 2004, 101(24):9103-9108). Protein aliquots were dialyzed overnight against PBS. An aliquot of the protein (15 µg) was mixed with sample rehydration buffer (8 M urea, 2% [w/v] 3-[(3-cholamidopropyl)dimethylammonio]-1-propanesulfonate hydrate (CHAPS), 50 mM DTT, 0.2% [w/v] BioLyte 3/10 ampholyte, 0.001% [w/v] bromophenol blue) and recombinant α-synuclein as an internal standard (predicted pI=4.67) and Bio-Rad protein standards in a total volume of 185 µl. The solution was added to an 11 cm IPG strip with a pH range of 4 to 7. Mineral oil was added to the top of the IPG strip to reduce evaporation during electrophoresis. The IPG strip was actively rehydrated at 20° C. for 12 hours and subjected to isoelectric focusing in a Protean IEF Cell (Bio-Rad) with the following voltage parameters: step one, 250 V for 15 minutes; step two, 8000 V for 2.5 hours; step 3, 8000 V for 4.4 hours. The 1PG strip was reduced with 2% [w/v] DTT in equilibration buffer (6 M urea, 0.375 M Tris HCl, pH 8.8, 2% [w/v] SDS, 20% [v/v] glycerol) for 15 minutes, followed by alkylation with 2.5% [w/v] iodoacetamide for 15 minutes. The IPG strip was loaded onto the top of a Criterion XT 12% Bis-Tris pre-cast gel (Bio-Rad) and sealed with 0.5% [w/v] agarose in 1×XT MOPS buffer to ensure an even transfer of protein. The second-dimension gel was stained with Coomassie Blue and analyzed with a Typhoon Imaging System. Spots on the 2D PAGE gel were quantified by measuring average pixel intensities. Approximate pI values were determined by calibration with the α-synuclein internal standard.

Proteolytic $^{18}O$ Labeling with Immobilized Trypsin.

Proteolysis and peptide labeling were carried out using a modified version of a previously described method (Brown et. al, *J Proteome Res*, 2004, 3(3):455-462). Each protein (approximately 10 µg) was dried, denatured in guanidine HCl (6 M, 15 minutes, 22° C.), reduced with TCEP (1 mM, 60 minutes, 60° C.), alkylated with iodoacetamide (IAA) (10 mM, 10 minutes, 22° C.), and mixed overnight with 1 µg of immobilized trypsin in (0.1 M ammonium bicarbonate pH 8.0) Prior to this step the immobilized trypsin was pre-washed four times with acetate buffer (pH 5), 20 volumes per wash, to eliminate any non-covalently bound protease on the surface of the agarose beads. After trypsin digestion, the samples were completely dried by vacuum centrifugation and resuspended in $H_2^{16}O$ or $H_2^{18}O$ in $CH_3CN$ (25%, v/v). The samples were then incubated in the presence of a fresh aliquot of immobilized trypsin (1 µg) in (25% (v/v) $CH_3CN$ pH 6.0) for at least seven hours at 22° C. Immobilized trypsin was used in both the digestion and labeling steps to prevent exchange of the $^{16}O$ and $^{18}O$ label that would occur if the labeled and unlabeled peptides were mixed in the presence of free protease. As previously described (Miyagi et al., *Spectrometry Reviews*, 2007, 26(1):121-136), the decoupling of the digestion and labeling procedures enabled us to carry out each step at its optimal pH (i.e. pH 8.0 and 6.0, respectively). The labeling reaction occurred at an acidic pH of 6.0 and in an aqueous solution containing 25% (v/v) $CH_3CN$ because previous studies showed that the addition of organic solvents accelerates trypsin-catalyzed oxygen exchange (Brown et. al, *J Proteome Res*, 2004, 3(3):455-462; Miyagi et al., *Spectrometry Reviews*, 2007, 26(1):121-136). After adding phenylmethylsulfonylfluoride (PMSF) to inhibit the trypsin, the mixture was filtered using Amicon Ultra-0.5 mL centrifugal filters (molecular weight cutoff, 10 kDa), and the labeled and unlabeled peptides were recovered from the filtrate.

Mass Spectrometry.

Aliquots of the labeled and unlabeled peptide pools were mixed and analyzed by online capillary chromatography mass spectrometry. Tryptic peptides were separated on an Agilent Zorbax C18 column (0.2 150 mm) using a nano-HPLC instrument (Waters Instruments Inc., Milford, Mass.) at 0.2 µL/min Solvent A was 0.01% TFA in deionized $H_2O$ (di-$H_2O$) and solvent B was 95% $CH_3CN$/0.01% TFA in di-$H_2O$. The nano-HPLC instrument is coupled to a Q-STAR workstation (Applied Biosystems, Inc., Framingham, Mass.) equipped with a nano-ESI source to ensure high sensitivity. An 85 min linear gradient (from 0% B to 60% B) was used in the separation of the peptides. MS/MS spectra were obtained in the positive ion mode via collision-induced dissociation using 2000 V of ionization voltage at a sampling rate of one spectrum per second. The top three peptides with charges ranging from 2 to 4 were monitored by MS/MS. The centroid value of MS/MS peaks was determined using the following parameters. The merge distance was set at 100 ppm with minimum and maximum widths of 10 ppm and 500 ppm, respectively. The percentage height was set at 50% and MASCOT was used for all searches.

Mascot Database Searching and Peptide Quantitation.

The files were then sent to an in-house mascot distiller software program connected to a MASCOT server (Version 2.2, Matrix Science (Perkins et al., *Electrophoresis*, 1999, 20(18):3551-3567)). The program's quantitation toolbox is designed to automatically recognize light and heavy peaks, calculate the clustered peak areas, and connect these to the MS/MS profile corresponding to the fragmentation of the peptides. The DJ-1 protein sequence in the NCBI database was searched with the following parameters: (i) the selected protease was trypsin, and (ii) the chemical modifications accounted for by the search were carbamidomethyl cysteine, threonine oxidation to 2-amino-3-oxo-butanoic acid, dioxidation of cysteine, oxidation of methionine, trioxidation of cysteine, and histidine to asparagine conversion. The precursor mass tolerance was set to 100 ppm, and the fragment mass tolerance was set to 0.6 Da. In each case the $^{18}O$ labeling quantitation method was specified. The software calculated the areas of the $^{16}O$ and $^{18}O$ monoisotopic peaks corresponding to the unlabeled and labeled peptides, respectively. These peak area values were then used to determine peak ratios. The software algorithm corrected for the incomplete incorporation of $^{18}O$ label to calculate the relative abundance ratio. Strict criteria were used to reduce the risk of false positives. The MS/MS spectra of any modification detected was manually examined in order to be considered a correct match. All modifications with ambiguous MS/MS spectra were rejected.

Example 5

Profiling of Oxidative Stress Inter and Intra Proteomic Signatures in the Plasma of Type II Diabetic Zucker Rats Materials Sodium cyanoborohydride, biotin hydrazide, ultralinked immobilized monomeric avidin, D-biotin, and Slide-A-Lyzer dialysis cassettes were purchased from Pierce Chemical Company (Rockford, Ill.). Iodoacetamide, dithiothreitol (DTT), trypsin, dimethylglycine, α-cyano-4-hydroxy-cinnamic acid (CHCA), proteomics grade N-p-tosyl-phenylalanine chloromethyl ketone (TPCK)-treated trypsin, ammonium bicarbonate, guanidine, dithiothreitol, iodoacetamide acid (IAA), and L-cysteine were obtained from Sigma Chemical Co. (St. Louis, Mo.). Protease inhibitor cocktail was purchased from Roche Diagnostics (Indianapolis, Ind.). The ABI 4700 Proteomics Analyzer Calibration Mixture (4700) Cal Mix, bradykinin, angiotensin I, glu1-fibrinopeptide B, ACTH fragment 1-17, ACTH fragment 18-39, and ACTH fragment 7-38) and iTRAQ™ reagent multiplex kit were purchased from Applied Biosystems, Inc. (Foster City, Calif.). Trifluoroacetic acid (TFA), and HPLC grade acetonitrile were purchased from Mallinckrodt Chemicals (Phillipsburg, N.J.). Sodium phosphate, sodium chloride and formic acid 88% were purchased from Mallinkrodt (St. Louis, Mo.). Amicon Ultra-4 and Microcon Ultracel YM-3 centrifugal filter devices were purchased from Millipore (Billerica, Mass.).

Methods

Animal Model.

The Zucker diabetic (ZDF) and Zucker lean rats provided the animal model for investigating oxidized proteins. Diabetic Zucker rats are homozygous for a leptin receptor defect, becoming obese and developing diabetes naturally at about seven weeks of age. The Zucker lean rat is genetically matched and is heterozygous for the leptin receptor defect (Peterson et al., *ILAR News* 1990, 32:16-19).

Glucose Assay.

Glucose assays were done in a 96-well format utilizing a glucose oxidase reagent from Pointe Scientific (Canton, Mich.). Both plasma and ultrafiltrate samples were analyzed using this method. Samples were stored at −80° C. until the assay was performed.

Briefly, samples from diabetic animals and their lean controls were thawed on ice and used to prepare a standard curve using 10 mg glucose solution in benzoic acid (RICCA Chemical Company, Arlington, Tex.) diluted to 0, 100, 300 and 500 mg/dl. A reagent blank and positive control were included on all assays. The positive control was Control Serum II™ obtained from Wako Chemicals USA, Inc. (Richmond, Va.) and was diluted according to the manufacturer's instructions. A microassay was utilized. Two µl of standard, positive control, and samples were loaded onto the plate in triplicate. Two hundred µl of pre-heated (37° C.) glucose oxidase reagent were pipetted into all the wells. The plate was incubated at 37° C. for five minutes and then read using a Powerwave X plate reader (Bio-Tek Instruments, Inc., Winooski, Vt.) at 500 nm. Baseline and lean rat samples were not diluted. All other samples were diluted 1:1 with deionized water to maintain the linearity specifications of the assay.

F2 Isoprostane Assay.

Urinary isoprostanes were measured in duplicate at baseline, 3 and 6 weeks of the supplementation protocol using a commercial competitive ELISA kit from Oxford Biomedical Research (Oxford, Mich.) according to the manufacturer's instructions. Briefly, two dilutions of the urine samples (1:4, 1:8) were prepared in the enhanced dilution buffer. Standards were prepared following the kit instruction and provided a range from 0 to 100 ng/mL. 100 µL of each of the sample dilutions and standards were added to the pre-coated ELISA plate. In addition, 100 µL of the diluted 15-isoprostane F2t horseradish peroxidase (HRP) conjugate was added to all wells except the blank. The plate was covered and incubated at room temperature with gentle shaking for two hours. After two hours, the plate was washed three times with the kit wash buffer. Next, 200 µL of the substrate was added to each well. This was allowed to incubate for 20 minutes. 50 µL of 3 M sulfuric acid was added to stop the reaction and the plate was read at an absorbance of 450 nm using a Powerwave X (Bio-Tek Instruments, Inc., Winooski, Vt.).

The data was analyzed by subtracting the average value for the reagent blank from all other wells. The % Bo was graphed on the y axis (linear) versus the standard concentrations on the x axis (logarithmic) to interpret the standard curve. Sample values were averaged and an acceptable dilution was chosen based on the B/Bo % being between 20 and 80% on the standard curve Biotinylation of the Plasma Samples.

Both diabetic and lean rats were scarified at the age of six months, blood was collected in BD Vacutainer™ venous blood collection tubes coated with EDTA (Fisher Scientific, Hanover Park, Ill.). Protease inhibitor cocktail was then added. Generally, each tablet of the protease inhibitor cocktail was dissolved in 1 ml of distilled water. Then the protease inhibitor solution was mixed with plasma in ratio of 1:10 (v/v) respectively. Because plasma samples were maintained at neutral pH during biotinylation and affinity selection there was no need to inhibit aspartate protease along with proteases that are only active at acidic pH. The samples were then centrifuged at 1500×g for 15 minutes. The supernatant was removed and centrifuged again at 2000×g for 15 minutes after which 50 mM biotin hydrazide (BH) was added to the plasma to a final concentration of 5 mM. The reaction of BH with carbonyl groups was allowed to proceed at room temperature for two hours after which sodium cyanoborohydride was added to a final concentration of 15 mM and incubated at 0°

C. for one hour. Samples were dialyzed three times against at least 200 volumes of PBS buffer to remove any unreacted BH.

Avidin Purification of the Biotinylated Proteins.

An Agilent 1100 series HPLC (Agilent Technologies) was used for packing the immobilized monomeric avidin and to purify biotinylated proteins. This ultralinked immobilized monomeric avidin was self-packed in a PEEK column (4.6 mm×100 mm). The column was then washed with PBS (0.15 M pH 7.4) followed by 2 mM biotin to block any non-reversible biotin binding sites. This was followed by washing with a regeneration buffer (0.1 M dimethylglycine, pH 2.5) and re-equilibration by PBS. The Bradford assay was used to estimate the protein concentration in rat plasma. For protein identification and quantification, samples were run individually, digested, and then labeled with the iTRAQ™ reagent as described below. In order to characterize and quantitate oxidative stress induced post-translational modifications, it was necessary to enrich the modifications by pooling the samples before applying to the avidin affinity column. A total of 5 mg of plasma proteins was applied to the column with PBS mobile phase (0.15 M phosphate buffered saline, pH 7.4) at a flow rate of 0.5 mL/min. To remove any unbound proteins, the column was washed thoroughly with more than 60 column volumes. Bound proteins were then eluted with regeneration buffer (0.1M dimethylglycine, pH 2.5) during which detection was achieved by absorbance at 280 nm.

Quantitative Comparison of Protein Abundance with iTRAQ™ and MALDI/TOF/TOF Analysis.

Tryptic digested proteins from avidin affinity fractions were labeled with iTRAQ™ reagent. The supplier's guidelines (ABI) were followed for both trypsin digestion and labeling with iTRAQ™ reagent. Lean and diabetic rat plasma samples were labeled with the 114-Da and 117-Da iTRAQ™ labeling reagents, respectively. The labeled peptides were then desalted and fractionated using an Agilent 1100 Series HPLC (Agilent Technologies). A Pepmap C18 trap column and a nano-column (Zorbax 300SB-C18, 3.5 µm, 100 µm i.d., 15 cm length, Agilent Technologies, Santa Clara, Calif.) were used. Two solvents were used for the reversed-phase separation, solvent A composed of 0.1% TFA in deionized water and solvent B composed of 0.1% TFA in acetonitrile. The RPC separation was achieved using a 40 min linear gradient from 98% solvent A: 2% solvent B to 60% solvent A: 40% solvent B at a flow rate of 800 mL/min. A mixing tee was used to mix the peptides separated with (α-cyano-4-hydroxycinnamic acid, 4 mg/mL in 60% ACN/0.1% TFA). A microfraction collector was used to spot the peptide matrix solution on the plate. The spotted peptides were analyzed using ABI 4800 plus (4800 MALDI/TOF/TOF) Proteomics Analyzer equipped with a 200 Hz Nd:Yag laser in the positive ion mode. 4000 Explorer software controlled the automated acquisition of MS and MS/MS analysis. Protein identification, based on the acquired MS/MS spectra, was carried out utilizing Protein Pilot software 2.0 using the ProGroup™ algorithm (ABI) for protein identification. The minimum acceptance criterion for peptide identification was the 95% confidence level. Protein Pilot software 2.0 with the ProGroup™ algorithm was used to perform automated MS/MS data analysis for protein identification and quantification of iTRAQ™ reporter ions.

Reversed-Phase Separation of Biotinylated Proteins.

To characterize the (OSi-PTMs), an Agilent Zorbax 300SB-C3 reversed-phase column was used to desalt and fractionate biotinylated proteins. The reversed-phase column was equilibrated with 5 column volumes of buffer A (99.5% deionized $H_2O$ (dI $H_2O$), 0.5% acetonitrile (ACN) and 0.1% TFA). After a 5 column volume wash, a linear 50 min gradient was applied from 100% buffer A to 75% buffer B (5% dI $H_2O$, 95% ACN and 0.1% TFA) to elute the proteins from the column. Collected fractions were vacuum dried and stored for digestion. A total of 12 fractions were collected for each of the pooled lean and diabetic samples.

Proteolysis.

The samples were reconstituted in 6 M guanidine HCl and 10 mM dithiothreitol. After a one-hour incubation at 70° C. iodoacetamide (at a final concentration of 10 mM) was added to the reaction and allowed to incubate for 30 minutes at 4° C. Ammonium bicarbonate (0.1 M, pH 8.0) was added to dilute samples six-fold. Sequence grade trypsin (2%) was added and the reaction mixture incubated at 37° C. for 18 hours. Proteolysis was stopped by addition of tosyl lysine chloroketone (TLCK) (trypsin:TLCK, 1:1 (w/w)). The tryptic peptides were then used for characterization of the oxidation sites using a nano-HPLC-QSTAR mass spectrometer and their relative quantitation using selective reaction monitoring (SRM) methods.

LC/MS/MS of Digested Fractions And Database Searches.

Tryptic peptides were separated on a nanoACQUITY HPLC BEH C18 Column, (1.7 µm, 75 µm×100 mm) using a nano HPLC instrument (Waters Instruments Inc., Milford, Mass.) at a flow rate of 0.2 µL/min. Solvent A was 0.01% TFA in deionized $H_2O$ (dI $H_2O$) and solvent B was 95% ACN/0.01% TFA in dI $H_2O$. The nano-HPLC instrument was coupled to a Q-STAR workstation (Applied Biosystems Inc., Framingham, Mass.) equipped with a nano ESI source. An 85 min linear gradient (from 0% B to 60% B) was used to separate the peptides. MS/MS spectra were obtained in the positive ion mode using an ionization voltage of 2000 V at a sampling rate of one spectrum per second. The top three peptides with charges ranging from 2 to 4 were monitored by MSMS. Previous ions were excluded for 60 seconds. The centroid value of MS/MS peaks was determined using the following parameters; the merge distance was set at 100 ppm with minimum and maximum widths of 10 ppm and 500 ppm, respectively. The percentage height was set a 50% and MASCOT was used for all searches.

Mascot Database Searching.

The files were then sent to the Mascot Daemon software (version 2.2.2) where a merged file for each of the lean and the diabetic pooled fractions was produced. The merged files were then sent to an in-house MASCOT server (Version 2.2, Matrix Science; Perkins et al., *Electrophoresis* 1999, 20:3551-3567). The *Rattus norvegicus* taxonomy (24123 sequences) in the NCBI database (5532021 sequences and 1915541870 residues) was searched. The enzyme selected was trypsin. The database was searched twice. In the first search, carbamidomethyl cysteine was selected as a fixed modification. The variable modifications selected were: biotinylated oxidized arginine, biotinylated oxidized lysine, biotinylated oxidized proline, biotinylated oxidized threonine and oxidized methionine. The second search included carbamidomethyl cysteine as a fixed modification. Biotinylated 3-deoxyglucosone adduct, biotinylated HNE adduct, biotinylated glyoxal adduct, biotinylated methyl glyoxal adduct and oxidized methionine were selected as variable modifications. The precursor mass tolerance was set to 100 ppm and the fragment mass tolerance was set to 0.6 Da. The fragmentation of biotin produces noise in the spectrum that increases the expectation value (Borisov Oleg et al., *Anal. Chem.* 2002, 74:2284-2292; Han et al., *Anal. Chem.* 2007, 79:3342-3354; Mirzaei and Regnier, *J. Chromatog., B.* 2008, 873:8-14). Consequently, the biotinylated carbonylated modifications were validated manually.

Relative Quantification of Carbonylation Sites Using Selective Reaction Monitoring (SRM).

A list of the tryptic peptides carrying carbonylation sites in each of the pooled lean and diabetic samples was made. Fractions containing these peptides were analyzed as follows; tryptic peptides were separated on an HPLC-polymeric Chip (Agilent Technologies, Santa Clara, Calif.): composed of a 40 nl enrichment column and a 75 μm×150 mm separation column packed with ZORBAX 300 SB-C18, 5 μm particles; using an Agilent series 1100 instrument (Agilent Technologies) at 0.4 μL/min. Solvent A was water, and solvent B was acetonitrile, both containing 0.1% (v/v) formic acid. The mobile phase gradient, started with 2% B, reached 35% B after six minutes, then reached 90% after another two minutes and was held constant for two minutes to rinse the column. The mobile phase was brought back to 2% within 0.1 minute. Finally the column was re-equilibrated with a post run time of five minutes. Prior to separation, analytes were enriched on the 40 nl enrichment column on the same chip using a capillary pump at 4 μL/min at 0% B. The chip was connected to a nanospray emitter tip, which was connected to an Agilent 6410 triple quadrupole mass spectrometer equipped with an electrospray source.

Maximum sensitivity was achieved by adjusting the position of the chip nanospray emitter tip and the capillary voltage to achieve a good direct spray. A capillary voltage of at least 1800 V was used. MS/MS spectra were acquired in the positive ionization mode. Drying gas flow was used a 4 L/min at 300° C. The delta electro multiplier voltage was set to 200 V. The Agilent Mass Hunter ChemStation software (version B02.01) was used for data acquisition and processing. The ESI signal stability was tested by injecting a standard peptide glu fibrinopeptide (100 fmole), precursor ion m/z 786 and monitoring the signal at both the total ion current level and the SRM signal of two fragment ions m/z 1171 and m/z 684, collision energy used was 30 and dwell time of 50 was used in both cases.

Agilent optimizer and skyline software were used to select the most prominent fragment ions for the SRM transitions. Two transitions were recorded for each carbonylated peptide in each time window for acquisition. SRM transitions were acquired at unit resolution for both the first and third quadrupoles. The mass hunter workstation qualitative analysis software was used for the integration of the area under the curve (AUC) for each of the transitions. The AUCs of the carbonylated peptides in the diabetic rat plasma were divided by the corresponding AUCs in the lean rat plasma.

Knowledge Assembly Analysis.

To determine whether the proteins that changed more than 1.5-fold could be correlated with specific diseases the GeneGo™ "disease biomarker networks" tool was used to reveal disease biomarkers as seed nodes for the network. The networks were set to the default value of 0.5 of significant level, which indicates a false positive value of no more than 5% for the list of significant networks. The list of oxidized proteins identified was uploaded along with their calculated fold changes. All distributions were sorted by the most statistically significant using a P-value of 0.5 as the cutoff.

Example 6

A Novel Oxidative Stress Induced Posttranslational Modifications Based Assay for Testing the In Vivo Efficacy of Antioxidants Materials As described in Madian et al., *J Proteome Res*, 2010, 9:3766-3780, sodium cyanoborohydride, Biotin hydrazide, ultralinked immobilized monomeric avidin, D-biotin, and Slide-A-Lyzer dialysis cassettes were purchased from Pierce (Rockford, Ill.). Iodoacetamide, dithiothreitol (DTI), trypsin, Glycine, α-Cyano-4-hydroxy-cinnamic acid (CHCA), proteomics grade N-p-tosyl-phenylalanine chloromethyl ketone (TPCK)-treated trypsin, ammonium bicarbonate, guanidine, dithiothreitol, iodoacetamide acid (IAA), and L-cysteine were obtained from Sigma Chemical Co. (St. Louis, Mo.). Protease inhibitor cocktail was purchased from Roche Diagnostics (Indianapolis, Ind.). Trifluoroacetic acid (TFA), and HPLC grade acetonitrile were purchased from Mallinckrodt Chemicals (Phillipsburg, N.J.). Sodium phosphate, sodium chloride and formic acid 88% were purchased from Mallinkrodt (St. Louis, Mo.). Amicon Ultra-4 and Microcon Ultracel YM-3 centrifugal filter devices and were purchased from Millipore (Billerica, Mass.).

Methods

Animal Model.

The Zucker diabetic (ZDF) and Zucker lean rats provide an excellent animal model for investigating oxidized proteins. The diabetic rat is homozygous for a leptin receptor defect and becomes obese and develops diabetes naturally at about seven weeks of age. The Zucker lean rat is genetically matched and is heterozygous for the leptin receptor defect. Rats were obtained at six weeks of age. Diabetic rats were divided into two groups: controls and green tea. The rats were gavaged with green tea or water for six weeks. Glucose tolerance tests were performed and blood was harvested at sacrifice for proteomic analysis.

Biotinylation of the Plasma Samples.

Blood was mixed with EDTA and protease inhibitor, centrifuged at 1500×g for 15 minutes, then the supernatant was removed and centrifuged again at 2000×g for 15 minutes. Immediately after that, 50 mM biotin hydrazide was added to the plasma to the final concentration of 5 mM and the reaction was allowed to occur at room temperature for two hours. Sodium cyanoborohydride was then added to a final concentration of 15 mM and the reaction was allowed at 0° C. for one hour. Dialysis for three times in at least 200×PBS buffer was performed to remove any unreacted biotin hydrazide.

Avidin Purification of the Biotinylated Proteins.

Agilent series 1100 (Agilent Technologies) was used for packing the immobilized monomeric avidin as well as the purification of biotinylated proteins. This ultralinked immobilized monomeric avidin was self-packed in a PEEK column (4.6 mm×100 mm). The column was then washed with PBS (0.15M pH 7.4) followed by 2 mM biotin to block any non-reversible biotin binding sites. This was followed by washing with a regeneration buffer (0.1 M glycine, pH 2.5) and re-equilibration by PBS. Bradford assay was used to estimate the concentration of the protein concentration of the proteins in the rat plasma. We had to enrich the oxidative modifications by pooling the samples together and then these samples were applied on the avidin affinity column. A total of 5 mg of plasma proteins was applied on the column with PBS mobile phase (0.15 M phosphate buffered saline, pH 7.4) at a flow rate of 0.5 mL/min. To remove any unbound proteins, the column was washed thoroughly with more than 60 column volumes. The bound proteins were then eluted with the regeneration buffer (0.1 M glycine, pH 2.5). The resulting chromatogram was monitored at 280 nm.

Reversed-Phase Separation of Biotinylated Proteins.

An Agilent Zorbax 300SB-C3 reversed-phase column was used to desalt and fractionate biotinylated proteins. The reversed-phase column was equilibrated with 5 column volumes of buffer A (99.5% deionized $H_2O$ (dl $H_2O$), 0.5% acetonitrile (ACN) and 0.1% TFA). After a 5 column volume wash a linear 50 min gradient was applied from 100% buffer A to 75% buffer B (5% dl $H_2O$, 95% ACN and 0.1% TFA) to elute proteins from the column. Collected fractions were vacuum dried and stored for digestion. A total of 12 fractions were collected for each of the pooled green tea fed diabetic rats and their control diabetic rats' plasma samples.

Proteolysis.

The samples were reconstituted in 6 M guanidine HCl and 10 mM dithiothreitol. This was incubated for one hour at 70° C. Iodoacetamide (with final concentration of 10 mM) was added to the reaction and allowed to incubate for 30 minutes at 4° C. 0.1 M ammonium bicarbonate (pH 8.0) was added to dilute the samples six times. Sequence grade trypsin (2%) was added and the reaction mixture incubated at 37° C. for 18 hours. Proteolysis was stopped by addition of tosyl lysine chloroketone (TLCK) (trypsin:TLCK ratio of 1:1 (w/w)). The tryptic peptides were then used for the characterization of the oxidation sites using a nano-HPLC-QSTAR mass spectrometer and their relative quantitation using selective reaction monitoring (SRM) technique.

LC/MS/MS of Digested Fractions and Database Searches.

Tryptic peptides were separated on nanoACQUITY HPLC BEH C18 Column, (1.7 µm, 75 µm×100 mm) using an nano HPLC instrument (Waters Instruments Inc., Milford, Mass.) at 0.2 µL/min. Solvent A was 0.01% TFA in deionized $H_2O$ (dI $H_2O$) and solvent B was 95% ACN/0.01% TFA in dI H2O. The nano-HPLC instrument is coupled to a Q-STAR workstation (Applied Biosystems Inc., Framingham, Mass.) equipped with a nano ESI source. An 85 min linear gradient (from 0% B to 60% B) was used in the separation of the peptides. MS/MS spectra were obtained in the positive ion mode using 2000 volts of ionization voltage at a sampling rate of one spectrum per second. The top three peptides with charges ranging from 2 to 4 were monitored by MSMS. Previous ions were excluded for 60 seconds. The centroid value of MSMS peaks was determined using the following parameters; the merge distance was set at 100 ppm with minimum and maximum widths of 10 ppm and 500 ppm, respectively. The percentage height was set a 50% and MASCOT was used for all searches.

Mascot Database Searching.

The files were then sent to the Mascot Daemon software (version 2.2.2) where a merged file for each of the lean and the diabetic pooled fractions were produced. The merged files were then sent to an in-house MASCOT server (Version 2.2, Matrix Science; Perkins et al., *Electrophoresis* 1999, 20(18): 3551-3567). The *Rattus norvegicus* taxonomy (24123 sequences) in the NCBI database (5532021 sequences and 1915541870 residues) was searched. Enzyme selected was trypsin. The database was searched twice. In the first search, carbamidomethyl cysteine was selected as a fixed modification. The variable modifications selected were: biotinylated oxidized arginine, biotinylated oxidized lysine, biotinylated oxidized proline, biotinylated oxidized threonine and oxidized methionine. The second search included carbamidomethyl cysteine as a fixed modification. Biotinylated 3-deoxyglucosone adduct, biotinylated HNE adduct, biotinylated glyoxal adduct, biotinylated methyl glyoxal adduct and oxidized methionine were selected as variable modifications. The precursor mass tolerance was set to 100 ppm and the fragment mass tolerance was set to 0.6 Da. The fragmentation of biotin produces noise in the spectrum that increases the expectation value (Borisov Oleg et al., *Anal. Chem.* 2002, 74(10):2284-92; Han et al., *Anal. Chem.* 2007, 79(9):3342-54; Mirzaei et al., *J. Chromatogr., B: Anal. Technol. Biomed. Life Sci.* 2008, 873(1):8-14). Consequently, the biotinylated carbonylated modifications were validated manually only.

Relative Quantitation of Carbonylation Sites Using Selective Reaction Monitoring (SRM).

A list of the tryptic peptides carrying carbonylation sites in each of the pooled green tea fed diabetic rat plasma samples and their control diabetic rat plasma samples was made. The fractions containing these peptides were analyzed as follows; tryptic peptides were separated on an HPLC-polymeric Chip (Agilent Technologies, Santa Clara, Calif.): composed of a 40 nl enrichment column and a separation column 75 µm×150 mm packed with ZORBAX 300 SB-C18, 5 µm particle size; using Agilent series 1100 instrument (Agilent Technologies) at 0.4 µL/min. Solvent A was water, and solvent B was acetonitrile, both containing 0.1% (v/v) formic acid. The mobile phase gradient, started with 2% B, reached 35% B after six minutes, then reached 90% after another two minutes and held constant for two minutes to rinse the column. This was brought back to 2% within 0.1 minute. Finally the column was re-equilibrated with a post run time of five minutes. Prior to this gradient, the analytes were enriched by the 40 nl enrichment column on the same chip using a capillary pump at 4 µL/min at 0% B.

The chip is connected to a nanospray emitter tip, which is connected to an Agilent 6410 triple quadrupole mass spectrometer equipped with an electrospray source.

Maximum sensitivity was achieved by adjusting the position of the chip nanospray emitter tip and the capillary voltage to achieve a good direct spray. A capillary voltage of at least 1800 V was used in our analyses. MS/MS spectra were acquired in the positive ionization mode. Drying gas flow was 4 L/min. Drying gas temperature was 300° C. The delta electro multiplier voltage was set to 200 V. The Agilent Mass Hunter ChemStation software (version B02.01) was used for data acquisition and processing. The ESI signal stability was tested by injecting a standard peptide glu fibrinopeptide (100 fmole), precursor ion m/z 786 and monitoring the signal at both the total ion current level and the MRM signal of two fragment ions m/z 1171 and m/z 684, collision energy used was 30 and dwell time of 50 was used in both cases.

Agilent optimizer and skyline software were used to select the most prominent fragment ions for the SRM transitions. Two transitions were recorded for each carbonylated peptide in each time window for acquisition. SRM transitions were acquired at unit resolution for both the first and third quadrupoles. The mass hunter workstation qualitative analysis software was used for the integration of the area under the curve (AUC) for each of the transitions. The AUCs of the carbonylated peptides in the green tea fed diabetic rat plasma were divided by the corresponding AUCs in the control diabetic rat plasma.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for determining whether a subject is afflicted with diabetes mellitus comprising:
- obtaining a blood or plasma sample from said subject comprising at least one carbonylated protein selected from Table 15, wherein the carbonylated protein comprises a plurality of carbonylated sites;
- isolating the carbonylated protein from the other oxidized proteins in the sample via an affinity purification technique, wherein the step of isolating comprises:
  - coupling a first member of a binding pair to the carbonylated protein;
  - contacting the sample to a chromatographic support matrix that comprises a second member of the binding pair such that the carbonylated protein is retained in the support matrix via a binding between the first and second members of the binding pair while the other oxidized proteins flow through the matrix;
- digesting the isolated carbonylated protein into a plurality of different carbonylated peptides;
- determining and quantitatively assessing by a liquid chromatography-mass spectrometry technique a degree of oxidation at each of a plurality of carbonylated sites found in one or more of the carbonylated peptides obtained from the following carbonylated proteins from as disclosed in Table 15: hemoglobin alpha 2 chain; major beta-hemoglobin; fibrinogen alpha chain; fatty acid binding protein, immunoglobulin heavy chain, and complement component 3;
- comparing the degree of oxidation at each of the plurality of carbonylated sites to a degree of oxidation at each of the same sites found in one or more reference peptides; and
- detecting a difference in the degree of oxidation at the plurality of the carbonylated sites between the one or more carbonylated peptides and the reference peptides, wherein a greater than 1.5 fold increase in the degree of oxidation at the plurality of the carbonylated sites is indicative of the subject being afflicted with diabetes mellitus.

2. The method of claim 1 wherein the carbonylated peptide, the reference peptide, or both are detectably labeled.

3. The method of claim 1 wherein comparing the carbonylated peptide with the reference peptides comprises using global internal standard technology.

4. The method of claim 1, further comprising: eluting the bound carbonylated protein from said chromatographic support matrix.

5. The method of claim 1, wherein the first member of the binding pair is biotin and the second member of the binding pair is avidin.

6. The method of claim 1 wherein the carbonylated protein originates from an organ and is shed into blood.

7. The method of claim 1 wherein the carbonylated protein results from:
- oxidative cleavage of an amino acid side chain;
- cleavage of the primary peptide structure;
- glycation;
- an AGE-peptide adduct; or
- addition of a lipid peroxidation product.

8. The method of claim 1 wherein the carbonylated peptide, the reference peptide, or both comprises an oxidative stress induced post-translational modification (OSi-PTM).

9. The method of claim 1, further comprising administering a therapeutically effective amount of a composition comprising an antioxidant to the subject determined to be afflicted with diabetes mellitus.

10. The method of claim 1, wherein the method is performed at least once at a later point in time to thereby monitor the progression of diabetes in the subject.

* * * * *

SEQUENCE LISTING

```
<160> NUMBER OF SEQ ID NOS: 6

<210> SEQ ID NO 1
<211> LENGTH: 24
<212> TYPE: PRT
<213> ORGANISM: Rattus rattus

<400> SEQUENCE: 1

Lys Gly Leu Ile Ala Ala Ile Cys Ala Gly Pro Thr Ala Leu Leu Ala
1               5                   10                  15

His Glu Ile Gly Phe Gly Ser Lys
            20

<210> SEQ ID NO 2
<211> LENGTH: 23
<212> TYPE: PRT
<213> ORGANISM: Rattus rattus

<400> SEQUENCE: 2

Gly Leu Ile Ala Ala Ile Cys Ala Gly Pro Thr Ala Leu Leu Ala His
1               5                   10                  15

Glu Ile Gly Phe Gly Ser Lys
            20

<210> SEQ ID NO 3
<211> LENGTH: 15
<212> TYPE: PRT
<213> ORGANISM: Rattus rattus

<400> SEQUENCE: 3

Asp Val Val Ile Cys Pro Asp Ala Ser Leu Glu Asp Ala Lys Lys
1               5                   10                  15

<210> SEQ ID NO 4
<211> LENGTH: 15
<212> TYPE: PRT
<213> ORGANISM: Rattus rattus

<400> SEQUENCE: 4

Gly Ala Glu Glu Met Glu Thr Val Ile Pro Val Asp Val Met Arg
1               5                   10                  15

<210> SEQ ID NO 5
<211> LENGTH: 18
<212> TYPE: PRT
<213> ORGANISM: Rattus rattus

<400> SEQUENCE: 5

Asp Lys Met Met Asn Gly Gly Met Tyr Thr Tyr Ser Glu Asn Arg Val
1               5                   10                  15

Glu Lys
```

```
<210> SEQ ID NO 6
<211> LENGTH: 8
<212> TYPE: PRT
<213> ORGANISM: Rattus rattus

<400> SEQUENCE: 6

Lys Val Ala Asp Ala Leu Ala Lys
 1               5
```